United States Patent
Bahadoor et al.

(10) Patent No.: US 9,346,769 B2
(45) Date of Patent: May 24, 2016

(54) TETRAZOLONES AS INHIBITORS OF FATTY ACID SYNTHASE

(71) Applicant: Infinity Pharmaceuticals, Inc., Cambridge, MA (US)

(72) Inventors: Adilah Bahadoor, Stittsville (CA); Alfredo C. Castro, Winchester, MA (US); Lawrence K. Chan, Brookline, MA (US); Gregg F. Keaney, Lexington, MA (US); Marta Nevalainen, Weymouth, MA (US); Vesa Nevalainen, Weymouth, MA (US); Stephane Peluso, Brookline, MA (US); Daniel A. Snyder, Somerville, MA (US); Thomas T. Tibbitts, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/975,236

(22) Filed: Aug. 23, 2013

(65) Prior Publication Data

US 2014/0079667 A1 Mar. 20, 2014

Related U.S. Application Data

(62) Division of application No. 13/101,978, filed on May 5, 2011, now Pat. No. 8,546,432.

(60) Provisional application No. 61/331,575, filed on May 5, 2010, provisional application No. 61/331,644, filed on May 5, 2010, provisional application No. 61/419,174, filed on Dec. 2, 2010, provisional application No. 61/437,564, filed on Jan. 28, 2011, provisional application No. 61/472,566, filed on Apr. 6, 2011.

(51) Int. Cl.

| | |
|---|---|
| A61K 31/7056 | (2006.01) |
| A61K 31/497 | (2006.01) |
| A61K 31/5377 | (2006.01) |
| A61K 31/4439 | (2006.01) |
| A61K 31/454 | (2006.01) |
| A61K 31/428 | (2006.01) |
| A61K 31/4184 | (2006.01) |
| A61K 31/4709 | (2006.01) |
| A61K 31/5415 | (2006.01) |
| A61K 31/55 | (2006.01) |
| A61K 31/41 | (2006.01) |
| A61K 38/21 | (2006.01) |
| A61K 45/06 | (2006.01) |
| C07D 257/04 | (2006.01) |
| C07D 401/06 | (2006.01) |
| C07D 401/12 | (2006.01) |
| C07D 403/06 | (2006.01) |
| C07D 403/12 | (2006.01) |

(Continued)

(52) U.S. Cl.
CPC .............. *C07D 257/04* (2013.01); *A61K 31/41* (2013.01); *A61K 31/4184* (2013.01); *A61K 31/428* (2013.01); *A61K 31/4439* (2013.01); *A61K 31/454* (2013.01); *A61K 31/4709* (2013.01); *A61K 31/497* (2013.01); *A61K 31/5377* (2013.01); *A61K 31/5415* (2013.01); *A61K 31/55* (2013.01); *A61K 31/7056* (2013.01); *A61K 38/21* (2013.01); *A61K 38/212* (2013.01); *A61K 38/217* (2013.01); *A61K 45/06* (2013.01); *C07D 295/185* (2013.01); *C07D 295/205* (2013.01); *C07D 401/06* (2013.01); *C07D 401/12* (2013.01); *C07D 401/14* (2013.01); *C07D 403/04* (2013.01); *C07D 403/06* (2013.01); *C07D 403/12* (2013.01); *C07D 405/12* (2013.01); *C07D 407/12* (2013.01); *C07D 413/06* (2013.01); *C07D 413/12* (2013.01); *C07D 417/04* (2013.01); *C07D 417/06* (2013.01)

(58) Field of Classification Search
None
See application file for complete search history.

(56) References Cited

U.S. PATENT DOCUMENTS

| | | | |
|---|---|---|---|
| 4,270,537 A | 6/1981 | Romaine et al. | |
| 4,596,556 A | 6/1986 | Morrow et al. | |

(Continued)

FOREIGN PATENT DOCUMENTS

| | | |
|---|---|---|
| DE | 4437197 | 4/1996 |
| EP | 0712850 | 5/1996 |

(Continued)

OTHER PUBLICATIONS

Kuhajda (Cancer Res 2006;66:5977-5980. Published online Jun. 15, 2006).*

(Continued)

*Primary Examiner* — Alicia L Otton
(74) *Attorney, Agent, or Firm* — Jones Day

(57) ABSTRACT

Provided herein are tetrazolone FASN inhibitors of the formula (I):

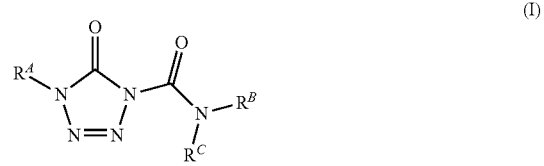

(I)

or a pharmaceutically acceptable form thereof; wherein the variables $R^A$, $R^B$ and $R^C$ are defined herein.
Also provided herein are pharmaceutical compositions of the compounds provided herein as well as methods of their use for the treatment of various disorders such as hyperproliferative disorders, inflammatory disorders, obesity-related disorders and microbial infections.

57 Claims, 2 Drawing Sheets

(51) Int. Cl.
   *C07D 407/12*     (2006.01)
   *C07D 413/06*     (2006.01)
   *C07D 413/12*     (2006.01)
   *C07D 417/04*     (2006.01)
   *C07D 417/06*     (2006.01)
   *C07D 295/185*    (2006.01)
   *C07D 295/205*    (2006.01)
   *C07D 401/14*     (2006.01)
   *C07D 403/04*     (2006.01)
   *C07D 405/12*     (2006.01)

(56) References Cited

U.S. PATENT DOCUMENTS

| | | |
|---|---|---|
| 4,598,089 A | 7/1986 | Hadvary et al. |
| 4,790,824 A | 12/1988 | Morrow et al. |
| 4,826,529 A | 5/1989 | Covey et al. |
| 4,886,499 A | 12/1989 | Cirelli et al. |
| 4,931,463 A | 6/1990 | Barbier et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,347,010 A | 9/1994 | Goto et al. |
| 5,362,704 A | 11/1994 | Goto et al. |
| 5,383,851 A | 1/1995 | McKinnon et al. |
| 5,417,662 A | 5/1995 | Hjertman et al. |
| 5,466,220 A | 11/1995 | Brenneman et al. |
| 5,466,708 A | 11/1995 | Derungs et al. |
| 5,480,381 A | 1/1996 | Weston et al. |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons et al. |
| 5,589,439 A | 12/1996 | Goto et al. |
| 5,599,302 A | 2/1997 | Lilley et al. |
| 5,605,920 A | 2/1997 | Goto et al. |
| 5,641,727 A | 6/1997 | Goto et al. |
| 5,649,912 A | 7/1997 | Peterson et al. |
| 5,650,374 A | 7/1997 | Goto et al. |
| 5,652,198 A | 7/1997 | Goto et al. |
| 5,654,257 A | 8/1997 | Goto et al. |
| 5,668,087 A | 9/1997 | Goto et al. |
| 5,686,392 A | 11/1997 | Stelzer et al. |
| 5,704,911 A | 1/1998 | Parsons et al. |
| 5,747,420 A | 5/1998 | Goto et al. |
| 5,759,837 A | 6/1998 | Kuhajda et al. |
| 5,767,286 A | 6/1998 | Yanagi et al. |
| 5,776,858 A | 7/1998 | Goto et al. |
| 5,893,397 A | 4/1999 | Peterson et al. |
| 5,981,575 A | 11/1999 | Kuhajda et al. |
| 5,993,412 A | 11/1999 | Deily et al. |
| 6,262,275 B1 | 7/2001 | Goto et al. |
| 6,277,790 B1 | 8/2001 | Zagar et al. |
| 6,498,187 B1 | 12/2002 | Christensen et al. |
| 6,548,450 B1 | 4/2003 | Watanabe et al. |
| 6,559,179 B1 | 5/2003 | Gaitanopoulos et al. |
| 6,608,059 B1 | 8/2003 | Daines et al. |
| 6,670,388 B1 | 12/2003 | Daines et al. |
| 6,723,749 B2 | 4/2004 | Christensen et al. |
| 6,919,376 B2 | 7/2005 | Llompart et al. |
| 7,410,976 B2 | 8/2008 | Yamakawa et al. |
| 7,445,794 B1 | 11/2008 | Newell et al. |
| 7,446,188 B2 | 11/2008 | Bao et al. |
| 7,449,482 B2 | 11/2008 | Cheng et al. |
| 7,491,381 B2 | 2/2009 | Kotani et al. |
| 7,531,521 B2 | 5/2009 | Burnett et al. |
| 7,572,783 B2 | 8/2009 | Chen et al. |
| 7,834,035 B2 | 11/2010 | Bessis et al. |
| 2002/0173447 A1 | 11/2002 | Pizer et al. |
| 2003/0220392 A1 | 11/2003 | Leber et al. |
| 2004/0024050 A1 | 2/2004 | Smith et al. |
| 2004/0058988 A1 | 3/2004 | Christensen, IV et al. |
| 2004/0120977 A1 | 6/2004 | Dodd et al. |
| 2004/0266732 A1 | 12/2004 | Galvez et al. |
| 2006/0241177 A1 | 10/2006 | Kuhajda et al. |
| 2006/0247302 A1 | 11/2006 | Kuhajda et al. |
| 2006/0258620 A1 | 11/2006 | Smith et al. |
| 2007/0142456 A1 | 6/2007 | Kuhajda et al. |
| 2007/0203236 A1 | 8/2007 | Smith et al. |
| 2007/0207975 A1 | 9/2007 | Menendez et al. |
| 2009/0013011 A1 | 1/2009 | Barker et al. |
| 2009/0023729 A1 | 1/2009 | Nakamura et al. |
| 2009/0042892 A1 | 2/2009 | Ali et al. |
| 2009/0042922 A1 | 2/2009 | Romo |
| 2009/0048276 A1 | 2/2009 | Goulet et al. |
| 2009/0048298 A1 | 2/2009 | Keyes et al. |
| 2009/0053804 A1 | 2/2009 | Ruiz et al. |
| 2009/0054478 A1 | 2/2009 | Zoller et al. |
| 2009/0054494 A1 | 2/2009 | Keil et al. |
| 2009/0061031 A1 | 3/2009 | Lee-Huang et al. |
| 2009/0062547 A1 | 3/2009 | Romo et al. |
| 2009/0069284 A1 | 3/2009 | Baker et al. |
| 2009/0069329 A1 | 3/2009 | McElroy et al. |
| 2009/0082339 A1 | 3/2009 | Schwink et al. |
| 2009/0082391 A1 | 3/2009 | Schwink et al. |
| 2009/0098224 A1 | 4/2009 | Cornelius et al. |
| 2009/0104210 A1 | 4/2009 | Tota et al. |
| 2009/0105305 A1 | 4/2009 | Butlin et al. |
| 2009/0118332 A1 | 5/2009 | Butlin et al. |
| 2009/0131395 A1 | 5/2009 | Antonelli et al. |
| 2009/0131409 A1 | 5/2009 | Mehlmann et al. |
| 2009/0131437 A1 | 5/2009 | Furet et al. |
| 2009/0131464 A1 | 5/2009 | Yamakawa et al. |
| 2009/0131475 A1 | 5/2009 | Uesugi et al. |
| 2009/0142335 A1 | 6/2009 | Kahn et al. |
| 2009/0149477 A1 | 6/2009 | Defossa et al. |
| 2009/0149486 A1 | 6/2009 | Defossa et al. |
| 2009/0149487 A1 | 6/2009 | Defossa et al. |
| 2009/0149519 A1 | 6/2009 | Defossa et al. |
| 2009/0155828 A1 | 6/2009 | Smith et al. |
| 2009/0162870 A1 | 6/2009 | Medghalchi et al. |
| 2009/0163433 A1 | 6/2009 | Grant et al. |
| 2009/0176786 A1 | 7/2009 | Konobe et al. |
| 2009/0186834 A1 | 7/2009 | Talley et al. |
| 2009/0192101 A1 | 7/2009 | Hung et al. |
| 2009/0202569 A1 | 8/2009 | Mashima et al. |
| 2009/0229015 A1 | 9/2009 | Metz et al. |
| 2009/0239253 A1 | 9/2009 | Watkins et al. |
| 2009/0253619 A1 | 10/2009 | Butler et al. |

FOREIGN PATENT DOCUMENTS

| | | |
|---|---|---|
| EP | 0902028 | 3/1999 |
| EP | 2097082 | 6/2008 |
| JP | 9-87281 A | 3/1997 |
| JP | 9087281 | 3/1997 |
| JP | 10-251238 A | 9/1998 |
| JP | 200951828 | 3/2009 |
| JP | 2009051827 | 3/2009 |
| WO | WO 97/13537 | 4/1997 |
| WO | WO 97/37705 | 10/1997 |
| WO | WO 98/25912 | 6/1998 |
| WO | WO 98/35961 | 8/1998 |
| WO | WO 98/51683 | 11/1998 |
| WO | WO 99/34850 | 7/1999 |
| WO | WO 99/48890 | 9/1999 |
| WO | WO 01/70673 | 9/2001 |
| WO | WO 02/28843 | 4/2002 |
| WO | 03/016290 A1 | 2/2003 |
| WO | WO 03/088975 | 10/2003 |
| WO | WO 2005/044797 | 5/2005 |
| WO | WO 2005/0103022 | 11/2005 |
| WO | WO 2006/067139 | 6/2006 |
| WO | WO 2006/123257 | 11/2006 |
| WO | WO 2007/019426 | 2/2007 |
| WO | WO 2007/088999 | 8/2007 |

(56) References Cited

FOREIGN PATENT DOCUMENTS

| WO | WO 2008/023266 | 2/2008 |
|---|---|---|
| WO | WO 2008/057585 | 5/2008 |
| WO | WO 2009/023059 | 2/2009 |
| WO | WO 2009/045313 | 4/2009 |
| WO | WO 2009/048249 | 4/2009 |
| WO | WO 2009/059046 | 5/2009 |
| WO | WO 2009/064927 | 5/2009 |
| WO | WO 2009/074829 | 6/2009 |
| WO | WO 2009/080182 | 7/2009 |
| WO | WO 2009/080223 | 7/2009 |
| WO | WO 2009/088931 | 7/2009 |
| WO | WO 2009/097995 | 8/2009 |
| WO | WO 2009/097996 | 8/2009 |
| WO | WO 2009/097997 | 8/2009 |
| WO | WO 2009/097998 | 8/2009 |
| WO | WO 2009/097999 | 8/2009 |
| WO | WO 2009/098000 | 8/2009 |
| WO | WO 2010/047956 | 4/2010 |
| WO | WO 2011/048018 | 4/2011 |
| WO | WO 2011/056635 | 5/2011 |

OTHER PUBLICATIONS

"Definition of Cancer," MedicineNet.com, 2004, Accessed Sep. 16, 2005, Obtained from <http://www.medterms.com>.*

Wang et al., J. Immunol. 2007, 179, pp. 5958-5965.*

Adams et al., "Rabbitpox virus and vaccinia virus infection of rabbits as a model for human smallpox," J Virol. 81(20):11084-11095, Epub Aug. 8, 2007.

Agostini et al., "Fatty acid synthase is required for the proliferation of human oral squamous carcinoma cells," Oral Oncol. 40(7):728-735 (2004).

Allen et al., "Identification and characterization of mutations in hepatitis B virus resistant to lamivudine. Lamivudine Clinical Investigation Group," Hepatology 27(6):1670-1677 (1998).

Alli et al., "Fatty acid synthase inhibitors are chemopreventive for mammary cancer in neu-N transgenic mice," Oncogene 24(1):39-46 (2005).

Alo et al., "Expression of fatty acid synthase (FAS) as a predictor of recurrence in stage I breast carcinoma patients," Cancer 77(3):474-482 (1996).

Alo et al., "Fatty acid synthase expression in Paget's disease of the vulva," Int J Gynecol Pathol. 24(4):404-408 (2005).

Alo et al., "Immunohistochemical study of fatty acid synthase in ovarian neoplasms," Oncol Rep. 7(6):1383-1388 (2000).

Amaral et al., "Intracerebral Infection with Dengue-3 Virus Induces Meningoencephalitis and Behavioral Changes that Precede Lethality in Mice," J. Neuroinflammation, 8:23 (2011).

Americo et al., "Identification of wild-derived inbred mouse strains highly susceptible to monkeypox virus infection for use as small animal models," J Virol. 84(16):8172-8180, Epub Jun. 2, 2010.

Angus et al., "Resistance to adefovir dipivoxil therapy associated with the selection of a novel mutation in the HBV polymerase," Gastroenterology 125(2):292-297 (2003).

Ashton et al., "The Mechanism of Inhibition of Fatty Acid Synthase by the Herbicide Diflufenican," Phytochemistry, 35(3): 587-590, 1994.

Ayash-Tashkovsky et al., "A novel small animal model for HIV-1 infection," FASEB J. 19(9):1149-1151, Epub Apr. 15, 2005.

Baldick et al., "A novel small molecule inhibitor of hepatitis C virus entry," PLoS Pathog. 6(9):e1001086 (2010).

Berge et al., "Pharmaceutical Salts," J. Pharmaceutical Sciences 66:1-19 (1977).

Blight et al., "Efficient initiation of HCV RNA replication in cell culture," Science 290(5498):1972-1974 (2000).

Blight et al., "Efficient replication of hepatitis C virus genotype 1a RNAs in cell culture," J Virol. 77(5):3181-3190 (2003).

Boger, et al., "Toward the primary targed of chloroacetamides," Pest Management Science, 56:497-508, 2000.

Bolger et al., "Cutaneously applied acyclovir acts systemically in the treatment of herpetic infection in the hairless mouse," Antiviral Res. 35(3):157-165 (1997).

Bonyhadi et al., "The SCID-hu mouse: an in vivo model for HIV-1 infection in humans," Mol Med Today 3(6):246-53 (1997).

Bourne et al., "Cyclic HPMPC is safe and effective against systemic guinea pig cytomegalovirus infection in immune compromised animals," Antiviral Res. 47(2):103-109 (2000).

Bravo et al., "An animal model of neonatal cytomegalovirus infection," Antiviral Res. 60(1):41-49 (2003).

Bravo et al., "Effect of maternal treatment with cyclic HPMPC in the guinea pig model of congenital cytomegalovirus infection," J Infect Dis. 193(4):591-597, Epub Jan. 13, 2006.

Browning et al., "Mice transgenic for human CD4 and CCR5 are susceptible to HIV infection," Proc Natl Acad Sci U S A. 94 26:14637-14641 (1997).

Butler et al., "Comparative reactions of benzonitrillium N-4-nitrophenylimide with some 1-substituted tetrazol-5-ones, tetrazole-5-thiones and tetraol-5-amines; a route to 1,2,4-triazole and 1,3,4-thiadiazole derivatives," J. Chem Research, 306-307 1993.

Camassei et al., Expression of the lipogenic enzyme fatty acid synthase (FAS) as a predictor of poor outcome in nephroblastoma: an interinstitutional stud Med Pediatr Oncol. 40(5):302-308 (2003).

Camassei et al., "Expression of the lipogenic enzyme fatty acid synthase (FAS) in retinoblastoma and its correlation with tumor aggressiveness," Invest Ophthalmol Vis Sci. 44(6):2399-2403 2003.

Carvalho et al., "Fatty acid synthase inhibition with Orlistat promotes apoptosis and reduces cell growth and lymph node metastasis in a mouse melanoma model," Int J Cancer. 123(11):2557-2565 (2008).

Cassagne et al., "Biosynthesis of Very Long Chain Fatty Acids in Higher Plants," Prog. Lipid Res. 33(1/2): 55-69, 1994.

Cavanaugh et al., "Interleukin-12 inhibits hepatitis B virus replication in transgenic mice," J Virol. 71(4):3236-3243 (1997).

Chakravarty et al., "Human Fatty Acid Synthase: Structure and Substrate Selectivity of the Thioesterase Domain," Proc. Natl. Acad. Sci. U.S.A., 101(44)L 15567-15572 (2004).

Chen et al., "Inhibition of dengue virus by an ester prodrug of an adenosine analog," Antimicrob Agents Chemother. 54(8):3255-3261, Epub Jun. 1, 2010.

Chen et al., "Prevention of genital herpes in a guinea pig model using a glycoprotein D-specific single chain antibody as a microbicide," Virol J., 1:11 (2004).

Cherry et al., "COPI activity coupled with fatty acid biosynthesis is required for viral replication," PLoS Pathog. 2(10):e102 (2006).

Christensen, "Cottontail rabbit papillomavirus (CRPV) model system to test antiviral and immunotherapeutic strategies," Antiviral Chemistry & Chemotherapy 16:283-294 (2005).

Consolazio et al., "Overexpression of fatty acid synthase in ulcerative colitis," Am J Clin Pathol. 126(1):113-118 (2006).

Courcambeck et al., "Resistance of hepatitis C virus to NS3-4A protease inhibitors: mechanisms of drug resistance induced by R155Q, A156T, D168A and D168V mutations," Antivir Ther. 11(7):847-855 (2006).

Cox et al., "Steady-state kinetic study of fatty acid synthase from chicken liver," Proc Natl Acad Sci U S A. 80(14):4233-4237 (1983).

Crute et al., "Herpes simplex virus helicase-primase inhibitors are active in animal models of human disease," Nat Med. 8(4):386-391 (2002).

De Schrijver et al., "RNA interference-mediated silencing of the fatty acid synthase gene attenuates growth and induces morphological changes and apoptosis of LNCaP prostate cancer cells," Cancer Res. 63(13):3799-3804 (2003).

Del Corona et al., "Synthesis and preliminary data on new selective and potent gastric prokinetic substituted benzamides," Eur. J. Med. Chem. 28:419-425 (1993).

Denecker et al., "Synthesis and Spectral Characteristics of Vinyltetrazolinones," Tetrahadron 31: 765-775 (1975).

Eckerman et al., "Covalent binding of chloroacetamide herbicides to the active site cysteine of plant type III polyketide synthases," Phytochemistry, 64: 1045-1054, (2003).

Epstein et al., "OA-519 (fatty acid synthase) as an independent predictor of pathologic state in adenocarcinoma of the prostate," Urology 45(1):81-86 (1995).

(56) References Cited

OTHER PUBLICATIONS

Evert et al., "Overexpression of fatty acid synthase in chemically and hormonally induced hepatocarcinogenesis of the rat," Lab Invest. 85(1):99-108 (2005).
Farasati et al., "Effect of leflunomide and cidofovir on replication of BK virus in an in vitro culture system," Transplantation 79(1):116-118 (2005).
Flavin et al., "Fatty Acid Synthase as a Potential Therapeutic Target in Cancer," Future Oncol. 6(4): 551-562 (2010).
Fors et al., "Water-mediated catalyst preactivation: an efficient protocol for C-n. cross-coupling reactions," Org. Lett. 10(16):3505-3508; Epub Jul. 12, 2008.
Freireich et al., "Quantitative comparison of toxicity of anticancer agents in mouse, rat, hamster, dog, monkey, and man," Cancer Chemother Rep. 50(4):219-244 (1966).
Fukusawa et al., "Enhancement of de novo fatty acid biosynthesis in hepatic cell line huh7 expressing Hepatitis C virus core protein," Biol. & Pharm. Bull. 29(9): 1958-1961 (2006).
Furuya et al., "Apoptosis of androgen-independent prostate cell line induced by inhibition of fatty acid synthesis," Anticancer Res. 17(6D):4589-4593 (1997).
Gabrielson et al., "Increased fatty acid synthase is a therapeutic target in mesothelioma," Clin. Cancer Research 7:153-157 (2001).
Gansler et al., "Increased expression of fatty acid synthase (OA-519) in ovarian neoplasms predicts shorter survival," Hum Pathol. 28(6):686-692 (1997).
Gao et al., "Chemical genetics strategy identifies an HCV NS5A inhibitor with a potent clinical effect," Nature 465(7294):96-100, Epub Apr. 21, 2010.
Gonzalez et al., "Selective monomethylation of anilines by Cu(OAc)2-promoted cross-coupling with MeB(OH)2," Org Lett. 11(8):1677-1680 (2009).
Goto et al., "Studies on herbicidal carbamoyltetrazolinone derivatives; Selection of fentrazamide," Weed Biology and Management, 2: 18-24 (2002).
Gotz et al., "The Very-Long-Chain Fatty Acid Synthase Is Inhibited by Chloroacetamides," Z. Naturforsch, 59: 549-553 (2004).
Guabiraba et al., "Role of the chemokine receptors CCR1, CCR2 and CCR4 in the pathogenesis of experimental dengue infection in mice," PLoS One 5(12):e15680 (2010).
Guidotti et al., "High-level hepatitis B virus replication in transgenic mice, J Virol. 69(10):6158-6169 (1995).
Haase et al., "Fatty acid synthase as a novel target for meningioma therapy," Neuro-Oncology Advance Access published Feb. 5, 2010, 1-11 (2010).
Heaton et al., "Dengue virus nonstructural protein 3 redistributes fatty acid synthase to sites of viral replication and increases cellular fatty acid synthesis," Proc Natl Acad Sci U.S.A. 107(40):17345-17350 (2010).
Hennigar et al., "Characterization of fatty acid synthase in cell lines derived from experimental mammary tumors," Biochim Biophys Acta. 1392(1):85-100 1998.
Herker et al., "Efficient hepatitis C virus particle formation requires diacylglycerol acyltransferase-1," Nat Med. 16 11 :1295-1298, Epub Oct. 10, 2010.
Huang et al., "Inhibitor of fatty acid synthase induced apoptosis in human colonic cancer cells," World J Gastroenterol. 6(2):295-297 (2000).
Innocenzi et al., "Fatty acid synthase expression in melanoma," J Cutan Pathol. 30(1):23-28 (2003).
Ishigami et al., "Enantioselective Synthesis of Phomallenic Acid C, an Inhibitor of FAS II Path way," Tetrahedron Letters, 1-12 (2008).
Iyer et al., "Phosphorothioate di- and trinucleotides as a novel class of anti-hepatitis B virus agents," Antimicrob Agents Chemother. 48(6):2199-2205 (2004).
Jakubowski et al., "Total Synthesis of (≠)-Cerulenin, (≠)-Tetrahydrocerulenin, and Related Compounds," J. Org. Chem. 47: 1221-1228 (1982).
Jayakumar et al., "Human fatty acid synthase: properties and molecular cloning," Proc Natl Acad Sci U S A. 92(19):8695-8699 (1995).
Johansson et al., "Inhibition of the fungal fatty acid synthase type I multienzyme complex," PNAS, 105 (35): 1203-12808 (2008).
Johnson et al., "New mouse model for dengue virus vaccine testing," J Virol. 73(1):783-786 (1999).
Jolicoeur et al., "A novel mouse model of HIV-1 disease," Leukemia 13 Suppl 1:S78-80 (1999).
Julander et al., "Characterizing antiviral activity of adefovir dipivoxil in transgenic mice expressing hepatitis B virus," Antiviral Res. 55(1):27-40 (2002).
Kapadia et al., "Hepatitis C virus RNA replication is regulated by host geranylgeranylation and fatty acids," Proc Natl Acad Sci U S A. 102(7): 2561-2566 (2005).
Kapur et al., "Fatty acid synthase expression in cutaneous melanocytic neoplasms," Mod Pathol. 18(8):1107-1112 (2005).
Kern et al., "Oral activity of a methylenecyclopropane analog, cyclopropavir, in animal models for cytomegalovirus infections," Antimicrob Agents Chemother. 48(12):4745-4753 (2004).
Knowles et al., "Inhibition of fatty-acid synthase induces caspase-8-mediated tumor cells apoptosis by up-regulating DDIT4," J. Biol. Chem. 283(46): 31378-84 (2008).
Koester, J., "Metabolism of fentrazamide (YRC 2388) in animals and plants," Pflanzenschutz-Nachrichten Bayer, 54: 51-74 (2001).
Korba et al., "Antisense oligonucleotides are effective inhibitors of hepatitis B virus replication in vitro," Antiviral Res. 28(3):225-242 (1995).
Korba et al., "Nitazoxanide, tizoxanide and other thiazolides are potent inhibitors of hepatitis B virus and hepatitis C virus replication," Antiviral Res. 77(1):56-63, Epub Sep. 4, 2007 (2008).
Korba et al., "Use of a standardized cell culture assay to assess activities of nucleoside analogs against hepatitis B virus replication," Antiviral Res. 19(1):55-70 (1992).
Korba. "In vitro evaluation of combination therapies against hepatitis B virus replication," Antiviral Res. 29(1):49-51 (1996).
Kridel et al., "Fatty acid synthase inhibitors: new directions for oncology," Expert Opin Investig Drugs 16(11):1817-29 (2007).
Kridel et al., "Fatty acid synthase with Antitumor Activity," Cancer Res. 64(6): 2070-2075 (2004).
Krieger et al., Enhancement of hepatitis C virus RNA replication by cell culture-adaptive mutations, J Virol. 75(10):4614-4624 (2001).
Krontiras et al., "Fatty acid synthase expression is increased in neoplastic lesions of the oral tongue," Head Neck 21(4):325-329 (1999).
Kuhajda, "Fatty Acid Synthase and Cancer: New Application of an Old Pathway," Cancer Res., 66(12): 5977-5980 (2006).
Kuhajda et al., "Synthesis and antitumor activity of an inhibitor of fatty acid synthase," Proc Natl Acad Sci U.S.A. 97(7):3450-3454 (2000).
Kusakabe et al., "Fatty acid synthase is highly expressed in carcinoma, adenoma and in regenerative epithelium and intestinal metaplasia of the stomach," Histopathology 40(1):71-79 (2002).
L'Abbe et al., "Reaction pathways in nucleophilic displacements with 1-benzyl-.DELTA.2-tetrazoline-5-thione and 1,2,3,4-thiatriazoline-5-thione," The Journal of Organic Chemistry, 39 (25): 3770-3772 (1974).
L'Abbe et al., "Synthesis of 1,4-Disubstituted Tetrazoline-5-thiones," Journal of Organic Chemistry, 41 (10): 1875-1876 (1976).
Lawrence et al., "Structure-Activity Studies of Cerulenin Analogues as Protein Palmitoylation Inhibitors," J. Med. Chem., 42: 4932-4941 (1999).
Li et al., "Fatty acid synthase expression is induced by the Epstein-Barr virus immediate-early protein BRLF1 and is required for lytic viral gene expression," J Virol. 78(8):4197-4206 (2004).
Li et al., "Fatty Acid Synthase Inhibitors from Plants: Isolation, Structure Elucidation, and SAR Studies," J. Nat. Prod., 65: 1909-1914 (2002).
Li et al., "Structure-Activity Relationship of Polyphenols That Inhibit Fatty Acid Synthase," J. Biochem., 138: 679-685 (2005).
Lim et al., "Action of fentrazamide on protein metabolism and cell division in plants," Journal of Pesticide Science, 32 (3): 249-254 (2007).
Liu et al., "A new mechanism of drug resistance in breast cancer cells: fatty acid synthase overexpression-mediated palmitate overproduction," Mol Cancer Ther. 7(2):263-270 (2008).

(56) References Cited

OTHER PUBLICATIONS

Llopart et al., "Lithiation of 1-arylimidazol-2(1H)-ones and 1-aryl-4,5-dihydroimidazol-2(1H)-ones," Canada Journal of Chemistry, 82: 1649-1661 (2004).
Loftus et al., "Reduced Food Intake and Body Weight in Mice Treated with Fatty Acid Synthase Inhibitors," Science 288:2379-2381 (2000).
Lupu et al., "Pharmacological inhibitors of Fatty Acid Synthase (FASN)—catalyzed endogenous fatty acid biogenesis: a new family of anti-cancer agents?," Curr Pharm Biotechnol. 7(6):483-493 (2006).
Lupu et al., "Targeting fatty acid synthase in breast and endometrial cancer: An alternative to selective estrogen receptor modulators?," Endocrinology 147(9):4056-4066 (2006).
Luo et al., "Discovery of a new insecticide lead by optimizing a target-diverse scaffold: Tetrazolinone derivatives," Bioorganic and Medicinal Chemistry, 15: 1716-1726 (2007).
Luo et al., "Synthesis and Herbicidal Activities of Tetrazolinone Derivatives Containing Oxime Ether," Chinese Journal of Organic Chemistry, 28(9): 1561-1565 (2008). (English translation of abstract provided).
Lyn et al., "Direct imaging of the disruption of hepatitis C virus replication complexes by inhibitors of lipid metabolism," Virology 394(1):130-142 (2009).
Maier et al., "The Crystal Structure of a Mammalian Fatty Acid Synthase," Science, 321: 1315-1322 (2008).
McCauley et al., "4-Guanidino-Neu5Ac2en fails to protect chickens from infection with highly pathogenic avian influenza virus," Antiviral Res. 27(1-2):179-186 (1995).
McHutchison et al., "Adherence to Combination Therapy Enhances Sustained Response in Genotype-1-Infected Patients with Chronic Hepatitis C," Gostroenterology 123(4): 1061-1069 (2002).
McManus, "Microtiter assay for interferon: microspectrophotometric quantitation of cytopathic effect," Appl Environ Microbiol. 31(1):35-8 (1976).
Menendez et al., "Ftty acid synthase and the lipogenic phenotype in cancer pathogenesis," Nat. Rev. Cancer 7(10): 763-777 (2007).
Menendez et al., "Obesity, fatty acid synthase, and cancer: serendipity or fogotten causual linkage?"Mol. Genet. Metab. 84(3): 293-295 (2005).
Migita et al., "Fatty acid synthase: a metabolic enzyme and candidate oncogene in prostate cancer," J Natl Cancer Inst. 101(7):519-532. Epub Mar. 24, 2009.
Milgraum et al., "Enzymes of the fatty acid synthesis pathway are highly expressed in in situ breast carcinoma," Clin Cancer Res. 3(11):2115-2120 (1997).
Mizutani et al., "Discovery of Novel Benzoxazinones as Potent and Orally Active Long Chain Fatty Acid Elongase 6 Inhibitors," Journal of Medical Chemistry (2009).
Morisaki et al., "Effect of side-chain structure on inhibition of yeast fatty-acid synthase by cerulenin analogues," Eur. J. Biochem., 211: 111-115 (1993).
Moseley et al., "Preparation of Dicarboxylate Analogues of Cerulenin," J. Heterocyclic Chem., 42: 819-830 (2005).
Mosier, "Modeling AIDS in a mouse," Hosp Pract (Minneap) 31(9):41-48, 53-55, 59-60 (1996).
Mosier, "Viral pathogenesis in hu-PBL-SCID mice," Semin Immunol. 8(4):255-262 (1996).
Muller et al., "Production of hepatitis B virus by stably transfected monocytic cell line U-937: a model for extrahepatic hepatitis B virus replication," J Infect Dis. 165(5):929-933 (1992).
Munger et al., "Systems-level metabolic flux profiling identifies fatty acid synthesis as a target for antiviral therapy," Nat Biotechnol. 26(10):1179-1186 (2008).
Nemoto et al., "Overexpression of fatty acid synthase in oesophageal squamous cell dysplasia and carcinoma," Pathobiology 69(6):297-303 (2001).
Okuse et al., "Enhancement of antiviral activity against hepatitis C virus in vitro by interferon combination therapy," Antiviral Res. 65(1):23-34 (2005).

Ortar et al., "Carbamoyl tetrazoles as inhibitors of endocannabinoid inactivation: A critical revisitation," European Journal of Medicinal Chemistry, 43:. 62-72 (2008).
Pemble et al., "Crystal structure of the thioesterase domain of human fatty acid synthase inhibited by Orlistat," Nat. Struct. Mol. Biol. 14(8):704-709 (2007).
Pierra et al., "NM 283, An Efficient Prodrug of the Potent Anti-HCV Agent 2'C'Methylcytidine," Nucleodides Nucleotides Nucleic Acids 24:767 (2005).
Piyathilake et al., "The expression of fatty acid synthase (FASE) is an early event in the development and progression of squamous cell carcinoma of the lung," Hum Pathol. 31(9):1068-1073 (2000).
Pizer et al., "Expression of fatty acid synthase is closely linked to proliferation and stromal decidualization in cycling endometrium," Int J Gynecol Pathol. 16(1):45-51 (1997).
Pizer et al., "Fatty acid synthase expression in endometrial carcinoma: correlation with cell proliferation and hormone receptors," Cancer 83(3):528-537 (1998).
Pizer et al. "Fatty acid synthase (FAS): a target for cytotoxic antimetabolites in HL60 promyelecytic leukemia cells," Cancer Res. 56(4): 745-751 (1996).
Pizer et al., "Increased fatty acid synthase as a therapeutic target in androgen-independent prostate cancer progression," Prostate 47(2):102-110 (2001).
Pizer et al., "Inhibition of fatty acid synthesis delays disease progression in a xenograft model of ovarian cancer," Cancer Res. 56(6):1189-1193 1996.
Pizer et al., "Malonyl-coenzyme-A is a potential mediator of cytotoxicity induced by fatty-acid synthase inhibition in human breast cancer cells and xenografts," Cancer Res. 60(2):213-218 (2000).
Porter et al., "Tetrahydroisoquinoline amide substituted phenyl pyraoles as selective Bcl-2 inhibitors," Bioorganic & Medicinal Chemistry Letters, 9: 230-233 (2009).
Raghavan et al., "Chemica probes for profiling fatty acid-associated proteins in living cells," Bioorganin & Medical Chemistry Letters (2008).
Rashid et al., "Elevated expression of fatty acid synthase and fatty acid synthetic activity in colorectal neoplasia," Am J Pathol. 150(1):201-208 (1997).
Rassmann et al., "The human fatty acid synthase: a new therapeutic target for coxsackievirus B3-induced diseases?," Antiviral Research 76(2):150-158 (2007).
Rice et al., "Efficacy of CMX001 as a prophylactic and presymptomatic antiviral agent in New Zealand white rabbits infected with rabbitpox virus, a model for orthopoxvirus infections of humans," Viruses 3(2):63-82 (2011).
Richardson et al., "Novel antagonists of the thioesterase domain of human fatty acid synthase," Mol. Cancer Ther. 6(7): 2120-2126 (2007).
Ritchie et al., "Characterization of Human Thioesterase II and Its Potential for Breast Cancer Drug Discovery," Center for Structural Biology, Abstract No. 2675 (2010).
Robertson, James G., "Mechanistic Basis of Enzyme-Targeted Drugs," Biochemistry, 44 (15): 5561-5571 (2005).
Rossi et al., "Fatty acid synthase expression defines distinct molecular signatures in prostate cancer," Mol Cancer Res. 1(10):707-715 (2003).
Rossi, "Gastrointestinal stromal tumours overexpress fatty acid synthase," J Pathol. 209(3):369-375 (2006).
Roy et al., "Use of the Aerosol Rabbitpox Virus Model for Evaluation of Anti-Poxvirus Agents," Viruses 2(9):2096-2107 (2010).
Sakamoto, "Host sphingolipid biosynthesis as a target for hepatitis C virus therapy," Nat Chem Biol. 1(6):333-337 (2005).
Samsa et al., "Dengue virus capsid protein usurps lipid droplets for viral particle formation," PLoS Pathog. 5(10):e1000632 (2009).
Sasaki et al., "Synthesis and evaluation of a novel 2-azabicyclo [2.2.2] octane class of long chain fatty acid elongase 6 (ELOVL6) inhibitors," Bioorganic & Medicinal Chemistry, 17: 5639-5647 (2009).
Sawada et al., "Disturbed CD4+ T cell homeostasis and in vitro HIV-1 susceptibility in transgenic mice expressing T cell line-tropic HIV-1 receptors," J Exp Med. 187(9):1439-1449 (1998).

(56) References Cited

OTHER PUBLICATIONS

Schito et al., "Preclinical evaluation of a zinc finger inhibitor targeting lentivirus nucleocapsid protein in SIV-infected monkeys," Curr HIV Res. 4(3):379-86 (2006).
Sebastiani et al., "Fatty acid synthase is a marker of increased risk of recurrence in endometrial carcinoma," Gynecol Oncol. 92(1):101-105 (2004).
Sekiguchi et al., "Biological characteristics and chemosensitivity profile of four human anaplastic thyroid carcinoma cell lines," Biomed Pharmacother. 55(8):466-474 (2001).
Sells et al., "Replicative intermediates of hepatitis B virus in HepG2 cells that produce infectious virions," J Virol. 62(8):2836-44 (1988).
Shafir et al., "Highly selective room-temperature copper-catalysed-C-N-coupling reactions," J. Am. Chem. Soc. 128(27):8742-8743 (2006).
Shah et al., "Fatty acid synthase gene overexpression and copy number gain in prostate adenocarcinoma," Hum Pathol. 37(4):401-409, Epub Feb. 7, 2006.
Sherman et al., "Combination Therapy with Thymosin α1 and Interferon for the Treatment of Chronic Hepatitis C Infection: A Randomized, Placebo-Controlled Double Blind Trial," Hepatology 27(4):1128-35 (1998).
Shimamura et al., "High Throughput Assay for Long Chain Fatty Acyl-CoA Elongase Using Homogen," Assay and Drug Development Technologies, 7(2): 124-132 (2009).
Shimamura et al., "Discovery and characterization of a novel potent, selective and orally active inhibitor for mammalian ELOVL6," Eur J Pharmacol. 630(1-3):34-41. Epub Jan. 4, 2010.
Shimazawa et al., "Syntheses of Cerulenin and Its Analogs. II Synthesis and Biological Activity of dl-Carbacerulenin, a Carbocylic Analog of Cerulenin," Chem Pharm Bull, 40 (11): 2954-2957 (1992).
Shurbaji et al., "Immunohistochemical detection of a fatty acid synthase (OA-519) as a predictor of progression of prostate cancer," Hum Pathol. 27(9):917-921 (1996).
Sidwell et al., "In vitro and in vivo assay systems for study of influenza virus inhibitors," Antiviral Res. 48(1):1-16 (2000).
Silva et al., "Fatty acid synthase expression in squamous cell carcinoma of the tongue: clinicopathological findings," Oral Diseases 14:376-382 (2007).
Slade et al., "Characterization and Inhibition of Fatty Acid Synthase in Pediatric Tumor Cell Lines," Anticancer Research 23:1235-1243 (2003).
Souza et al., "Essential role of platelet-activating factor receptor in the pathogenesis of Dengue virus infection," Proc Natl Acad Sci U S A. 106(33):14138-14143, Epub Jul. 30, 2009.
Stuyver et al., "Nomenclature for antiviral-resistant human hepatitis B virus mutations in the polymerase region," Hepatology 33(3):751-757 (2001).
Sun et al., "A substantive substrate for measurements of 3-ketoacyl reductases in two fatty acid synthase systems," Journal of Biochemical and Biophysical Methods, 70: 850-856 (2008).
Swinnen et al., "Overexpression of fatty acid synthase is an early and common event in the development of prostate cancer," Int J Cancer. 98(1):19-22 (2002).
Syed et al., "Hepatitis C virus hijacks host lipid metabolism," Trends Endocrinol Metab. 21(1):33-40 (2009).
Takahashi et al. "Inhibition of Very-Long-Chain Fatty Acid Biosynthesis by 2-Chloro-N-(3-methoxy-2-thenyl)-2',6'-dimethylacetanilide, Thenylchlor, and Its Analogs," Pesticide Biochemistry and Physiology, 71: 140-146 (2001).
Takahashi et al. "Sythesis and Evaluation of a Novel Indoledione Class of Long Chain Fatty Acid Elongase 6 (ELOVL6) Inhibitors," J. Med. Chem., 52: 3142-3145 (2009).
Takahiro et al., "Expression of fatty acid synthase as a prognostic indicator in soft tissue sarcomas," Clin Cancer Res. 9(6):2204-2212 (2003).
Theodoridis et al., "Sythesis and Structure-Activity Relationships of 1-Aryl-4-substituted-1,4-dihydro-5H-tetrazol-5-ones, a Novel Class of Pre-and Post-emergence Herbicides," Pestic. Sci., 30: 259-274 (1990).
Tian, Wei-Xi, "Inhibition of Fatty Acid Synthase by Polyphenols," Current Medicinal Chemistry, 13: 967-977 (2006).
Trenkamp et al., "Specific and differential inhibition of very-long-chain fatty acid elongases from Arabidopsis thaliana by different herbicides," PNAS, 101(32): 11903-11908 (2004).
Tsuge et al., "Reactions of Trimethylsilyl Azide with Heterocumulenes," Journal of Organic Chemistry, 45: 5130-5136 (1980).
Uddin et al., "Fatty acid synthase and AKT pathway signaling in a subset of papillary thyroid cancers," J Clin Endocrinol Metab. 93(10):4088-4097, Epub Aug. 5, 2008.
Vazquez et al., "Discovery of GSK837149A, an inhibitor of human fatty acid synthase targeting the βketoacyl reductase reaction," FEBS Journal, 275: 1556-1567 (2008).
Vinayavekhin et al., "Exploring Disease through Metabolomics," ACS Chemical Biology, 5(1): 91-103 (2010).
Visca et al., "Fatty acid synthase (FAS) is a marker of increased risk of recurrence in lung carcinoma," Anticancer Res. 24(6):4169-4173 (2004).
Visca et al., "Immunohistochemical Expression and Prognostic Significance of FAS and GLUT1 in Bladder Carcinoma" Anticancer Res. 23:335-339 (2003).
Vishwanath et al., "Biosynthesis of Very Long Chain Fatty Acids in Microsomes from Epidermal Cells of Allium porrum L.," Archives of Biochemistry and Biophysics, 230(2): 580-589 (1984).
Vlad et al., "Fatty acid synthase is highly expressed in aggressive thyroid tumors," Mod. Path. 88$^{th}$ Annual Meeting Abstracts, 12(1): 70A (1999).
Walter et al., "Serum fatty acid synthase as a marker of pancreatic neoplasia," Cancer Epidemiol Biomarkers Prev. 18(9):2380-2385, Epub Sep. 1, 2009.
Wang et al, "A Mutant of Hepatitis B Virus X Protein (HBxΔ127) Promotes Cell Growth Through a Positive Feedback Loop Involving 5-Lipoxygenase and Fatty Acid Synthase," Neoplasia 12(2): 103-115 (2010).
Wang et al., "Fatty acid synthase (FAS) expression in human breast cancer cell culture supernatants and in breast cancer patients," Cancer Lett. 167(1):99-104 (2001).
Wang et al., "The galloyl moiety of green tea catechins is the critical structural feature to inhibit fatty-acid sythase," Biochemical Pharmacology, 66: 2039-2047 (2003).
Wang et al., "Positive feedback regulation between AKT activation and fatty acid synthase expression in ovarian carcinoma cells," Oncogene 24(22):3574-3582 (2005).
Wang et al., "Novel fatty acid synthase (FAS) inhibitors; design, synthesis, biological evaluation and molecular docking studies," Bioorganinc & Medicinal Chemistry, 1-20 (2008).
Wang et al., "Increased Fatty Acid Synthase as a Potential Therapeutic Target in Multiple Myeloma," Zhejiang Univ. Sci B 9(6):441-447 (2008).
Weerapana et al., "Disparate proteome reactivity profiles of carbon electrophiles: Supplementary Information," 1-31 (2008).
Weiss et al. "Characterization of fatty acid synthase activity using scintillation proximity," Assay Drug Dev Technol. 1(1 Pt 2):161-166 (2003).
Wilen et al., "Strategies in Optical Resolutions," Tetrahedron 33:2725 (1977).
Wu et al., "Antidiabetic and antisteatotic effects of the selective fatty acid synthase (FAS) inhibitor platensimycin in mouse models of diabetes," www.pnas.org/lookup/suppl/doi:10.1073/pnas.1002588108, PNAS Early edition 1-6 (2011).
Yanagi, Akihiko, "Fentrazamide—A novel selective paddy herbicide from the chemical class of carbamoyltetrazolinones," Pflanzenshutz-Nachrichten, 54: 5-12 (2001).
Yang et al., "Fatty acid synthase is up-regulated during hepatitis C virus infection and regulates hepatitis C virus entry and production," Hepatology 48(5):1396-1403 (2008).
Young et al., "Discovery of FabH/FabF Inhibitors from Natural Products," Antimicrobial Agents and Chemotherapy, 50(2): 519-526 (2006).
Zhan et al., "Control of cell growth and survival by enzymes of the fatty acid synthesis pathway in HCT-116 colon cancer cells," Clin Cancer Res. 14(18):5735-5742 (2008).

(56) References Cited

OTHER PUBLICATIONS

Zhao et al., "Fatty acid synthase: a novel target for antiglioma therapy," Br. J. Cancer 95(7):869-878 (2006).
Zhou et al., "Fatty acid synthase inhibition activates AMP-activated protein kinase in SKOV3 human ovarian cancer cells," Cancer Res. 67(7):2964-2971 (2007).
Zoeteweij et al., "Identification and rapid quantification of early- and late-lytic human herpesvirus 8 infection in single cells by flow cytometric analysis: characterization of antiherpesvirus agents," J Virol. Jul. 1999;73(7):5894-5902 (1999).
Patani et al., "Bioisosterism: A Rational Approach in Drug Design," Chem. Rev. 96(8):3147-3176 (1996).

* cited by examiner

SEQUENCE LISTING

<160> NUMBER OF SEQ ID NOS: 1

<210> SEQ ID NO 1
<211> LENGTH: 2511
<212> TYPE: PRT
<213> ORGANISM: Homo sapiens

<400> SEQUENCE: 1

```
Met Glu Glu Val Val Ile Ala Gly Met Ser Gly Lys Leu Pro Glu Ser
 1               5                  10                  15

Glu Asn Leu Gln Glu Phe Trp Asp Asn Leu Ile Gly Gly Val Asp Met
            20                  25                  30

Val Thr Asp Asp Asp Arg Arg Trp Lys Ala Gly Leu Tyr Gly Leu Pro
        35                  40                  45

Arg Arg Ser Gly Lys Leu Lys Asp Leu Ser Arg Phe Asp Ala Ser Phe
50                  55                  60

Phe Gly Val His Pro Lys Gln Ala His Thr Met Asp Pro Gln Leu Arg
65                  70                  75                  80

Leu Leu Leu Glu Val Thr Tyr Glu Ala Ile Val Asp Gly Gly Ile Asn
                85                  90                  95

Pro Asp Ser Leu Arg Gly Thr His Thr Gly Val Trp Val Gly Val Ser
            100                 105                 110

Gly Ser Glu Thr Ser Glu Ala Leu Ser Arg Asp Pro Glu Thr Leu Val
        115                 120                 125

Gly Tyr Ser Met Val Gly Cys Gln Arg Ala Met Met Ala Asn Arg Leu
    130                 135                 140

Ser Phe Phe Phe Asp Phe Arg Gly Pro Ser Ile Ala Leu Asp Thr Ala
145                 150                 155                 160

Cys Ser Ser Ser Leu Met Ala Leu Gln Asn Ala Tyr Gln Ala Ile His
                165                 170                 175

Ser Gly Gln Cys Pro Ala Ala Ile Val Gly Gly Ile Asn Val Leu Leu
            180                 185                 190

Lys Pro Asn Thr Ser Val Gln Phe Leu Arg Leu Gly Met Leu Ser Pro
        195                 200                 205

Glu Gly Thr Cys Lys Ala Phe Asp Thr Ala Gly Asn Gly Tyr Cys Arg
    210                 215                 220

Ser Glu Gly Val Val Ala Val Leu Leu Thr Lys Lys Ser Leu Ala Arg
225                 230                 235                 240

Arg Val Tyr Ala Thr Ile Leu Asn Ala Gly Thr Asn Thr Asp Gly Phe
                245                 250                 255

Lys Glu Gln Gly Val Thr Phe Pro Ser Gly Asp Ile Gln Glu Gln Leu
            260                 265                 270

Ile Arg Ser Leu Tyr Gln Ser Ala Gly Val Ala Pro Glu Ser Phe Glu
        275                 280                 285

Tyr Ile Glu Ala His Gly Thr Gly Thr Lys Val Gly Asp Pro Gln Glu
    290                 295                 300

Leu Asn Gly Ile Thr Arg Ala Leu Cys Ala Thr Arg Gln Glu Pro Leu
305                 310                 315                 320

Leu Ile Gly Ser Thr Lys Ser Asn Met Gly His Pro Glu Pro Ala Ser
                325                 330                 335

Gly Leu Ala Ala Leu Ala Lys Val Leu Leu Ser Leu Glu His Gly Leu
            340                 345                 350

Trp Ala Pro Asn Leu His Phe His Ser Pro Asn Pro Glu Ile Pro Ala
        355                 360                 365
```

```
Leu Leu Asp Gly Arg Leu Gln Val Val Asp Gln Pro Leu Pro Val Arg
    370                 375                 380
Gly Gly Asn Val Gly Ile Asn Ser Phe Gly Phe Gly Gly Ser Asn Val
385                 390                 395                 400
His Ile Ile Leu Arg Pro Asn Thr Gln Pro Pro Ala Pro Ala Pro
                405                 410                 415
His Ala Thr Leu Pro Arg Leu Leu Arg Ala Ser Gly Arg Thr Pro Glu
            420                 425                 430
Ala Val Gln Lys Leu Leu Glu Gln Gly Leu Arg His Ser Gln Asp Leu
        435                 440                 445
Ala Phe Leu Ser Met Leu Asn Asp Ile Ala Ala Val Pro Ala Thr Ala
    450                 455                 460
Met Pro Phe Arg Gly Tyr Ala Val Leu Gly Gly Glu Arg Gly Gly Pro
465                 470                 475                 480
Glu Val Gln Gln Val Pro Ala Gly Glu Arg Pro Leu Trp Phe Ile Cys
                485                 490                 495
Ser Gly Met Gly Thr Gln Trp Arg Gly Met Gly Leu Ser Leu Met Arg
            500                 505                 510
Leu Asp Arg Phe Arg Asp Ser Ile Leu Arg Ser Asp Glu Ala Val Lys
        515                 520                 525
Pro Phe Gly Leu Lys Val Ser Gln Leu Leu Leu Ser Thr Asp Glu Ser
    530                 535                 540
Thr Phe Asp Asp Ile Val His Ser Phe Val Ser Leu Thr Ala Ile Gln
545                 550                 555                 560
Ile Gly Leu Ile Asp Leu Leu Ser Cys Met Gly Leu Arg Pro Asp Gly
                565                 570                 575
Ile Val Gly His Ser Leu Gly Glu Val Ala Cys Gly Tyr Ala Asp Gly
            580                 585                 590
Cys Leu Ser Gln Glu Glu Ala Val Leu Ala Ala Tyr Trp Arg Gly Gln
        595                 600                 605
Cys Ile Lys Glu Ala His Leu Pro Pro Gly Ala Met Ala Ala Val Gly
    610                 615                 620
Leu Ser Trp Glu Glu Cys Lys Gln Arg Cys Pro Pro Gly Val Val Pro
625                 630                 635                 640
Ala Cys His Asn Ser Lys Asp Thr Val Thr Ile Ser Gly Pro Gln Ala
                645                 650                 655
Pro Val Phe Glu Phe Val Glu Gln Leu Arg Lys Glu Gly Val Phe Ala
            660                 665                 670
Lys Glu Val Arg Thr Gly Gly Met Ala Phe His Ser Tyr Phe Met Glu
        675                 680                 685
Ala Ile Ala Pro Pro Leu Leu Gln Glu Leu Lys Lys Val Ile Arg Glu
    690                 695                 700
Pro Lys Pro Arg Ser Ala Arg Trp Leu Ser Thr Ser Ile Pro Glu Ala
705                 710                 715                 720
Gln Trp His Ser Ser Leu Ala Arg Thr Ser Ser Ala Glu Tyr Asn Val
                725                 730                 735
Asn Asn Leu Val Ser Pro Val Leu Phe Gln Glu Ala Leu Trp His Val
            740                 745                 750
Pro Glu His Ala Val Val Leu Glu Ile Ala Pro His Ala Leu Leu Gln
        755                 760                 765
Ala Val Leu Lys Arg Gly Leu Lys Pro Ser Cys Thr Ile Ile Pro Leu
    770                 775                 780
Met Lys Lys Asp His Arg Asp Asn Leu Glu Phe Phe Leu Ala Gly Ile
```

```
785                 790                 795                 800
Gly Arg Leu His Leu Ser Gly Ile Asp Ala Asn Pro Asn Ala Leu Phe
                805                 810                 815

Pro Pro Val Glu Phe Pro Ala Pro Arg Gly Thr Pro Leu Ile Ser Pro
                820                 825                 830

Leu Ile Lys Trp Asp His Ser Leu Ala Trp Asp Val Pro Ala Ala Glu
                835                 840                 845

Asp Phe Pro Asn Gly Ser Gly Ser Pro Ser Ala Ala Ile Tyr Asn Ile
850                 855                 860

Asp Thr Ser Ser Glu Ser Pro Asp His Tyr Leu Val Asp His Thr Leu
865                 870                 875                 880

Asp Gly Arg Val Leu Phe Pro Ala Thr Gly Tyr Leu Ser Ile Val Trp
                885                 890                 895

Lys Thr Leu Ala Arg Ala Leu Gly Leu Gly Val Glu Gln Leu Pro Val
                900                 905                 910

Val Phe Glu Asp Val Val Leu His Gln Ala Thr Ile Leu Pro Lys Thr
                915                 920                 925

Gly Thr Val Ser Leu Glu Val Arg Leu Leu Glu Ala Ser Arg Ala Phe
                930                 935                 940

Glu Val Ser Glu Asn Gly Asn Leu Val Val Ser Gly Lys Val Tyr Gln
945                 950                 955                 960

Trp Asp Asp Pro Asp Pro Arg Leu Phe Asp His Pro Glu Ser Pro Thr
                965                 970                 975

Pro Asn Pro Thr Glu Pro Leu Phe Leu Ala Gln Ala Glu Val Tyr Lys
                980                 985                 990

Glu Leu Arg Leu Arg Gly Tyr Asp Tyr Gly Pro His Phe Gln Gly Ile
                995                1000                1005

Leu Glu Ala Ser Leu Glu Gly Asp Ser Gly Arg Leu Leu Trp Lys Asp
                1010                1015                1020

Asn Trp Val Ser Phe Met Asp Thr Met Leu Gln Met Ser Ile Leu Gly
1025                1030                1035                1040

Ser Ala Lys His Gly Leu Tyr Leu Pro Thr Arg Val Thr Ala Ile His
                1045                1050                1055

Ile Asp Pro Ala Thr His Arg Gln Lys Leu Tyr Thr Leu Gln Asp Lys
                1060                1065                1070

Ala Gln Val Ala Asp Val Val Ser Arg Trp Leu Arg Val Thr Val
                1075                1080                1085

Ala Gly Gly Val His Ile Ser Gly Leu His Thr Glu Ser Ala Pro Arg
                1090                1095                1100

Arg Gln Gln Glu Gln Gln Val Pro Ile Leu Glu Lys Phe Cys Phe Thr
1105                1110                1115                1120

Pro His Thr Glu Glu Gly Cys Leu Ser Glu Arg Ala Ala Leu Gln Glu
                1125                1130                1135

Glu Leu Gln Leu Cys Lys Gly Leu Val Gln Ala Leu Gln Thr Lys Val
                1140                1145                1150

Thr Gln Gln Gly Leu Lys Met Val Val Pro Gly Leu Asp Gly Ala Gln
                1155                1160                1165

Ile Pro Arg Asp Pro Ser Gln Gln Glu Leu Pro Arg Leu Leu Ser Ala
                1170                1175                1180

Ala Cys Arg Leu Gln Leu Asn Gly Asn Leu Gln Leu Glu Leu Ala Gln
1185                1190                1195                1200

Val Leu Ala Gln Glu Arg Pro Lys Leu Pro Glu Asp Pro Leu Leu Ser
                1205                1210                1215
```

```
Gly Leu Leu Asp Ser Pro Ala Leu Lys Ala Cys Leu Asp Thr Ala Val
            1220                1225                1230

Glu Asn Met Pro Ser Leu Lys Met Lys Val Val Glu Val Leu Ala Gly
            1235                1240                1245

His Gly His Leu Tyr Ser Arg Ile Pro Gly Leu Leu Ser Pro His Pro
        1250                1255                1260

Leu Leu Gln Leu Ser Tyr Thr Ala Thr Asp Arg His Pro Gln Ala Leu
1265                1270                1275                1280

Glu Ala Ala Gln Ala Glu Leu Gln Gln His Asp Val Ala Gln Gly Gln
                1285                1290                1295

Trp Asp Pro Ala Asp Pro Ala Pro Ser Ala Leu Gly Ser Ala Asp Leu
            1300                1305                1310

Leu Val Cys Asn Cys Ala Val Ala Ala Leu Gly Asp Pro Ala Ser Ala
            1315                1320                1325

Leu Ser Asn Met Val Ala Ala Leu Arg Glu Gly Gly Phe Leu Leu Leu
            1330                1335                1340

His Thr Leu Leu Arg Gly His Pro Leu Gly Asp Ile Val Ala Phe Leu
1345                1350                1355                1360

Thr Ser Thr Glu Pro Gln Tyr Gly Gln Gly Ile Leu Ser Gln Asp Ala
            1365                1370                1375

Trp Glu Ser Leu Phe Ser Arg Val Ser Leu Arg Leu Val Gly Leu Lys
            1380                1385                1390

Lys Ser Phe Tyr Gly Ser Thr Leu Phe Leu Cys Arg Arg Pro Thr Pro
            1395                1400                1405

Gln Asp Ser Pro Ile Phe Leu Pro Val Asp Asp Thr Ser Phe Arg Trp
            1410                1415                1420

Val Glu Ser Leu Lys Gly Ile Leu Ala Asp Glu Asp Ser Ser Arg Pro
1425                1430                1435                1440

Val Trp Leu Lys Ala Ile Asn Cys Ala Thr Ser Gly Val Val Gly Leu
            1445                1450                1455

Val Asn Cys Leu Arg Arg Glu Pro Gly Gly Asn Arg Leu Arg Cys Val
            1460                1465                1470

Leu Leu Ser Asn Leu Ser Ser Thr Ser His Val Pro Glu Val Asp Pro
            1475                1480                1485

Gly Ser Ala Glu Leu Gln Lys Val Leu Gln Gly Asp Leu Val Met Asn
            1490                1495                1500

Val Tyr Arg Asp Gly Ala Trp Gly Ala Phe Arg His Phe Leu Leu Glu
1505                1510                1515                1520

Glu Asp Lys Pro Glu Glu Pro Thr Ala His Ala Phe Val Ser Thr Leu
            1525                1530                1535

Thr Arg Gly Asp Leu Ser Ser Ile Arg Trp Val Cys Ser Ser Leu Arg
            1540                1545                1550

His Ala Gln Pro Thr Cys Pro Gly Ala Gln Leu Cys Thr Val Tyr Tyr
            1555                1560                1565

Ala Ser Leu Asn Phe Arg Asp Ile Met Leu Ala Thr Gly Lys Leu Ser
            1570                1575                1580

Pro Asp Ala Ile Pro Gly Lys Trp Thr Ser Gln Asp Ser Leu Leu Gly
1585                1590                1595                1600

Met Glu Phe Ser Gly Arg Asp Ala Ser Gly Lys Arg Val Met Gly Leu
            1605                1610                1615

Val Pro Ala Lys Gly Leu Ala Thr Ser Val Leu Leu Ser Pro Asp Phe
            1620                1625                1630
```

```
Leu Trp Asp Val Pro Ser Asn Trp Thr Leu Glu Glu Ala Ala Ser Val
        1635                1640                1645

Pro Val Val Tyr Ser Thr Ala Tyr Tyr Ala Leu Val Val Arg Gly Arg
        1650                1655                1660

Val Arg Pro Gly Glu Thr Leu Leu Ile His Ser Gly Ser Gly Gly Val
1665                1670                1675                1680

Gly Gln Ala Ala Ile Ala Ile Ala Leu Ser Leu Gly Cys Arg Val Phe
                1685                1690                1695

Thr Thr Val Gly Ser Ala Glu Lys Arg Ala Tyr Leu Gln Ala Arg Phe
            1700                1705                1710

Pro Gln Leu Asp Ser Thr Ser Phe Ala Asn Ser Arg Asp Thr Ser Phe
            1715                1720                1725

Glu Gln His Val Leu Trp His Thr Gly Gly Lys Gly Val Asp Leu Val
        1730                1735                1740

Leu Asn Ser Leu Ala Glu Glu Lys Leu Gln Ala Ser Val Arg Cys Leu
1745                1750                1755                1760

Ala Thr His Gly Arg Phe Leu Glu Ile Gly Lys Phe Asp Leu Ser Gln
                1765                1770                1775

Asn His Pro Leu Gly Met Ala Ile Phe Leu Lys Asn Val Thr Phe His
            1780                1785                1790

Gly Val Leu Leu Asp Ala Phe Phe Asn Glu Ser Ser Ala Asp Trp Arg
        1795                1800                1805

Glu Val Trp Ala Leu Val Gln Ala Gly Ile Arg Asp Gly Val Val Arg
        1810                1815                1820

Pro Leu Lys Cys Thr Val Phe His Gly Ala Gln Val Glu Asp Ala Phe
1825                1830                1835                1840

Arg Tyr Met Ala Gln Gly Lys His Ile Gly Lys Val Val Val Gln Val
                1845                1850                1855

Leu Ala Glu Glu Pro Glu Ala Val Leu Lys Gly Ala Lys Pro Lys Leu
            1860                1865                1870

Met Ser Ala Ile Ser Lys Thr Phe Cys Pro Ala His Lys Ser Tyr Ile
            1875                1880                1885

Ile Ala Gly Gly Leu Gly Gly Phe Gly Leu Glu Leu Ala Gln Trp Leu
        1890                1895                1900

Ile Gln Arg Gly Val Gln Lys Leu Val Leu Thr Ser Arg Ser Gly Ile
1905                1910                1915                1920

Arg Thr Gly Tyr Gln Ala Lys Gln Val Arg Arg Trp Arg Arg Gln Gly
                1925                1930                1935

Val Gln Val Gln Val Ser Thr Ser Asn Ile Ser Ser Leu Glu Gly Ala
            1940                1945                1950

Arg Gly Leu Ile Ala Glu Ala Ala Gln Leu Gly Pro Val Gly Gly Val
            1955                1960                1965

Phe Asn Leu Ala Val Val Leu Arg Asp Gly Leu Leu Glu Asn Gln Thr
        1970                1975                1980

Pro Glu Phe Phe Gln Asp Val Cys Lys Pro Lys Tyr Ser Gly Thr Leu
1985                1990                1995                2000

Asn Leu Asp Arg Val Thr Arg Glu Ala Cys Pro Glu Leu Asp Tyr Phe
                2005                2010                2015

Val Val Phe Ser Ser Val Ser Cys Gly Arg Gly Asn Ala Gly Gln Ser
            2020                2025                2030

Asn Tyr Gly Phe Ala Asn Ser Ala Met Glu Arg Ile Cys Glu Lys Arg
            2035                2040                2045

Arg His Glu Gly Leu Pro Gly Leu Ala Val Gln Trp Gly Ala Ile Gly
```

-continued

```
            2050                2055                2060
Asp Val Gly Ile Leu Val Glu Thr Met Ser Thr Asn Asp Thr Ile Val
2065                2070                2075                2080

Ser Gly Thr Leu Pro Gln Arg Met Ala Ser Cys Leu Glu Val Leu Asp
            2085                2090                2095

Leu Phe Leu Asn Gln Pro His Met Val Leu Ser Ser Phe Val Leu Ala
            2100                2105                2110

Glu Lys Ala Ala Ala Tyr Arg Asp Arg Asp Ser Gln Arg Asp Leu Val
            2115                2120                2125

Glu Ala Val Ala His Ile Leu Gly Ile Arg Asp Leu Ala Ala Val Asn
            2130                2135                2140

Leu Asp Ser Ser Leu Ala Asp Leu Gly Leu Asp Ser Leu Met Ser Val
2145                2150                2155                2160

Glu Val Arg Gln Thr Leu Glu Arg Glu Leu Asn Leu Val Leu Ser Val
            2165                2170                2175

Arg Glu Val Arg Gln Leu Thr Leu Arg Lys Leu Gln Glu Leu Ser Ser
            2180                2185                2190

Lys Ala Asp Glu Ala Ser Glu Leu Ala Cys Pro Thr Pro Lys Glu Asp
            2195                2200                2205

Gly Leu Ala Gln Gln Gln Thr Gln Leu Asn Leu Arg Ser Leu Leu Val
            2210                2215                2220

Asn Pro Glu Gly Pro Thr Leu Met Arg Leu Asn Ser Val Gln Ser Ser
2225                2230                2235                2240

Glu Arg Pro Leu Phe Leu Val His Pro Ile Glu Gly Ser Thr Thr Val
            2245                2250                2255

Phe His Ser Leu Ala Ser Arg Leu Ser Ile Pro Thr Tyr Gly Leu Gln
            2260                2265                2270

Cys Thr Arg Ala Ala Pro Leu Asp Ser Ile His Ser Leu Ala Ala Tyr
            2275                2280                2285

Tyr Ile Asp Cys Ile Arg Gln Val Gln Pro Glu Gly Pro Tyr Arg Val
            2290                2295                2300

Ala Gly Tyr Ser Tyr Gly Ala Cys Val Ala Phe Glu Met Cys Ser Gln
2305                2310                2315                2320

Leu Gln Ala Gln Gln Ser Pro Ala Pro Thr His Asn Ser Leu Phe Leu
            2325                2330                2335

Phe Asp Gly Ser Pro Thr Tyr Val Leu Ala Tyr Thr Gln Ser Tyr Arg
            2340                2345                2350

Ala Lys Leu Thr Pro Gly Cys Glu Ala Glu Ala Glu Thr Glu Ala Ile
            2355                2360                2365

Cys Phe Phe Val Gln Gln Phe Thr Asp Met Glu His Asn Arg Val Leu
            2370                2375                2380

Glu Ala Leu Leu Pro Leu Lys Gly Leu Glu Glu Arg Val Ala Ala Ala
2385                2390                2395                2400

Val Asp Leu Ile Ile Lys Ser His Gln Gly Leu Asp Arg Gln Glu Leu
            2405                2410                2415

Ser Phe Ala Ala Arg Ser Phe Tyr Tyr Lys Leu Arg Ala Ala Glu Gln
            2420                2425                2430

Tyr Thr Pro Lys Ala Lys Tyr His Gly Asn Val Met Leu Leu Arg Ala
            2435                2440                2445

Lys Thr Gly Gly Ala Tyr Gly Glu Asp Leu Gly Ala Asp Tyr Asn Leu
            2450                2455                2460

Ser Gln Val Cys Asp Gly Lys Val Ser Val His Val Ile Glu Gly Asp
2465                2470                2475                2480
```

```
His Arg Thr Leu Leu Glu Gly Ser Gly Leu Glu Ser Ile Ile Ser Ile
            2485                2490                2495

Ile His Ser Ser Leu Ala Glu Pro Arg Val Ser Val Arg Glu Gly
                2500                2505            2510
```

TETRAZOLONES AS INHIBITORS OF FATTY ACID SYNTHASE

This application is a divisional of U.S. application Ser. No. 13/101,978, filed May 5, 2011, now allowed, which claims priority to U.S. Provisional Application Nos. 61/331,575, filed May 5, 2010; 61/331,644, filed May 5, 2010; 61/419,174, filed Dec. 2, 2010, 61/437,564, filed Jan. 28, 2011; and 61/472,566, filed Apr. 6, 2011, all of which are incorporated herein in their entireties.

The present specification is being filed with a computer readable form (CRF) copy of the Sequence Listing. The CRF entitled 12928-122-999 seqlisting.txt, which was created on Aug. 23, 2013 and is 21,177 bytes in size, is identical to the paper copy of the Sequence Listing and is incorporated Herein by reference in its entirety.

BACKGROUND

Fatty acid synthase (FASN) is a key enzyme for the synthesis of long-chain fatty acids from acetyl-coenzyme A (CoA) and malonyl-CoA that uses reduced nicotinamide adenine dinucleotidephosphate as a cofactor. FASN is minimally expressed in most normal human tissues except the liver and adipose tissue, where it is expressed at high levels. Since FASN expression is markedly increased in several human cancers compared with the corresponding normal tissue, and FASN overexpression in tumors has been associated with a poor prognosis, FASN inhibitors have long been viewed as potential therapeutics for the treatment of cancer. FASN inhibitors have also shown promise in the treatment of other FASN-mediated diseases, disorders or conditions, such as obesity, lack of appetite control and inflammatory conditions.

Furthermore, FASN has been identified as a target for treatment of microbial infections. In particular, it was reported that fatty acid synthesis or the level of fatty acid is critical in viral pathogenesis. For example, it was reported that the formation of a novel vesicular compartment (i.e., remodelled golgi apparatus), on the surface of which viral RNA replication takes place, requires fatty acid biosynthesis. (See Cherry et al., *PLoS Pathogens*, 2(10): e102 (2006)). In addition, fatty acid biosynthesis has been identified as a target for anti-viral therapy using a metabolic profiling of the hosts upon viral infection. (See Munger et al., *Nature Biotechnology*, 26: 1179-1186 (2008). It was also reported that inhibition of fatty acid biosynthesis (e.g., inhibition of fatty acid synthase) results in reduced replication of human cytomegalomous virus (HCMV) and influenza A viruses. (Id.).

Reports establishing FASN as a valid target for the treatment of viral infections are available for various viruses. For example, the role of FASN has been implicated in the pathogenesis of an enveloped virus such as human cytomegalomous virus (HCMV), influenza A and Hepatitis C (HCV). (See Munger et al., *Nature Biotechnology*, 26: 1179-1186 (2008); Syed et al., *Trends in Endocrinology and Metabolism*, 21: 33-40 (2009); Sakamoto et al., *Nature Chemical Biology*, 1: 333-337 (2005); Yang et al., *Hepatology*, 48: 1396-1403 (2008)). With regard to HCV, it was reported that an elevated level of fatty acid biosynthesis enzymes, including FASN, contributes to liver steatosis, leading to cirrhosis and hepatocellular carcinoma, upon HCV infection. (Fukusawa et al., *Biol. Pharm. Bull.*, 29(9): 1958-1961 (2006)). HCV replication was reported to be regulated by, among others, fatty acid biosynthesis. (Kapadia et al., *Proc. Natl. Acad. Sci.*, 102(7): 2561-2566 (2005)). Other reports establishing FASN as a potential host-target against HCV have also been published. (See, e.g., *Hepatology*, 48: 1396 (2008); *Trends Endocrine Metabol.*, 21: 33 (2010); and *Virology*, 394: 130 (2009)).

With regard to other various viruses, it was reported that the FASN expression is increased in the cells infected by coxsackievirus B3 (CVB3), a picornavirus, and the replication of CVB3 is blocked by FASN inhibitors. (See Rassmann et al., *Antiviral Research*, 76: 150-158 (2007)). FASN was reported to be important in lytic viral replication of Epstein-Barr virus (EBV), and it was suggested that FASN inhibition may be a novel approach for blocking the EBV replication. (Li et al., *Journal of Virology*, 78(8): 4197-4206 (2004)). The role of FASN in the replication of dengue virus has also been implicated. (See, e.g., Heaton et al., *Proc. Natl. Acad. Sci.*, 107(40): 17345-17350 (2010); and Samsa et al., *PLoS Pathogens*, 5(10): e1000632 (2009)). Moreover, aside from being a potential target for anti-viral therapy, the role of FASN has also been implicated in diabetes or regulation of the general wellness of the liver. (See, e.g., Wu et al., *PNAS Early Edition*, www.pnas.org/cgi/doi/10.1073/pnas.1002588108 (2011)). Thus, there is a need for effective inhibitors of FASN, which can be potentially used as therapies for microbial infections, including, but not limited to viral infections, or other diseases and disorders.

SUMMARY

Provided herein are tetrazolone FASN inhibitors of the formula (I):

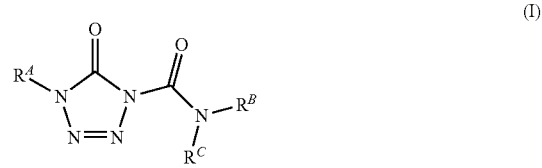

(I)

or a pharmaceutically acceptable form thereof, wherein the variables $R^A$, $R^B$ and $R^C$ are defined below and herein.

Also provided herein are pharmaceutical compositions comprising at least one compound of formula (I) or a pharmaceutically acceptable form thereof. Also provided herein are methods of treating cancer comprising administering at least one compound of formula (I) or a pharmaceutically acceptable form thereof, or a pharmaceutical composition thereof, to a subject in need thereof. Also provided herein are methods of treating microbial infections comprising administering at least one compound of formula (I) or a pharmaceutically acceptable form thereof, or a pharmaceutical composition thereof, to a subject in need thereof.

The details of additional or alternative embodiments are set forth in the accompanying Detailed Description and Exemplification as described below. Other features, objects, and advantages will be apparent from this description and from the claims.

SEQUENCE IDENTIFICATION NUMBERS

SEQ ID NO. 1: *Homo sapiens* FASN amino acid sequence:

```
MEEVVIAGMSGKLPESENLQEFWDNLIGGVDMVTDDDRRWKAGLYGLPRRSGKLKDL

SRFDASFFGVHPKQAHTMDPQLRLLLEVTYEAIVDGGINPDSLRGTHTGVWVGVSGSET
```

-continued

```
SEALSRDPETLVGYSMVGCQRAMMANRLSFFFDFRGPSIALDTACSSSLMALQNAYQAI
HSGQCPAAIVGGINVLLKPNTSVQFLRLGMLSPEGTCKAFDTAGNGYCRSEGVVAVLLT
KKSLARRVYATILNAGTNIDGFKEQGVTFPSGDIQEQLIRSLYQSAGVAPESFEYIEAHG
TGTKVGDPQELNGITRALCATRQEPLLIGSTKSNMGHPEPASGLAALAKVLLSLEHGLW
APNLHFHSPNPEIPALLDGRLQVVDQPLPVRGGNVGINSFGFGGSNVHIILRPNTQPPPAP
APHATLPRLLRASGRTPEAVQKLLEQGLRHSQDLAFLSMLNDIAAVPATAMPFRGYAVL
GGERGGPEVQQVPAGERPLWFICSGIVIGTQWRGMGLSLMRLDRFRDSILRSDEAVKPFG
LKVSQLLLSTDESTFDDIVHSFVSLTAIQIGLIDLLSCMGLRPDGIVGHSLGEVACGYADG
CLSQEEAVLAAYWRGQCIKEAHLPPGAMAAVGLSWEECKQRCPPGVVPACHNSKDTV
TISGPQAPVFEFVEQLRKEGVFAKEVRTGGMAFHSYFMEAIAPPLLQELKKVIREPKPRS
ARWLSTSIPEAQWHSSLARTSSAEYNVNNLVSPVLFQEALWHVPEHAVVLEIAPHALLQ
AVLKRGLKPSCTIIPLMKKDHRDNLEFFLAGIGRLHLSGIDANPNALFPPVEFPAPRGTPLI
SPLIKWDHSLAWDVPAAEDFPNGSGSPSAAIYNIDTSSESPDHYLVDHTLDGRVLFPATG
YLSIVWKTLARALGLGVEQLPVVFEDVVLHQATILPKTGTVSLEVRLLEASRAFEVSEN
GNLVVSGKVYQWDDPDPRLFDHPESPTPNPTEPLFLAQAEVYKELRLRGYDYGPHFQGI
LEASLEGDSGRLLWKDNWVSFMDTMLQMSILGSAKHGLYLPTRVTAIHIDPATHRQKL
YTLQDKAQVADVVVSRWLRVTVAGGVHISGLHTESAPRRQQEQQVPILEKFCFTPHTEE
GCLSERAALQEELQLCKGLVQALQTKVTQQGLKMVVPGLDGAQIPRDPSQQELPRLLS
AACRLQLNGNLQLELAQVLAQERPKLPEDPLLSGLLDSPALKACLDTAVENMPSLKMK
VVEVLAGHGHLYSRIPGLLSPHPLLQLSYTATDRHPQALEAAQAELQQHDVAQGQWDP
ADPAPSALGSADLLVCNCAVAALGDPASALSNMVAALREGGFLLLHTLLRGHPLGDIV
AFLTSTEPQYGQGILSQDAWESLFSRVSLRLVGLKKSFYGSTLFLCRRPTPQDSPIFLPVD
DTSFRWVESLKGILADEDSSRPVWLKAINCATSGVVGLVNCLRREPGGNRLRCVLLSNL
SSTSHVPEVDPGSAELQKVLQGDLVMNVYRDGANVGAFRHELLEEDKPEEPTAHAFVST
LTRGDLSSIRWVCSSLRHAQPTCPGAQLCTVYYASLNFRDIMLATGKLSPDAIPGKWTS
QDSLLGMEFSGRDASGKRVMGLVPAKGLATSVLLSPDFLWDVPSNWTLEEAASVPVVY
STAYYALVVRGRVRPGETLLIHSGSGGVGQAAIAIALSLGCRVETTVGSAEKRAYLQAR
FPQLDSTSFANSRDTSFEQHVLWHTGGKGVDLVLNSLAEEKLQASVRCLATHGRFLEIG
KFDLSQNHPLGMAIFLKNVTFHGVLLDAFFNESSADWREVWALVQAGIRDGVVRPLKC
TVETIGAQVEDAFRYMAQGKHIGKVVVQVLAEEPEAVLKGAKPKLMSAISKTFCPAHKS
YIIAGGLGGFGLELAQWLIQRGVQKLVLTSRSGIRTGYQAKQVRRWRRQGVQVQVSTS
NISSLEGARGLIAEAAQLGPVGGVFNLAVVLRDGLLENQTPEFFQDVCKPKYSGTLNLD
RVTREACPELDYFVVFSSVSCGRGNAGQSNYGFANSAMERICEKRRHEGLPGLAVQWG
AIGDVGILVETMSTNDTIVSGTLPQRMASCLEVLDLFLNQPHMVLSSFVLAEKAAAYRD
RDSQRDLVEAVAHILGIRDLAAVNLDSSLADLGLDSLMSVEVRQTLERELNLVLSVREV
RQLTLRKLQELSSKADEASELACPTPKEDGLAQQQTQLNLRSLLVNPEGPTLMRLNSVQ
SSERPLFLVHPIEGSTTVFHSLASRLSIPTYGLQCTRAAPLDSIHSLAAYYIDCIRQVQPEG
PYRVAGYSYGACVAFEMCSQLQAQQSPAPTHNSLFLEDGSPTYVLAYTQSYRAKLTPG
CEAEAETEAICFFVQQFTDMEHNRVLEALLPLKGLEERVAAAVDLIIKSHQGLDRQELSF
```

-continued

AARSFYYKLRAAEQYTPKAKYHGNVMLLRAKTGGAYGEDLGADYNLSQVCDGKVSV

HVIEGDHRTLLEGSGLESIISIIHSSLAEPRVSVREG

DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers. *Some Modern Methods of Organic Synthesis*, 3$^{rd}$ Edition, Cambridge University Press, Cambridge, 1987.

Certain compounds provided herein can comprise one or more asymmetric centers, and thus can exist in various isomeric forms, e.g., enantiomers and/or diastereomers and/or stereoisomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds provided herein are enantiopure compounds. In certain other embodiments, mixtures of stereoisomers are provided.

Furthermore, certain compounds, as described herein can have one or more double bonds that can exist as either the cis or trans, or the E or Z isomer, unless otherwise indicated. Also encompassed are the compounds as individual isomers substantially free of other isomers, and alternatively, as mixtures of various isomers, e.g., racemic mixtures of E/Z isomers or mixtures enriched in one E/Z isomer.

The terms "optically enriched", "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). In addition, the term "non-racemic" can apply more broadly to mixtures of stereoisomers, diastereomers or olefin E/Z isomers. For example, an enantiomerically enriched preparation of the (S)-enantiomer, means a preparation of the compound having greater than 50% by weight of the (S)-enantiomer relative to the (R)-enantiomer, such as at least 75% by weight, and even such as at least 80% by weight. In some embodiments, the enrichment can be much greater than 80% by weight, providing a "substantially optically enriched," "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, and such as at least 95% by weight. In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or enantiomers can be prepared by asymmetric syntheses. See, for example, Jacques, et al., *Enantiomers, Racemates and Resolutions* (Wiley Interscience, New York, 1981); Wilen, S. H., et al., Tetrahedron 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed. Univ. of Notre Dame Press, Notre Dame, Ind. 1972).

As used herein, alone or as part of another group, "halo" and "halogen" refer to fluorine (fluoro, —F), chlorine (chloro, —Cl), bromine (bromo, —Br), or iodine (iodo, —I).

As used herein, alone or as part of another group, "alkyl" refers to a monoradical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with 1, 2, 3, 4, or 5 substituents as described herein. In certain embodiments, the alkyl group is an unsubstituted $C_{1-10}$ alkyl (e.g. —$CH_3$). In certain embodiments, the alkyl group is a substituted $C_{1-10}$ alkyl.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Perhaloalkyl" as defined herein refers to an alkyl group having from 1 to 10 carbon atoms wherein all of the hydrogen atoms are each independently replaced by a halogen, e.g., selected from fluoro, bromo, chloro or iodo ("$C_{1-10}$ perhaloalkyl"). In some embodiments, the alkyl moiety has 1 to 9 carbon atoms ("$C_{1-9}$ perhaloalkyl"). In some embodiments, the alkyl moiety has 1 to 8 carbon atoms ("$C_{1-8}$ perhaloalkyl"). In some embodiments, the alkyl moiety has 1 to 7 carbon atoms ("$C_{1-7}$ perhaloalkyl"). In some embodiments, the alkyl moiety has 1 to 6 carbon atoms ("$C_{1-6}$ perhaloalkyl"). In some embodiments, the alkyl moiety has 1 to 5 carbon atoms ("$C_{1-5}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl and the like.

As used herein, alone or as part of another group, "alkenyl" refers to a monoradical of a straight-chain or branched hydrocarbon group having from 2 to 10 carbon atoms and one or more carbon-carbon double bonds ("C$_{2-10}$ alkenyl"). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$) and the like. Examples of C$_{2-6}$ alkenyl groups include the aforementioned C$_{2-4}$ alkenyl groups as well as pentenyl (C$_5$), pentadienyl (C$_5$), hexenyl (C$_6$) and the like. Additional examples of alkenyl include heptenyl (C$_7$), octenyl (C$_8$), octatrienyl (C$_8$) and the like. Unless otherwise specified, each instance of an alkenyl group is independently unsubstituted (an "unsubstituted alkenyl") or substituted (a "substituted alkenyl") with 1, 2, 3, 4, or 5 substituents as described herein. In certain embodiments, the alkenyl group is an unsubstituted C$_{2-10}$ alkenyl. In certain embodiments, the alkenyl group is a substituted C$_{2-10}$ alkenyl.

As used herein, alone or as part of another group, "alkynyl" refers to a monoradical of a straight-chain or branched hydrocarbon group having from 2 to 10 carbon atoms and one or more carbon-carbon triple bonds ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$) and the like. Examples of C$_{2-6}$ alkenyl groups include the aforementioned C$_{2-4}$ alkynyl groups as well as pentynyl (C$_5$), hexynyl (C$_6$) and the like. Additional examples of alkynyl include heptynyl (C$_7$), octynyl (C$_8$) and the like. Unless otherwise specified, each instance of an alkynyl group is independently unsubstituted (an "unsubstituted alkynyl") or substituted (a "substituted alkynyl") with 1, 2, 3, 4, or 5 substituents as described herein. In certain embodiments, the alkynyl group is an unsubstituted C$_{2-10}$ alkynyl. In certain embodiments, the alkynyl group is a substituted C$_{2-10}$ alkynyl.

As used herein, alone or as part of another group, "heteroaliphatic" refers to a monoradical of an acyclic 3- to 14-membered straight-chain or branched-chain having from 2 to 13 carbon atoms and 1 to 4 heteroatoms selected from oxygen, sulfur, phosphorous, and nitrogen, and wherein the point of attachment is a carbon atom ("3-14 membered heteroaliphatic"). In some embodiments, "heteroaliphatic" is a saturated group ("heteroalkyl"). In some embodiments, "heteroaliphatic" is a group containing one or more double bonds ("heteroalkenyl"). In some embodiments, "heteroaliphatic" is a group containing one or more triple bonds ("heteroalkynyl"). Exemplary heteroaliphatic groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy)methanyl (—CH$_2$OCH$_2$OCH$_3$) and (methoxyethoxy)methanyl (—CH$_2$OCH$_2$ CH$_2$OCH$_3$) and the like; amines such as —CH$_2$CH$_2$NHCH$_3$—CH$_2$CH$_2$N (CH$_3$)$_2$, —CH$_2$NHCH$_2$CH$_3$, —CH$_2$N(CH$_2$CH$_3$)(CH$_3$) and the like. Unless otherwise specified, each instance of a heteroaliphatic group is independently unsubstituted (an "unsubstituted heteroaliphatic") or substituted (a "substituted heteroaliphatic") with 1-5 substituents as described herein. In certain embodiments, the heteroaliphatic group is an unsubstituted 3-14 membered heteroaliphatic. In certain embodiments, the heteroaliphatic group is a substituted 3-14 membered heteroaliphatic.

As used herein, alone or as part of another group, "carbocyclyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 9 ring carbon atoms ("C$_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 3 to 5 ring carbon atoms ("C$_{3-5}$ carbocyclyl"). In some embodiments, a carbocyclyl group has 3 to 4 ring carbon atoms ("C$_{3-4}$ carbocyclyl"). In some embodiments, a carbocyclyl group has 5 to 10 ring carbon atoms ("C$_{5-10}$ carbocyclyl"). Examples of C$_{3-6}$ carbocyclyl groups include, without limitation, cyclopropyl (C$_3$), cyclobutyl (C$_4$), cyclopentyl (C$_5$), cyclopentenyl (C$_5$), cyclohexyl (C$_6$), cyclohexenyl (C$_6$), cyclohexadienyl (C$_6$) and the like. Examples of C$_{3-8}$ carbocyclyl groups include the aforementioned C$_{3-6}$ carbocyclyl groups as well as cycloheptyl (C$_7$), cycloheptadienyl (C$_7$), cycloheptatrienyl (C$_7$), cyclooctyl (C$_8$), bicyclo [2.2.1]heptanyl, bicyclo[2.2.2]octanyl, and the like. Examples of C$_{3-10}$ carbocyclyl groups include the aforementioned C$_{3-8}$ carbocyclyl groups as well as octahydro-1H-indenyl, decahydronaphthalenyl, spiro[4.5]decanyl and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring. Unless otherwise specified, each instance of a carbocyclyl group is independently unsubstituted (an "unsubstituted carbocyclyl") or substituted (a "substituted carbocyclyl") with 1, 2, 3, 4, or 5 substituents as described herein. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with 1, 2, 3, 4, or 5 substituents as described herein. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, alone or as part of another group, "heterocyclyl" refers to a radical of a 3- to 14-membered non-aromatic ring system having ring carbon atoms and 1 to 4 ring heteroatoms, wherein each heteroatom is independently selected from nitrogen, oxygen, phosphorous, and sulfur ("3-14 membered heterocyclyl"). In heterocyclyl groups that contain one or more nitrogen or phosphorous atoms, the point of attachment can be a carbon, nitrogen, or phosphorous atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring. In some embodiments, a heterocyclyl group is a 5-10 membered non-aromatic ring system having ring carbon atoms and 1-4 ring heteroatoms, wherein each heteroatom is independently selected from nitrogen, oxygen, phosphorous, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous, and sulfur ("5-6 membered heterocyclyl"). In some embodiments, the 5-6 membered heterocyclyl has 1-3 ring heteroatoms selected from nitrogen, oxygen, phosphorous, and sulfur. In some embodiments, the 5-6 membered heterocyclyl has 1-2 ring heteroatoms selected from nitrogen, oxygen, phosphorous, and sulfur. In some embodiments, the 5-6 membered heterocyclyl has 1 ring heteroatom selected from nitrogen, oxygen, phosphorous, and sulfur. Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetra-hydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Unless otherwise specified, each instance of heterocyclyl is independently unsubstituted (an "unsubstituted heterocyclyl") or substituted (a "substituted heterocyclyl") with 1, 2, 3, 4, or 5 substituents as described herein. In certain embodiments, the heterocyclyl group is an unsubstituted 3-14 membered heterocyclyl. In certain embodiments, the heterocyclyl group is a substituted 3-14 membered heterocyclyl.

As used herein, alone or as part of another group, "aryl" refers to a radical of a monocyclic or polycyclic (e.g., bicyclic or tricyclic) aromatic ring system (e.g., having 6, 10 or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl, such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring. Unless otherwise specified, each instance of an aryl group is independently unsubstituted (an "unsubstituted aryl") or substituted (a "substituted aryl") with 1, 2, 3, 4, or 5 substituents as described herein. In certain embodiments, the aryl group is an unsubstituted $C_{6-14}$ aryl. In certain embodiments, the aryl group is a substituted $C_{6-14}$ aryl.

As used herein, alone or part of another group, "aralkyl" refers to a $C_{1-10}$ alkyl group as defined herein substituted by a $C_{6-14}$ aryl group as defined herein, wherein the point of attachment is on the alkyl group ("$C_{1-10}$ aralkyl").

As used herein, alone or as part of another group, "heteroaryl" refers to a radical of a 5-14 membered monocyclic or polycyclic (e.g., bicyclic or tricyclic) aromatic ring system (e.g., having 6, 10 or 14 π electrons shared in a cyclic array) having ring carbon atoms and 1-4 ring heteroatoms provided in the aromatic ring system, wherein each heteroatom is independently selected from nitrogen, oxygen, phosphorous, and sulfur ("5-14 membered heteroaryl"). In heteroaryl groups that contain one or more nitrogen or phosphorous atoms, the point of attachment can be a carbon, phosphorous or nitrogen atom, as valency permits. Heteroaryl polycyclic ring systems can include one or more heteroatoms in one or both rings. "Heteroaryl" also includes ring systems wherein the heteroaryl ring, as defined above, is fused with one or more aryl groups wherein the point of attachment is either on the aryl or on the heteroaryl ring, or wherein the heteroaryl ring, as defined above, is fused with one or more carbocycyl or heterocycyl groups wherein the point of attachment is on the heteroaryl ring. For polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, and thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Exemplary tricyclic heteroaryls include, without limitation, phenanthridinyl, dibenzofuranyl, carbazolyl, acridinyl, phenothiazinyl, phenoxazinyl and phenazinyl. Unless otherwise specified, each instance of a heteroaryl group is independently unsubstituted (an "unsubstituted heteroaryl") or substituted (a "substituted heteroaryl") with 1, 2, 3, 4, or 5 substituents as described herein. In certain embodiments, the heteroaryl group is an unsubstituted 5-14 membered heteroaryl. In certain embodiments, the heteroaryl group is a substituted 5-14 membered heteroaryl.

As used herein, alone or part of another group, "heteroaralkyl" refers to a $C_{1-10}$ alkyl group as defined herein substituted by a 5-14 membered heteroaryl group as defined herein, wherein the point of attachment is on the alkyl group ("$C_{1-10}$ heteroaralkyl").

As used herein, a "covalent bond" or "direct bond" refers to a single bond joining two groups.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein a "divalent" group, such as a divalent alkyl, divalent alkenyl, divalent alkynyl, divalent heteroaliphatic, divalent carbocyclyl, divalent heterocyclyl, divalent aryl or divalent heteroaryl group, refers to a bis-radical of the group, as defined herein.

Monovalent or divalent alkyl, alkenyl, alkynyl, heteroaliphatic, carbocyclyl, heterocyclyl, aryl and heteroaryl groups, as defined herein, are either "substituted" or "unsubstituted" alkyl, "substituted" or "unsubstituted" alkenyl, "substituted" or "unsubstituted" alkynyl, "substituted" or "unsubstituted" heteroaliphatic, "substituted" or "unsubstituted" carbocyclyl, "substituted" or "unsubstituted" heterocyclyl, "substituted" or "unsubstituted" aryl or "substituted" or "unsubstituted" heteroaryl groups. In general, the term "substituted" means that at least one hydrogen present on a group (e.g., a carbon or nitrogen atom, etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. A group referred to as "not hydrogen" indicates that the group is an exemplary and permissible substituent as described herein.

Exemplary substituents include, but are not limited to, halogen (i.e., fluoro (—F), bromo (—Br), chloro (—Cl), and iodo (—I)), —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(S)SR$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$), —OP(R$^{cc}$)$_3$, —B(OR$^{cc}$)$_2$, or —BR$^{aa}$(OR$^{cc}$), =O, =S, =NN(R$^{bb}$)$_2$, =NNR$^{bb}$C(O) R$^{aa}$, =NNR$^{bb}$CO$_2$R$^{aa}$, =NNR$^{bb}$S(O)$_2$R$^{aa}$, =NR$^{bb}$, =NOR$^{cc}$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently unsubstituted or substituted with 1-5 R$^{dd}$ groups;

wherein:

each instance of R$^{aa}$ is, independently, selected from C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, wherein each alkyl, alkenyl, alkynyl, heteroaliphatic, carbocyclyl, heterocyclyl, aryl, and heteroaryl is independently unsubstituted or substituted with 1-5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroaliphatic, carbocyclyl, heterocyclyl, aryl, and heteroaryl is independently unsubstituted or substituted with 1-5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroaliphatic carbocyclyl, heterocyclyl, aryl, and heteroaryl is independently unsubstituted or substituted with 1-5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(OR$^{ee}$)R$^{ff}$, —SH, —SR$^{ee}$, —SSR$^{ee}$, —C(O)R$^{ee}$, —CO$_2$H, —CO$_2$R$^{ee}$, —OC(O)R$^{ee}$, —OCO$_2$R$^{ee}$, —C(O)N(R$^{ff}$)$_2$, —OC(O)N(R$^{ff}$)$_2$, —NR$^{ff}$C(O)R$^{ee}$, —NR$^{ff}$CO$_2$R$^{ee}$, NR$^{ff}$C(O)N(R$^{ff}$)$_2$, —C(NR$^{ff}$) OR$^{ee}$, —OC(NR$^{ff}$)R$^{ee}$, —OC(NR$^{ff}$)OR$^{ee}$, —C(NR$^{ff}$)N(R$^{ff}$)$_2$, —OC(NR$^{ff}$)N(R$^{ff}$)$_2$, —NR$^{ff}$C(NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —SOR$^{ee}$, —Si(R$^{ee}$)$_3$, —OSi(R$^{ee}$)$_3$, —C(S)N(R$^{ff}$)$_2$, —C(O) SR$^{ee}$, —C(S)SR$^{ee}$, —SC(S)SR$^{ee}$, —P(O)$_2$R$^{ee}$, —P(O)(R$^{ee}$)$_2$, —OP(O)(R$^{ee}$)$_2$, —OP(O)(OR$^{ee}$)$_2$, =O, =S, C$_{1-6}$ alkyl, C$_{1-6}$ perhaloalkyl, C$_{2-6}$ alkenyl, C$_{2-4}$ alkynyl, 3-14 membered heteroaliphatic, C$_{3-10}$ carbocyclyl, 3-10 membered heterocyclyl, C$_{6-10}$ aryl, 5-10 membered heteroaryl, wherein each alkyl, alkenyl, alkynyl, heteroaliphatic, carbocyclyl, heterocyclyl, aryl, and heteroaryl is independently unsubstituted or substituted with 1-5 R$^{gg}$ groups;

each instance of R$^{ee}$ is, independently, selected from C$_{1-6}$ alkyl, C$_{1-6}$ perhaloalkyl, C$_{2-6}$ alkenyl, C$_{2-6}$ alkynyl, 3-14 membered heteroaliphatic, C$_{3-10}$ carbocyclyl, C$_{6-10}$ aryl, 3-10 membered heterocyclyl, and 3-10 membered heteroaryl, wherein each alkyl, alkenyl, alkynyl, heteroaliphatic, carbocyclyl, heterocyclyl, aryl, and heteroaryl is independently unsubstituted or substituted with 1-5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, 3-14 membered heteroaliphatic, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroaliphatic, carbocyclyl, heterocyclyl, aryl, and heteroaryl is independently unsubstituted or substituted with 1-5 R$^{gg}$ groups; and each instance of R$^{gg}$ is, independently, halogen, —CN, —NO$_2$, —N3, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —S(C$_{1-6}$ alkyl), —SS(C$_{1-6}$ alkyl), —C(O)(C$_{1-6}$ alkyl), —CO$_2$H, —CO$_2$(C$_{1-6}$ alkyl), —OC(O)(C$_{1-6}$ alkyl), —OCO$_2$(C$_{1-6}$ alkyl), —C(O)NH$_2$, —C(O)N(C$_{1-6}$ alkyl)$_2$, —OC(O)NH(C$_{1-6}$ alkyl), —NHC(O)(C$_{1-6}$ alkyl), —N(C$_{1-6}$ alkyl)C(O)(C$_{1-6}$ alkyl), —NHCO$_2$(C$_{1-6}$ alkyl), —NHC(O)N(C$_{1-6}$ alkyl)$_2$, —NHC(O)NH(C$_{1-6}$ alkyl), —NHC(O)NH$_2$, —C(NH)O(C$_{1-6}$ alkyl), —OC(NH)(C$_{1-6}$ alkyl), —OC(NH)OC$_{1-6}$ alkyl, —C(NH)N(C$_{1-6}$ alkyl)$_2$, —C(NH)NH(C$_{1-6}$ alkyl), —C(NH)NH$_2$, —OC(NH)N(C$_{1-6}$ alkyl)$_2$, —OC(NH)NH(C$_{1-6}$ alkyl), —OC(NH)NH$_2$, —NHC(NH)NH(C$_{1-6}$ alkyl)$_2$, —NHC(NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$C$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(S)N(C$_{1-6}$ alkyl)$_2$, —C(S)NH(C$_{1-6}$ alkyl), —C(S)NH$_2$, —C(O)S(C$_{1-6}$ alkyl), —C(S)SC$_{1-6}$ alkyl, —SC(S)SC$_{1-6}$ alkyl, —P(O)$_2$(C$_{1-6}$ alkyl), —P(O)(C$_{1-6}$ alkyl)$_2$, —OP(O)(C$_{1-6}$ alkyl)$_2$, —OP(O)(OC$_{1-16}$ alkyl)$_2$, C$_{1-6}$ alkyl, C$_{1-6}$ perhaloalkyl, C$_{2-6}$ alkenyl, C$_{2-6}$ alkynyl, 3-14 membered heteroaliphatic, C$_{3-10}$ carbocyclyl, C$_{6-10}$ aryl, 3-10 membered heterocyclyl, 5-10 membered heteroaryl, =O or =S.

These and other exemplary substituents are described in more detail in the Detailed Description, the Exemplification and in the claims. The term "substituents" is not intended to be limited in any manner by the above exemplary listing of substituents.

As used herein, a "pharmaceutically acceptable form thereof" includes pharmaceutically acceptable salts, hydrates, solvates, prodrugs, tautomers, isomers, and/or polymorphs of a compound provided herein, as defined below and herein.

In certain embodiments, the pharmaceutically acceptable form thereof is a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In certain embodiments, the pharmaceutically acceptable form thereof is a hydrate or solvate. As used herein, the term "hydrate" refers to a compound non-covalently associated with one or more molecules of water, which in some embodiments can be crystalline. Likewise, "solvate" refers to a compound non-covalently associated with one or more molecules of an organic solvent, which in some embodiments can be crystalline.

In certain embodiments, the pharmaceutically acceptable form thereof is a prodrug. As used herein, the term "prodrug" refers to a derivative of a parent compound that requires transformation within the body in order to release the parent compound.

The term "prodrug" refers to compounds that are transformed in vivo to yield a disclosed compound or a pharmaceutically acceptable form of the compound. The transformation can occur by various mechanisms, such as, but not limited to, through hydrolysis in blood. In certain cases, a prodrug has improved physical and/or delivery properties over the parent compound. Prodrugs are typically designed to enhance pharmaceutically and/or pharmacokinetically based properties associated with the parent compound. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

For example, if a disclosed compound or a pharmaceutically acceptable form of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$ alkylcarbamoyl-$(C_1-C_2)$alkyl and piperidino-, pyrrolidino- or morpholino$(C_2-C_3)$alkyl.

Similarly, if a disclosed compound or a pharmaceutically acceptable form of the compound contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —P(O)(O$(C_1-C_6)$alkyl$)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino, morpholino, piperidin-1-yl or pyrrolidin-1-yl.

In certain embodiments, the pharmaceutically acceptable form thereof is a tautomer. As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations.

In certain embodiments, the pharmaceutically acceptable form thereof is an isomer. As used herein, the term "isomer" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of this disclosure. For instance, an isomer/enantiomer can, in some embodiments, be provided substantially free of the corresponding enantiomer, and may also be referred to as "optically enriched." "Optically-enriched," as used herein, means that the compound is made up of a significantly greater proportion of one enantiomer. In certain embodiments, the compound provided herein is made up of at least about 90% by weight of one enantiomer. In other embodiments the compound is made up of at least about 95%, 98%, or 99% by weight of one enantiomer. Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, NY, 1962); and *Tables of Resolving Agents and*

*Optical Resolutions* p. 268 (E. L. Eliel, Ed., Univ. of Notre Dame Press, Notre Dame, Ind. 1972).

In certain embodiments, the pharmaceutically acceptable form thereof is a polymorph. As used herein, "polymorph" refers to a compound having more than one crystal structure, e.g., resulting from differences in molecular packing and/or molecular conformation of the compound in the solid state.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}H$, $^{3}H$, $^{3}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{4}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by following procedures analogous to those disclosed in the Exemplification section herein by substituting an isotopically labeled reagent for a non-isotopically labeled reagent.

DETAILED DESCRIPTION

1. Brief Description of Figures

2. Compounds

Figure 1:
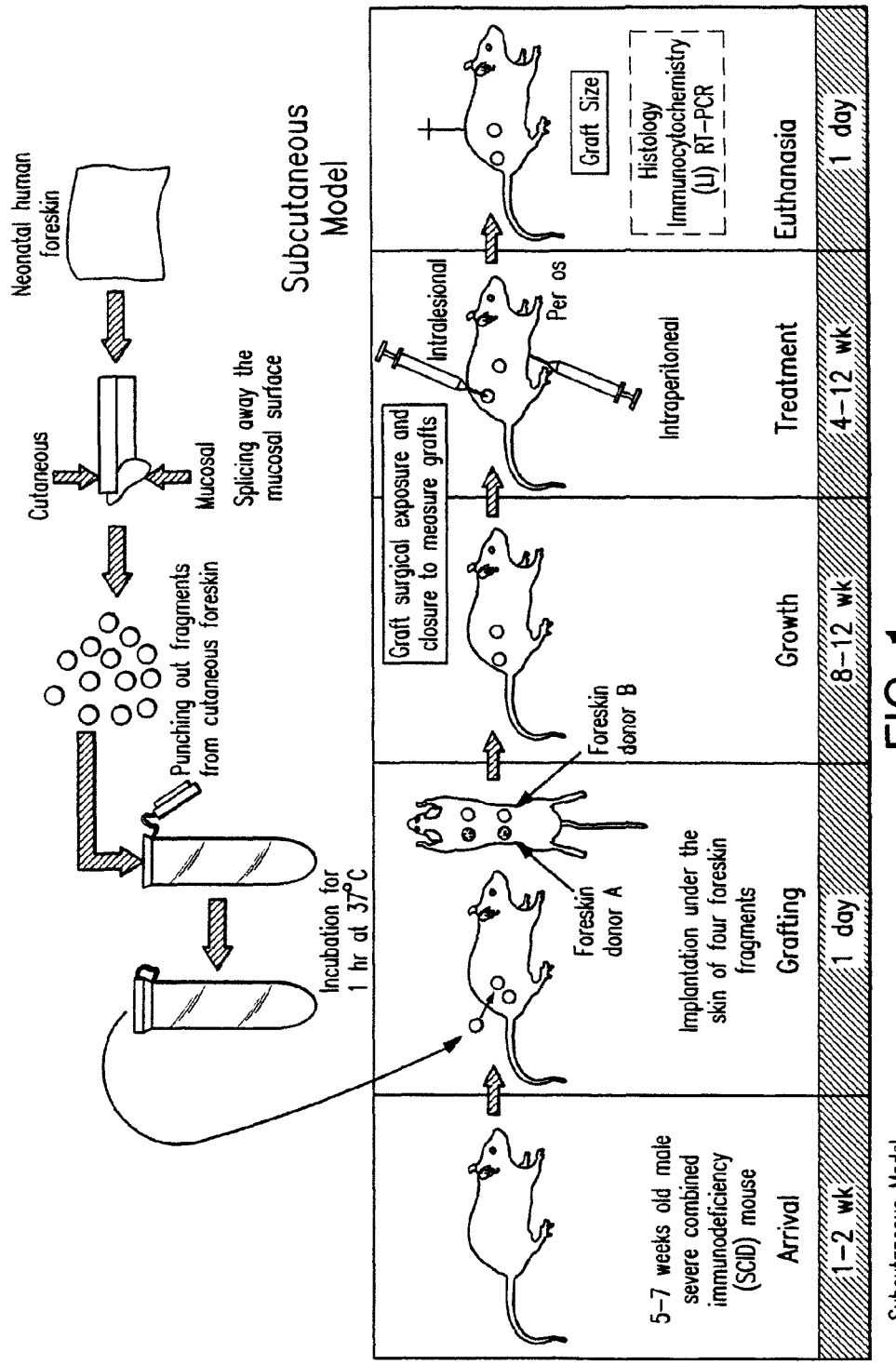
FIG. 1 illustrates a schematic diagram of subcutaneous mouse xenograft model for assaying papillomaviruses.

Without being limited by a particular theory, the present disclosure is based on the discovery that tetrazolones are inhibitors of human fatty acid synthase (FASN) and thus are useful in the treatment of FASN-mediated diseases, disorders or conditions. Further, without being limited by a particular theory, in certain embodiments, the compounds provided herein can inhibit long chain fatty acid elongase (ELOVL) such as ELOVL 6. Thus, in some embodiments, compounds provided herein are useful in the treatment of ELOVL-mediated diseases, disorders or conditions.

For example, in one aspect, provided herein is a compound of formula (I):

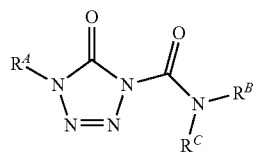

or a pharmaceutically acceptable form thereof;
wherein:
$R^{A}$ is selected from $C_{3-10}$ carbocyclyl, 3-14 membered heterocyclyl, $C_{6-14}$ aryl and 5-14 membered heteroaryl;
$R^{B}$ is selected from $C_{1-10}$ alkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl and 5-14 membered heteroaryl;

$R^{C}$ is selected from hydrogen, —OH, —OR$^{C1}$, —ON(R$^{C2}$)$_{2}$, —N(R$^{C2}$)$_{2}$, —C(=O)R$^{C1}$, —CHO, —CO$_{2}$R$^{C1}$, —C(=O)N(R$^{C2}$)$_{2}$, —C(=NR$^{C2}$)OR$^{C1}$, —C(=NR$^{C2}$)N(R$^{C2}$)$_{2}$, —SO$_{2}$R$^{C1}$, —S(=O)R$^{C1}$, —Si(R$^{C1}$)$_{3}$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;
wherein:
each instance of $R^{C1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; and
each instance of $R^{C2}$ is, independently, selected from hydrogen, —OH, —OR$^{C1}$, —N(R$^{C3}$)$_{2}$, —CN, —C(=O)R$^{C1}$, —C(=O)N(R$^{C3}$)$_{2}$, —CO$_{2}$R$^{C1}$, —SO$_{2}$R$^{C1}$, —C(=NR$^{C3}$)OR$^{C1}$, —C(=NR$^{C3}$)N(R$^{C3}$)$_{2}$, —SO$_{2}$N(R$^{C3}$)$_{2}$, —SO$_{2}$R$^{C3}$, —SO$_{2}$OR$^{C3}$, —SOR$^{C1}$, —C(=S)N(R$^{C3}$)$_{2}$, —C(=O)SR$^{C3}$, —C(=S)SR$^{C3}$, —P(=O)$_{2}$R$^{C1}$, —P(=O)(R$^{C1}$)$_{2}$, —P(=O)$_{2}$N(R$^{C3}$)$_{2}$, —P(=O)(NR$^{C3}$)$_{2}$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{C2}$ groups are joined to form a 3-14 membered heterocyclyl or 5-14 membered heteroaryl ring;
or $R^{B}$ and $R^{C}$ together with the nitrogen (N) atom to which each is attached are joined to form a 5-14 membered heterocyclyl or heteroaryl ring.

In one embodiment, provided herein is a compound of formula (I):

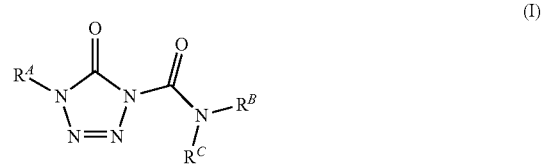

or a pharmaceutically acceptable form thereof;
wherein:
$R^{A}$ is selected from $C_{6-14}$ aryl and 5-14 membered heteroaryl;
$R^{B}$ is selected from $C_{6-14}$ aryl and 5-14 membered heteroaryl;
$R^{C}$ is selected from —OH, —OR$^{C1}$, —ON(R$^{C2}$)$_{2}$—N(R$^{C2}$)$_{2}$, —C(=O)R$^{C1}$, —CHO, —CO$_{2}$R$^{C1}$, —C(=O)N(R$^{C2}$)$_{2}$, —C(=NR$^{C2}$)OR$^{C1}$, —C(=NR$^{C2}$)N(R$^{C2}$)$_{2}$, —SO$_{2}$R$^{C1}$, —S(=O)R$^{C1}$, —Si(R$^{C1}$)$_{3}$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, with the proviso that $R^{C}$ is not —CH$_{3}$;
each instance of $R^{C1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;
each instance of $R^{C2}$ is, independently, selected from hydrogen, —OH, —OR$^{C1}$, —N(R$^{C3}$)$_{2}$, —CN, —C(=O)R$^{C1}$, —C(=O)N(R$^{C3}$)$_{2}$, —CO$_{2}$R$^{C1}$, —SO$_{2}$R$^{C1}$, —C(=NR$^{C3}$)OR$^{C1}$, —C(=NR$^{C3}$)N(R$^{C3}$)$_{2}$, —SO$_{2}$N(R$^{C3}$)$_{2}$, —SO$_{2}$R$^{C3}$, —SO$_{2}$OR$^{C3}$, —SOR$^{C1}$, —C(=S)N(R$^{C3}$)$_{2}$, —C(=O)SR$^{C3}$, —C(=S)SR$^{C3}$, —P(=O)$_{2}$R$^{C1}$, —P(=O)(R$^{C1}$)$_{2}$, —P(=O)$_{2}$N(R$^{C3}$)$_{2}$, —P(=O)(NR$^{C3}$)$_{2}$, $C_{2-10}$ alkyl, $C_{2-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{C2}$ groups are joined to form a 3-14 membered heterocyclyl or 5-14 membered heteroaryl ring;

or $R^B$ and $R^C$ together with the nitrogen (N) atom to which each is attached are joined to form a 5-14 membered ring;

wherein:

$R^B$ is substituted with the group:

-L-$R^D$ wherein:

L is a covalent bond or a divalent $C_{1-10}$ hydrocarbon chain, wherein one, two or three methylene units of L are optionally and independently replaced with one or more —O—, —S—, —NR$^{B8}$—, —(C=NR$^{B8}$)—, —C(=O)—, —C(=S)—, —S(=O)—, —S(=O)$_2$—, divalent carbocyclyl, divalent heterocyclyl, divalent aryl or divalent heteroaryl group;

$R^D$ is selected from —CN, —NO$_2$, —N$_3$, —SO$_2$H, —SO$_3$H, —C(=O)R$^{B7}$, —CO$_2$H, —CHO, —C(OR$^{B9}$)$_2$, —CO$_2$R$^{B7}$, —OC(=O)R$^{B7}$, —OCO$_2$R$^{B7}$, —C(=O)N(R$^{B8}$)$_2$, —OC(=O)N(R$^{B8}$)$_2$, —NR$^{B8}$C(=O)R$^{B7}$, —NR$^{B8}$CO$_2$R$^{B7}$, —NR$^{B8}$C(=O)N(R$^{B8}$)$_2$, —C(=NR$^{B8}$)OR$^{B7}$, —OC(=NR$^{B8}$)R$^{B7}$, —OC(=NR$^{B8}$)OR$^{B7}$, —C(=NR$^{B8}$)N(R$^{B8}$)$_2$, —OC(=NR$^{B8}$)N(R$^{B8}$)$_2$, —NR$^{B8}$C(=NR$^{B8}$)N(R$^{B8}$)$_2$, —C(=O)NR$^{B8}$SO$_2$R$^{B7}$, —NR$^{B8}$SO$_2$R$^{B7}$, —SO$_2$N(R$^{B8}$)$_2$, —SO$_2$R$^{B7}$, —SO$_2$OR$^{B7}$, —OSO$_2$R$^{B7}$, —S(=O)R$^{B7}$, —OS(=O)R$^{B7}$, —C(=S)N(R$^{B8}$)$_2$, —C(=O)SR$^{B7}$, —C(=S)SR$^{B7}$, —SC(=S)SR$^{B7}$, —P(=O)$_2$R$^{B7}$, —OP(=O)$_2$R$^{B7}$, —P(=O)(R$^{B7}$)$_2$, —OP(=O)(R$^{B7}$)$_2$, —OP(=O)(OR$^{B9}$)$_2$, —P(=O)$_2$N(R$^{B8}$)$_2$, —OP(=O)$_2$N(R$^{B8}$)$_2$, —P(=O)(NR$^{B8}$)$_2$, —OP(=O)(NR$^{B8}$)$_2$, —NR$^{B8}$P(=O)(OR$^{B9}$)$_2$, —NR$^{B8}$P(=O)(NR$^{B8}$)$_2$, —B(OR$^{B9}$)$_2$, —BR$^{B7}$(OR$^{B9}$), and tetrazolyl;

each instance of $R^{B7}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{B8}$ is, independently, selected from hydrogen, —OH, —OR$^{B7}$, —N(R$^{B9}$)$_2$, —CN, —C(=O)R$^{B7}$, —C(=O)N(R$^{B9}$)$_2$, —CO$_2$R$^{B7}$, —SO$_2$R$^{B7}$, —C(=NR$^{B9}$)OR$^{B7}$, —C(=NR$^{B9}$)N(R$^{B9}$)$_2$, —SO$_2$N(R$^{B9}$)$_2$, —SO$_2$R$^{B9}$, —SO$_2$OR$^{B9}$, —SOR$^{B7}$, —C(=S)N(R$^{B9}$)$_2$, —C(=O)SR$^{B9}$, —C(=S)SR$^{B9}$, —P(=O)$_2$R$^{B7}$, —P(=O)(R$^{B7}$)$_2$, —P(=O)$_2$N(R$^{B9}$)$_2$, —P(=O)(NR$^{B9}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B8}$ groups are joined to form a 3-14 membered heterocyclyl or 5-14 membered heteroaryl ring; and each instance of $R^{B9}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl and 5-14 membered heteroaryl, or two $R^{B9}$ groups are joined to form a 3-14 membered heterocyclyl or 5-14 membered heteroaryl ring.

In one embodiment, provided herein is a compound of formula (I):

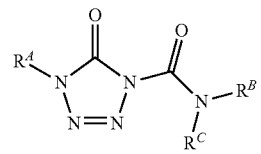

(I)

or a pharmaceutically acceptable form thereof;

wherein:

$R^A$ is selected from $C_{3-10}$ carbocyclyl, 3-14 membered heterocyclyl, $C_{6-14}$ aryl and 5-14 membered heteroaryl;

$R^B$ is selected from $C_{1-10}$ alkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl and 5-14 membered heteroaryl;

$R^C$ is selected from hydrogen, —OH, —OR$^{C1}$, —ON(R$^{C2}$)$_2$, —N(R$^{C2}$)$_2$, —C(=O)R$^{C1}$, —CHO, —CO$_2$R$^{C1}$, —C(=O)N(R$^{C2}$)$_2$, —C(=NR$^{C2}$)OR$^{C1}$, —C(=NR$^{C2}$)N(R$^{C2}$)$_2$, —SO$_2$R$^{C1}$, —S(=O)R$^{C1}$, —Si(R$^{C1}$)$_3$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{C1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; and each instance of $R^{C2}$ is, independently, selected from hydrogen, —OH, —OR$^{C1}$, —N(R$^{C3}$)$_2$, —CN, —C(=O)R$^{C1}$, —C(=O)N(R$^{C3}$)$_2$, —CO$_2$R$^{C1}$, —SO$_2$R$^{C1}$, —C(=NR$^{C3}$)OR$^{C1}$, —C(=NR$^{C3}$)N(R$^{C3}$)$_2$, —SO$_2$N(R$^{C3}$)$_2$, —SO$_2$R$^{C3}$, —SO$_2$OR$^{C3}$, —SOR$^{C1}$, —C(=S)N(R$^{C3}$)$_2$, —C(=O)SR$^{C3}$, —C(=S)SR$^{C3}$, —P(=O)$_2$R$^{C1}$, —P(=O)(R$^{C1}$)$_2$, —P(=O)$_2$N(R$^{C3}$)$_2$, —P(=O)(NR$^{C3}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{C2}$ groups are joined to form a 3-14 membered heterocyclyl or 5-14 membered heteroaryl ring;

or $R^B$ and $R^C$ together with the nitrogen (N) atom to which each is attached are joined to form a 5-14 membered ring.

Group $R^A$

As described generally above, $R^A$ is selected from $C_{3-10}$ carbocyclyl, 3-14 membered heterocyclyl, $C_{6-14}$ aryl, and 5-14 membered heteroaryl.

In certain embodiments, $R^A$ is $C_{3-10}$ carbocyclyl. Exemplary carbocyclyl groups include, but are not limited to, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptadienyl ($C_7$), cycloheptatrienyl ($C_7$) and cyclooctyl ($C_8$).

In certain embodiments, $R^A$ is 3-14 membered heterocyclyl. Exemplary heterocyclyl groups include, but are not limited to, azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, dioxolanyl, oxathiolanyl, dithiolanyl, piperidinyl, tetrahydropyranyl, dihydropyridinyl, thianyl, piperazinyl, morpholinyl, dithianyl, dioxanyl, azepanyl, oxepanyl thiepanyl, azocanyl, oxecanyl and thiocanyl.

In certain embodiments, $R^A$ is $C_{6-14}$ aryl. Exemplary aryl groups include, but are not limited to, phenyl, naphthyl and anthracyl. In certain embodiments, $R^A$ is phenyl ($C_6$ aryl). In certain embodiments, $R^A$ is naphthyl ($C_{10}$ aryl).

In certain embodiments, $R^4$ is 5-14 membered heteroaryl. In certain embodiments, $R^4$ is 5-10 membered heteroaryl. In certain embodiments, $R^4$ is 5-6 membered heteroaryl. In certain embodiments, $R^4$ is 5,6-bicyclic heteroaryl. In certain embodiments, $R^4$ is 6,6-bicyclic heteroaryl.

In certain embodiments, $R^4$ is a 5-membered heteroaryl group. Exemplary 5-membered heteroaryl groups include, but are not limited to, pyrrolyl, furanyl, thiophenyl, imidazolyl, pyrazolyl, oxazolyl, isoxazolyl, thiazolyl, isothiazolyl, triazolyl, oxadiazolyl, thiadiazolyl and tetrazolyl.

In certain embodiments, $R^4$ is a 6-membered heteroaryl group. Exemplary 6-membered heteroaryl groups include, but are not limited to, pyridinyl, pyridazinyl, pyrimidinyl, pyrazinyl, triazinyl and tetrazinyl.

In certain embodiments, $R^4$ is a 5,6-bicyclic heteroaryl group. Exemplary 5,6-bicyclic heteroaryl groups include, but are not limited to, indolyl, isoindolyl, indazolyl, benztriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl.

In certain embodiments, $R^4$ is a 6,6-bicyclic heteroaryl group. Exemplary 6,6-bicyclic heteroaryl groups include, but are not limited to, naphthyridinyl, pteridinyl, quinolinyl, isoquinolinyl, cinnolinyl, quinoxalinyl, phthalazinyl and quinazolinyl.

In certain embodiments, $R^4$ is a group of the formula (i):

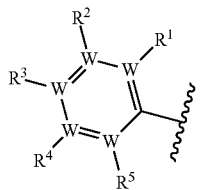

(i)

wherein each group W—$R^1$, W—$R^2$, W—$R^3$, W—$R^4$, and W—$R^5$ independently represents either a nitrogen atom (N) or C—$R^1$, C—$R^2$, C—$R^3$, C—$R^4$, or C—$R^5$, respectively; and wherein $R^1$, $R^2$, $R^3$, $R^4$ and $R^5$ are independently selected from the group consisting of hydrogen, halogen, —CN, —NO$_2$, —N$_3$, —SO$_2$H, —SO$_3$H, —OH, —OR$^{41}$, —ON(R$^{42}$)$_2$, —N(R$^{42}$)$_2$, —N(OR$^{43}$)R$^{43}$, —SH, —SR$^{41}$, —SSR$^{43}$, —C(=O)R$^{41}$, —CO$_2$H, —CHO, —C(OR$^{43}$)$_2$, —CO$_2$R$^{41}$, —OC(=O)R$^{41}$, —OCO$_2$R$^{41}$, —C(=O)N(R$^{42}$)$_2$, —OC(=O)N(R$^{42}$)$_2$, —NR$^{42}$C(=O)R$^{41}$, —NR$^{42}$CO$_2$R$^{41}$, —NR$^{42}$C(=O)N(R$^{42}$)$_2$, —C(=NR$^{42}$)OR$^{41}$, —OC(=NR$^{42}$)R$^{41}$, —OC(=NR$^{42}$)OR$^{41}$, —C(=NR$^{42}$)N(R$^{42}$)$_2$, —OC(=NR$^{42}$)N(R$^{42}$)$_2$, —NR$^{42}$C(=NR$^{42}$)N(R$^{42}$)$_2$, —C(=O)NR$^{42}$SO$_2$R$^{41}$, —NR$^{42}$SO$_2$R$^{41}$, —SO$_2$N(R$^{42}$)$_2$, —SO$_2$R$^{41}$, —SO$_2$OR$^{41}$, —OSO$_2$R$^{41}$, —S(=O)R$^{41}$, —OS(=O)R$^{41}$, —Si(R$^{41}$)$_3$, —OSi(R$^{41}$)$_3$—C(=S)N(R$^{42}$)$_2$, —C(=O)SR$^{41}$, —C(=S)SR$^{41}$, —SC(=S)SR$^{41}$, —P(=O)$_2$R$^{41}$, —OP(=O)$_2$R$^{41}$, —P(=O)(R$^{41}$)$_2$, —OP(=O)(R$^{41}$)$_2$, —OP(=O)(OR$^{43}$)$_2$, —P(=O)$_2$N(R$^{42}$)$_2$, —OP(=O)$_2$N(R$^{42}$)$_2$, —P(=O)(NR$^{42}$)$_2$, —OP(=O)(NR$^{42}$)$_2$, —NR$^{42}$P(=O)(OR$^{43}$)$_2$, —NR$^{42}$P(=O)(NR$^{42}$)$_2$, —P(R$^{43}$)$_2$, —P(R$^{43}$)$_3$, —OP(R$^{43}$)$_2$, —OP(R$^{43}$)$_3$, —B(OR$^{43}$)$_2$, or —BR$^{41}$(OR$^{43}$), $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; or one or more of $R^1$ and $R^2$, $R^2$ and $R^3$, $R^3$ and $R^4$ or $R^4$ and $R^5$ are joined to form a $C_{3-10}$ carbocyclyl, 3-14 membered heterocyclyl, $C_{6-14}$ aryl or 5-14 membered heteroaryl ring;

each instance of $R^{41}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{42}$ is, independently, selected from hydrogen, —OH, —OR$^{41}$, —N(R$^{43}$)$_2$, —CN, —C(=O)R$^{41}$, —C(=O)N(R$^{43}$)$_2$, —CO$_2$R$^{41}$, —SO$_2$R$^{41}$, —C(=NR$^{43}$)OR$^{41}$, —C(=NR$^{43}$)N(R$^{43}$)$_2$, —SO$_2$N(R$^{43}$)$_2$, —SO$_2$R$^{43}$, —SO$_2$OR$^{43}$, —SOR$^{41}$, —C(=S)N(R$^{43}$)$_2$, —C(=O)SR$^{43}$, —C(=S)SR$^{43}$, —P(=O)$_2$R$^{41}$, —P(=O)(R$^{41}$)$_2$, —P(=O)$_2$N(R$^{43}$)$_2$, —P(=O)(NR$^{43}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{42}$ groups are joined to form a 3-14 membered heterocyclyl or 5-14 membered heteroaryl ring; and each instance of $R^{43}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{43}$ groups are joined to form a 3-14 membered heterocyclyl or 5-14 membered heteroaryl ring.

In certain embodiments, the group of formula (i) represents a $C_{6-14}$ aryl group or a 6-14 membered heteroaryl group. In certain embodiments, the group of formula (i) represents a 6-14 membered heteroaryl group. In certain embodiments, the group of formula (i) represents a $C_{6-14}$ aryl group. In certain embodiments, the $C_{6-14}$ aryl group of formula (i) represents a phenyl group.

As used herein, when one or more of $R^1$, $R^2$, $R^3$, $R^4$ and $R^5$ is referred to as "not hydrogen", it is meant that one or more of $R^1$, $R^2$, $R^3$, $R^4$ and $R^5$ is independently selected from a group consisting of halogen, —CN, —NO$_2$, —N$_3$, —SO$_2$H, —SO$_3$H, —OH, —OR$^{41}$, —ON(R$^{42}$)$_2$, —N(R$^{42}$)$_2$, —N(OR$^{43}$)R$^{43}$, —SH, —SR$^{41}$, —SSR$^{43}$, —C(=O)R$^{41}$, —CO$_2$H, —CHO, —C(OR$^{43}$)$_2$, —CO$_2$R$^{41}$, —OC(=O)R$^{41}$, —OCO$_2$R$^{41}$, —C(=O)N(R$^{42}$)$_2$, —OC(=O)N(R$^{42}$)$_2$, —NR$^{42}$C(=O)R$^{41}$, —NR$^{42}$CO$_2$R$^{41}$, —NR$^{42}$C(=O)N(R$^{42}$)$_2$, —C(=NR$^{42}$)OR$^{41}$, —OC(=NR$^{42}$)R$^{41}$, —OC(=NR$^{42}$)OR$^{41}$, —C(=NR$^{42}$)N(R$^{42}$)$_2$, —OC(=NR$^{42}$)N(R$^{42}$)$_2$, —NR$^{42}$C(=NR$^{42}$)N(R$^{42}$)$_2$, —C(=O)NR$^{42}$SO$_2$R$^{41}$, —NR$^{42}$SO$_2$R$^{41}$, —SO$_2$N(R$^{42}$)$_2$, —SO$_2$R$^{41}$, —SO$_2$OR$^{41}$, —OSO$_2$R$^{41}$, —S(=O)R$^{41}$, —OS(=O)R$^{41}$, —Si(R$^{41}$)$_3$, —OSi(R$^{41}$)$_3$—C(=S)N(R$^{42}$)$_2$, —C(=O)SR$^{41}$, —C(=S)SR$^{41}$, —SC(S)SR$^{41}$, —P(=O)$_2$R$^{41}$, —OP(=O)$_2$R$^{41}$, —P(=O)(R$^{41}$)$_2$, —OP(=O)(R$^{41}$)$_2$, —OP(=O)(OR$^{43}$)$_2$, —P(=O)$_2$N(R$^{42}$)$_2$, —OP(=O)$_2$N(R$^{42}$)$_2$, —P(=O)(NR$^{42}$)$_2$, —OP(=O)(NR$^{42}$)$_2$, —NR$^{42}$P(=O)(OR$^{43}$)$_2$, —NR$^{42}$P(=O)(NR$^{42}$)$_2$, —P(R$^{43}$)$_2$, —P(R$^{43}$)$_3$, —OP(R$^{43}$)$_2$, —OP(R$^{43}$)$_3$, —B(OR$^{43}$)$_2$, or —BR$^{41}$(OR$^{43}$), $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; or one or more of $R^1$ and $R^2$, $R^2$ and $R^3$, $R^3$ and $R^4$ or $R^4$ and $R^5$ are joined to form a $C_{3-10}$ carbocyclyl, 3-14 membered heterocyclyl, $C_{6-14}$ aryl or 5-14 membered heteroaryl ring.

In certain embodiments, $R^1$, $R^2$, $R^3$, $R^4$ and $R^5$ are independently selected from the group consisting of hydrogen, halogen, —CN, —NO$_2$, —SO$_2$H, —SO$_3$H, —OH, —OR$^{41}$, —N(R$^{42}$)$_2$, —C(=O)R$^{41}$, —CO$_2$H, —CHO, —C(OR$^{43}$)$_2$, —CO$_2$R$^{41}$, —OC(=O)R$^{41}$, —OCO$_2$R$^{41}$, —C(=O)N(R$^{42}$)$_2$, —OC(=O)N(R$^{42}$)$_2$, —NR$^{42}$C(=O)R$^{41}$, —NR$^{42}$CO$_2$R$^{41}$, —NR$^{42}$C(=O)N(R$^{42}$)$_2$, —C(=NR$^{42}$)

$OR^{A1}$, $-OC(=NR^{A2})R^{A1}$, $-OC(=NR^{A2})OR^{A1}$, $-C(=NR^{A2})N(R^{A2})_2$, $-OC(=NR^{A2})N(R^{A2})_2$, $-NR^{A2}C(=NR^{A2})N(R^{A2})_2$, $-C(=O)NR^{A2}SO_2R^{A1}$, $-NR^{A2}SO_2R^{A1}$, $-SO_2N(R^{A2})_2$, $-SO_2R^{A1}$, $-SO_2OR^{A1}$, $-OSO_2R^{A1}$, $-S(=O)R^{A1}$, $-OS(=O)R^{A1}$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; or one or more of $R^1$ and $R^2$, $R^2$ and $R^3$, $R^3$ and $R^4$ or $R^4$ and $R^5$ are joined to form a $C_{3-10}$ carbocyclyl, 3-14 membered heterocyclyl, $C_{6-14}$ aryl or 5-14 membered heteroaryl ring.

In certain embodiments, $R^1$, $R^2$, $R^3$, $R^4$ and $R^5$ are independently selected from the group consisting of hydrogen, halogen, $-CN$, $-OR^{A1}$, $-N(R^{A2})_2$, $-CO_2H$, $-CO_2R^{A1}$, $-C(=O)N(R^{A2})_2$, $-SO_2R^{A1}$, $C_{1-10}$ alkyl, $C_{2-10}$ alkynyl, 3-14 membered heterocyclyl, and $C_{6-14}$ aryl; or one or more of $R^1$ and $R^2$, $R^2$ and $R^3$, $R^3$ and $R^4$ or $R^4$ and $R^5$ are joined to form a 5-14 membered heteroaryl ring.

In certain embodiments, $R^1$, $R^2$, $R^3$, $R^4$ and $R^5$ are independently selected from the group consisting of hydrogen, halogen, $-OR^{A1}$, $-N(R^{A2})_2$, $-CO_2H$, $-C(=O)N(R^{A2})_2$, $-SO_2R^{A1}$, and 3-14 membered heterocyclyl; or $R^4$ and $R^5$ are joined to form a 5-14 membered heteroaryl ring.

In certain embodiments, $R^1$, $R^2$, $R^3$, $R^4$ and $R^5$ are independently selected from the group consisting of hydrogen, halogen, $-OR^{A1}$, and $-C(=O)N(R^{A2})_2$; or $R^4$ and $R^5$ are joined to form a 5-14 membered heteroaryl ring.

In certain embodiments, $R^1$, $R^2$, $R^3$, $R^4$ and $R^5$ are independently selected from the group consisting of hydrogen, halogen, $-OR^{A1}$, and $-C(=O)N(R^{A2})_2$; or $R^4$ and $R^5$ are joined to form a 5-14 membered heteroaryl ring.

In certain embodiments, $R^1$, $R^2$, $R^3$, $R^4$ and $R^5$ are independently selected from the group consisting of hydrogen, halogen, and $-OR^{A1}$. In certain embodiments, $R^1$, $R^2$, $R^3$, $R^4$ and $R^5$ re independently selected from the group consisting of hydrogen, fluoro, chloro, and $-OR^{A1}$. In certain embodiments, $R^1$, $R^2$, $R^3$, $R^4$ and $R^5$ are independently selected from the group consisting of hydrogen, fluoro, chloro, and $-OMe$. In certain embodiments. $R^1$, $R^2$, $R^3$, $R^4$ and $R^5$ are independently selected from the group consisting of hydrogen, fluoro and $-OR^{A1}$. In certain embodiments, $R^1$, $R^2$, $R^3$, $R^4$ and $R^5$ are independently selected from the group consisting of hydrogen, fluoro and $-OMe$. In certain embodiments, $R^1$, $R^2$, $R^3$, $R^4$ and $R^5$ are independently selected from the group consisting of hydrogen and fluoro. In certain embodiments, $R^1$, $R^2$, $R^3$, $R^4$ and $R^5$ are independently selected from the group consisting of hydrogen and chloro.

In certain embodiments, $R^4$ and $R^5$ are joined to form a 5-14 membered heteroaryl ring.

In certain embodiments, $R^4$ is a group of the formula (ii):

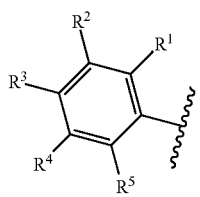
(ii)

wherein $R^1$, $R^2$, $R^3$, $R^4$ and $R^5$ are as defined above and herein.

In certain embodiments, the group of formula (ii) represents a $C_{6-14}$ aryl group. In certain embodiments, the $C_{6-14}$ aryl group of formula (ii) represents a phenyl group.

In certain embodiments, $R^A$ is a monosubstituted, disubstituted or trisubstituted group of the formula (ii). In certain embodiments, $R^A$ is a monosubstituted or disubstituted group of the formula (ii).

In certain embodiments, $R^A$ is a monosubstituted group of the formula (ii).

For example, in certain embodiments, $R^A$ is an ortho-substituted group of the formula (ii), e.g., wherein $R^1$-$R^4$ are hydrogen, and $R^5$ is not hydrogen, e.g., of the formula (ii-a).

In certain embodiments, $R^A$ is a meta-substituted group of the formula (ii), e.g., wherein $R^1$-$R^3$ and $R^5$ are hydrogen and $R^4$ is not hydrogen, e.g., of the formula (ii-b).

In certain embodiments, $R^A$ is a para-substituted group of the formula (ii), e.g., wherein $R^1$, $R^2$, $R^4$ and $R^5$ are hydrogen and $R^3$ is not hydrogen, e.g., of the formula (ii-c).

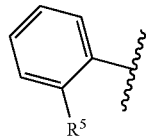
(ii-a)

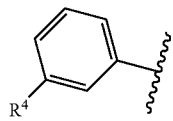
(ii-b)

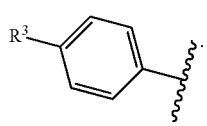
(ii-c)

In certain embodiments, $R^A$ is a disubstituted group of the formula (ii).

For example, in certain embodiments, $R^A$ is a 2,6-disubstituted group of the formula (ii), e.g., wherein $R^2$, $R^3$ and $R^4$ are hydrogen, and $R^1$ and $R^5$ are not hydrogen, e.g. of the formula (ii-d).

In certain embodiments, $R^A$ is a 2,5-disubstituted group of the formula (ii), e.g., wherein $R^2$, $R^3$ and $R^5$ are hydrogen, and $R^1$ and $R^4$ are not hydrogen, e.g., of the formula (ii-e).

In certain embodiments, $R^A$ is a 2,4-disubstituted group of the formula (ii), e.g., wherein $R^2$, $R^5$ and $R^5$ are hydrogen, and $R^1$ and $R^3$ are not hydrogen, e.g., of the formula (ii-f).

In certain embodiments, $R^A$ is a 2,3-disubstituted group of the formula (ii), e.g., wherein $R^1$, $R^2$ and $R^3$ are hydrogen, and $R^4$ and $R^5$ are not hydrogen, e.g., of the formula (ii-g).

In certain embodiments, $R^A$ is a 3,4-disubstituted group of the formula (ii), e.g., wherein $R^1$, $R^4$ and $R^5$ are hydrogen, and $R^2$ and $R^3$ are not hydrogen, e.g., of the formula (ii-h).

In certain embodiments, $R^A$ is a 3,5-disubstituted group of the formula (ii), e.g., wherein $R^1$, $R^3$ and $R^5$ are hydrogen, and $R^2$ and $R^4$ are not hydrogen, e.g., of the formula (ii-i).

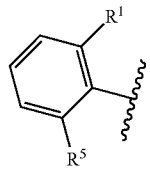
(ii-d)

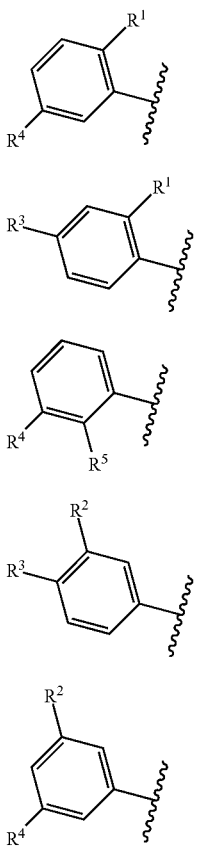

For example, in certain embodiments, $R^4$ is a 2,6-disubstituted group as described herein, e.g., of the formula (ii-d):

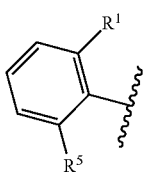

wherein $R^1$ and $R^5$ are as defined above and herein.

In certain embodiments, one of $R^1$ and $R^5$ is halogen, —CN, —$OR^{41}$, —$N(R^{A2})_2$, —$CO_2H$, —$CO_2R^{41}$, —C(=O)N($R^{A2})_2$, —$SO_2R^{41}$, $C_{1-10}$ alkyl, $C_{2-10}$ alkynyl, 3-14 membered heterocyclyl, and $C_{6-14}$ aryl, and the other of $R^1$ and $R^5$ is halogen, —CN, —$OR^{41}$, —$N(R^{A2})_2$, $CO_2H$, —$CO_2R^{41}$, —C(=O)N($R^{A2})_2$, —$SO_2R^{41}$, $C_{1-10}$ alkyl, $C_{2-10}$ alkynyl, 3-14 membered heterocyclyl, and $C_{6-14}$ aryl.

In certain embodiments, one of $R^1$ and $R^5$ is halogen, —$OR^{41}$, $C_{1-10}$ alkyl, or —C(=O)N($R^{A2})_2$, and the other of $R^1$ and $R^5$ is halogen, —$OR^{41}$, $C_{1-10}$ alkyl, or —C(=O)N($R^{A2})_2$.

In certain embodiments, each of $R^1$ and $R^5$ is independently halogen. For example, each of $R^1$ and $R^5$ is independently selected from fluoro and chloro.

In certain embodiments, $R^4$ is a trisubstituted group of the formula (ii).

For example, in certain embodiments, $R^4$ is a 2,4,6-trisubstituted group of the formula (ii), e.g., wherein $R^2$ and $R^4$ are hydrogen, and $R^1$, $R^3$ and $R^5$ are not hydrogen, e.g., of the formula (ii-j).

In certain embodiments, $R^4$ is a 2,3,6-trisubstituted group of the formula (ii), e.g., wherein $R^2$ and $R^3$ are hydrogen, and $R^1$, $R^4$ and $R^5$ are not hydrogen, e.g., of the formula (ii-k).

In certain embodiments, $R^4$ is a 2,4,5-trisubstituted group of the formula (ii), e.g., wherein $R^2$ and $R^5$ are hydrogen, and $R^1$, $R^3$ and $R^4$ are not hydrogen, e.g., of the formula (ii-l).

In certain embodiments, $R^4$ is a 2,3,4-trisubstituted group of the formula (ii), e.g., wherein $R^4$ and $R^5$ are hydrogen, and $R^1$, $R^2$ and $R^3$ are not hydrogen, e.g., of the formula (ii-m).

In certain embodiments, $R^4$ is a 3,4,5-trisubstituted group of the formula (ii), e.g., wherein $R^1$ and $R^5$ are hydrogen, and $R^2$, $R^3$ and $R^4$ are not hydrogen, e.g., of the formula (ii-n).

In certain embodiments, $R^4$ is heteroaryl selected from a 5-6-membered heteroaryl, a 5,6-bicyclic heteroaryl or a 6,6-bicyclic heteroaryl.

In certain embodiments, $R^4$ is a 6-membered heteroaryl. In certain embodiments, $R^4$ is a 6-membered heteroaryl selected from pyridinyl. In certain embodiments, $R^4$ is 2-pyridinyl, 3-pyridinyl or 4-pyridinyl.

In certain embodiments, $R^4$ is a 2-pyridinyl wherein W—$R^1$ is N, and W—$R^2$, W—$R^3$, W—$R^4$, and W—$R^5$ are C—$R^2$, C—$R^3$, C—$R^4$ and C—$R^5$, respectively, e.g., of the formula (iii).

In certain embodiments, $R^4$ is a 3-pyridinyl wherein W—$R^2$ is N, and W—$R^1$, W—$R^3$, W—$R^4$, and W—$R^5$ are C—$R^1$, C—$R^3$, C—$R^4$ and C—$R^5$, respectively, e.g., of the formula (iv).

In certain embodiments, $R^4$ is a 4-pyridinyl wherein W—$R^3$ is N, and W—$R^1$, W—$R^2$, W—$R^4$, and W—$R^5$ are C—$R^1$, C—$R^2$, C—$R^4$ and C—$R^5$, respectively, e.g., of the formula (v).

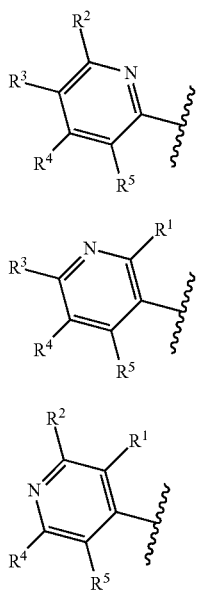

wherein $R^1$, $R^2$, $R^3$, $R^4$ and $R^5$ are as defined above and herein.

In certain embodiments, $R^4$ is a monosubstituted or disubstituted pyridinyl.

In certain embodiments, $R^4$ is a monosubstituted pyridinyl.

In certain embodiments, $R^4$ is a monosubstituted pyridinyl of the formula (iii) wherein $R^3$, $R^4$, $R^5$ are hydrogen and $R^2$ is not hydrogen, e.g. of the formula (iii-a).

in certain embodiments, $R^4$ is a monosubstituted pyridinyl of the formula (iii) wherein $R^2$, $R^4$, $R^5$ are hydrogen and $R^3$ is not hydrogen, e.g., of the formula (iii-b).

In certain embodiments, $R^4$ is a monosubstituted pyridinyl of the formula (iii) wherein $R^2$, $R^3$, $R^5$ are hydrogen and $R^4$ is not hydrogen, e.g., of the formula (iii-c).

In certain embodiments, $R^4$ is a monosubstituted pyridinyl of the formula (iii) wherein $R^2$, $R^3$, $R^4$ are hydrogen and $R^5$ is not hydrogen, e.g., of the formula (iii-d).

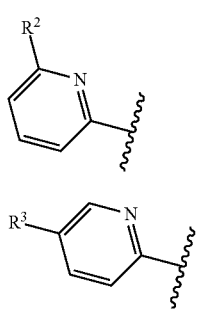

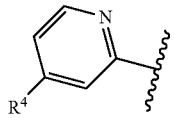

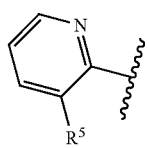

In certain embodiments, $R^4$ is a monosubstituted pyridinyl of the formula (iv) wherein $R^3$, $R^4$. $R^5$ are hydrogen and $R^1$ is not hydrogen, e.g., of the formula (iv-a).

In certain embodiments, $R^4$ is a monosubstituted pyridinyl of the formula (iv) wherein $R^1$, $R^4$, $R^5$ are hydrogen and $R^3$ is not hydrogen, e.g., of the formula (iv-b).

In certain embodiments, $R^4$ is a monosubstituted pyridinyl of the formula (iv) wherein $R^1$, $R^3$, $R^5$ are hydrogen and $R^4$ is not hydrogen, e.g., of the formula (iv-c).

In certain embodiments, $R^4$ is a monosubstituted pyridinyl of the formula (iv) wherein $R^1$, $R^3$, $R^4$ are hydrogen and $R^5$ is not hydrogen. e.g., of the formula (iv-d).

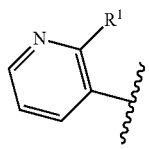

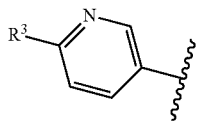

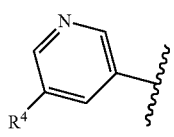

In certain embodiments, $R^4$ is a monosubstituted pyridinyl of the formula (v) wherein $R^2$, $R^4$, $R^5$ are hydrogen and $R^1$ is not hydrogen, e.g., of the formula (v-a).

In certain embodiments, $R^4$ is a monosubstituted pyridinyl of the formula (v) wherein $R^1$, $R^4$, $R^5$ are hydrogen and $R^2$ is not hydrogen, e.g., of the formula (v-b).

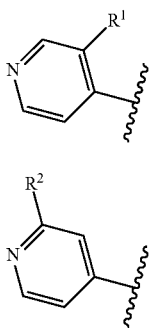

(v-a)

(v-b)

In certain embodiments, $R^A$ is a disubstituted pyridinyl.

In certain embodiments, $R^A$ is a disubstituted pyridinyl of the formula (iii) wherein $R^3$ and $R^4$ are hydrogen and $R^2$ and $R^5$ are not hydrogen, e.g., of the formula (iii-e).

In certain embodiments, $R^A$ is a disubstituted pyridinyl of the formula (iii) wherein $R^2$ and $R^4$ are hydrogen and $R^3$ and $R^5$ are not hydrogen, e.g., of the formula (iii-f).

In certain embodiments, $R^A$ is a disubstituted pyridinyl of the formula (iii) wherein $R^2$ and $R^3$ are hydrogen and $R^4$ and $R^5$ are not hydrogen, e.g., of the formula (iii-g).

In certain embodiments, $R^A$ is a disubstituted pyridinyl of the formula (iii) wherein $R^3$ and $R^5$ are hydrogen and $R^2$ and $R^4$ are not hydrogen, e.g., of the formula (iii-h).

In certain embodiments, $R^A$ is a disubstituted pyridinyl of the formula (iii) wherein $R^4$ and $R^5$ are hydrogen and $R^2$ and $R^3$ are not hydrogen, e.g., of the formula (iii-i).

In certain embodiments, $R^A$ is a disubstituted pyridinyl of the formula (iii) wherein $R^2$ and $R^5$ are hydrogen and $R^3$ and $R^4$ are not hydrogen, e.g., of the formula (iii-j).

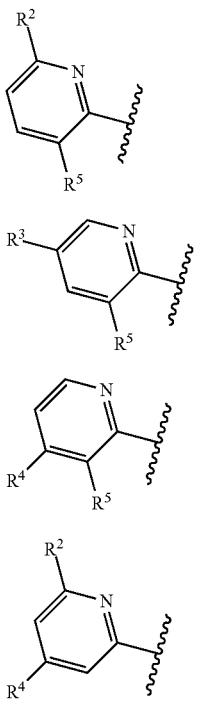

(iii-e)

(iii-f)

(iii-g)

(iii-h)

(iii-i)

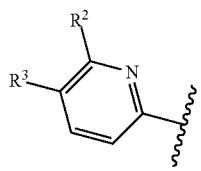

(iii-j)

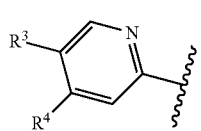

In certain embodiments, $R^A$ is a disubstituted pyridinyl of the formula (iv) wherein $R^3$ and $R^4$ are hydrogen and $R^1$ and $R^5$ are not hydrogen, e.g., of the formula (iv-e).

In certain embodiments, $R^A$ is a disubstituted pyridinyl of the formula (iv) wherein $R^3$ and $R^5$ are hydrogen and $R^1$ and $R^4$ are not hydrogen, e.g., of the formula (iv-f).

In certain embodiments, $R^A$ is a disubstituted pyridinyl of the formula (iv) wherein $R^4$ and $R^5$ are hydrogen and $R^1$ and $R^3$ are not hydrogen, e.g., of the formula (iv-g).

In certain embodiments, $R^A$ is a disubstituted pyridinyl of the formula (iv) wherein $R^1$ and $R^4$ are hydrogen and $R^3$ and $R^5$ are not hydrogen, e.g., of the formula (iv-h).

In certain embodiments, $R^A$ is a disubstituted pyridinyl of the formula (iv) wherein $R^1$ and $R^5$ are hydrogen and $R^3$ and $R^4$ are not hydrogen, e.g., of the formula (iv-i).

In certain embodiments, $R^A$ is a disubstituted pyridinyl of the formula (iv) wherein $R^1$ and $R^3$ are hydrogen and $R^4$ and $R^5$ are not hydrogen, e.g., of the formula (iv-j).

(iv-e)

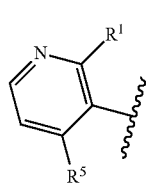

(iv-f)

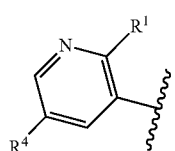

(iv-g)

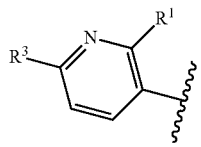

(iv-h)

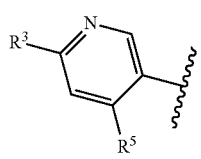

(iv-i)

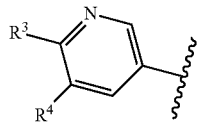

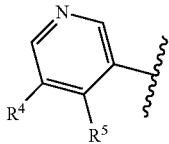
(iv-j)

In certain embodiments, $R^4$ is a disubstituted pyridinyl of the formula (v) wherein $R^2$ and $R^4$ are hydrogen and $R^1$ and $R^5$ are not hydrogen, e.g., of the formula (v-c).

In certain embodiments, $R^4$ is a disubstituted pyridinyl of the formula (v) wherein $R^4$ and $R^5$ are hydrogen and $R^1$ and $R^2$ are not hydrogen, e.g., of the formula (v-d).

In certain embodiments, $R^4$ is a disubstituted pyridinyl of the formula (v) wherein $R^2$ and $R^5$ are hydrogen and $R^1$ and $R^4$ are not hydrogen, e.g., of the formula (v-e).

In certain embodiments, $R^4$ is a disubstituted pyridinyl of the formula (v) wherein $R^2$ and $R^5$ are hydrogen and $R^2$ and $R^4$ are not hydrogen, e.g. of the formula (v-f).

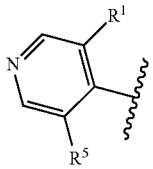
(v-c)

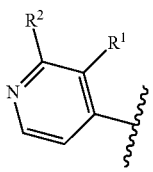
(v-d)

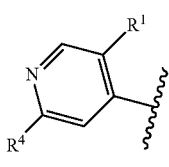
(v-e)

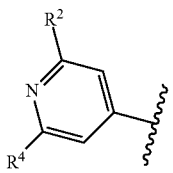
(v-f)

In certain embodiments, $R^4$ is a 5,6-bicyclic heteroaryl.

For example, in certain embodiments, $R^4$ is a 5,6-bicyclic heteroaryl group of the formula (vi) (which is a subset of a group of the formula (ii-g)):

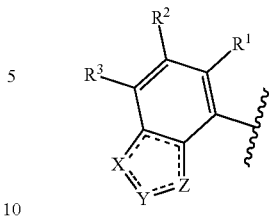
(vi)

wherein $R^1$, $R^2$, $R^3$ are as defined above and herein and $R^4$ and $R^5$ are joined to form a 5-membered heteroaryl ring;

X, Y and Z are independently selected from $CR^{44}$, O, S, N, or $NR^{45}$;

each instance of $R^{44}$ is, independently, selected from hydrogen, halogen, —CN, —$NO_2$, —$N_3$, —$SO_2H$, —$SO_3H$, —OH, —$OR^{46}$, —$ON(R^{47})_2$, —$N(R^{47})_2$, —$N(OR^{46})R^{48}$, —SH, —$SR^{46}$, —$SSR^{48}$, —C(=O)$R^{46}$, —$CO_2H$, —CHO, —C($OR^{48})_2$, —$CO_2R^{46}$, —OC(=O)$R^{46}$, —$OCO_2R^{46}$, —C(=O)N($R^{47})_2$, —OC(=O)N($R^{47})_2$, —$NR^{47}$C(=O)$R^{46}$, —$NR^{47}CO_2R^{46}$, —$NR^{47}$C(=O)N($R^{47})_2$, —C(=$NR^{47}$)$OR^6$, —OC(=$NR^{47}$)$R^{46}$, —OC(=$NR^{47}$)$OR^{46}$, —C(=$NR^{47}$)N($R^{47})_2$, —OC(=$NR^{47}$)N($R^{47})_2$, —$NR^{47}$C(=$NR^{47}$)N($R^{47})_2$, —C(=O)$NR^{47}SO_2R^{46}$, —$NR^{47}SO_2R^{46}$, —$SO_2N(R^{47})_2$, —$SO_2R^{46}$, —$SO_2OR^{46}$, —$OSO_2R^{46}$, —S(=O)$R^{46}$, —OS(=O)$R^{46}$, —Si($R^{46})_3$, —OSi($R^{46})_3$, —C(=S)N($R^{47})_2$, —C(=O)$SR^{46}$, —C(=S)$SR^{46}$, —SC(=S)$SR^{46}$, —P(=O)$_2R^{46}$, —OP(=O)$_2R^{46}$, —P(=O)($R^{46})_2$, —OP(=O)($R^{46})_2$, —OP(=O)($OR^{48})_2$, —P(=O)$_2N(R^{47})_2$, —OP(=O)$_2N(R^{47})_2$, —P(=O)(N$R^{47})_2$, —OP(=O)(N$R^{47})_2$, —$NR^{47}$P(=O)($OR^{48})_2$, —$NR^{47}$P(=O)(N$R^{47})_2$, —P($R^{48})_2$, —P($R^{48})_3$, —OP($R^{48})_2$, —OP($R^{48})_3$, —B($OR^{48})_2$, or —$BR^{46}(OR^{48})$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{46}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{45}$ and $R^{47}$ is, independently, selected from hydrogen, —OH, —$OR^{46}$, —N($R^{47})_2$, —CN, —C(=O)$R^{46}$, —C(=O)N($R^{47})_2$, —$CO_2R^{46}$, —$SO_2R^{47}$, —C(=$NR^{43}$)$OR^{46}$, —C(=$NR^{47}$)N($R^{47})_2$, —$SO_2N(R^{43})_2$, —$SO_2R^{46}$—, $SO_2OR^{48}$, —$SOR^{46}$, —C(=S)N($R^{47})_2$, —C(=O)$SR^{48}$, —C(=S)$SR^{48}$, —P(=O)$_2R^{46}$, —P(=O)($R^{46})_2$, —P(=O)$_2N(R^{48})_2$, —P(=O)(N$R^{48})_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{47}$ groups are joined to form a 3-14 membered heterocyclyl or 5-14 membered heteroaryl ring;

each instance of $R^{48}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{48}$ groups are joined to form a 3-14 membered heterocyclyl or 5-14 membered heteroaryl ring; and the dashed line represents a double or single bond.

In certain embodiments, $R^1$ is hydrogen. In certain embodiments, $R^2$ is hydrogen. In certain embodiments, $R^3$ is hydrogen. In certain embodiments, $R^1$, $R^2$ and $R^3$ are hydrogen.

In certain embodiments, $R^4$ is a heteroaryl group of the formulae (vi-a) or (vi-b):

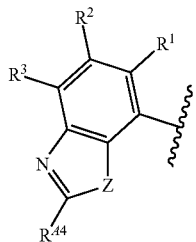

(vi-a)

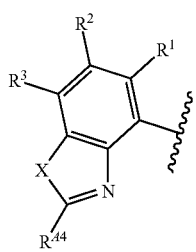

(vi-b)

wherein $R^1$, $R^2$, $R^3$ are as defined above and X and Z are independently selected from O, S and $NR^{45}$.

In certain embodiments, wherein $R^4$ is a heteroaryl group of the formulae (vi-a) or (vi-b), X and Z are O (i.e., benzoxazolyl). In certain embodiments, X and Z are S (i.e., benzthiazolyl). In certain embodiments, X and Z are $NR^{45}$ (i.e., imidazolyl).

In certain embodiments, $R^4$ is a heteroaryl group of the formulae (vi-c) or (vi-d):

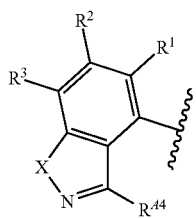

(vi-c)

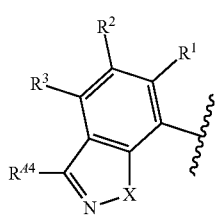

(vi-d)

wherein $R^1$, $R^2$, $R^3$ are as defined above and X is independently selected from O, S and $NR^{45}$.

In certain embodiments, wherein $R^4$ is a heteroaryl group of the formulae (vi-c) or (vi-d), X is O (i.e., benzisoxazolyl). In certain embodiments, X is S (i.e., benzisothiazolyl). In certain embodiments, X is $NR^{45}$ (i.e., indazolyl).

In certain embodiments, $R^4$ is a heteroaryl group of the formulae (vi-e), (vi-f) or (vi-g):

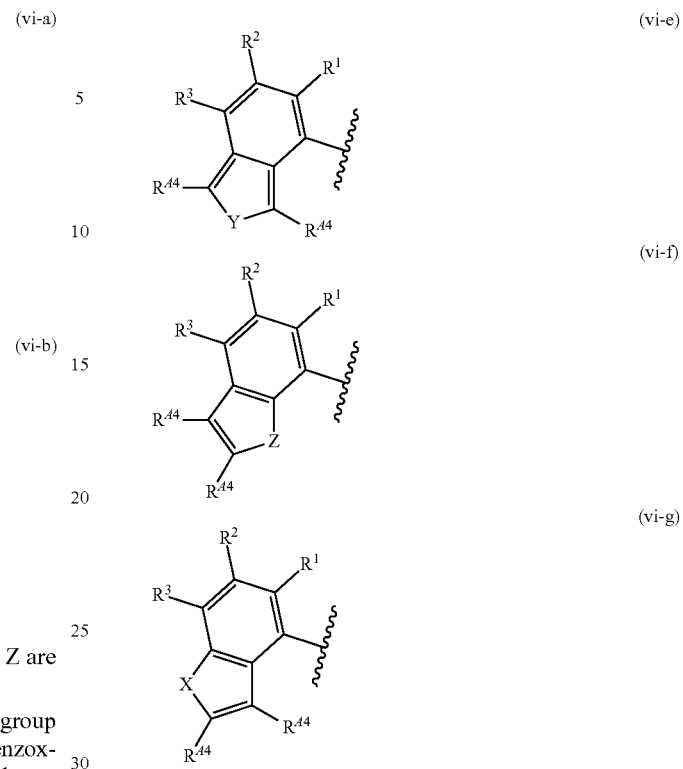

wherein $R^1$, $R^2$, $R^3$ and $R^{44}$ are as defined above and X, Y and Z are independently selected from O, S and $NR^{45}$.

In certain embodiments, wherein $R^4$ is a heteroaryl group of the formulae (vi-e), (vi-f) or (vi-g), Y is O (i.e., benzofuranyl or isobenzofuranyl). In certain embodiments, Y is S (i.e., benzothiophenyl or isobenzothiophenyl). In certain embodiments, Y is $NR^{45}$ (i.e., indolyl or isoindolyl).

In certain embodiments, $R^4$ is a heteroaryl group of the formula (vi-h):

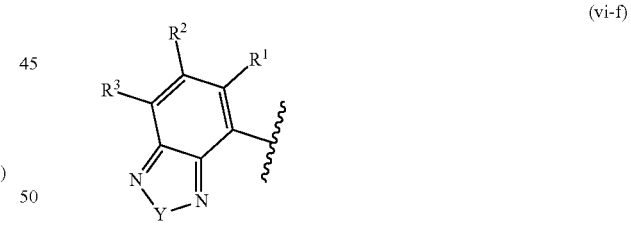

(vi-f)

wherein $R^1$, $R^2$, $R^3$ are as defined above and Y is independently selected from O, S and $NR^{45}$.

In certain embodiments, wherein $R^4$ is a heteroaryl group of the formula (vi-e), Y is O (i.e., benzoxadiazolyl). In certain embodiments, Y is S (i.e., benzthiadiazolyl). In certain embodiments, Y is $NR^{45}$ (i.e., benztriazolyl).

Group $R^B$

As described generally above, $R^B$ is selected from $C_{1-10}$ alkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl and 5-14 membered heteroaryl; or $R^B$ and $R^C$ together with the nitrogen (N) atom to which each is attached are joined to form a 5-14 membered ring.

In certain embodiments, $R^B$ is selected from $C_{1-10}$ alkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl and 5-14 membered heteroaryl.

In certain embodiments, $R_B$ is an acyclic group, i.e., selected from $C_{1-10}$ alkyl, $C_{2-10}$ alkenyl, $C_{2-10}$ alkynyl and 3-14 membered heteroaliphatic. In certain embodiments, $R^B$ is $C_{1-10}$ alkyl. In certain embodiments, $R^B$ is a substituted $C_{1-10}$ alkyl, e.g., a $C_{1-10}$ aralkyl group. In certain embodiments, $R^B$ is a $C_{1-2}$ aralkyl, e.g. for example, a substituted or unsubstituted benzyl group ($C_1$ aralkyl) or substituted or unsubstituted phenylethyl group ($C_2$ aralkyl). In certain embodiments, $R^B$ is a $C_{1-10}$ heteroaralkyl. In certain embodiments, $R^B$ is alkenyl. In certain embodiments, $R^B$ is alkynyl. In certain embodiments, $R^B$ is 3-14 membered heteroaliphatic.

Alternatively, in certain embodiments, $R^B$ is a cyclic group, i.e., selected from $C_{3-10}$ carbocyclyl, 3-14 membered heterocyclyl, $C_{6-14}$ aryl and 5-14 membered heteroaryl.

In certain embodiments, $R^B$ is $C_{3-10}$ carbocyclyl or 3-14 membered heterocyclyl.

In certain embodiments, $R^B$ is $C_{3-10}$ carbocyclyl. Exemplary carbocyclyl groups include, but are not limited to, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptadienyl ($C_7$), cycloheptatrienyl ($C_7$) and cyclooctyl ($C_8$).

In certain embodiments, $R^B$ is 3-14 membered heterocyclyl. Exemplary heterocyclyl groups include, but are not limited to, azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, dioxolanyl, oxathiolanyl, dithiolanyl, piperidinyl, tetrahydropyranyl, dihydropyridinyl, thianyl, piperazinyl, morpholinyl, dithianyl, dioxanyl, azepanyl, oxepanyl thiepanyl, azocanyl, oxecanyl and thiocanyl.

In certain embodiments, $R^B$ is $C_{6-14}$ aryl or 5-14 membered heteroaryl.

In certain embodiments, $R^B$ is $C_{6-14}$ aryl. Exemplary aryl groups include, but are not limited to phenyl, naphthyl and anthracyl. In certain embodiments, $R^B$ is phenyl ($C_6$ aryl). In certain embodiments, $R^B$ is naphthyl ($C_{10}$ aryl).

In certain embodiments, $R^B$ is 5-14 membered heteroaryl. In certain embodiments, $R^B$ is 5-10 membered heteroaryl. In certain embodiments, $R^B$ is 5-6 membered heteroaryl. In certain embodiments, $R^B$ is a 5,6-bicyclic heteroaryl. In certain embodiments, $R^B$ is a 6,6-bicyclic heteroaryl.

In certain embodiments, $R^B$ is a 5-membered heteroaryl group. Exemplary 5-membered heteroaryl groups include, but are not limited to, pyrrolyl, furanyl, thiophenyl, imidazolyl, pyrazolyl, oxazolyl, isoxazolyl, thiazolyl, isothiazolyl, triazolyl, oxadiazolyl, thiadiazolyl and tetrazolyl.

In certain embodiments, $R^B$ is a 6-membered heteroaryl group. Exemplary 6-membered heteroaryl groups include, but are not limited to, pyridinyl, pyridazinyl, pyrimidinyl, pyrazinyl, triazinyl and tetrazinyl.

In certain embodiments, $R^B$ is a 5,6-bicyclic heteroaryl group. Exemplary 5,6-bicyclic heteroaryl groups include, but are not limited to, indolyl, isoindolyl, indazolyl, benztriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl.

In certain embodiments, $R^B$ is a 6,6-bicyclic heteroaryl group. Exemplary 6,6-bicyclic heteroaryl groups include, but are not limited to naphthyridinyl, pteridinyl, quinolinyl, isoquinolinyl, cinnolinyl, quinoxalinyl, phthalazinyl and quinazolinyl.

In certain embodiments, $R^B$ is substituted with the group:
-L-$R^D$ wherein:

L is a covalent bond or a divalent $C_{1-10}$ hydrocarbon chain, wherein one, two or three methylene units of L are optionally and independently replaced with one or more —O—, —S—, —$NR^{B8}$—, —(C=$NR^{B8}$)—, —C(=O)—, —C(=S)—, —S(=O)—, —S(=O)$_2$—, divalent $C_{3-10}$ carbocyclyl, divalent 3-14 membered heterocyclyl, divalent $C_{6-14}$ aryl or divalent 5-14 membered heteroaryl group; and $R^D$ is selected from —CN, —$NO_2$, —$N_3$, —$SO_2H$, —$SO_3H$, —C(=O)$R^{B7}$, —$CO_2H$, —CHO, —C(O$R^{B9}$)$_2$, —$CO_2R^{B7}$, —OC(=O)$R^{B7}$, —$OCO_2R^{B7}$, —C(=O)N($R^{B8}$)$_2$, —OC(=O)N($R^{B8}$)$_2$, —$NR^{B8}$C(=O)$R^{B7}$, —$NR^{B8}CO_2R^{B7}$, —$NR^{B8}$C(=O)N($R^{B8}$)$_2$, —C(=$NR^{B8}$)$OR^{B7}$, —OC(=$NR^{B8}$)$R^{B7}$, —OC(=$NR^{B8}$)$OR^{B7}$, —C(=$NR^{B8}$)N($R^{B8}$)$_2$, —OC(=$NR^{B8}$)N($R^{B8}$)$_2$, —$NR^{B8}$C(=$NR^{B8}$)N($R^{B8}$)$_2$, —C(=O)$NR^{B8}SO_2R^{B7}$, —$NR^{B8}SO_2R^{B7}$, —$SO_2$N($R^{B8}$)$_2$, —$SO_2R^{B7}$, —$SO_2OR^{B7}$, —$OSO_2R^{B7}$, —S(=O)$R^{B7}$, —OS(=O)$R^{B7}$, —C(=S)N($R^{B8}$)$_2$, —C(=O)$SR^{B7}$, —C(=S)$SR^{B7}$, —SC(=S)$SR^{B7}$, —P(=O)$_2R^{B7}$, —OP(=O)$_2R^{B7}$, —P(=O)($R^{B7}$)$_2$, —OP(=O)($R^{B7}$)$_2$, —OP(=O)(O$R^{B9}$)$_2$, —P(=O)$_2$N($R^{B8}$)$_2$, —OP(=O)$_2$N($R^{B8}$)$_2$, —P(=O)(N$R^{B8}$)$_2$, —OP(=O)(N$R^{B8}$)$_2$, —$NR^{B8}P$(=O)(O$R^{B9}$)$_2$, —$NR^{B8}$P(=O)(N$R^{B8}$)$_2$, —B(O$R^{B9}$)$_2$, —B$R^{B7}$(O$R^{B9}$), and tetrazolyl;

each instance of $R^{B7}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{B8}$ is, independently, selected from hydrogen, —OH, —O$R^{B7}$, —N($R^{B9}$)$_2$, —CN, —C(=O)$R^{B7}$, —C(=O)N($R^{B9}$)$_2$, —$CO_2R^{B7}$, —$SO_2R^{B7}$, —C(=$NR^{B9}$)$OR^{B7}$, —C(=$NR^{B9}$)N($R^{B9}$)$_2$, —$SO_2$N($R^{B9}$)$_2$, —$SO_2R^{B9}$, —$SO_2R^{B9}$, —SO$R^{B7}$, —C(=S)N($R^{B9}$)$_2$, —C(=O)$SR^{B9}$, —C(=S)$SR^{B9}$, —P(=O)$_2R^{B7}$, —P(=O)($R^{B7}$)$_2$, —P(=O)$_2$N($R^{B9}$)$_2$, —P(=O)(N$R^{B9}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$aryl, and 5-14 membered heteroaryl, or two $R^{B8}$ groups are joined to form a 3-14 membered heterocyclyl or a 5-14 membered heteroaryl ring; and each instance of $R^{B9}$ is, independently, selected from hydrogen, $C_{1-10}$alkyl, $C_{1-10}$ perhaloalkyl, $C_{2-10}$ alkenyl, $C_{2-10}$ alkynyl, 3-14 membered heteroaliphatic, $C_{3-10}$carbocyclyl, 3-14 membered heterocyclyl, $C_{6-14}$ aryl, and 5-14 membered heteroaryl, or two $R^{B9}$ groups are joined to form a 3-14 membered heterocyclyl or a 5-14 membered heteroaryl ring.

In certain embodiments, L is a covalent bond.

In certain embodiments, L is a divalent $C_{1-10}$ hydrocarbon chain, wherein one, two or three methylene units of L are optionally and independently replaced with one or more —O—, —S—, —$NR^{B8}$—, —(C=$NR^{B8}$)—, —C(=O)—, —C(=S)—, —S(=O)—, —S(=O)$_2$—, divalent carbocyclyl, divalent heterocyclyl, divalent aryl or divalent heteroaryl group.

In certain embodiments, L is a divalent $C_{1-10}$ hydrocarbon chain, wherein one, two or three methylene units of L are optionally and independently replaced with one or more —O—, —S—, —$NR^{B8}$—, —(C=$NR^{B8}$)—, —C(=O)—, —C(=S)—, —S(=O)—, —S(=O)$_2$—, divalent $C_{3-10}$ carbocyclyl, divalent 3-14 membered heterocyclyl, divalent $C_{6-14}$ aryl or divalent 5-14 membered heteroaryl group.

As generally described above, $R^D$ is selected from the group consisting of —CN, —$NO_2$, —$SO_2H$, —$SO_3H$, —C(=O)$R^{B7}$, —$CO_2H$, —CHO, —C(O$R^{B9}$)$_2$, —$CO_2R^{B7}$, —OC(=O)R$^{B7}$, —OCO$_2$R$^{B7}$, —C(=O)N(R$^{B8}$)$_2$, —OC(=O)N(R$^{B8}$)$_2$, —NR$^{B8}$C(=O)R$^{B7}$, —NR$^{B8}$CO$_2$R$^{B7}$, NR$^{B8}$C(=O)N(R$^{B9}$)$_2$, —C(=NR$^{B8}$)OR$^{B7}$, —OC(=NR$^{B8}$)R$^{B7}$, —OC(=NR$^{B8}$)OR$^{B7}$, —C(=NR$^{B8}$)N(R$^{B8}$)$_2$, —OC(=NR$^{B8}$)N(R$^{B8}$)$_2$, —NR$^{B8}$C(=NR$^{B8}$)N(R$^{B8}$)$_2$, —C(=O)NR$^{B8}$SO$_2$R$^{B7}$, —NR$^{B8}$SO$_2$R$^{B7}$, —SO$_2$N(R$^{B8}$)$_2$, —SO$_2$R$^{B7}$, —SO$_2$OR$^{B7}$, —OSO$_2$R$^{B7}$, —S(=O)R$^{B7}$, —OS(=O)R$^{B7}$, —C(=S)N(R$^{B7}$)$_2$, —C(=O)SR$^{B7}$, —C(=S)SR$^{B7}$, —SC(=S)SR$^{B7}$, —P(=O)$_2$R$^{B7}$, —OP(=O)$_2$R$^{B7}$, —P(=O)(R$^{B7}$)$_2$, —OP(=O)(R$^{B7}$)$_2$, —OP(=O)(OR$^{B9}$)$_2$, —P(=O)$_2$N(R$^{B8}$)$_2$, —OP(=O)$_2$N(R$^{B8}$)$_2$, —P(=O)(NR$^{B8}$)$_2$, —OP(=O)(NR$^{B8}$)$_2$, —NR$^{B8}$P(=O)(OR$^{B9}$)$_2$, —NR$^{B8}$P(=O)(NR$^{B8}$)$_2$, —B(OR$^{B9}$)$_2$, —BR$^{B7}$(OR$^{B9}$) and tetrazolyl.

However, in certain embodiments, R$^D$ is not —CO$_2$R$^7$(e.g., CO$_2$Me, CO$_2$Et, CO$_2$nPr, CO$_2$iPr, or CO$_2$tBu), but can be selected from any of the other substituents listed above. In certain embodiments, R$^D$ is not —C(=O)R$^{B7}$), but can be selected from any of the other substituents listed above. In certain embodiments, R$^D$ is not —CHO, but can be selected from any of the other substituents listed above. In certain embodiments, R$^D$ is not —C(OR$^{B9}$)$_2$), but can be selected from any of the other substituents listed above. In certain embodiments, R$^D$ is not —CN, but can be selected from any of the other substituents listed above. In certain embodiments, R$^D$ is not —NO$_2$), but can be selected from any of the other substituents listed above. In certain embodiments, R$^D$ is not any one of —SO$_2$H, —SO$_3$H, —SO$_2$N(R$^{B8}$)$_2$, —NR$^{B8}$SO$_2$R$^{B7}$, —SO$_2$R$^{B7}$, —SO$_2$OR$^{B7}$, —OSO$_2$R$^{B7}$, —S(=O)R$^{B7}$ or —OS(=O)R$^{B7}$), but can be selected from any of the other substituents listed above. In certain embodiments, R$^D$ is not any one of —OC(=O)R$^{B7}$, —OCO$_2$R$^{B7}$, —OC(=O)N(R$^{B8}$)$_2$, —NR$^{B8}$C(=O)R$^{B7}$, —NR$^{B8}$CO$_2$R$^{B7}$, —NR$^{B8}$C(=O)N(R$^{B8}$)$_2$, —OC(=NR$^{B8}$)R$^{B7}$, —OC(=NR$^{B8}$)OR$^{B7}$, —OC(=NR$^{B8}$)N(R$^{B8}$)$_2$ or —NR$^{B8}$C(=NR$^{B8}$)N(R$^{B8}$)$_2$), but can be selected from any of the other substituents listed above. In certain embodiments, R$^D$ is not any one of —C(=S)N(R$^{B8}$)$_2$, —C(=O)SR$^{B7}$, —C(=S)SR$^{B7}$ or —SC(=S)SR$^{B7}$), but can be selected from any of the other substituents listed above. In certain embodiments, R$^D$ is not any one of —P(=O)$_2$R$^{B7}$, —OP(=O)$_2$R$^{B7}$, —P(=O)(R$^{B7}$)$_2$, —OP(=O)(R$^{B7}$)$_2$, —OP(=O)(OR$^{B9}$)$_2$, —P(=O)$_2$N(R$^{B8}$)$_2$, —OP(=O)$_2$N(R$^{B8}$)$_2$, —P(=O)(NR$^{B8}$)$_2$, —OP(=O)(NR$^{B8}$)$_2$, —NR$^{B8}$P(=O)(OR$^{B9}$)$_2$ or —NR$^{B8}$P(=O)(NR$^{B8}$)$_2$), but can be selected from any of the other substituents listed above. In certain embodiments, R$^D$ is not any one of —B(OR$^{B9}$)$_2$ or —BR$^{B7}$(OR$^{B9}$)), but can be selected from any of the other substituents listed above. In certain embodiments, R$^D$ is not tetrazolyl), but can be selected from any of the other substituents listed above.

In certain embodiments, R$^D$ is selected from —CN, —NO$_2$, —SO$_2$H, —SO$_3$H, —C(=O)R$^{B7}$, —CO$_2$H, —CHO, —CO$_2$R$^{B7}$, —C(=O)N(R$^{B8}$)$_2$, —C(=NR$^{B8}$)OR$^{B7}$, —C(=NR$^{B8}$)N(R$^{B8}$)$_2$, —C(=O)NR$^{B8}$SO$_2$R$^{B7}$, —SO$_2$N(R$^{B8}$)$_2$, —SO$_2$R$^{B7}$, —SO$_2$OR$^{B7}$, —S(=O)R$^{B7}$, —C(=S)N(R$^{B8}$)$_2$, —C(=O)SR$^{B7}$, —C(=S)SR$^{B7}$, —P(=O)$_2$R$^{B7}$, —P(=O)(R$^{B7}$)$_2$, —P(=O)$_2$N(R$^{B8}$)$_2$, —P(=O)(NR$^{B8}$)$_2$, —B(OR$^{B9}$)$_2$, —BR$^{B7}$(OR$^{B9}$) and tetrazolyl. In certain embodiments, L is a covalent bond.

In certain embodiments, R$^D$ is selected from —C(=O)R$^{B7}$, —CO$_2$H, —CHO, —CO$_2$R$^{B7}$, —C(=O)N(R$^{B8}$)$_2$, —C(=NR$^{B8}$)OR$^{B7}$, —C(=NR$^{B8}$)N(R$^{B8}$)$_2$, —C(=O)NR$^{B8}$SO$_2$R$^{B7}$, —C(=S)N(R$^{B8}$)$_2$, —C(=O)SR$^{B7}$ and —C(=S)SR$^{B7}$. In certain embodiments, L is a covalent bond.

In certain embodiments, R$^D$ is selected from —C(=O)R$^{B7}$, —CO$_2$H, —CHO, and —CO$_2$R$^{B7}$. In certain embodiments, L is a covalent bond.

In certain embodiments, R$^D$ is —CO$_2$H. In certain embodiments, L is a covalent bond.

In certain embodiments, wherein R$^B$ is substituted with L-R$^D$, R$^B$ is further substituted with the group:

—R$^E$ wherein:

R$^E$ is selected from halogen, —OH, —OR$^{B10}$, —ON(R$^{B11}$)$_2$, —N(R$^{B11}$)$_2$, —N(OR$^{B12}$)R$^{B12}$, —SH, —SR$^{B10}$, —SSR$^{B12}$, —OC(=O)R$^{B10}$, —OCO$_2$R$^{B10}$, —OC(=O)N(R$^{B11}$)$_2$, —NR$^{B11}$C(=O)R$^{B10}$, —NR$^{B11}$CO$_2$R$^{B10}$, —NR$^{B11}$C(=O)N(R$^{B11}$)$_2$, —OC(=NR$^{B11}$)R$^{B10}$, —OC(=NR$^{B11}$)OR$^{B10}$, —OC(=NR$^{B11}$)N(R$^{B11}$)$_2$, —NR$^{B11}$C(=NR$^{B11}$)N(R$^{B11}$)$_2$, —NR$^{B11}$SO$_2$R$^{B10}$, —OSO$_2$R$^{B10}$, —OS(=O)R$^{B10}$, —Si(R$^{B10}$)$_3$, —OSi(R$^{B10}$)$_3$, —SC(S)SR$^{10}$, —OP(=O)$_2$R$^{B10}$, —OP(=O)(R$^{B10}$)$_2$, —OP(=O)(OR$^{B12}$)$_2$, —OP(=O)$_2$N(R$^{B11}$)$_2$, —OP(=O)(NR$^{B11}$)$_2$, —NR$^{B11}$P(=O)(OR$^{B12}$)$_2$, —NR$^{B11}$P(=O)(NR$^{B11}$)$_2$, —P(R$^{B12}$)$_2$, —P(R$^{B12}$)$_3$, —OP(R$^{B12}$)$_2$, —OP(R$^{B12}$)$_3$, 3-14 membered heterocyclyl and 5-14 membered heteroaryl, wherein the point of attachment of the 3-14 membered heterocyclyl or 5-14 membered heteroaryl group is on a nitrogen atom;

each instance of R$^{B10}$ is, independently, selected from C$_{1-10}$ alkyl, C$_{1-10}$ perhaloalkyl, C$_{2-10}$ to alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl;

each instance of R$^{B11}$ is, independently, selected from hydrogen, —OH, —OR$^{B10}$, —N(R$^{B12}$)$_2$, —CN, —C(=O)R$^{B10}$, —C(=O)N(R$^{B12}$)$_2$, —CO$_2$R$^{B10}$, —SO$_2$R$^{B10}$, —C(=NR$^{B12}$)OR$^{B10}$, —C(=NR$^{B12}$)N(R$^{B12}$)$_2$, —SO$_2$N(R$^{B12}$)$_2$, —SO$_2$R$^{B12}$, —SO$_2$OR$^{B12}$, —SOR$^{B10}$, —C(=S)N(R$^{B12}$)$_2$, —C(=O)SR$^{B12}$, —C(=S)SR$^{B12}$, —P(=O)$_2$R$^{B10}$, —P(=O)(R$^{B10}$)$_2$, —P(=O)$_2$N(R$^{B12}$)$_2$, —P(=O)(NR$^{B12}$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two R$^{B11}$ groups are joined to form a 3-14 membered heterocyclyl or 5-14 membered heteroaryl ring; and each instance of R$^{B12}$ is, independently, selected from hydrogen, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two R$^{B12}$ groups are joined to form a 3-14 membered heterocyclyl or 5-14 membered heteroaryl ring.

In certain embodiments, R$^E$ is selected from halogen, —OH, —OR$^{B10}$, —ON(R$^{B11}$)$_2$, —N(R$^{B11}$)$_2$, —N(OR$^{B12}$)R$^{B12}$, —SH, —SR$^{B10}$, —SSR$^{B12}$, —Si(R$^{B10}$)$_3$, —OSi(R$^{B10}$), —P(R$^{B12}$)$_2$, —P(R$^{B12}$)$_3$, —OP(R$^{B12}$)$_2$, —OP(R$^{B12}$)$_3$, 3-14 membered heterocyclyl and 5-14 membered heteroaryl, wherein the point of attachment of the 3-14 membered heterocyclyl or 5-14 membered heteroaryl group is on a nitrogen atom.

In certain embodiments, R$^E$ is selected from halogen, —OH, —OR$^{B10}$, —N(R$^{B11}$)$_2$, 3-14 membered heterocyclyl and 5-14 membered heteroaryl, wherein the point of attachment of the 3-14 membered heterocyclyl or 5-14 membered heteroaryl group is on a nitrogen atom.

In certain embodiments, R$^E$ is selected from halogen, —OR$^{B10}$ and —N(R$^{B11}$)$_2$. In certain embodiments, R$^E$ is halogen. In certain embodiments, R$^E$ is —OR$^{B10}$. In certain embodiments, R$^E$ is —N(R$^{B11}$)$_2$.

In certain embodiments, -L-R$^D$ and —R$^E$ are vicinal R$^B$ substituents (i.e., attached to two adjacent atoms on the group R$^B$; e.g., ortho to each other). In certain embodiments, -L-R$^D$ and —R$^E$ are ortho to each other.

In certain embodiments, -L-$R^D$ and —$R^E$ are not vicinal $R^B$ substituents (i.e., not attached to two adjacent atoms on the group $R^B$; e.g. meta or para to each other). In certain embodiments, -L-$R^D$ and —$R^E$ are meta to each other. In certain embodiments, -L-$R^D$ and —$R^E$ are para to each other.

In certain embodiments, the $R^B$ is a group of the formula (vii):

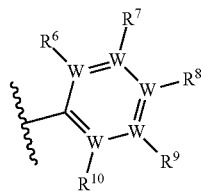

(vii)

wherein each group W—$R^6$, W—$R^7$, W—$R^8$, W—$R^9$, and W—$R^{10}$ independently represents either a nitrogen atom (N) or C—$R^6$, C—$R^7$, C—$R^8$, C—$R^9$, or C—$R^{10}$, respectively; and wherein $R^6$, $R^7$, $R^8$, $R^9$ and $R^{10}$ are independently selected from the group consisting of hydrogen, halogen, —CN, —$NO_2$, —$N_3$, —$SO_2H$, —$SO_3H$, —OH, —$OR^{B1}$, —$ON(R^{B2})_2$, —$N(R^{B2})_2$, —$N(OR^{B3})R^{B3}$, —SH, —$SR^{B1}$, —$SSR^{B3}$, —C(=O)$R^{B1}$, —$CO_2H$, —CHO, —C($OR^{B3})_2$, —$CO_2R^{B1}$, —OC(=O)$R^{B1}$, —$OCO_2R^{B1}$, —OC(=O)N($R^{B2})_2$, —$NR^{B2}$C(=O)$R^{B1}$, —$NR^{B2}CO_2R^{B1}$, —$NR^{B2}$C(=O)N($R^{B2})_2$, —C(=$NR^{B2}$)$OR^{B1}$, —OC(=$NR^{B2}$)$R^{B1}$, —OC(=$NR^{B2}$)$OR^{B1}$, —C(=$NR^{B2}$)N($R^{B2})_2$, —OC(=$NR^{B2}$)N($R^{B2})_2$, —$NR^{B2}$C(=$NR^{B2}$)N($R^{B2})_2$, —C(=O)$NR^{B2}SO_2R^{B1}$, —$NR^{B2}SO_2R^{B1}$, —$SO_2N(R^{B2})_2$, —$SO_2R^{B1}$, —$SO_2OR^{B1}$, —$OSO_2R^{B1}$, —S(=O)$R^{B1}$, —OS(=O)$R^{B1}$, —Si($R^{B1})_3$, —OSi($R^{B1})_3$—C(=S)N($R^{B2})_2$, —C(=O)$SR^{B1}$, —C(=S)$SR^{B1}$, —SC(S)$SR^{B1}$, —P(=O)$_2R^{B1}$, —OP(=O)$_2R^{B1}$, —P(=O)($R^{B1})_2$, —OP(=O)($R^{B1})_2$, —OP(=O)($OR^{B3})_2$, —P(=O)$_2N(R^{B2})_2$, —OP(=O)$_2N(R^{B2})_2$, —P(=O)(N$R^{B2})_2$, —OP(=O)(N$R^{B2})_2$, —$NR^{B2}$P(=O)($OR^{B3})_2$, —$NR^{B2}$P(=O)(N$R^{B2})_2$, —P($R^{B3})_2$, —P($R^{B3})_3$, —OP($R^{B3})_2$, —OP($R^{B3})_3$, —B($OR^{B3})_2$, or —$BR^{B1}(OR^{B3})$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, 5-14 membered heteroaryl, -L-$R^D$ and —$R^E$ or one or more of $R^6$ and $R^7$, $R^7$ and $R^8$, $R^8$ and $R^9$ or $R^9$ and $R^{10}$ are joined to form a $C_{3-10}$ carbocyclyl, 3-14 membered heterocyclyl, $C_{6-14}$ aryl or 5-14 membered heteroaryl ring; or $R^{10}$ and $R^C$ are joined to form a 3-14 membered heterocyclyl or 5-14 membered heteroaryl ring;

each instance of $R^{B1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{B2}$ is, independently, selected from hydrogen, —OH, —$OR^{B1}$, —N($R^{B3})_2$—CN, —C(=O)$R^{B1}$, —C(=O)N($R^{B3})_2$, —$CO_2R^{B1}$, —$SO_2R^{B1}$, —C(=$NR^{B3}$)$OR^{B1}$, —C(=$NR^{B3}$)N($R^{B3})_2$, —$SO_2N(R^{B3})_2$, —$SO_2R^{B3}$, —$SO_2OR^{B3}$, —$SOR^{B1}$, —C(=S)N($R^{B3})_2$, —C(=O)$SR^{B3}$, —C(=S)$SR^{B3}$, —P(=O)$_2R^{B1}$, —P(=O)($R^{B1})_2$, —P(=O)$_2N(R^{B3})_2$, —P(=O)(N$R^{B3})_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B2}$ groups are joined to form a 3-14 membered heterocyclyl or 5-14 membered heteroaryl ring;

each instance of $R^{B3}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B3}$ groups are joined to form a 3-14 membered heterocyclyl or 5-14 membered heteroaryl ring;

and L, $R^D$ and $R^E$ are as defined above and herein.

As used herein, when one or more of $R^6$, $R^7$, $R^8$, $R^9$ and $R^{10}$ is referred to as "not hydrogen", it is meant that one or more of $R^6$, $R^7$, $R^8$, $R^9$ and $R^{10}$ is independently selected from the group consisting of halogen, —CN, —$NO_2$, —$N_3$, —$SO_2H$, —$SO_3H$, —OH, —$OR^{B1}$, —$ON(R^{B2})_2$, —$N(R^{B2})_2$, —$N(OR^{B3})R^{B3}$, —SH, —$SR^{B1}$, —$SSR^{B3}$, —C(=O)$R^{B1}$, —$CO_2H$, —CHO, —C($OR^{B3})_2$, —$CO_2R^{B1}$, —OC(=O)$R^{B1}$, —$OCO_2R^{B1}$, —C(=O)N($R^{B2})_2$, —OC(=O)N($R^{B2})_2$, —$NR^{B2}$C(=O)$R^{B1}$, —$NR^{B2}CO_2R^{B1}$, —$NR^{B2}$C(=O)N($R^{B2})_2$, —C(=$NR^{B2}$)$OR^{B1}$, —OC(=$NR^{B2}$)$R^{B1}$, —OC(=$NR^{B2}$)$OR^{B1}$, —C(=$NR^{B2}$)N($R^{B2})_2$, —OC(=$NR^{B2}$)N($R^{B2})_2$, —$NR^{B2}$C(=$NR^{B2}$)N($R^{B2})_2$, —C(=O)$NR^{B2}SO_2R^{B1}$, —$NR^{B2}SO_2R^{B1}$, —$SO_2N(R^{B2})_2$, —$SO_2R^{B1}$, —$SO_2OR^{B1}$, —$OSO_2R^{B1}$, —S(=O)$R^{B1}$, —OS(=O)$R^{B1}$, —Si($R^{B1})_3$, —OSi($R^{B1})_3$—C(=S)N($R^{B2})_2$, —C(=O)$SR^{B1}$, —C(=S)$SR^{B1}$, —SC(=S)$SR^{B1}$, —P(=O)$_2R^{B1}$, —OP(=O)$_2R^{B1}$, —P(=O)($R^{B1})_2$, —OP(=O)($R^{B1})_2$, —OP(=O)($OR^{B3})_2$, —P(=O)$_2N(R^{B2})_2$, —OP(=O)$_2N(R^{B2})_2$, —P(=O)(N$R^{B2})_2$, —OP(=O)(N$R^{B2})_2$, —$NR^{B2}$P(=O)($OR^{B3})_2$, —$NR^{B2}$P(=O)(N$R^{B2})_2$, —P($R^{B3})_2$, —P($R^{B3})_3$, —OP($R^{B3})_2$, —OP($R^{B3})_3$, —B($OR^{B3})_2$, —$BR^{B1}(OR^{B3})$, -L-$R^D$, —$R^E$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; or wherein one or more of $R^6$ and $R^7$, $R^7$ and $R^8$, $R^8$ and $R^9$ or $R^9$ and $R^{10}$ are joined to form a $C_{3-10}$ carbocyclyl, 3-14 membered heterocyclyl, $C_{6-14}$ aryl or 5-14 membered heteroaryl ring, or wherein $R^{10}$ and $R^C$ are joined to form a 3-14 membered heterocyclyl or 5-14 membered heteroaryl ring.

In certain embodiments, at least one of $R^6$, $R^7$, $R^8$, $R^9$, and $R^{10}$ is the group -L-$R^D$ as defined above and herein. In certain embodiments, at least one of $R^6$, $R^7$, $R^8$, $R^9$, and $R^{10}$ is the group —$R^E$ as defined herein.

In certain embodiments, the group of formula (vii) represents a $C_{6-14}$ aryl or a 6-14 membered heteroaryl group. In certain embodiments, the group of formula (vii) represents a 6-14 membered heteroaryl group. In certain embodiments, the group of formula (vii) represents a $C_{6-14}$ aryl group. In certain embodiments, the group of formula (vii) represents a phenyl group.

In certain embodiments, W—$R^6$, W—$R^7$, W—$R^8$, W—$R^9$, and W—$R^{10}$ represent C—$R^6$, C—$R^7$, C—$R^8$, C—$R^9$, or C—$R^{10}$, respectively. For example, in certain embodiments, $R^B$ is a group of the formula (viii):

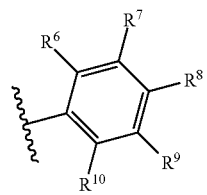

(viii)

wherein $R^6$, $R^7$, $R^8$, $R^9$ and $R^{10}$ are as defined above and herein.

In certain embodiments, at least one of $R^6$, $R^7$, $R^8$, $R^9$, and $R^{10}$ is the group -L-$R^D$ as defined above and herein. In certain embodiments, at least one of $R^6$, $R^7$, $R^8$, $R^9$, and $R^{10}$ is the group —$R^E$ as defined herein.

In certain embodiments, the group of the formula (viii) represents a $C_{6-14}$ aryl group. In certain embodiments, the $C_{6-14}$ aryl group of the formula (viii) represents a phenyl group.

In certain embodiments, $R^B$ is a monosubstituted, disubstituted or trisubstituted group of the formula (viii). In certain embodiments, $R^B$ is a monosubstituted or disubstituted group of the formula (viii).

In certain embodiments, $R^B$ is a monosubstituted group of the formula (viii).

For example, in certain embodiments, $R^B$ is an ortho-substituted group of formula (viii), e.g., wherein $R^6$-$R^9$ are hydrogen, and $R^{10}$ is not hydrogen, e.g., of the formula (viii-a).

In certain embodiments, $R^B$ is a meta-substituted group of the formula (viii), e.g., wherein $R^6$-$R^8$ and $R^{10}$ are hydrogen and $R^9$ is not hydrogen, e.g., of the formula (viii-b).

In certain embodiments, $R^B$ is a para-substituted group of the formula (viii), e.g., wherein $R^6$, $R^7$, $R^9$ and $R^{10}$ are hydrogen and $R^8$ is not hydrogen, e.g., of the formula (viii-c).

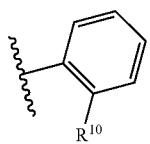
(viii-a)

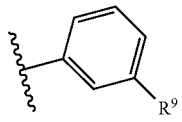
(viii-b)

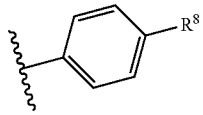
(viii-c)

In certain embodiments, $R^B$ is a disubstituted group of the formula (viii).

For example, in certain embodiments, $R^B$ is a 2,6-disubstituted group of the formula (viii), e.g., wherein $R^7$, $R^8$ and $R^9$ are hydrogen, and $R^6$ and $R^{10}$ are not hydrogen, e.g., of the formula (viii-d).

In certain embodiments, $R^B$ is a 2,5-disubstituted group of the formula (viii), e.g., wherein $R^6$, $R^8$ and $R^9$ are hydrogen, and $R^7$ and $R^{10}$ are not hydrogen, e.g., of the formula (viii-e).

In certain embodiments, $R^B$ is a 2,4-disubstituted group of the formula (viii), e.g., wherein $R^6$, $R^7$ and $R^9$ are hydrogen, and $R^8$ and $R^{10}$ are not hydrogen, e.g., of the formula (viii-f).

In certain embodiments, $R^B$ is a 2,3-disubstituted group of formula (viii), e.g., wherein $R^6$, $R^7$ and $R^8$ are hydrogen, and $R^9$ and $R^{10}$ are not hydrogen, e.g., of the formula (viii-g).

In certain embodiments, $R^B$ is a 3,4-disubstituted group of the formula (viii), e.g., wherein $R^6$, $R^7$ and $R^{10}$ are hydrogen, and $R^8$ and $R^9$ are not hydrogen, e.g., of the formula (viii-h).

In certain embodiments, $R^B$ is a 3,5-disubstituted group of the formula (viii), e.g., wherein $R^6$, $R^7$ and $R^{10}$ are hydrogen, and $R^7$ and $R^9$ are not hydrogen, e.g., of the formula (viii-i).

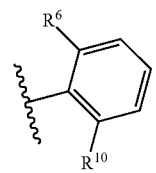
(viii-d)

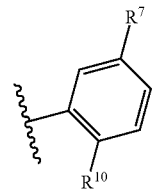
(viii-e)

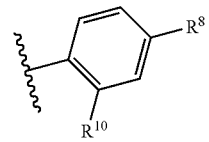
(viii-f)

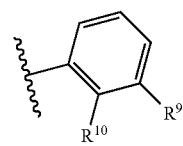
(viii-g)

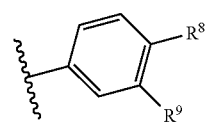
(viii-h)

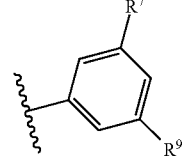
(viii-i)

In certain embodiments, $R^B$ is a trisubstituted group of the formula (viii).

For example, in certain embodiments, $R^B$ is a 2,4,6-trisubstituted group of formula (viii), e.g., wherein $R^7$ and $R^9$ are hydrogen, and $R^6$, $R^8$ and $R^{10}$ are not hydrogen, e.g., of the formula (viii-j).

In certain embodiments, $R^B$ is a 2,3,6-trisubstituted group of the formula (viii), e.g., wherein $R^2$ and $R^3$ are hydrogen, and $R^1$, $R^4$ and $R^5$ are not hydrogen, e.g., of the formula (viii-k).

In certain embodiments, $R^B$ is a 2,4,5-trisubstituted group of the formula (viii), e.g., wherein $R^8$ and $R^9$ are hydrogen, and $R^6$, $R^7$ and $R^{10}$ are not hydrogen, e.g., of the formula (viii-l).

In certain embodiments, $R^B$ is a 2,3,4-trisubstituted group of the formula (viii), e.g., wherein $R^6$ and $R^9$ are hydrogen, and $R^7$, $R^8$ and $R^{10}$ are not hydrogen, e.g., of the formula (viii-m).

In certain embodiments, $R^B$ is a 3,4,5-trisubstituted group of the formula (viii), e.g., wherein $R^6$ and $R^{10}$ are hydrogen, and $R^7$, $R^8$ and $R^9$ are not hydrogen, e.g., of the formula (viii-n).

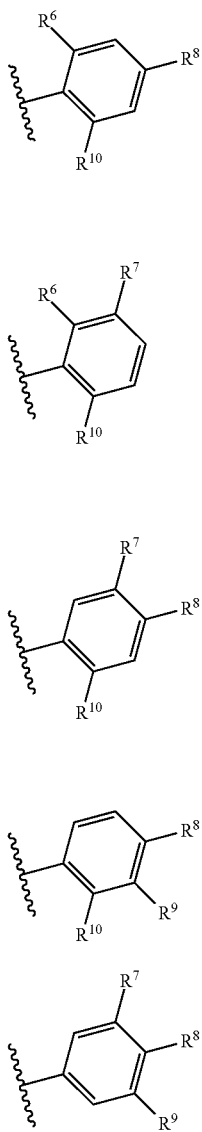

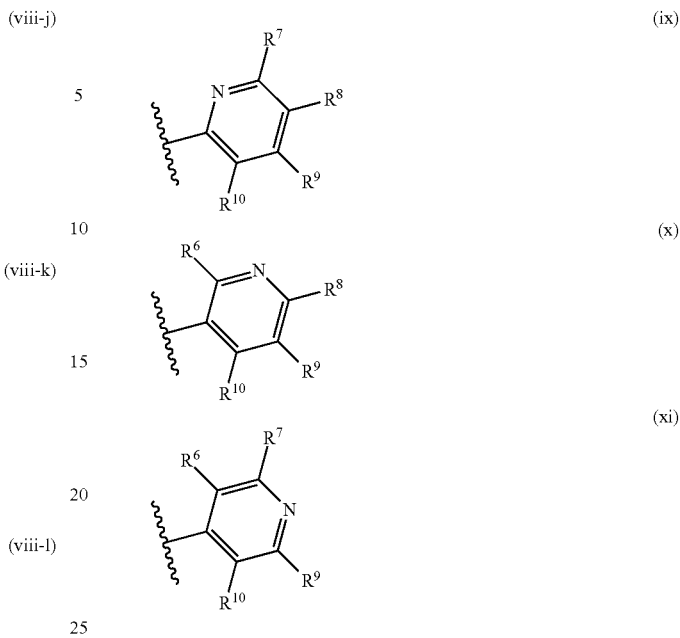

In certain embodiments, $R^B$ is heteroaryl selected from a 5-6-membered heteroaryl, a 5,6-bicyclic heteroaryl, or a 6,6-bicyclic heteroaryl.

In certain embodiments, $R^B$ is a 6-membered heteroaryl. In certain embodiments, $R^A$ is a 6-membered heteroaryl selected from pyridinyl. In certain embodiments, $R^B$ is 2-pyridinyl, 3-pyridinyl or 4-pyridinyl.

In certain embodiments, $R^B$ is a 2-pyridinyl wherein W—$R^6$ is N, and W—$R^7$, W—$R^8$, W—$R^9$, and W—$R^{10}$ are C—$R^7$, C—$R^8$, C—$R^9$ and C—$R^{10}$, respectively, e.g. of the formula (ix).

In certain embodiments, $R^B$ is a 3-pyridinyl wherein W—$R^7$ is N, and W—$R^6$, W—$R^8$, W—$R^9$, and W—$R^{10}$ are C—$R^6$, C—$R^8$, C—$R^9$ and C—$R^{10}$, respectively, e.g., of the formula (x).

In certain embodiments, $R^B$ is a 4-pyridinyl wherein W—$R^8$ is N, and W—$R^6$, W—$R^7$, W—$R^9$, and W—$R^{10}$ are C—$R^6$, C—$R^7$, C—$R^9$ and C—$R^{10}$, respectively, e.g., of the formula (xi).

wherein $R^6$, $R^7$, $R^8$, $R^9$ and $R^{10}$ are as defined above and herein.

In certain embodiments, at least one of $R^6$, $R^7$, $R^9$, $R^9$, and $R^{10}$ is the group -L-$R^D$ as defined above and herein. In certain embodiments, at least one of $R^6$, $R^7$, $R^8$, $R^9$, and $R^{10}$ is the group —$R^E$ as defined herein.

In certain embodiments, $R^B$ is a monosubstituted or disubstituted pyridinyl.

In certain embodiments, $R^B$ is a monosubstituted pyridinyl.

In certain embodiments, $R^B$ is a monosubstituted pyridinyl of the formula (ix) wherein $R^8$, $R^9$, $R^{10}$ are hydrogen and $R^7$ is not hydrogen, e.g., of the formula (ix-a).

In certain embodiments, $R^B$ is a monosubstituted pyridinyl of the formula (ix) wherein $R^7$, $R^9$, $R^{10}$ are hydrogen and $R^8$ is not hydrogen, e.g., of the formula (ix-b).

In certain embodiments, $R^B$ is a monosubstituted pyridinyl of the formula (ix) wherein $R^7$, $R^8$, $R^{10}$ are hydrogen and $R^9$ is not hydrogen, e.g., of the formula (ix-c).

In certain embodiments, $R^B$ is a monosubstituted pyridinyl of the formula (ix) wherein $R^7$, $R^8$, $R^9$ are hydrogen and $R^{10}$ is not hydrogen, e.g., of the formula (ix-d).

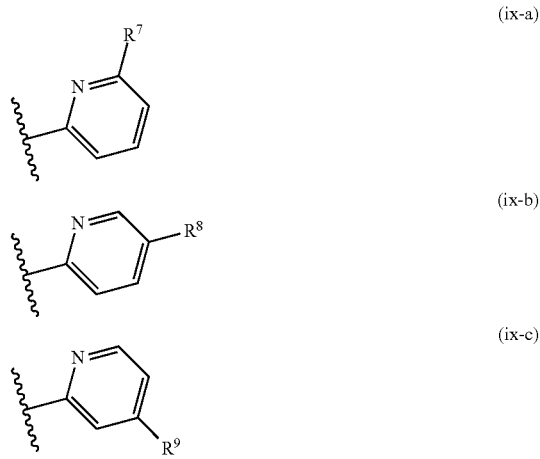

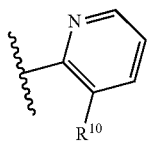
(ix-d)

In certain embodiments, $R^B$ is a monosubstituted pyridinyl of the formula (x) wherein $R^8$, $R^9$, $R^{10}$ are hydrogen and $R^6$ is not hydrogen, e.g., of the formula (x-a).

In certain embodiments, $R^B$ is a monosubstituted pyridinyl of the formula (x) wherein $R^6$, $R^9$, $R^{10}$ are hydrogen and $R^8$ is not hydrogen, e.g., of the formula (x-b).

In certain embodiments, $R^B$ is a monosubstituted pyridinyl of the formula (x) wherein $R^6$, $R^8$, $R^{10}$ are hydrogen and $R^9$ is not hydrogen, e.g., of the formula (x-c).

In certain embodiments, $R^B$ is a monosubstituted pyridinyl of the formula (x) wherein $R^6$, $R^8$, $R^9$ are hydrogen and $R^{10}$ is not hydrogen, e.g., of the formula (x-d).

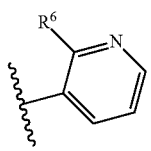
(x-a)

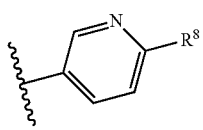
(x-b)

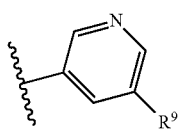
(x-c)

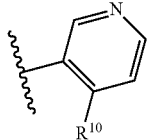
(x-d)

In certain embodiments, $R^B$ is a monosubstituted pyridinyl of the formula (xi) wherein $R^6$, $R^7$, $R^9$ are hydrogen and $R^{10}$ is not hydrogen, e.g., of the formula (xi-a).

In certain embodiments, $R^B$ is a monosubstituted pyridinyl of the formula (v) wherein $R^6$, $R^7$, $R^{10}$ are hydrogen and $R^9$ is not hydrogen, e.g., of the formula (xi-b).

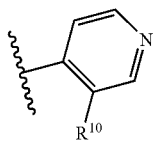
(xi-a)

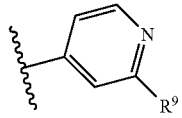
(xi-b)

In certain embodiments, $R^B$ is a disubstituted pyridinyl.

In certain embodiments, $R^B$ is a disubstituted pyridinyl of the formula (ix) wherein $R^8$ and $R^9$ are hydrogen and $R^7$ and $R^{10}$ are not hydrogen, e.g., of the formula (ix-e).

In certain embodiments, $R^B$ is a disubstituted pyridinyl of the formula (ix) wherein $R^7$ and $R^9$ are hydrogen and $R^8$ and $R^{10}$ are not hydrogen, e.g., of the formula (ix-f).

In certain embodiments, $R^B$ is a disubstituted pyridinyl of the formula (ix) wherein $R^7$ and $R^8$ are hydrogen and $R^9$ and $R^{10}$ are not hydrogen. e.g., of the formula (ix-g).

In certain embodiments, $R^B$ is a disubstituted pyridinyl of the formula (ix) wherein $R^8$ and $R^{10}$ are hydrogen and $R^7$ and $R^9$ are not hydrogen, e.g., of the formula (ix-h).

In certain embodiments, $R^B$ is a disubstituted pyridinyl of the formula (ix) wherein $R^9$ and $R^{10}$ are hydrogen and $R^7$ and $R^8$ are not hydrogen, e.g., of the formula (ix-i).

In certain embodiments. $R^B$ is a disubstituted pyridinyl of the formula (ix) wherein $R^7$ and $R^{10}$ are hydrogen and $R^8$ and $R^9$ are not hydrogen, e.g., of the formula (ix-j).

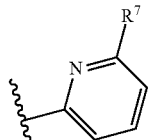
(ix-e)

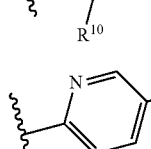
(ix-f)

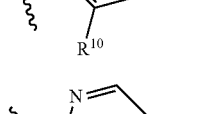
(ix-g)

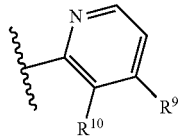
(ix-h)

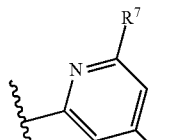
(ix-i)

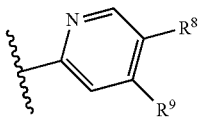
(ix-j)

In certain embodiments, $R^B$ is a disubstituted pyridinyl of the formula (x) wherein $R^8$ and $R^9$ are hydrogen and $R^6$ and $R^{10}$ are not hydrogen, e.g., of the formula (x-e).

In certain embodiments, $R^B$ is a disubstituted pyridinyl of the formula (x) wherein $R^8$ and $R^{10}$ are hydrogen and $R^6$ and $R^9$ are not hydrogen, e.g., of the formula (x-f).

In certain embodiments, $R^B$ is a disubstituted pyridinyl of the formula (x) wherein $R^9$ and $R^{10}$ are hydrogen and $R^6$ and $R^8$ are not hydrogen, e.g., of the formula (x-g).

In certain embodiments, $R^B$ is a disubstituted pyridinyl of the formula (x) wherein $R^6$ and $R^9$ are hydrogen and $R^8$ and $R^{10}$ are not hydrogen, e.g., of the formula (x-h).

In certain embodiments, $R^B$ is a disubstituted pyridinyl of the formula (x) wherein $R^6$ and $R^{10}$ are hydrogen and $R^8$ and $R^9$ are not hydrogen, e.g., of the formula (x-i).

In certain embodiments, $R^B$ is a disubstituted pyridinyl of the formula (x) wherein $R^6$ and $R^8$ are hydrogen and $R^9$ and $R^{10}$ are not hydrogen, e.g., of the formula (x-j).

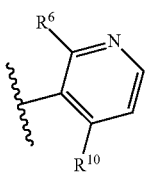
(x-e)

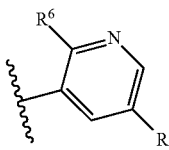
(x-f)

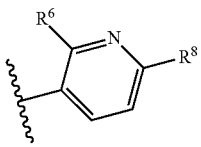
(x-g)

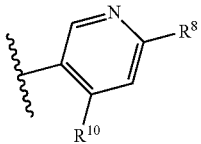
(x-h)

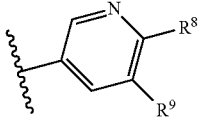
(x-i)

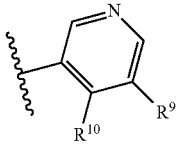
(x-j)

In certain embodiments, $R^B$ is a disubstituted pyridinyl of the formula (xi) wherein $R^7$ and $R^9$ are hydrogen and $R^6$ and $R^{10}$ are not hydrogen, e.g., of the formula (xi-c).

In certain embodiments, $R^B$ is a disubstituted pyridinyl of the formula (xi) wherein $R^6$ and $R^7$ are hydrogen and $R^9$ and $R^{10}$ are not hydrogen, e.g., of the formula (xi-d).

In certain embodiments, $R^B$ is a disubstituted pyridinyl of the formula (xi) wherein $R^6$ and $R^8$ are hydrogen and $R^7$ and $R^{10}$ are not hydrogen, e.g., of the formula (xi-e).

In certain embodiments, $R^B$ is a disubstituted pyridinyl of the formula (xi) wherein $R^6$ and $R^{10}$ are hydrogen and $R^7$ and $R^9$ are not hydrogen, e.g., of the formula (xi-f).

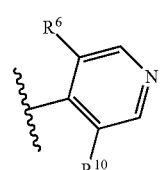
(ix-c)

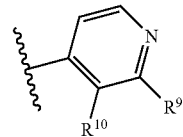
(ix-d)

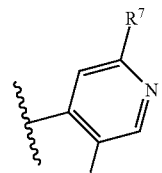
(xi-e)

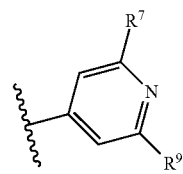
(xi-f)

In certain embodiments, $R^B$ is $C_{5-10}$ carbocyclyl or 5-10 membered heterocyclyl of the formula (xii):

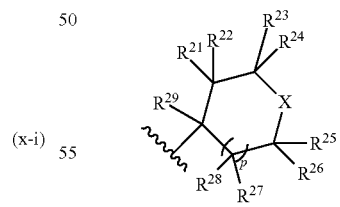
(xii)

wherein:
X is N, $NR^{30}$, O, S or $CR^{31}R^{32}$;
p is 0, 1 or 2;
each instance of $R^{21}$, $R^{22}$, $R^{23}$, $R^{24}$, $R^{25}$, $R^{26}$, $R^{27}$, $R^{28}$, $R^{29}$, $R^{31}$ and $R^{32}$ is independently selected from hydrogen, halogen, —CN, —NO$_2$, —N$_3$, —SO$_2$H, —SO$_3$H, —OH, —OR$^{B1}$, —ON(R$^{B2}$)$_2$, —N(R$^{B2}$)$_2$, —N(OR$^{B3}$)R$^{B3}$, —SH, —SR$^{B1}$, —SSR$^{B3}$, —C(=O)R$^{B1}$, —CO$_2$H, —CHO, —C(OR$^{B3}$)$_2$, —CO$_2$R$^{B1}$, —OC(=O)R$^{B1}$, —OCO$_2$R$^{B1}$, —C(=O)N(R^{B2})_2, —OC(=O)N(R^{B2})_2, —NR^{B2}C(=O)R^{B1}, —NR^{B2}CO_2R^{B1}, —NR^{B2}C(=O)N(R^{B2})_2, —C(=NR^{B2})OR^{B1}, —OC(=NR^{B2})R^{B1}, —OC(=NR^{B2})OR^{B1}, —C(=NR^{B2})N(R^{B2})_2, —OC(=NR^{B2})N(R^{B2})_2, —NR^{B2}C(=NR^{B2})N(R^{B2})_2, —C(=O)NR^{B2}SO_2R^{B1}, NR^{B2}SO_2R^{B1}, —SO_2N(R^{B2})_2, —SO_2R^{B1}, —SO_2OR^{B1}, —OSO_2R^{B1}, —S(=O)R^{B1}, —OS(=O)R^{B1}, Si(R^{B1})_3, —OSi(R^{B1})_3 —C(=S)N(R^{B2})_2, —C(=O)SR^{B1}, —C(=S)SR^{B1}, —SC(=S)SR^{B1}, —P(=O)_2R^{B1}, —OP(=O)_2R^{B1}, —P(=O)(R^{B1})_2, —OP(=O)(R^{B1})_2, —OP(=O)(OR^{B3})_2, —P(=O)_2N(R^{B2})_2, —OP(=O)_2N(R^{B2})_2, —P(=O)(NR^{B2})_2, —OP(=O)(NR^{B2})_2, —NR^{B2}P(=O)(OR^{B3})_2, —NR^{B2}P(=O)(NR^{B2})_2, —P(R^{B3})_2, —P(R^{B3})_3, —OP(R^{B3})_2, —OP(R^{B3})_3, —B(OR^{B3})_2, or —BR^{B1}(OR^{B3}), C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, 5-14 membered heteroaryl, -L-R^D and —R^E; or one or more of R^{29} and R^{21}, R^{22} and R^{23}, R^{24} and R^{31}, R^{32} and R^{25}, R^{26} and R^{27}, R^{28} and R^{29}, or R^{26} and R^{29}, are joined to form a double bond or a C_{3-10} carbocyclyl, 3-14 membered heterocyclyl, C_{6-14} aryl or 5-14 membered heteroaryl ring; optionally wherein X is N, then N and R^{23} or N and R^{25} are joined to form a double bond;

R^{30} is selected from hydrogen, —OH, —OR^{B1}, —N(R^{B3})_2, —CN, —C(=O)R^{B1}, —C(=O)N(R^{B3})_2, —CO_2R^{B1}, —SO_2R^{B1}, —C(=NR^{B3})OR^{B1}, —C(=NR^{B3})N(R^{B3})_2, —SO_2N(R^{B3})_2, —SO_2R^{B3}, —SO_2OR^{B3}, —S(=O)R^{B1}, —C(=S)N(R^{B3})_2, —C(=O)SR^{B3}, —C(=S)SR^{B3}, —P(=O)_2R^{B1}, —P(=O)(R^{B1})_2, —P(=O)_2N(R^{B3})_2, —P(=O)(NR^{B3})_2, C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, and 5-14 membered heteroaryl, optionally wherein R^{24} and R^{30} or R^{30} and R^{25} are joined to form a 3-14 membered heterocyclyl or 5-14 membered heteroaryl ring;

wherein:

each instance of R^{B1} is, independently, selected from C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, and 5-14 membered heteroaryl;

each instance of R^{B2} is, independently, selected from hydrogen, —OH, —OR^{B1}, —N(R^{B3})_2, —CN, —C(=O)R^{B1}, —C(=O)N(R^{B3})_2, —CO_2R^{B1}, —SO_2R^{B1}, —C(=NR^{B3})OR^{B1}, —C(=NR^{B3})N(R^{B3})_2, —SO_2N(R^{B3})_2, —SO_2R^{B3}, —SO_2OR^{B3}, —SOR^{B1}, —C(=S)N(R^{B3})_2, —C(=O)SR^{B3}, —C(=S)SR^{B3}, —P(=O)_2R^{B1}, —P(=O)(R^{B1})_2, —P(=O)_2N(R^{B3})_2, —P(=O)(NR^{B3})_2, C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, and 5-14 membered heteroaryl, or two R^{B2} groups are joined to form a 3-14 membered heterocyclyl or 5-14 membered heteroaryl ring;

each instance of R^{B3} is, independently, selected from hydrogen, C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, and 5-14 membered heteroaryl, or two R^{B3} groups are joined to form a 3-14 membered heterocyclyl or 5-14 membered heteroaryl ring;

and L, R^D and R^E are as defined above and herein.

In certain embodiments, at least one of R^{21}, R^{22}, R^{23}, R^{24}, R^{25}, R^{26}, R^{27}, R^{28}, R^{29}, R^{30}, R^{31}, and R^{32} is the group -L-R^D as defined above and herein. In certain embodiments, at least one of R^{21}, R^{22}, R^{23}, R^{24}, R^{25}, R^{26}, R^{27}, R^{28}, R^{29}, R^{30}, R^{31}, and R^{32} is selected from the group —R^E as defined herein.

In certain embodiments, p is 0. In certain embodiments, p is 1. In certain embodiments, p is 2.

In certain embodiments, X is N. In certain embodiments, X is NR^{30}. In certain embodiments, X is O. In certain embodiments, X is S. In certain embodiments, X is CR^{31}R^{32}

In certain embodiments, R^B is C_{5-10} carbocyclyl or 5-10 membered heterocylyl of the formula (xiii):

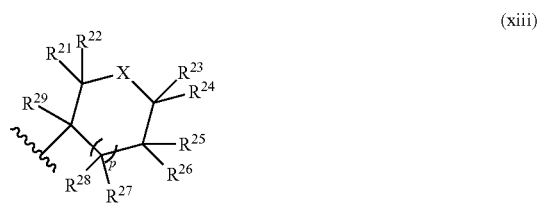

(xiii)

wherein:

X is N, NR^{30}, O, S or CR^{31}R^{32};

p is 0, 1 or 2;

each instance of R^{21}, R^{22}, R^{23}, R^{24}, R^{25}, R^{26}, R^{27}, R^{28}, R^{29}, R^{31} and R^{32} is independently selected from hydrogen, halogen, —CN, —NO_2, —N_3, —SO_2H, —SO_3H, —OH, —OR^{B1}, —ON(R^{B2})_2, —N(R^{B2})_2, —N(OR^{B3})R^{B3}, —SH, —SR^{B1}, —SSR^{B3}, —C(=O)R^{B1}, —CO_2H, —CHO, —C(OR^{B3})_2, —CO_2R^{B1}, —OC(=O)R^{B1}, —OCO_2R^{B1}, —C(=O)N(R^{B2})_2, —OC(=O)N(R^{B2})_2, —NR^{B2}C(=O)R^{B1}, —NR^{B2}CO_2R^{B1}, —NR^{B2}C(=O)N(R^{B2})_2, —C(=NR^{B2})OR^{B1}, —OC(=NR^{B2})R^{B1}, —OC(=NR^{B2})OR^{B1}, —C(=NR^2)N(R^{B2})_2, —OC(=NR^{B2})N(R^{B2})_2, —NR^{B2}C(=NR^{B2})N(R^{B2})_2, —C(=O)NR^{B2}SO_2R^{B1}, —NR^{B2}SO_2R^{B1}, —SO_2N(R^{B2})_2, —SO_2R^{B1}, SO_2OR^{B1}, —OSO_2R^{B1}, —S(=O)R^{B1}, —OS(=O)R^{B1}, —Si(R^{B1})_3, —OSi(R^{B1})_3 —C(=S)N(R^{B2})_2, —C(=O)SR^{B1}, —C(=S)SR^{B1}, —SC(=S)SR^{B1}, —P(=O)_2R^{B1}, —OP(=O)_2R^{B1}, —P(=O)(R^{B1})_2, —OP(=O)(R^{B1})_2, —OP(=O)(OR^{B3})_2, —P(=O)_2N(R^{B2})_2, —OP(=O)_2N(R^{B2})_2, —P(=O)(NR^{B2})_2, —OP(=O)(NR^{B2})_2, —NR^{B2}P(=O)(OR^{B3})_2, —NR^{B2}P(=O)(NR^{B2})_2, —P(R^{B3})_2, —P(R^{B3})_3, —OP(R^{B3})_2, —OP(R^{B3}), —B(OR^{B3})_2, or —BR^{B1}(OR^{B3}), C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, 5-14 membered heteroaryl, -L-R^D and —R^E; or one or more of R^{29} and R^{21}, R^{22} and R^{31}, R^{32} and R^{23}, R^{24} and R^{25}, R^{26} and R^{27}, R^{28} and R^{29}, and R^{26} and R^{29}, are joined to form a double bond or a C_{3-10} carbocyclyl, 3-14 membered heterocyclyl, C_{6-14} aryl or 5-14 membered heteroaryl ring; optionally wherein X is N, then N and R^{21} or N and R^{23} are joined to form a double bond;

R^{30} is selected from hydrogen, —OH, —OR^{B1}, —N(R^{B3})_2, —CN, —C(=O)R^{B1}, —C(=O)N(R^{B3})_2, —CO_2R^{B1}, —SO_2R^{B1}, —C(=NR^{B3})OR^{B1}, —C(=NR^{B3})N(R^{B3})_2, —SO_2N(R^{B3})_2, —SO_2R^{B3}, —SO_2OR^{B3}, —S(=O)R^{B1}, —C(=S)N(R^{B3})_2, —C(=O)SR^{B3}, —C(=S)SR^{B3}, —P(=O)_2R^{B1}, —P(=O)(R^{B1})_2, —P(=O)_2N(R^{B3})_2, —P(=O)(NR^{B3})_2, C_{1-10} alkyl, C_{1-10} perhaloalkyl, C_{2-10} alkenyl, C_{2-10} alkynyl, 3-14 membered heteroaliphatic, C_{3-10} carbocyclyl, 3-14 membered heterocyclyl, C_{6-14} aryl, and 5-14 membered heteroaryl, or R^{22} and R^{30} or R^{30} and R^{23} are joined to form a 3-14 membered heterocyclyl or 5-14 membered heteroaryl ring;

wherein:

each instance of R^{B1} is, independently, selected from C_{1-10} alkyl, C_{1-10} perhaloalkyl, C_{2-10} alkenyl, C_{2-10} alkynyl, C_{3-10} carbocyclyl, 3-14 membered heterocyclyl, C_{6-14} aryl, and 5-14 membered heteroaryl;

each instance of R^{B2} is, independently, selected from hydrogen, —OH, —OR^{B1}, —N(R^{B3})_2, —CN, —C(=O)R^{b1}, —C(=O)N($R^{B3}$)$_2$, —CO$_2$$R^{B1}$, —SO$_2$$R^{B1}$, —C(=N$R^{B3}$)O$R^{B1}$, —C(=N$R^{B3}$)N($R^{B3}$)$_2$, —SO$_2$N($R^{B3}$)$_2$, —SO$_2$$R^{B3}$, —SO$_2$O$R^{B3}$, —S(=O)$R^{B1}$, —C(=S)N($R^{B3}$)$_2$, —C(=O)S$R^{B3}$, —C(=S)S$R^{B3}$, —P(=O)$_2$$R^{B1}$, —P(=O)($R^{B1}$)$_2$, —P(=O)$_2$N($R^{B3}$)$_2$, —P(=O)(N$R^{B3}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B2}$ groups are joined to form a 3-14 membered heterocyclyl or 5-14 membered heteroaryl ring;

each instance of $R^{B3}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B3}$ groups are joined to form a 3-14 membered heterocyclyl or 5-14 membered heteroaryl ring;

and L, $R^D$ and $R^E$ are as defined above and herein.

In certain embodiments, at least one of $R^{21}$, $R^{22}$, $R^{23}$, $R^{24}$, $R^{23}$, $R^{26}$, $R^{27}$, $R^{28}$, $R^{29}$, $R^{30}$, $R^{31}$, and $R^{32}$ is the group -L-$R^D$ as defined above and herein. In certain embodiments, at least one of at least one of $R^{21}$, $R^{22}$, $R^{23}$, $R^{24}$, $R^{25}$, $R^{26}$, $R^{27}$, $R^{28}$, $R^{29}$, $R^{30}$, $R^{31}$, and $R^{32}$ is selected from —$R^E$ as defined herein.

In certain embodiments, p is 0. In certain embodiments, p is 1. In certain embodiments, p is 2.

In certain embodiments, X is N. In certain embodiments, X is $NR^{30}$. In certain embodiments, X is O. In certain embodiments, X is S. In certain embodiments, X is $CR^{31}R^{32}$.

For example, in certain embodiments, X is O. In certain embodiments, $R^B$ is a 5-10 membered heterocyclyl of the formulae (xii-a) or (xiii-a):

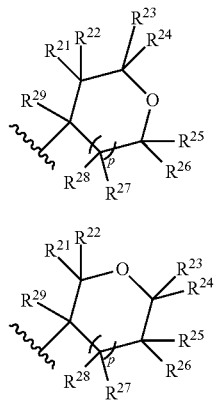

wherein p, $R^{21}$, $R^{22}$, $R^{23}$, $R^{24}$, $R^{25}$, $R^{26}$, $R^{27}$, $R^{28}$ and $R^{29}$ are as defined above and herein.

In certain embodiments, X is $NR^{30}$. For example, in certain embodiments, $R^B$ is heterocyclyl of the formulae (xii-b) or (xiii-b):

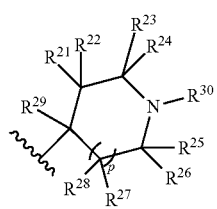

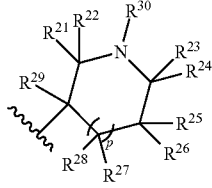

wherein p, $R^{21}$, $R^{22}$, $R^{23}$, $R^{24}$, $R^{25}$, $R^{26}$, $R^{27}$, $R^{28}$, $R^{29}$ and $R^{30}$ are as defined above and herein.

In certain embodiments, X is $CR^{31}R^{32}$. For example, in certain embodiments, $R^B$ is $C_{1-10}$ carbocyclyl of the formula (xii-c):

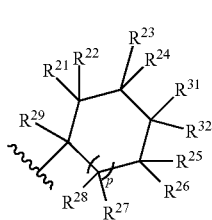

wherein p, $R^{21}$, $R^{22}$, $R^{23}$, $R^{24}$, $R^{25}$, $R^{26}$, $R^{27}$, $R^{28}$, $R^{29}$, $R^{31}$ and $R^{32}$ are as defined above and herein.

Joined Groups $R^B$ and $R^C$

As described generally above, in certain embodiments, $R^B$ and $R^C$ together with the nitrogen (N) atom to which each is attached are joined to form a 5-14 membered ring.

For example, in certain embodiments, $R^B$ and $R^C$ together with the nitrogen (N) atom to which each is attached are joined to form a 5-14 membered ring of the formula (xiv):

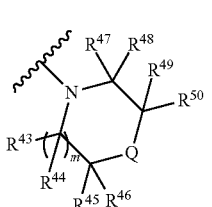

wherein:
Q is N, $NR^{40}$, O, S, or $CR^{41}R^{42}$
m is 0, 1 or 2; and
each instance of $R^{41}$, $R^{42}$, $R^{43}$, $R^{44}$, $R^{45}$, $R^{46}$, $R^{47}$, $R^{48}$, $R^{49}$ and $R^{50}$ is independently selected from hydrogen, halogen, —CN, —NO$_2$, —N$_3$, —SO$_2$H, —SO$_3$H, —OH, —O$R^{F1}$, —ON($R^{F2}$)$_2$, —N($R^{F2}$)$_2$, —N(O$R^{F3}$)$R^{F3}$, —SH, —S$R^{F1}$, —SS$R^{F3}$, —C(=O)$R^{F1}$, —CO$_2$H, —CHO, —C(O$R^{F3}$)$_2$, —CO$_2$$R^{F1}$, OC(=O)$R^{F1}$, —OCO$_2$$R^{F1}$, —C(=O)N($R^{F2}$)$_2$, —OC(=O)N($R^{F2}$)$_2$, —N$R^{F2}$C(=O)$R^{F1}$, —N$R^{F2}$CO$_2$$R^{F1}$, —N$R^{F2}$C(=O)N($R^{F2}$)$_2$, —C(=N$R^{F2}$)O$R^{F1}$, —OC(=N$R^{F2}$)$R^{F1}$, —OC(=N$R^{F2}$)O$R^{F1}$, —C(=N$R^{F2}$)N($R^{F2}$)$_2$, —OC(=N$R^{F2}$)N($R^{F2}$)$_2$, —N$R^{F2}$C(=N$R^{F2}$)N($R^{F2}$)$_2$, —C(=O)N$R^{F2}$SO$_2$$R^{BC1}$, —N$R^{F2}$SO$_2$$R^{F1}$, —SO$_2$N($R^{F2}$)$_2$, —SO$_2$$R^{F1}$, —SO$_2$O$R^{F1}$, —OSO$_2$$R^{F1}$, —S(=O)$R^{F1}$, —OS(=O)$R^{F1}$, —Si($R^{F1}$)$_3$, —OSi($R^{F1}$)$_3$ —C(=S)N($R^{F2}$)$_2$, —C(=O)S$R^{F1}$, —C(=S)S$R^{F1}$, —SC(=S)S$R^{F1}$, —P(=O)$_2$$R^{F1}$, —OP(=O)$_2$$R^{F1}$, —P(=O)($R^{F1}$)$_2$, —OP(=O)($R^{F1}$)$_2$, —OP(=O)(O$R^{F3}$)$_2$, —P(=O)$_2$N($R^{F2}$)$_2$, —OP(=O)$_2$N(R$^{F2}$)$_2$, —P(=O)(NR$^{F2}$)$_2$, —OP(=O)(NR$^{F2}$)$_2$, —NR$^{F2}$P(=O)(OR$^{F3}$)$_2$, —NR$^{F2}$P(=O)(NR$^{F2}$)$_2$, —P(R$^{F3}$)$_2$, —P(R$^{F3}$)$_3$, —OP(R$^{F3}$)$_2$, —OP(R$^{F3}$)$_3$, —B(OR$^{F3}$)$_2$, or —BR$^{F1}$(OR$^{F3}$), C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, 5-14 membered heteroaryl, -L-R$^D$ and —R$^E$; or one or more of R$^{47}$ and R$^{49}$, R$^{48}$ and R$^{50}$, R$^{49}$ and R$^{41}$, R$^{50}$ and R$^{42}$, R$^{41}$ and R$^{45}$, R$^{42}$ and R$^{46}$, R$^{45}$ and R$^{43}$, and R$^{46}$ and R$^{44}$, are joined to form a double bond or a C$_{3-10}$ carbocyclyl, 3-14 membered heterocyclyl, C$_{6-14}$ aryl or 5-14 membered heteroaryl ring; optionally wherein Q is N, then N and R$^{49}$ or N and R$^{46}$ are joined to form a double bond;

R$^{40}$ is selected from hydrogen, —OH, —OR$^{F1}$, —N(R$^{F3}$)$_2$, —CN, —C(=O)R$^{F1}$, —C(=O)N(R$^{F3}$)$_2$, —CO$_2$R$^{F1}$, —SO$_2$R$^{F1}$, —C(=NR$^{F3}$)OR$^{F1}$, —C(=NR$^{F3}$)N(R$^{F3}$)$_2$, —SO$_2$N(R$^{F3}$)$_2$, —SO$_2$R$^{F3}$, —SO$_2$OR$^{F3}$, —SOR$^{F1}$, —C(=S)N(R$^{F3}$)$_2$, —C(=O)SR$^{F3}$, —C(=S)SR$^{F3}$, —P(=O)$_2$R$^{F1}$, —P(=O)(R$^{F1}$)$_2$, —P(=O)$_2$N(R$^{F3}$)$_2$, —P(=O)(NR$^{F3}$)$_2$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, optionally wherein R$^{49}$ and R$^{40}$ or R$^{40}$ and R$^{45}$ are joined to form a 3-14 membered heterocyclyl, or 5-14 membered heteroaryl ring;

wherein:

each instance of R$^{F1}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl;

each instance of R$^{12}$ is, independently, selected from hydrogen, —OH, —OR$^{F1}$, —N(R$^{F3}$)$_2$, —CN, —C(=O)R$^{F1}$, —C(=O)N(R$^{F3}$)$_2$, —CO$_2$R$^{F1}$, —SO$_2$R$^{F1}$, —C(=NR$^{F3}$)OR$^{F1}$, —C(=NR$^{F3}$)N(R$^{F3}$)$_2$, —SO$_2$N(R$^{F3}$)$_2$, —SO$_2$R$^{F3}$, —SO$_2$OR$^{F3}$, —S(=O)R$^{F1}$, —C(=S)N(R$^{F3}$)$_2$, —C(=O)SR$^{F3}$, —C(=S)SR$^{F3}$, —P(=O)$_2$R$^{F1}$, —P(=O)(R$^{F1}$)$_2$, —P(=O)$_2$N(R$^{F3}$)$_2$, —P(=O)(NR$^{F3}$)$_2$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two R$^2$ groups are joined to form a 3-14 membered heterocyclyl or 5-14 membered heteroaryl ring;

each instance of R$^{F3}$ is independently, selected from hydrogen, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two R$^{F3}$ groups are joined to form a 3-14 membered heterocyclyl or 5-14 membered heteroaryl ring;

and L, R$^D$ and R$^E$ are as defined above and herein.

In certain embodiments, at least one of R$^{40}$, R$^{41}$, R$^{42}$, R$^{43}$, R$^{44}$, R$^{45}$, R$^{46}$, R$^{47}$, R$^{48}$, R$^{49}$ and R$^{50}$ is the group -L-R$^D$ as defined above and herein. In certain embodiments, at least one of R$^{40}$, R$^{41}$, R$^{42}$, R$^{43}$, R$^{44}$, R$^{45}$, R$^{46}$, R$^{47}$, R$^{48}$, R$^{49}$ and R$^{50}$ is selected from —R$^E$ as defined herein.

In certain embodiments, m is 0. In certain embodiments, m is 1. In certain embodiments, m is 2.

In certain embodiments, Q is N. In certain embodiments, Q is NR$^{40}$. In certain embodiments, Q is O. In certain embodiments, Q is S. In certain embodiments, Q is CR$^{41}$R$^{42}$.

In certain embodiments, R$^{47}$ and R$^{49}$ are joined to form a double bond and R$^{48}$ and R$^{50}$ are joined to form a C$_{6-14}$ aryl or 5-14 membered heteroaryl. For example, in certain embodiments, R$^B$ and R$^C$ together with the nitrogen (N) atom to which each is attached are joined to form a 5-14 membered ring of the formula (xv):

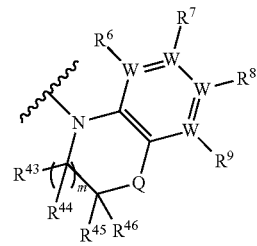

(xv)

wherein Q, m, W, R$^{41}$, R$^{42}$, R$^{43}$, R$^{44}$, R$^{45}$, R$^{46}$, R$^6$, R$^7$, R$^8$ and R$^9$ are as defined above and herein.

In certain embodiments, Q is CR$^{41}$R$^{42}$, R$^{49}$ and R$^{41}$ are joined to form a double bond and R$^{50}$ and R$^{42}$ are joined to form a C$_{6-14}$ aryl or 5-14 membered heteroaryl. For example, in certain embodiments, R$^B$ and R$^C$ together with the nitrogen (N) atom to which each is attached are joined to form a group of the formula (xvi):

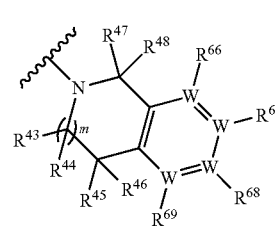

(xvi)

wherein m, W, R$^{43}$, R$^{44}$, R$^{45}$, R$^{46}$, R$^{47}$ and R$^{48}$ are as defined above and herein; and wherein R$^{66}$, R$^{67}$, R$^{68}$ and R$^{69}$ are independently selected from the group consisting of hydrogen, halogen, —CN, —NO$_2$, —N$_3$, —SO$_2$H, —SO$_3$H, —OH, —OR$^{F4}$, —ON(R$^{F5}$)$_2$, —N(R$^{F5}$)$_2$, —N(OR$^{F6}$)R$^{F6}$, —SH, —SR$^{F4}$, —SSR$^{F6}$, —C(=O)R$^{F4}$, —CO$_2$H, —CHO, —C(OR$^{F6}$)$_2$, —CO$_2$R$^{F4}$, —OC(=O)R$^{F4}$, —OCO$_2$R$^{F4}$, —C(=O)N(R$^{F5}$)$_2$, —OC(=O)N(R$^{F5}$)$_2$, —NR$^{F5}$C(=O)R$^{F4}$, —NR$^{F5}$CO$_2$R$^{F4}$, —NR$^{F5}$C(=O)N(R$^{F5}$)$_2$, —C(=NR$^{F5}$)OR$^{F4}$, —OC(=NR$^{F5}$)R$^{F4}$, —OC(=NR$^{F5}$)OR$^{F4}$, —C(=NR$^{F5}$)N(R$^{F5}$)$_2$, —OC(=NR$^{F5}$)N(R$^{F5}$)$_2$, —NR$^{F5}$C(=NR$^{F5}$)N(R$^{F5}$)$_2$, —C(=O)NR$^{F5}$SO$_2$R$^{F4}$, —NR$^{F5}$SO$_2$R$^{F4}$, —SO$_2$N(R$^{F5}$)$_2$, —SO$_2$R$^{F4}$, —SO$_2$OR$^{F4}$, —OSO$_2$R$^{F4}$, —S(=O)R$^{F4}$, —OS(=O)R$^{F4}$, —Si(R$^{F4}$)$_3$, —OSi(R$^{F4}$)$_3$ —C(=S)N(R$^{F5}$)$_2$, —C(=O)SR$^{F4}$, —C(=S)SR$^{F4}$, —SC(S)SR$^{F4}$, —P(=O)$_2$R$^{F4}$, —OP(=O)$_2$R$^{F4}$, —P(=O)(R$^{F4}$)$_2$, —OP(=O)(R$^{F4}$)$_2$, —OP(=O)(OR$^{F6}$)$_2$, —P(=O)$_2$N(R$^{F5}$)$_2$, —OP(=O)$_2$N(R$^{F5}$)$_2$, —P(=O)(NR$^{F5}$)$_2$, —OP(=O)(NR$^{F5}$)$_2$, —NR$^{F5}$P(=O)(OR$^{F6}$)$_2$, —NR$^{F5}$P(=O)(NR$^{F5}$)$_2$, —P(R$^{F6}$)$_2$, —P(R$^{F6}$)$_3$, —OP(R$^{F6}$)$_2$, —OP(R$^{F6}$)$_3$, —B(OR$^{F6}$)$_2$, or —BR$^{F4}$(OR$^{F6}$), C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, 5-14 membered heteroaryl, -L-R$^D$ and —R$^E$; or one or more of R$^{66}$ and R$^{67}$, R$^{67}$ and R$^{68}$, and R$^{68}$ and R$^{69}$ are joined to form a C$_{3-10}$ carbocyclyl, 3-14 membered heterocyclyl, C$_{6-14}$ aryl or 5-14 membered heteroaryl ring;

each instance of R$^{F4}$ is, independently, selected from C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl;

each instance of $R^{F5}$ is, independently, selected from hydrogen, —OH, —OR$^{F4}$, —N(R$^{F6}$)$_2$, —CN, —C(=O)R$^{F4}$, —C(=O)N(R$^{F6}$)$_2$, —CO$_2$R$^{F4}$, —SO$_2$R$^{F4}$, —C(=NR$^{F6}$)OR$^{F4}$, —C(=NR$^{F6}$)N(R$^{F6}$)$_2$, —SO$_2$N(R$^{F6}$)$_2$, —SO$_2$R$^{F6}$, —SO$_2$OR$^{F6}$, —SOR$^{F4}$, —C(=S)N(R$^{F6}$)$_2$, —C(=O)SR$^{F6}$, —C(=S)SR$^{F6}$, —P(=O)$_2$R$^{F4}$, —P(=O)(R$^{F4}$)$_2$, —P(=O)$_2$N(R$^{F6}$)$_2$, —P(=O)(NR$^{F6}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{F5}$ groups are joined to form a 3-14 membered heterocyclyl or 5-14 membered heteroaryl ring; and each instance of $R^{F6}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{F6}$ groups are joined to form a 3-14 membered heterocyclyl or 5-14 membered heteroaryl ring.

In certain embodiments, at least one of $R^{43}$, $R^{44}$, $R^{45}$, $R^{46}$, $R^{47}$, $R^{48}$, $R^{66}$, $R^{67}$, $R^{68}$ and $R^{69}$ is the group -L-R$^D$ as defined above and herein. In certain embodiments, at least one of $R^{43}$, $R^{44}$, $R^{45}$, $R^{46}$, $R^{47}$, $R^{48}$, $R^{66}$, $R^{67}$, $R^{68}$ and $R^{69}$ is selected from —R$^E$ as defined herein.

In certain embodiments, m is 0. In certain embodiments, m is 1. In certain embodiments, m is 2.

Group $R^C$

As described generally above, $R^C$ is selected from hydrogen, —OH, —OR$^{C1}$, —ON(R$^{C2}$)$_2$, —N(R$^{C2}$)$_2$, —C(=O)R$^{C1}$, —CHO, —CO$_2$R$^{C1}$, —C(=O)N(R$^{C2}$)$_2$, —C(=NR$^{C2}$)OR$^{C1}$, —C(=NR$^{C2}$)N(R$^{C2}$)$_2$, —SO$_2$R$^{C1}$, —S(=O)R$^{C1}$, —Si(R$^{C1}$)$_3$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

wherein:

each instance of $R^{C1}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl; and each instance of $R^{C2}$ is, independently, selected from hydrogen, —OH, —OR$^{C1}$, —N(R$^{C3}$)$_2$, —CN, —C(=O)R$^{C1}$, —C(=O)N(R$^{C3}$)$_2$, —CO$_2$R$^{C1}$, —SO$_2$R$^{C1}$, —C(=NR$^{C3}$)OR$^{C1}$, —C(=NR$^{C3}$)N(R$^{C3}$)$_2$, —SO$_2$N(R$^{C3}$)$_2$, —SO$_2$R$^{C3}$, —SO$_2$OR$^{C3}$, —SOR$^{C1}$, —C(=S)N(R$^{C3}$)$_2$, —C(=O)SR$^{C3}$, —C(=S)SR$^{C3}$, —P(=O)$_2$R$^{C1}$, —P(=O)(R$^{C1}$)$_2$, —P(=O)$_2$N(R$^{C3}$)$_2$, —P(=O)(NR$^{C3}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{C2}$ groups are joined to form a 3-14 membered heterocyclyl or 5-14 membered heteroaryl ring;

or $R^B$ and $R^C$ together with the nitrogen (N) atom to which each is attached are joined to form a 5-14 membered ring.

In certain embodiments, $R^C$ is selected from $C_{1-10}$ alkyl, $C_{1-10}$ perhaloalkyl, $C_{2-10}$ alkenyl, $C_{2-10}$ alkynyl, 3-14 membered heterocyclyl, $C_{3-10}$ carbocyclyl, 3-14 membered heterocyclyl, $C_{6-14}$ aryl, and 5-14 membered heteroaryl.

In certain embodiments, $R^C$ is an unsubstituted group, e.g., selected from unsubstituted $C_{1-10}$ alkyl, unsubstituted $C_{2-10}$ alkenyl, unsubstituted $C_{2-10}$ alkynyl, unsubstituted 3-14 membered heteroaliphatic, unsubstituted $C_{3-10}$ carbocyclyl, unsubstituted 3-14 membered heterocyclyl, unsubstituted $C_{6-14}$ aryl and unsubstituted 5-14 membered heteroaryl. However, in certain embodiments, $R^C$ is an unsubstituted group wherein —CH$_3$ and —CH$_2$CH$_3$ are excluded.

In certain embodiments, $R^C$ is a group having 2 or more carbon atoms, e.g., selected from $C_{2-10}$ alkyl, $C_{2-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl. In certain embodiments, $R^C$ is an unsubstituted group having 2 or more carbon atoms. However, in certain embodiments, $R^C$ is a group having 2 or more carbon atoms wherein —CH$_2$CH$_3$ is excluded.

In certain embodiments, $R^C$ is a group having 3 or more carbon atoms, e.g., selected from $C_{3-10}$ alkyl, $C_{3-10}$ perhaloalkyl, $C_{3-10}$ alkenyl, $C_{3-10}$ alkynyl, 3-14 membered heteroaliphatic, $C_{3-10}$ carbocyclyl, 3-14 membered heterocyclyl, $C_{6-14}$ aryl, and 5-14 membered heteroaryl. In certain embodiments, $R^C$ is an unsubstituted group having 3 or more carbon atoms. However, in certain embodiments, $R^C$ is a group having 3 or more carbon atoms wherein —CH(CH$_3$)$_2$ is excluded.

In certain embodiments, $R^C$ is a group having 4 or more carbon atoms, e.g., selected from $C_{4-10}$ alkyl, $C_{4-10}$ perhaloalkyl, $C_{4-10}$ alkenyl, $C_{4-10}$ alkynyl, 5-14 membered heteroaliphatic, $C_{5-10}$ carbocyclyl, 5-14 membered heterocyclyl, $C_{6-14}$ aryl, and 5-14 membered heteroaryl. In certain embodiments, $R^C$ is an unsubstituted group having 4 or more carbon atoms.

In certain embodiments, $R^C$ is an acyclic group, e.g., selected from $C_{1-10}$ alkyl, $C_{2-10}$ alkenyl, $C_{2-10}$ alkynyl and 3-14 membered heteroaliphatic. In certain embodiments, $R^C$ is an unsubstituted acyclic group, e.g., selected from unsubstituted $C_{1-10}$ alkyl, unsubstituted $C_{2-10}$ alkenyl, unsubstituted $C_{2-10}$ alkynyl and unsubstituted 3-14 membered heteroaliphatic. However, in certain embodiments, $R^C$ is an acyclic group, wherein —CH$_3$ and —CH$_2$CH$_3$ are excluded.

In certain embodiments, $R^C$ is $C_{1-10}$ alkyl. In certain embodiments, $R^C$ is an unsubstituted $C_{1-10}$ alkyl. In certain embodiments, $R^C$ is $C_{1-10}$ alkyl, wherein —CH$_3$ is excluded. In certain embodiments, $R^C$ is $C_{1-10}$ alkyl, wherein —CH$_2$CH$_3$ is excluded. In certain embodiments, $R^C$ is $C_{1-10}$ alkyl, wherein —CH(CH$_3$)$_2$ is excluded.

In certain embodiments, $R^C$ is $C_{2-10}$ alkyl, e.g., selected from ethyl, n-propyl, isopropyl, n-butyl, tert-butyl, sec-butyl, iso-butyl, n-pentyl, pentan-3-yl, amyl, neopentyl, 3-methyl-2-butanyl, tertiary amyl and n-hexyl. In certain embodiments, $R^C$ is an unsubstituted $C_{2-10}$ alkyl. In certain embodiments, $R^C$ is $C_{2-10}$ alkyl, wherein —CH$_2$CH$_3$ is excluded. In certain embodiments, $R^C$ is $C_{2-10}$ alkyl, wherein —CH(CH$_3$)$_2$ is excluded.

In certain embodiments, $R^C$ is $C_{3-10}$ alkyl, e.g., selected from n-propyl, isopropyl, n-butyl, tert-butyl, sec-butyl, iso-butyl, n-pentyl, pentan-3-yl, amyl, neopentyl, 3-methyl-2-butanyl, tertiary amyl and n-hexyl. In certain embodiments, $R^C$ is an unsubstituted $C_{3-10}$ alkyl. In certain embodiments, $R^C$ is $C_{3-10}$ alkyl, wherein —CH(CH$_3$)$_2$ is excluded.

In certain embodiments, $R^C$ is $C_{4-10}$ alkyl, e.g., selected from n-butyl, tert-butyl, sec-butyl, iso-butyl, n-pentyl, pentan-3-yl, amyl, neopentyl, 3-methyl-2-butanyl, tertiary amyl and n-hexyl. In certain embodiments, $R^C$ is an unsubstituted $C_{4-10}$ alkyl.

In certain embodiments, $R^C$ is $C_{2-10}$ alkenyl. In certain embodiments, $R^C$ is an unsubstituted $C_{2-10}$ alkenyl. In certain embodiments, $R^C$ is $C_{2-10}$ alkenyl selected from allyl.

In certain embodiments, $R^C$ is $C_{2-10}$ alkynyl. In certain embodiments, $R^C$ is an unsubstituted $C_{2-10}$ alkynyl.

In certain embodiments, $R^C$ is 3-14 membered heteroaliphatic. In certain embodiments, $R^C$ is an unsubstituted 3-14 membered heteroaliphatic.

In certain embodiments, $R^C$ is a cyclic group, e.g., selected from $C_{3-10}$ carbocyclyl, 3-14 membered heterocyclyl, $C_{6-14}$ aryl and 5-14 membered heteroaryl. In certain embodiments, $R^C$ is an unsubstituted cyclic group, e.g., selected from unsubstituted $C_{3-10}$ carbocyclyl, unsubstituted 3-14 membered heterocyclyl, unsubstituted $C_{6-14}$ aryl and unsubstituted 5-14 membered heteroaryl.

In certain embodiments, $R^C$ is $C_{3-10}$ carbocyclyl. In certain embodiments, $R^C$ is $C_{4-10}$ carbocyclyl. In certain embodiments, $R^C$ is $C_{5-10}$ carbocyclyl. In certain embodiments, $R^C$ is $C_{5-8}$ carbocyclyl. In certain embodiments, $R^C$ is $C_{3-10}$ carbocyclyl selected from cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptadienyl ($C_7$), cycloheptatrienyl ($C_7$) and cyclooctyl ($C_8$). In certain embodiments, $R^C$ is $C_{3-10}$ carbocyclyl selected from cyclopentyl and cyclohexyl. In certain embodiments, $R^C$ is an unsubstituted $C_{3-10}$ carbocyclyl.

In certain embodiments, $R^C$ is 3-14 membered heterocyclyl. In certain embodiments, $R^C$ is 5-10 membered heterocyclyl. In certain embodiments, $R^C$ is 5-6 membered heterocyclyl. In certain embodiments, $R^C$ is 3-14 membered heterocyclyl selected from azirdinyl, oxiranyl, thiorenyl, azetidinyl, oxetanyl, thietanyl, tetrahydrofuranyl, dihydrofuranyl, tetrahydrothiophenyl, dihydrothiophenyl, pyrrolidinyl, dihydropyrrolyl, dioxolanyl, oxathiolanyl, dithiolanyl, piperidinyl, tetrahydropyranyl, dihydropyridinyl, thianyl, piperazinyl, morpholinyl, dithianyl, dioxanyl, azepanyl, oxepanyl thiepanyl, azocanyl, oxecanyl and thiocanyl. In certain embodiments, $R^C$ is 3-14 membered heterocyclyl selected from tetrahydropyranyl. In certain embodiments, $R^C$ is an unsubstituted 3-14 membered heterocyclyl.

In certain embodiments, $R^C$ is $C_{6-14}$ aryl. In certain embodiments, $R^C$ is a $C_{6-14}$ aryl selected from phenyl, naphthyl and anthracyl. In certain embodiments, $R^C$ a $C_{6-14}$ aryl selected from phenyl. In certain embodiments, $R^C$ is an unsubstituted $C_{6-14}$ aryl.

In certain embodiments, $R^C$ is 5-14 membered heteroaryl. In certain embodiments, $R^C$ is 5-10 membered heteroaryl. In certain embodiments, $R^C$ is 5-6 membered heteroaryl. In certain embodiments, $R^C$ is a 5-membered heteroaryl, e.g., selected from pyrrolyl, furanyl, thiophenyl, imidazolyl, pyrazolyl, oxazolyl, isoxazolyl, thiazolyl, isothiazolyl, triazolyl, oxadiazolyl, thiadiazolyl and tetrazolyl. In certain embodiments, $R^A$ is a 6-membered heteroaryl, e.g. selected from pyridinyl, pyridazinyl, pyrimidinyl, pyrazinyl, triazinyl and tetrazinyl. In certain embodiments, $R^C$ is an unsubstituted 5-14 membered heteroaryl.

Exemplary Combinations of Groups $R^A$, $R^B$ and $R^C$

Various combinations of $R^A$, $R^B$ and/or $R^C$ are contemplated herein, and are described in more detail below and herein.

For example, in certain embodiments, both $R^B$ and $R^C$ are cyclic, i.e., $R^B$ is selected from $C_{3-10}$ carbocyclyl, 3-14 membered heterocyclyl, $C_{6-14}$ aryl and 5-14 membered heteroaryl, and $R^C$ is selected from $C_{3-10}$ carbocyclyl, 3-14 membered heterocyclyl, $C_{6-14}$ aryl, and 5-14 membered heteroaryl. In certain embodiments, $R^C$ is a group having 2 or more carbon atoms. In certain embodiments, $R^C$ is a group having 3 or more carbon atoms. In certain embodiments, $R^C$ is a group having 4 or more carbon atoms. In certain embodiments, $R^C$ is an unsubstituted cyclic group.

In certain embodiments, $R^B$ is cyclic and $R^C$ is acyclic, i.e., $R^B$ is selected from $C_{3-10}$ carbocyclyl, 3-14 membered heterocyclyl, $C_{6-14}$ aryl and 5-14 membered heteroaryl, and $R^C$ is selected from —OH, —OR$^{C1}$, —ON(R$^{C2}$)$_2$, —N(R$^{C2}$)$_2$, —C(=O)R$^{C1}$, —CHO, —CO$_2$R$^{C1}$, —C(=O)N(R$^{C2}$)$_2$, —C(=NR$^{C2}$)OR$^{C1}$, —C(=NR$^{C2}$)N(R$^{C2}$)$_2$, —SO$_2$R$^{C1}$, —S(=O)R$^{C1}$, —Si(R$^{C1}$)$_3$, $C_{1-10}$ alkyl, $C_{1-10}$ perhaloalkyl, $C_{2-10}$ alkenyl, $C_{2-10}$ alkynyl, 3-14 membered heteroaliphatic, where R$^{C1}$ and R$^{C2}$ are as defined above and herein. In certain embodiments, $R^C$ is an acyclic group having 2 or more carbon atoms. In certain embodiments, $R^C$ is an acyclic group having 3 or more carbon atoms. In certain embodiments, $R^C$ is an acyclic group having 4 or more carbon atoms. In certain embodiments, $R^C$ is an unsubstituted acyclic group.

In certain embodiments, $R^A$ and $R^B$ are independently selected from $C_{6-14}$ aryl and 5-14 membered heteroaryl. In certain embodiments, $R^A$ is $C_{6-14}$ aryl, and $R^B$ is $C_{6-14}$ aryl or 5-14 membered heteroaryl. In certain embodiments, $R^A$ is 5-14 membered heteroaryl, and $R^B$ is $C_{6-14}$ aryl or 5-14 membered heteroaryl. In certain embodiments, $R^A$ is $C_{6-14}$ aryl or 5-14 membered heteroaryl, and $R^B$ is $C_{6-14}$ aryl. In certain embodiments, $R^A$ is $C_{6-14}$ aryl or 5-14 membered heteroaryl, and $R^B$ is 5-14 membered heteroaryl.

In certain embodiments, both $R^A$ and $R^B$ are $C_{6-14}$ aryl. In certain embodiments, both $R^A$ and $R^B$ are phenyl ($C_6$ aryl). In certain embodiments, $R^A$ is $C_{6-14}$ aryl and $R^B$ is $C_{3-10}$ carbocyclyl.

In certain embodiments, $R^A$ is $C_{6-14}$ aryl and $R^B$ is 5-14 membered heteroaryl.

In certain embodiments, $R^A$ is $C_{6-14}$ aryl and $R^B$ is 3-14 membered heterocyclyl.

In certain embodiments, $R^A$ is $C_{6-14}$ aryl and $R^B$ and $R^C$ together with the nitrogen (N) atom to which each is attached are joined to form a 5-14 membered ring.

In certain embodiments, both $R^A$ and $R^B$ are 5-14 membered heteroaryl.

In certain embodiments, $R^A$ is 5-14 membered heteroaryl and $R^B$ is $C_{3-10}$ carbocyclyl.

In certain embodiments, $R^A$ is 5-14 membered heteroaryl and $R^B$ is $C_{6-14}$ aryl.

In certain embodiments, $R^A$ is 5-14 membered heteroaryl and $R^B$ is 3-14 membered heterocyclyl.

In certain embodiments, $R^A$ is 5-14 membered heteroaryl, and $R^B$ and $R^C$ together with the nitrogen (N) atom to which each is attached are joined to form a 5-14 membered ring.

In certain embodiments, the compound is of the formula (II):

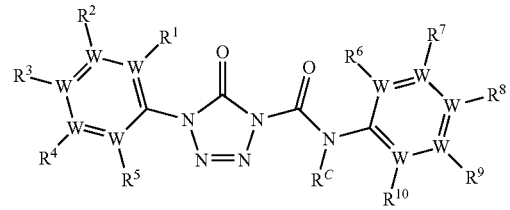

(II)

or a pharmaceutically acceptable form thereof;

wherein $R^C$, W—R$^1$, W—R$^2$, W—R$^3$, W—R$^4$, W—R$^5$, W—R$^6$, W—R$^7$, W—R$^8$, W—R$^9$, and W—R$^{10}$ are as defined above and herein.

In certain embodiments, at least one of R$^6$, R$^7$, R$^8$, R$^9$ and R$^{10}$ of the formula (II) is the group -L-R$^D$ as defined above and herein. In certain embodiments, at least one of R$^6$, R$^7$, R$^8$, R$^9$ and R$^{10}$ of the formula (II) is further selected from the group —R$^E$ as defined above and herein.

In certain embodiments, the compound is of the formulae (II-a), (II-b) or (II-c):

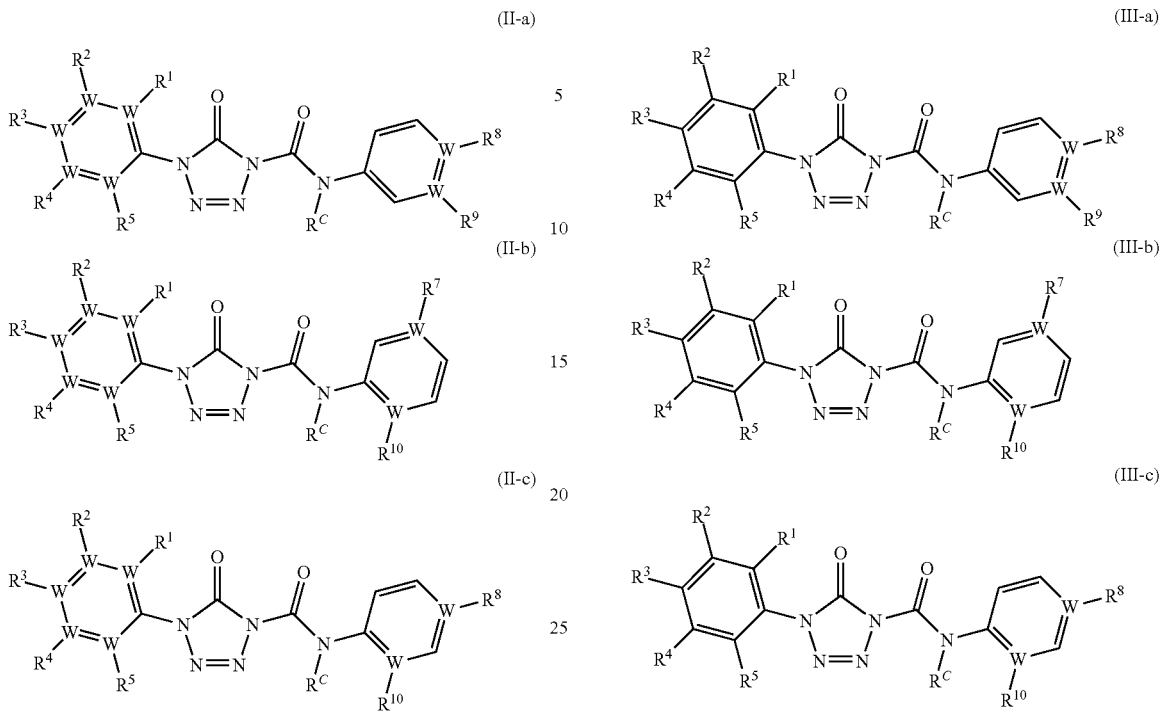

or a pharmaceutically acceptable form thereof;

wherein $R^C$, W—$R^1$, W—$R^2$, W—$R^3$, W—$R^4$, W—$R^5$, W—$R^7$, W—$R^8$, W—$R^9$, and W—$R^{10}$ are as defined above and herein.

In certain embodiments, at least one of $R^7$, $R^8$, $R^9$ and $R^{10}$ of the formulae (II-a), (II-b) or (II-c) is the group -L-$R^D$ as defined above and herein. In certain embodiments, at least one of $R^7$, $R^8$, $R^9$ and $R^{10}$ of the formulae (II-a), (II-b) or (II-c) is further selected from the group —$R^E$ as defined above and herein.

In certain embodiments, the compound is of the formula (III):

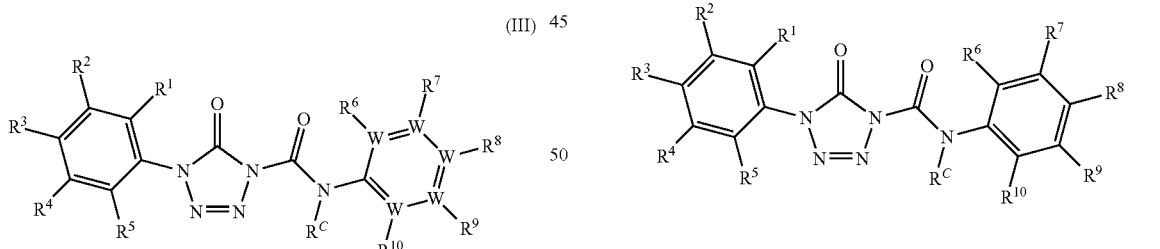

or a pharmaceutically acceptable form thereof, wherein $R^C$, $R^1$, $R^2$, $R^3$, $R^4$, $R^5$, W—$R^6$, W—$R^7$, W—$R^8$, W—$R^9$, and W—$R^{10}$ are as defined above and herein.

In certain embodiments, at least one of $R^6$, $R^7$, $R^8$, $R^9$ and $R^{10}$ of the compound of formula (III) is the group -L-$R^D$ as defined above and herein. In certain embodiments, at least one of $R^6$, $R^7$, $R^8$, $R^9$ and $R^{10}$ of the compound of formula (III) is further selected from the group —$R^E$ as defined above and herein.

In certain embodiments, the compound is of the formulae (III-a), (III-b) or (III-c):

or a pharmaceutically acceptable form thereof, wherein $R^C$, $R^1$, $R^2$, $R^3$, $R^4$, $R^5$, W—$R^7$, W—$R^8$, W—$R^9$, and W—$R^{10}$ are as defined above and herein.

In certain embodiments, at least one of $R^7$, $R^8$, $R^9$ and $R^{10}$ of the formulae (III-a), (III-b) or (III-c) is the group -L-$R^D$ as defined above and herein. In certain embodiments, at least one of $R^7$, $R^8$, $R^9$ and $R^{10}$ of formulae (III-a), (III-b) or (III-c) is further selected from the group —$R^E$ as defined above and herein.

In certain embodiments, the compound is of the formula (IV):

or a pharmaceutically acceptable form thereof;

wherein $R^C$, $R^1$, $R^2$, $R^3$, $R^4$, $R^5$, $R^6$, $R^7$, $R^8$, $R^9$, and $R^{10}$ are as defined above and herein.

In certain embodiments, at least one of $R^6$, $R^7$, $R^8$, $R^9$ and $R^{10}$ of the formula (IV) is the group -L-$R^D$ as defined above and herein. In certain embodiments, at least one of $R^6$, $R^7$, $R^8$, $R^9$ and $R^{10}$ of the formula (IV) is further selected from the group —$R^E$ as defined above and herein. In certain embodiments, $R^1$-$R^5$ are independently H, $C_{1-10}$ alkyl, $C_{1-10}$ alkyloxy, $C_{6-14}$ aryloxy, CN, —$SO_2N(R^{A7})_2$, —$SO_2R^{A6}$, and —$SO_2OR^{A6}$; $R^C$ is unsubstituted $C_{1-10}$ alkyl or unsubstituted $C_{3-10}$ carbocyclyl; and $R^6$-$R^{10}$ are independently selected from H, $C_{1-10}$ alkyl, $C_{1-10}$ alkyloxy, $C_{6-14}$ aryloxy, COOH, and —$CO_2R^{A6}$. In certain embodiments, $R^1$-$R^5$ are independently H, methyl, methoxy, CN, and SO$_2$Me; R$^C$ is unsubstituted C$_{1-3}$ alkyl or unsubstituted C$_{5-6}$ cycloalkyl; and R$^6$-R$^{10}$ are independently selected from H, methyl, methoxy, phenoxy, COOH, and CO$_2$Me.

In certain embodiments, the compound is of the formulae (IV-a), (IV-b), (IV-c) or (IV-d):

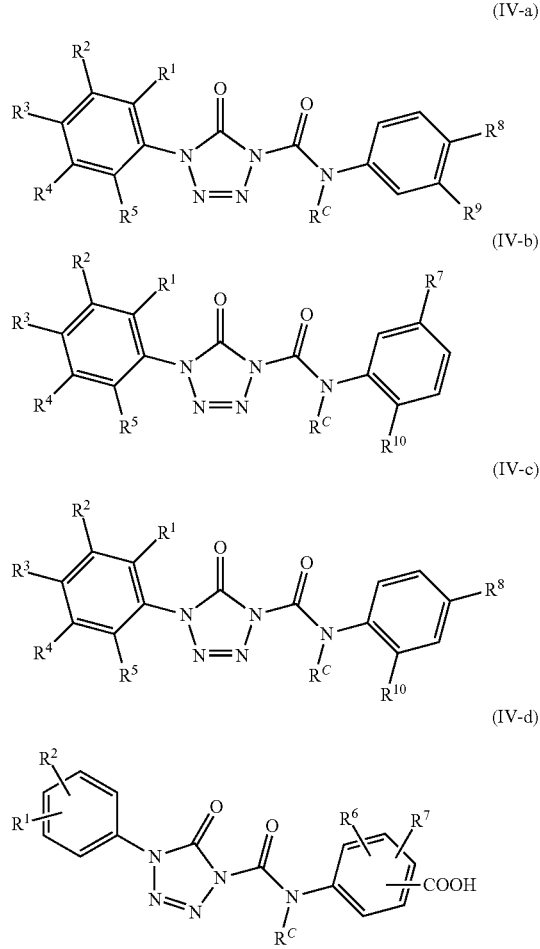

or a pharmaceutically acceptable form thereof;
wherein R$^C$, R$^1$, R$^2$, R$^3$, R$^4$, R$^5$, R$^6$, R$^7$, R$^8$, R$^9$, and R$^{10}$ are as defined above and herein.

In certain embodiments, at least one of R$^7$, R$^8$, R$^9$ and R$^{10}$ of the formulae (IV-a), (IV-b) or (IV-c) is the group -L-R$^D$ as defined above and herein. In certain embodiments, at least one of R$^7$, R$^8$, R$^9$ and R$^{10}$ of the formulae (IV-a), (IV-b), (IV-c) or (IV-d) is further selected from the group —R$^E$ as defined above and herein.

In one embodiment, provided herein is a compound of formula (IV-d), or a pharmaceutically acceptable form thereof. In one embodiment where the compound is of formula (IV-d), R$^C$ is C$_{1-10}$alkyl or C$_{3-10}$carbocyclyl. In one embodiment, R$^C$ is ethyl, isopropyl, cyclopentyl or cyclohexyl.

In another embodiment where the compound is of formula (IV-d), R$^1$ and R$^2$ are each independently hydrogen, halogen, —CN, —OR$^{A1}$ or —SO$_2$R$^{A1}$, wherein R$^{A1}$ is C$_{1-10}$alkyl. In another embodiment, R$^1$ and R$^2$ are each independently hydrogen, fluoro, methoxy, —CN or —SO$_2$CH$_3$.

In another embodiment where the compound is of formula (IV-d), R$^6$ and R$^7$ are each independently hydrogen, halogen or —O—R$^{B1}$, wherein R$^{B1}$ is C$_{1-10}$alkyl or C$_{6-14}$aryl. In another embodiment, R$^6$ and R$^7$ are each independently hydrogen, fluoro, methoxy or phenyloxy.

In certain embodiments, the compound is of the formula (V):

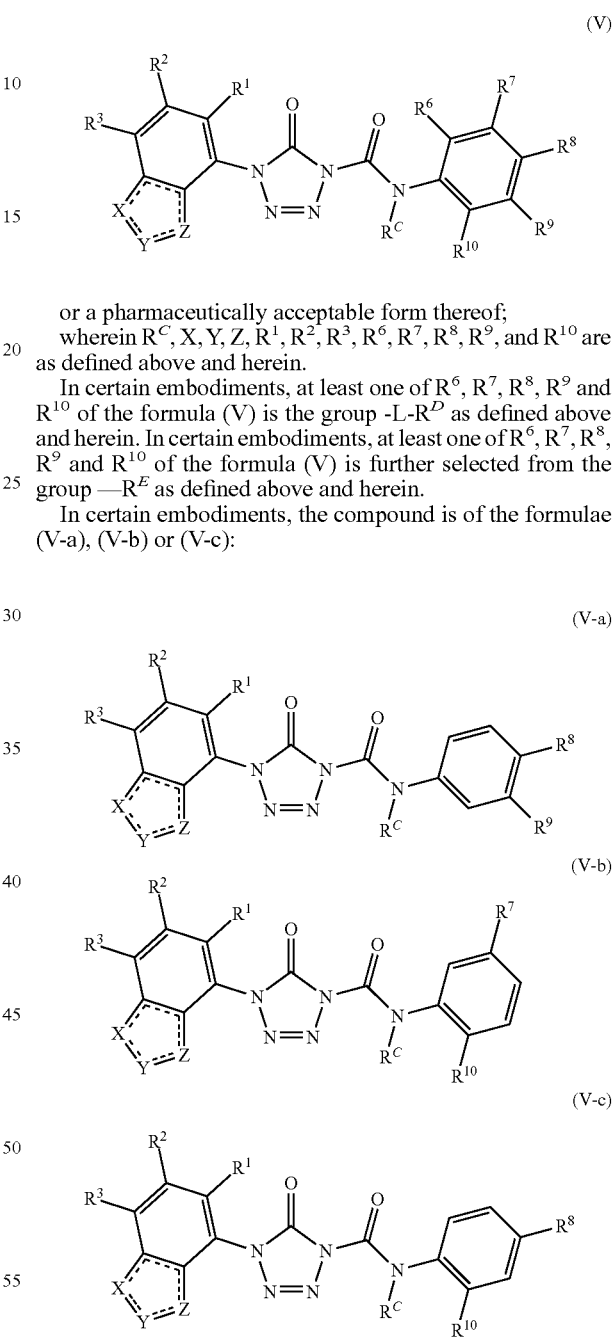

or a pharmaceutically acceptable form thereof;
wherein R$^C$, X, Y, Z, R$^1$, R$^2$, R$^3$, R$^6$, R$^7$, R$^8$, R$^9$, and R$^{10}$ are as defined above and herein.

In certain embodiments, at least one of R$^6$, R$^7$, R$^8$, R$^9$ and R$^{10}$ of the formula (V) is the group -L-R$^D$ as defined above and herein. In certain embodiments, at least one of R$^6$, R$^7$, R$^8$, R$^9$ and R$^{10}$ of the formula (V) is further selected from the group —R$^E$ as defined above and herein.

In certain embodiments, the compound is of the formulae (V-a), (V-b) or (V-c):

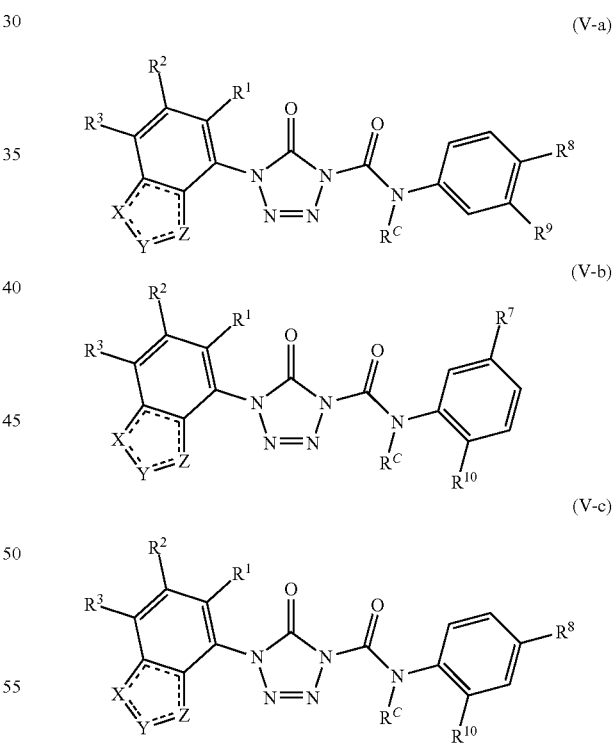

or a pharmaceutically acceptable form thereof;
wherein R$^C$, X, Y, Z, R$^1$, R$^2$, R$^3$, R$^7$, R$^8$, R$^9$, and R$^{10}$ are as defined above and herein.

In certain embodiments, at least one of R$^7$, R$^8$, R$^9$ and R$^{10}$ of the formulae (V-a), (V-b) or (V-c) is the group -L-R$^D$ as defined above and herein. In certain embodiments, at least one of R$^7$, R$^8$, R$^9$ and R$^{10}$ of the formulae (V-a), (V-b) or (V-c) is further selected from the group —R$^E$ as defined above and herein.

In certain embodiments, the compound is of the formula (VI):

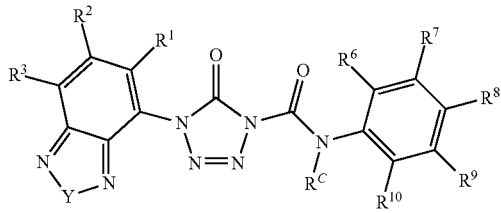

(VI)

or a pharmaceutically acceptable form thereof;
wherein $R^C$, Y, $R^1$, $R^2$, $R^3$, $R^6$, $R^7$, $R^8$, $R^9$, and $R^{10}$ are as defined above and herein.

In certain embodiments, at least one of $R^6$, $R^7$, $R^8$, $R^9$ and $R^{10}$ of the formula (VI) is the group -L-$R^D$ as defined above and herein. In certain embodiments, at least one of $R^6$, $R^7$, $R^8$, $R^9$ and $R^{10}$ of the formula (VI) is further selected from the group —$R^E$ as defined above and herein. In certain embodiments, $R^1$-$R^3$ are independently H, $C_{1-10}$ alkyl, $C_{1-10}$ alkyloxy, $C_{6-14}$ aryloxy, CN, —$SO_2N(R^{A7})_2$, —$SO_2R^{A6}$, and —$SO_2OR^{A6}$; $R^C$ is unsubstituted $C_{1-10}$ alkyl or unsubstituted $C_{3-10}$ carbocyclyl; and $R^6$-$R^{10}$ are independently selected from H, $C_{1-10}$ alkyl, $C_{1-10}$ alkyloxy, $C_{6-14}$ aryloxy, COOH, and —$CO_2R^{A6}$. In certain embodiments, $R^1$-$R^3$ are independently H, methyl, methoxy, and CN; $R^C$ is unsubstituted $C_{5-6}$ cycloalkyl; and $R^6$-$R^{10}$ are independently selected from H, methyl, methoxy, phenoxy, COOH, and $CO_2Me$.

In certain embodiments, the compound is of the formulae (VI-a), (VI-b) or (VI-c):

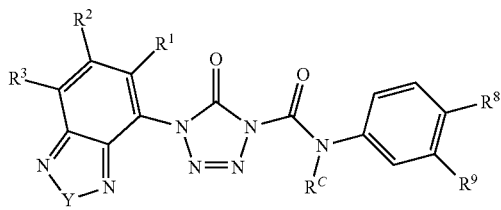

(VI-a)

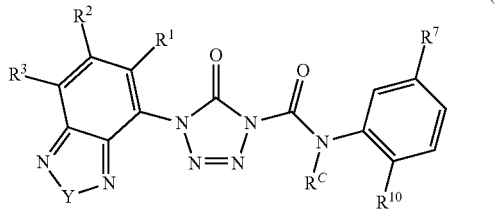

(VI-b)

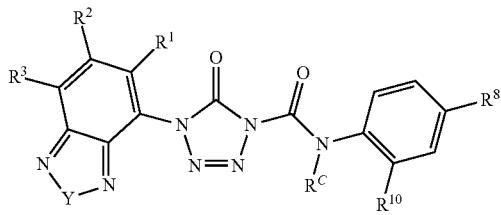

(VI-c)

or a pharmaceutically acceptable form thereof;
wherein $R^C$, Y, $R^1$, $R^2$, $R^3$, $R^7$, $R^8$, $R^9$, and $R^{10}$ are as defined above and herein.

In certain embodiments, at least one of $R^7$, $R^8$, $R^9$ and $R^{10}$ of the formulae (VI-a), (VI-b) or (VI-c) is the group -L-$R^D$ as defined above and herein. In certain embodiments, at least one of $R^7$, $R^8$, $R^9$ and $R^{10}$ of the formulae (VI-a), (VI-b) or (VI-c) is further selected from the group —$R^E$ as defined above and herein.

Exemplary Compounds

Exemplary compounds are set forth in the Exemplification and listed in Tables 1, 2, 3 and 4 provided therein.

In certain embodiments, a compound of formula (I) is selected from any of the compounds provided in Tables 1, 2, 3 or 4. In certain embodiments, a compound of formula (I) is selected from any of the compounds provided in Table 1. In certain embodiments, a compound of formula (I) is selected from any of the compounds provided in Table 2. In certain embodiments, a compound of formula (I) is selected from any of the compounds provided in Table 3. In certain embodiments, a compound of formula (I) is selected from any of the compounds provided in Table 4.

In certain embodiments, a compound of formula (I) is selected from any of the compounds provided in Tables 1, 2 or 3. In certain embodiments, a compound of formula (I) is selected from any of the compounds provided in Tables 1 or 2. In certain embodiments, a compound of formula (I) is selected from any of the compounds provided in Tables 1 or 3. In certain embodiments, a compound of formula (I) is selected from any of the compounds provided in Tables 1 or 4. In certain embodiments, a compound of formula (I) is selected from any of the compounds provided in Tables 2 or 3. In certain embodiments, a compound of formula (I) is selected from any of the compounds provided in Tables 2 or 4.

Activities provided from the FASN NADPH Consumption Assay are designated in Tables 1, 2, 3 and 4 with a star (*), wherein "A*" refers to compounds having an $IC_{50}$ of less than 60 nM; "B*" refers to compounds having an $IC_{50}$ of 60 nM to 250 nM, inclusive; "C*" refers to compounds having an $IC_{50}$ of greater than 250 nM to 1000 nM, inclusive; "D*" refers to compounds having an $IC_{50}$ of greater than 1000 nM to 10,000 nM, inclusive; and "E*" refers to compounds having an $IC_{50}$ of greater than 10,000 nM, as measured by the assay.

Activities provided from the FASN Scintillation Proximity Flashplate Assay are provided in Tables 1, 2, 3 and 4, wherein "A" refers to compounds having an $IC_{50}$ of less than 15 nM/mL; "B" refers to compounds having an $IC_{50}$ of 15 nM to 100 nM, inclusive; "C" refers to compounds having an $IC_{50}$ of greater than 100 nM to 200 nM, inclusive; "D" refers to compounds having an $IC_{50}$ of greater than 200 nM to 5000 nM, inclusive; and "E" refers to compounds having an $IC_{50}$ of greater than 5000 nM, as measured by the assay.

In certain embodiments, a compound of formula (I) is any of the compounds provided in Tables 1, 2 or 3 having an activity of "A", "A*", "B". "B*", "C" or "C*". In certain embodiments, a compound of formula (I) is any of the compounds provided in Tables 1, 2 or 3 having an activity of "A" or "A*". In certain embodiments, a compound of formula (I) is any of the compounds provided in Tables 1, 2 or 3 having an activity of "B" or "B*". In certain embodiments, a compound of formula (I) is any of the compounds provided in Tables 1, 2 or 3 having an activity of "C" or "C*".

In certain embodiments, compounds provided herein include any of the compounds provided in Tables 1, 2 or 3 substituted with a group -L-$R^D$, as defined above and herein, and having an activity of "A", "A*", "B" or "B*".

For example, in certain embodiments, the compound of formula (I) is a compound selected from the group consisting of:

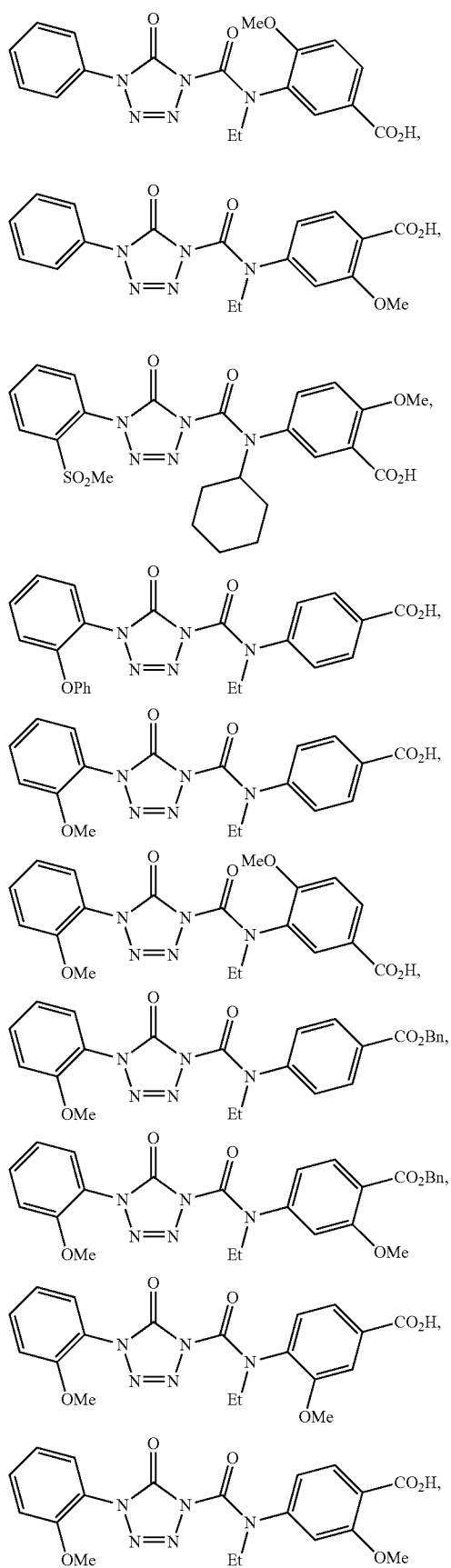
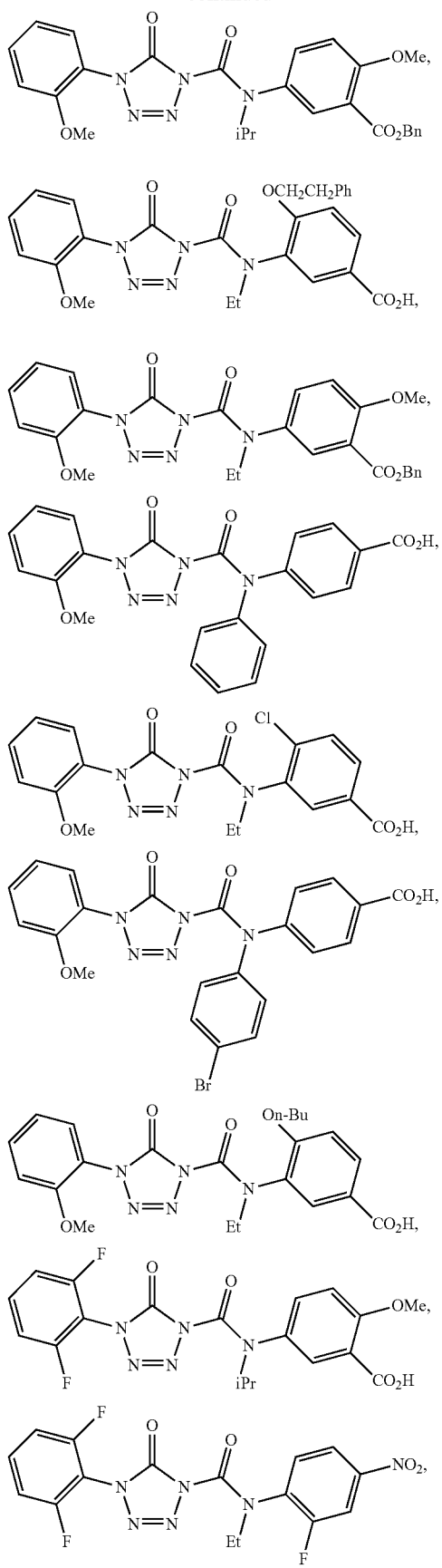

67
-continued
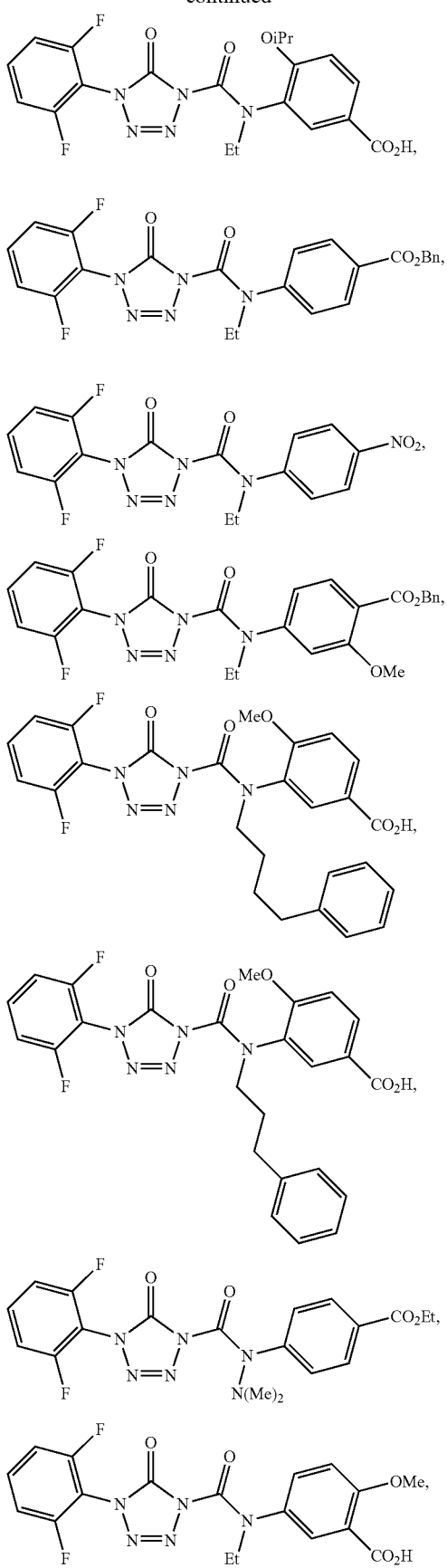
68
-continued
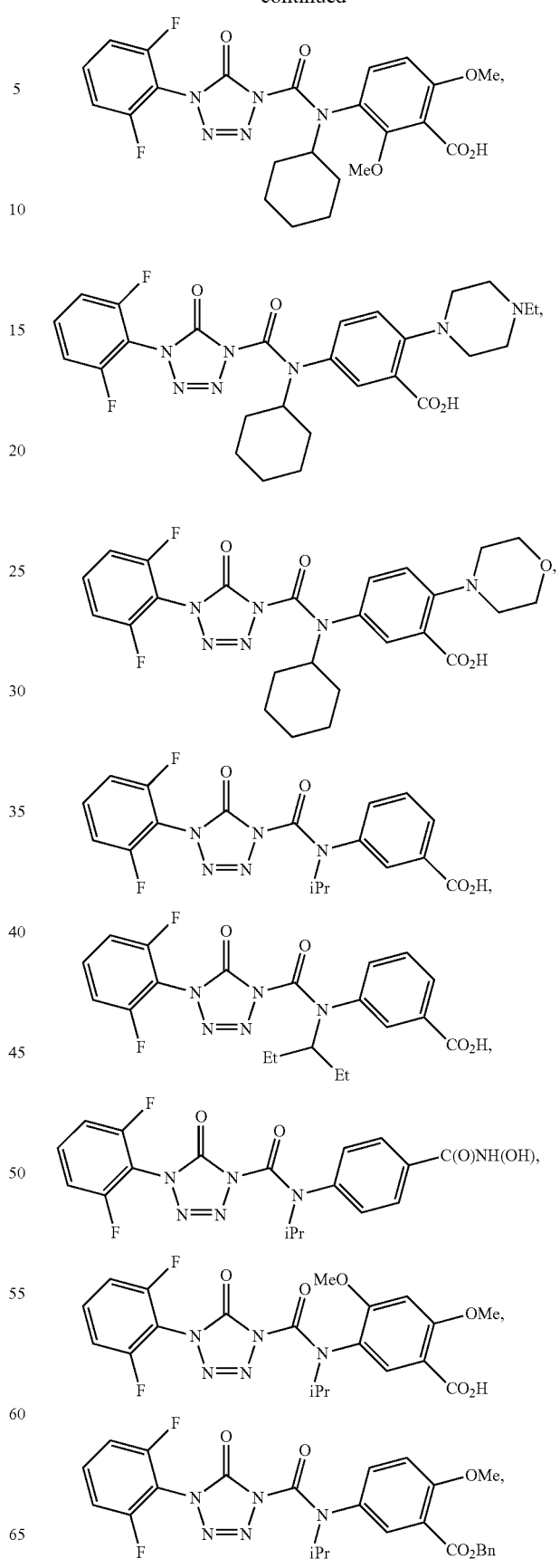

69
-continued
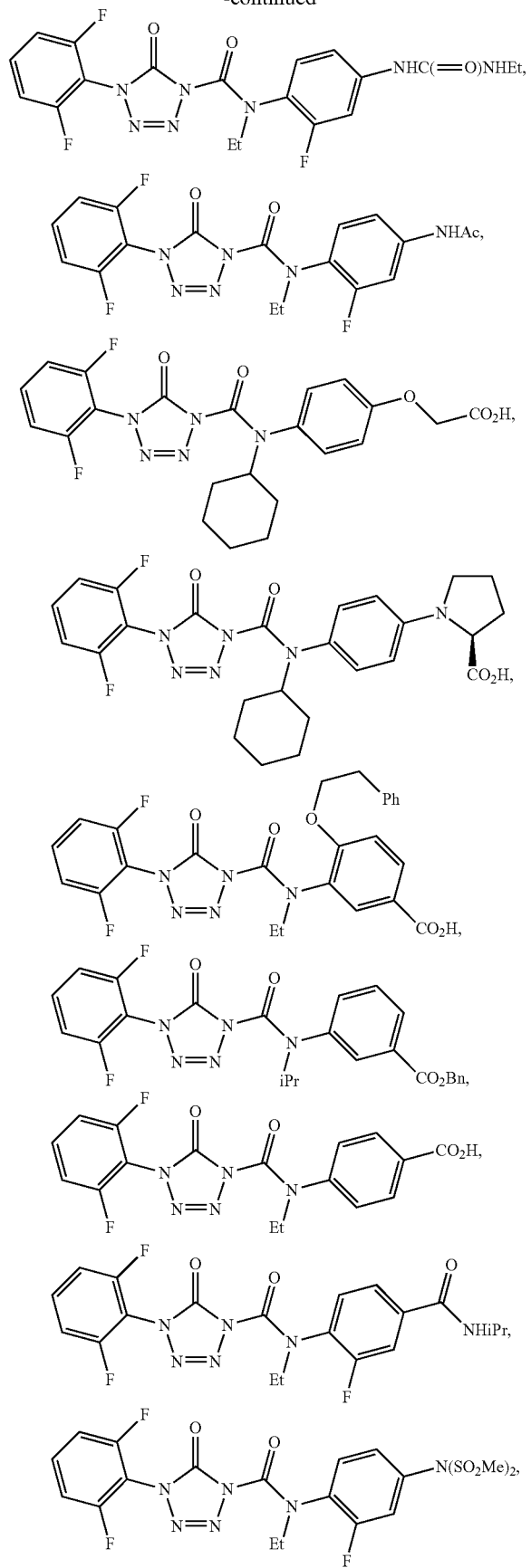
70
-continued
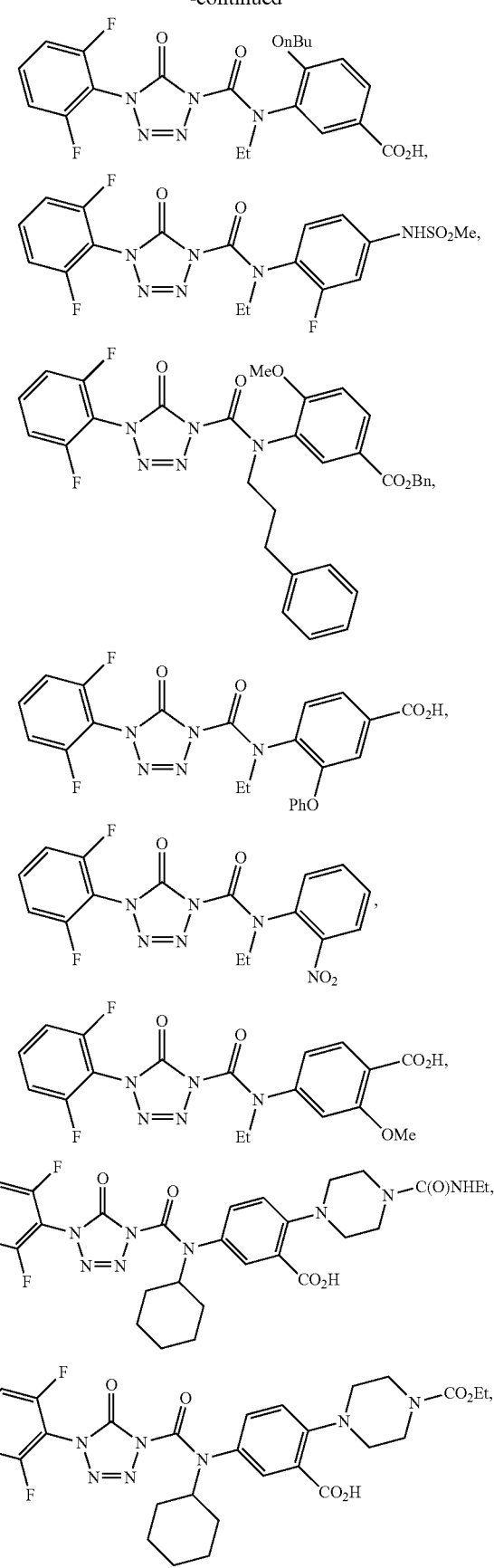

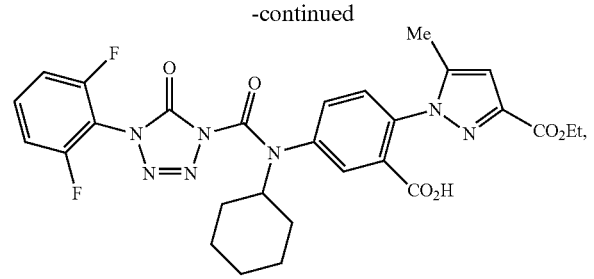
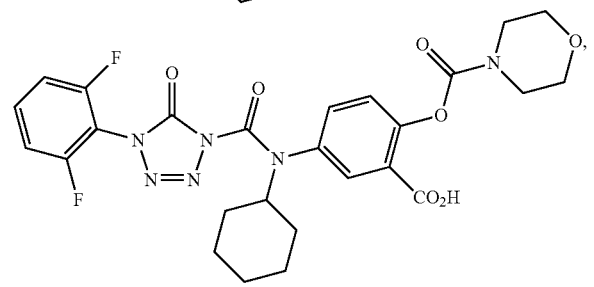
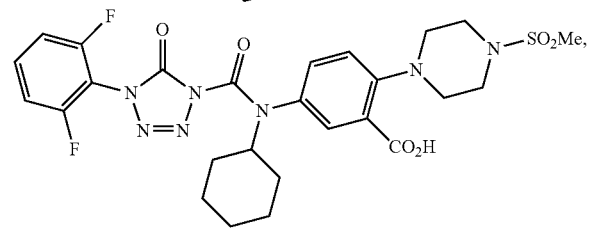
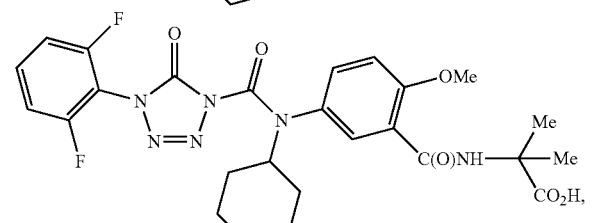
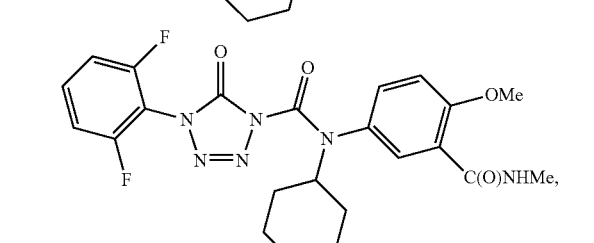
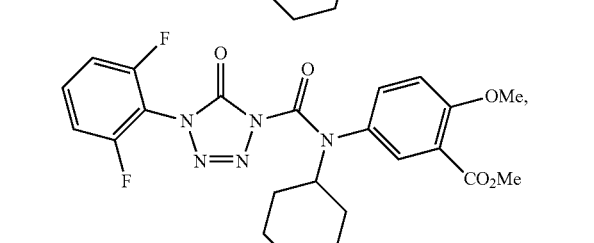
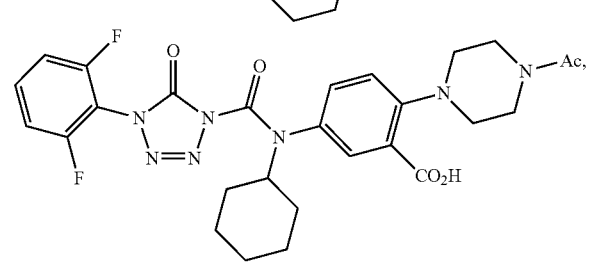
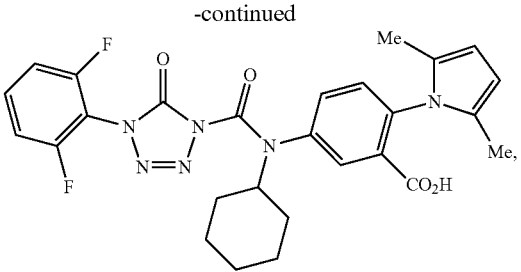
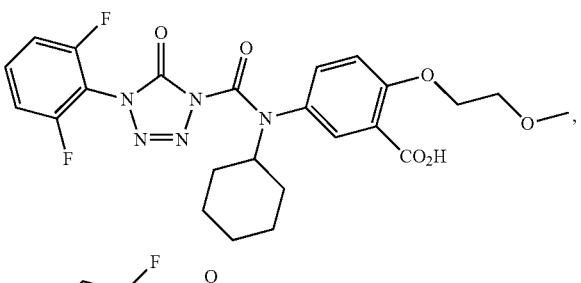
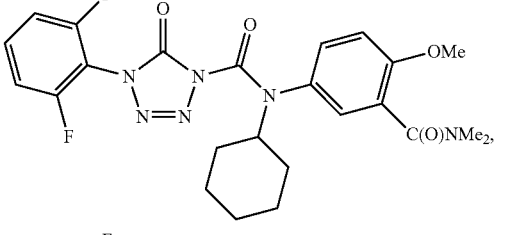
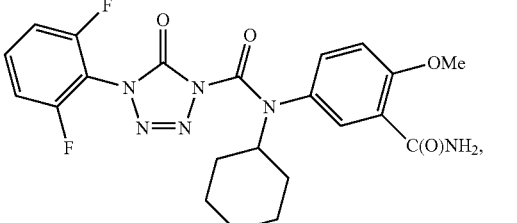
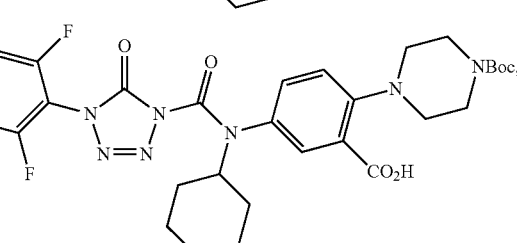
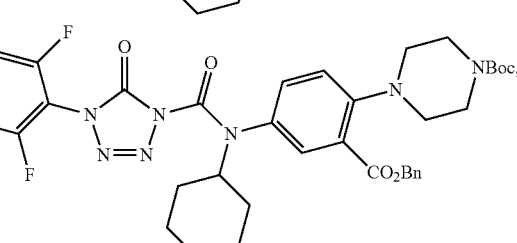
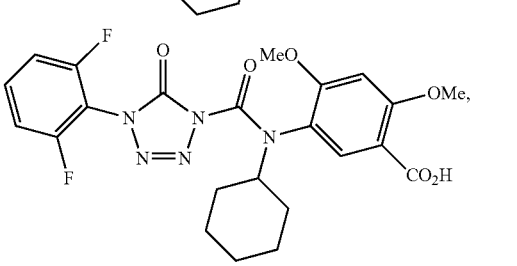

73
-continued
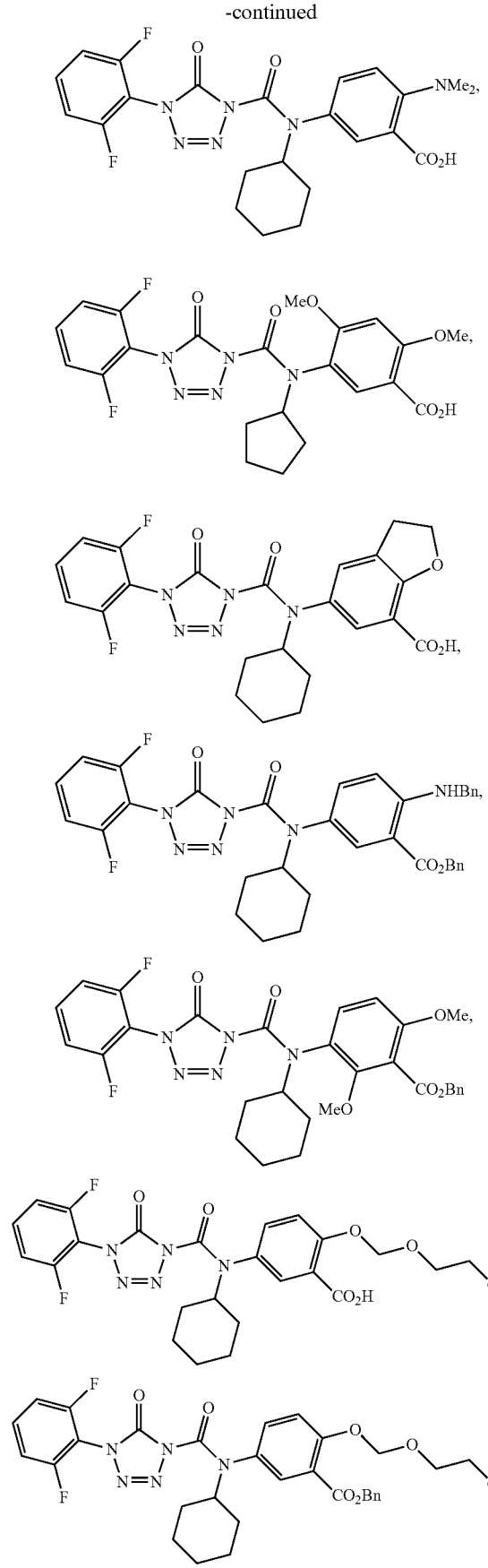
74
-continued
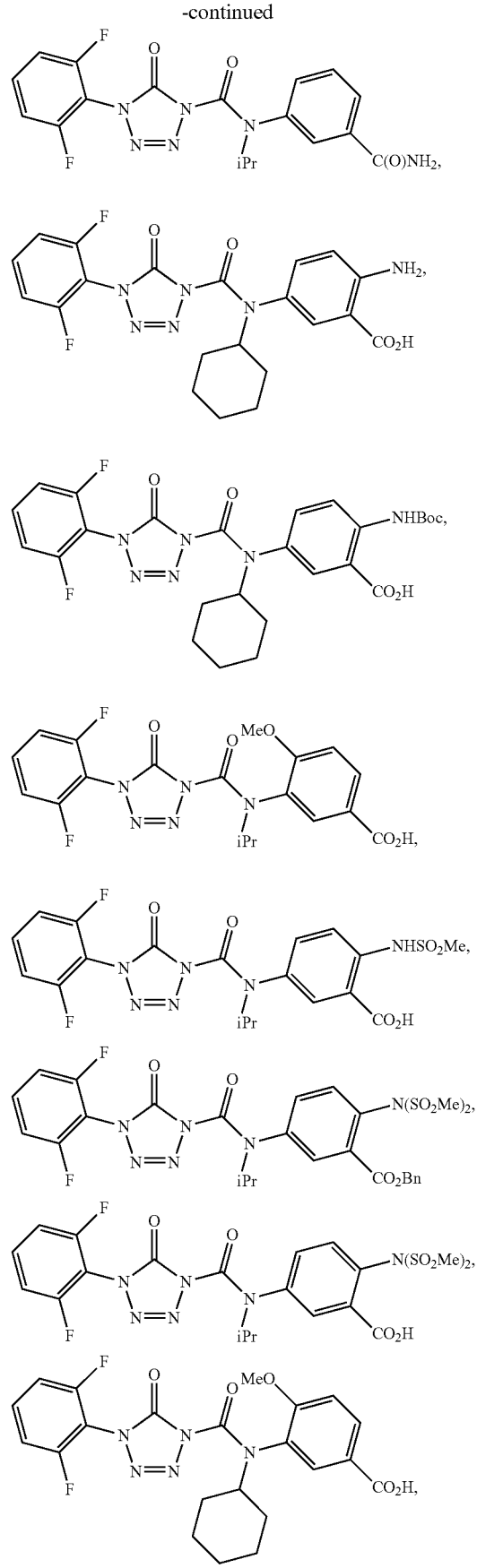

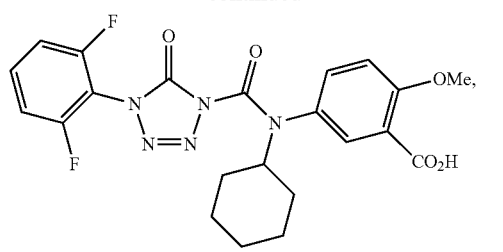
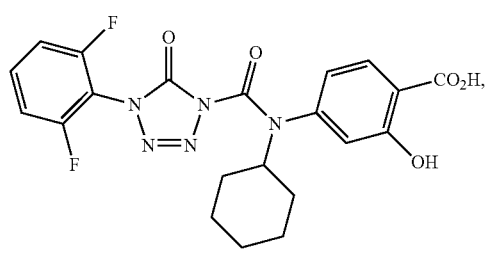
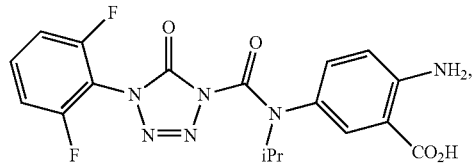
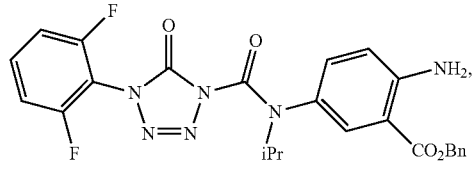
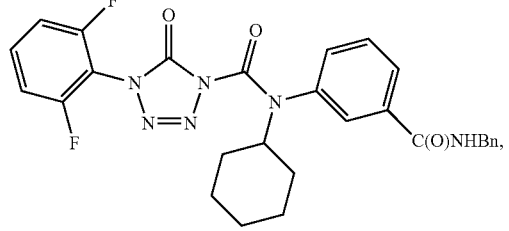
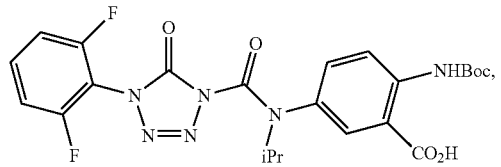
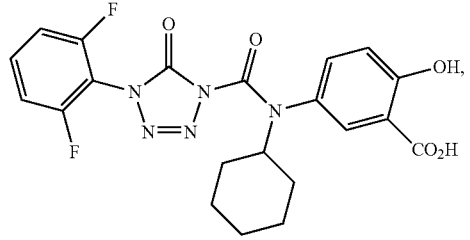
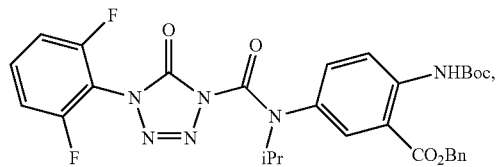
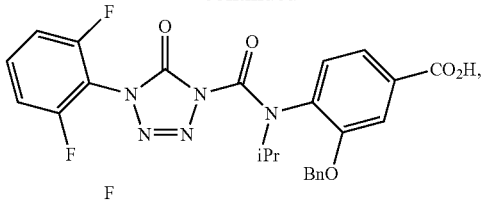
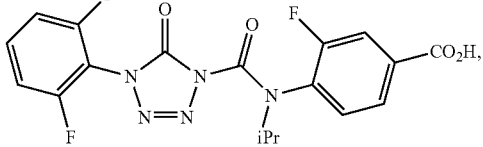
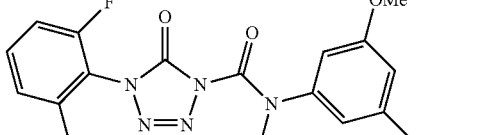
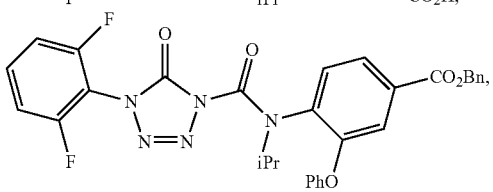
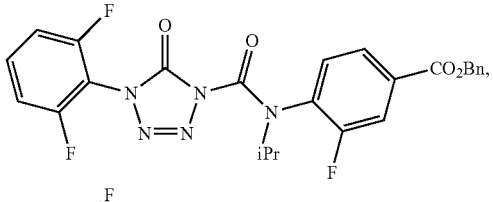
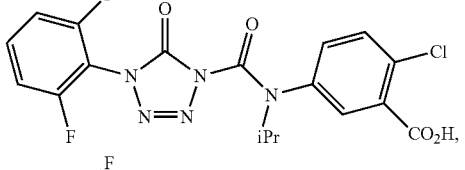
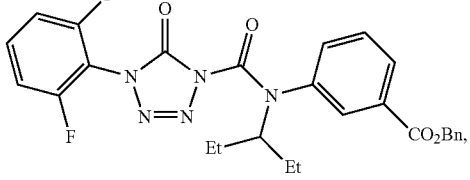
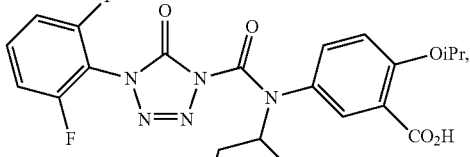
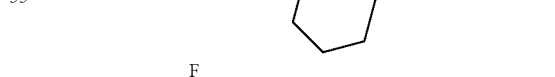
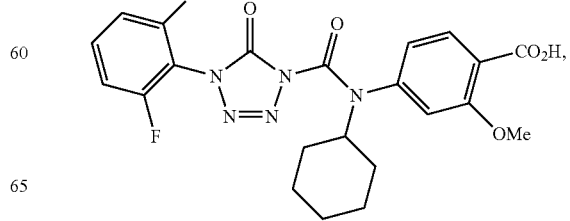

77
-continued
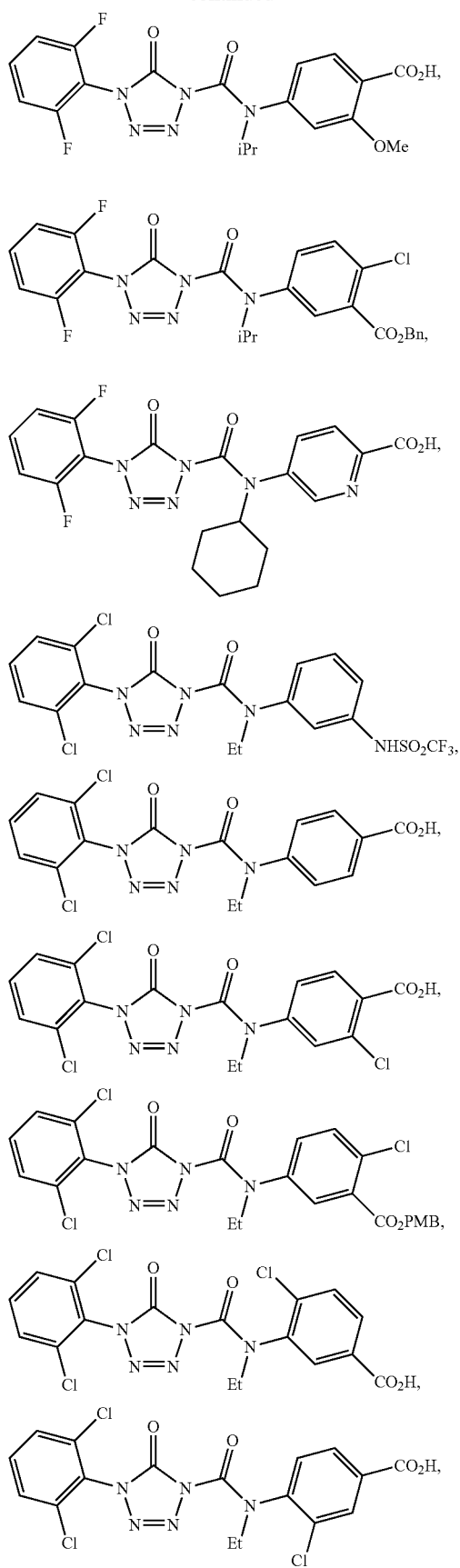
78
-continued
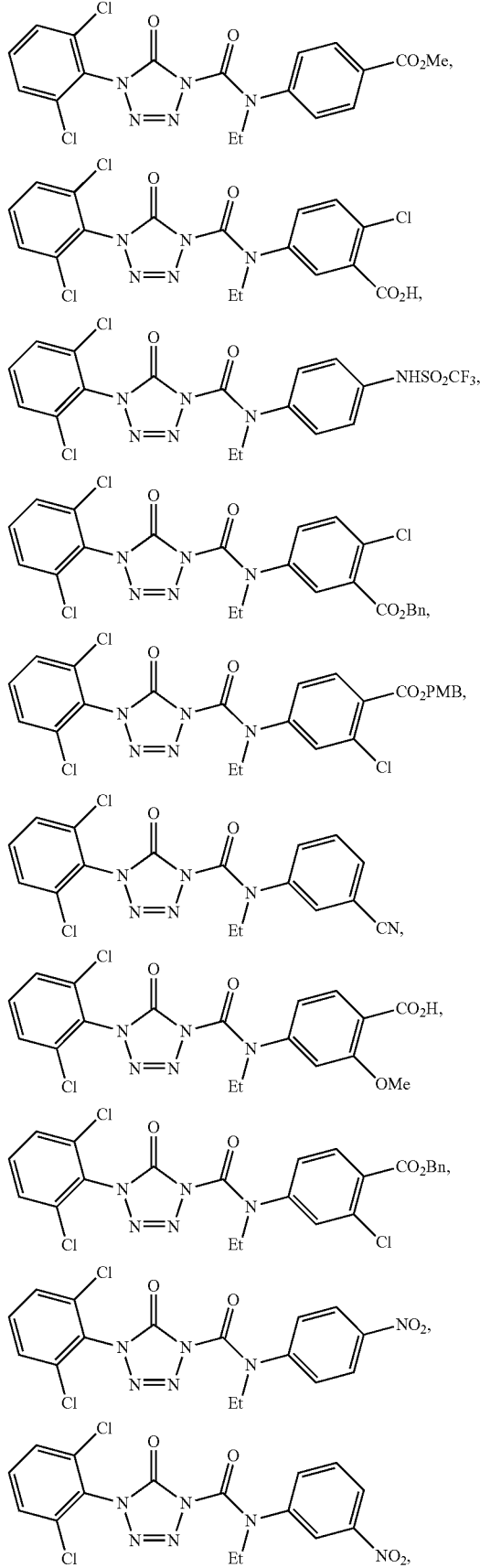

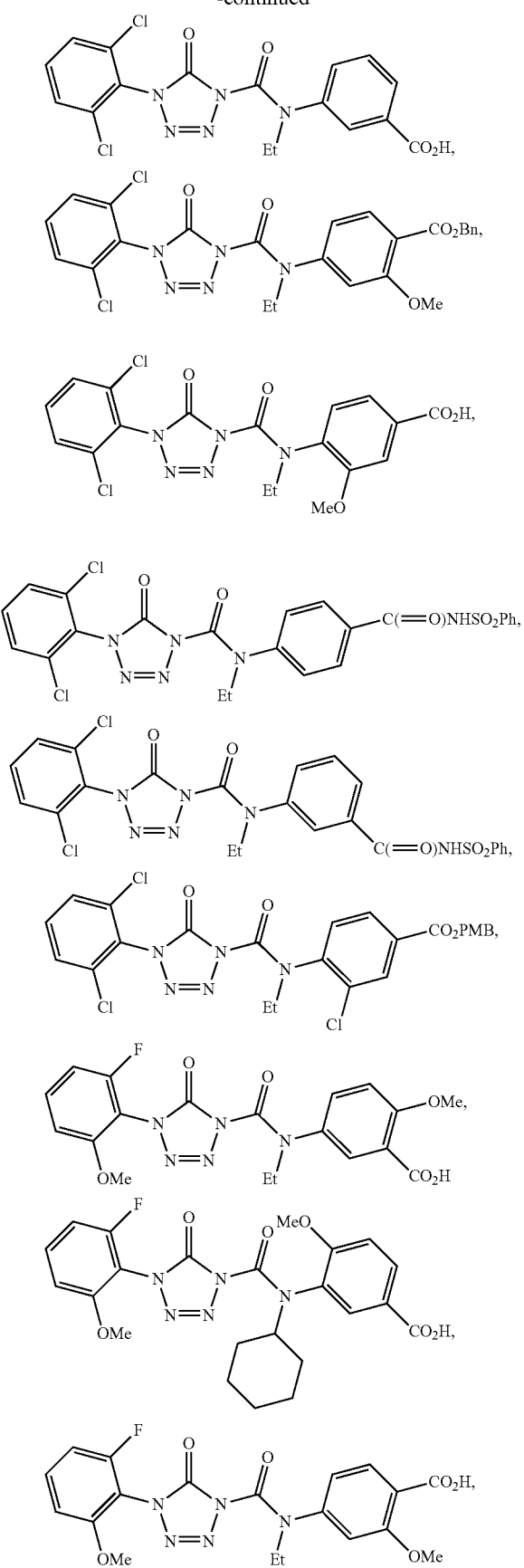
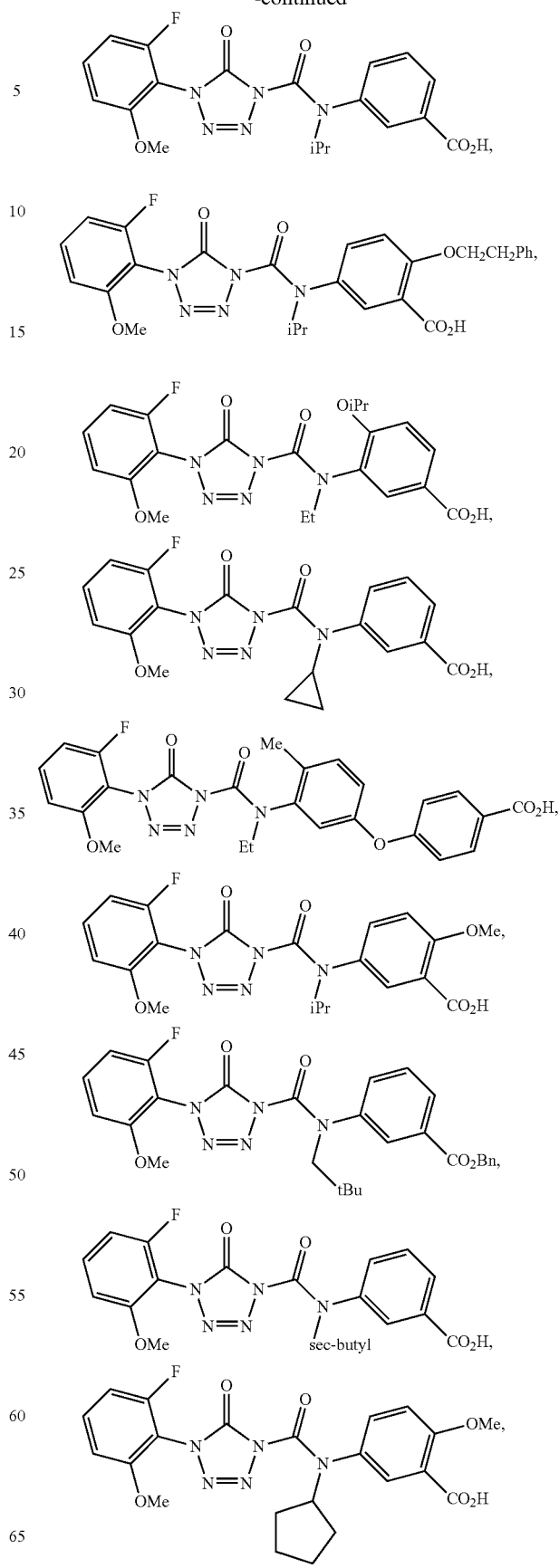

81
-continued
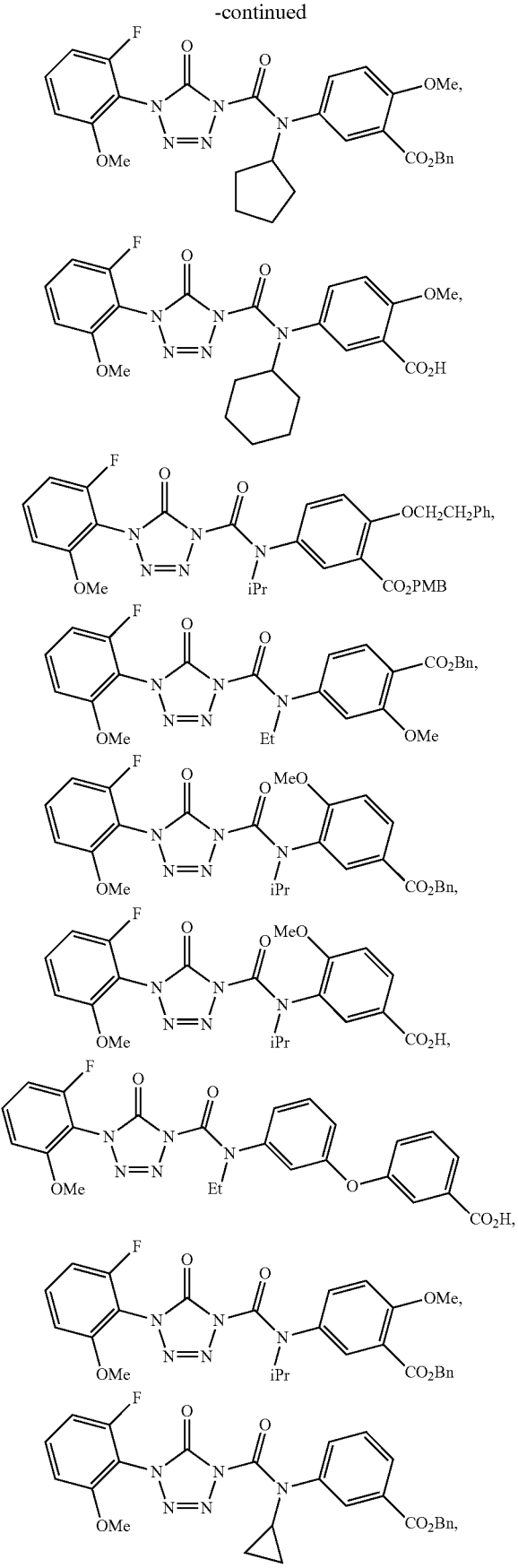
82
-continued
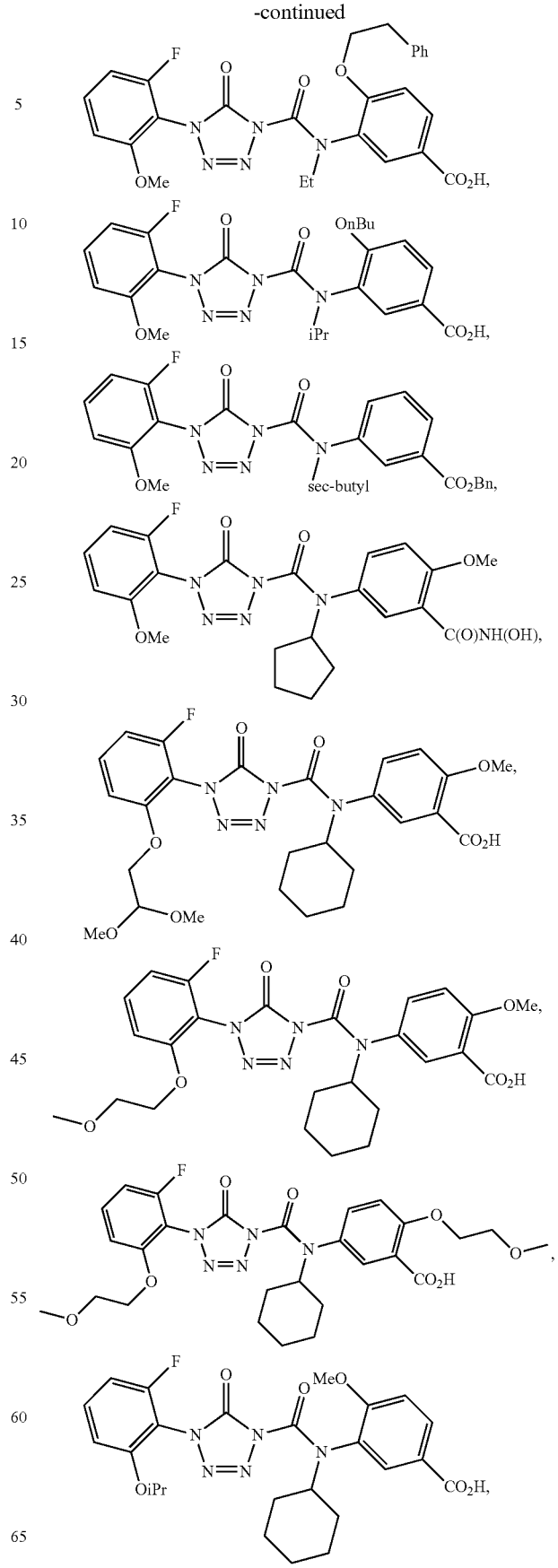

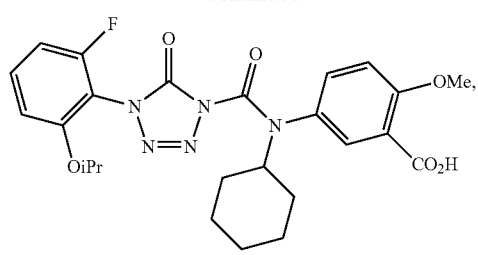
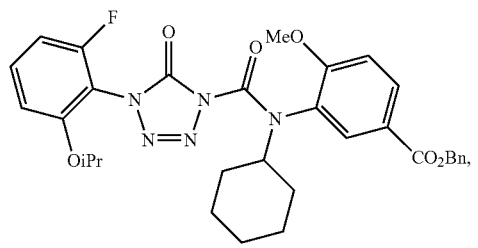
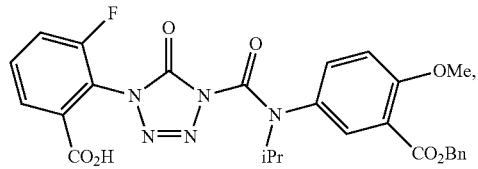
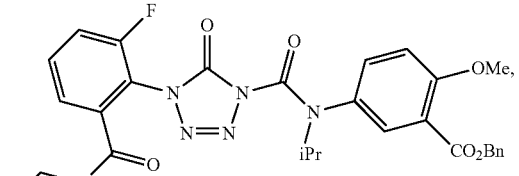
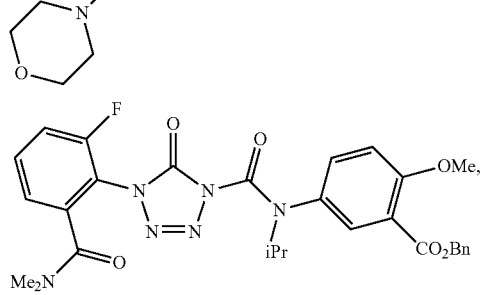
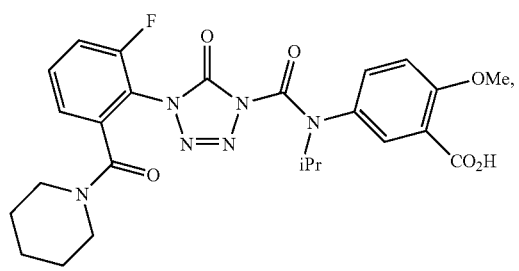
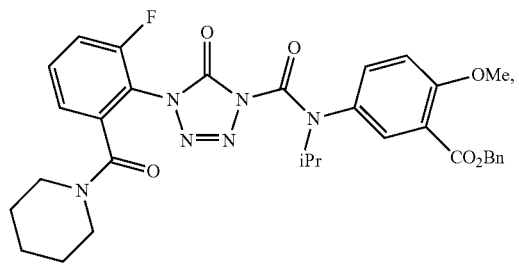
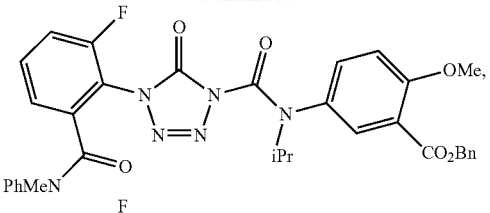
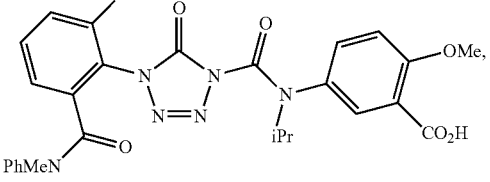
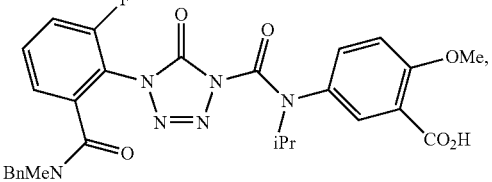
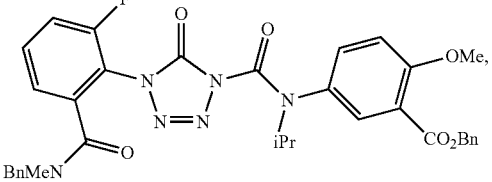
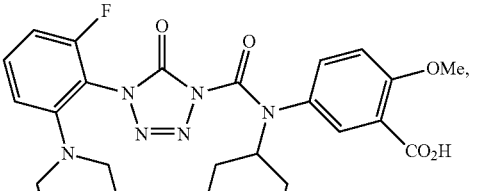
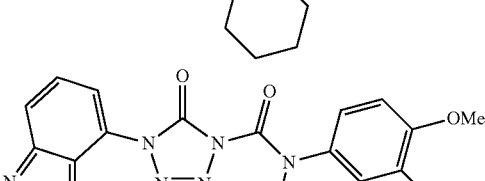
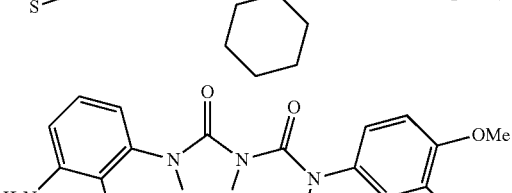
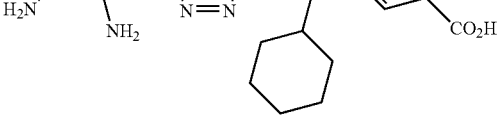

or a pharmaceutically acceptable form thereof.
In certain embodiments, the compound of formula (I) is a compound selected from the group consisting of:
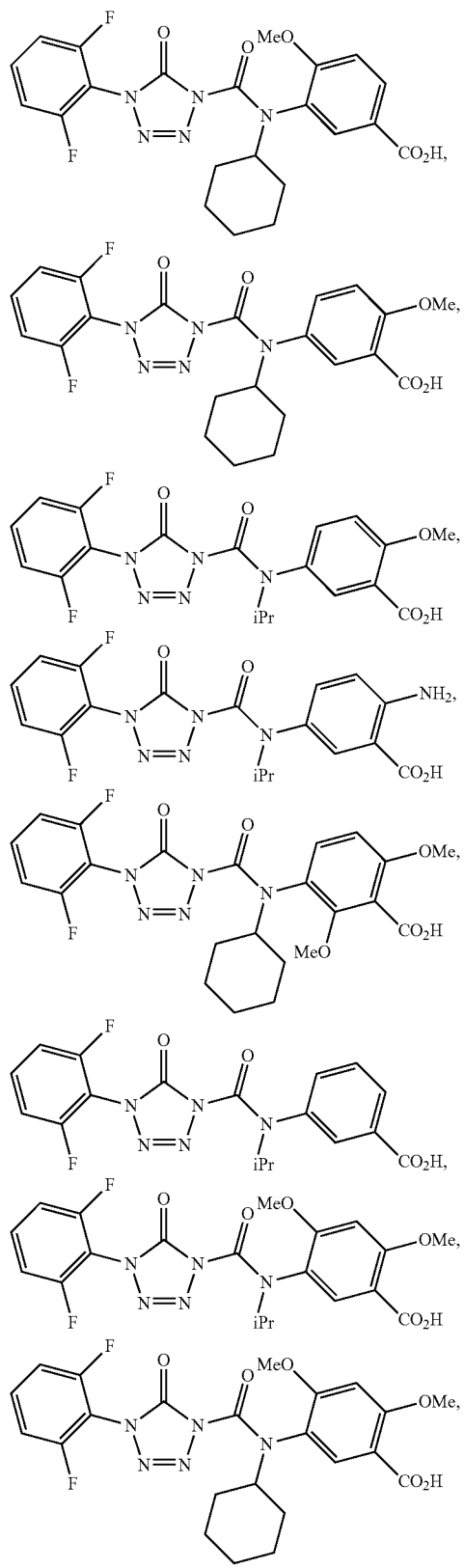
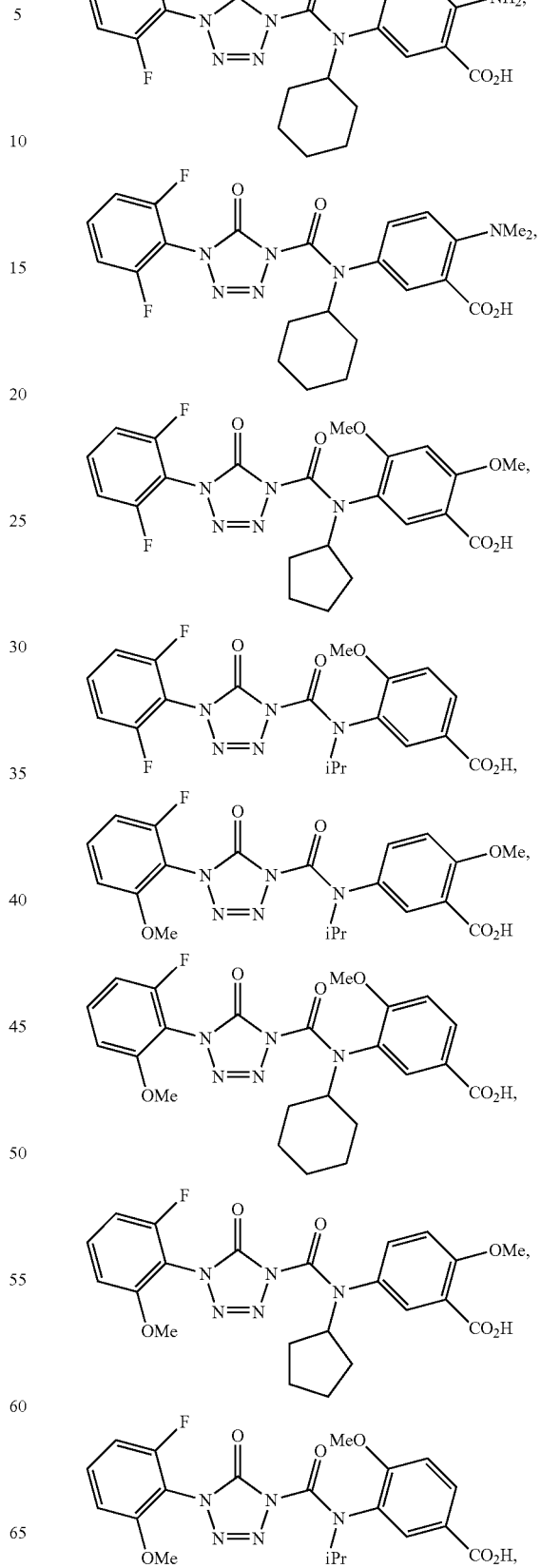

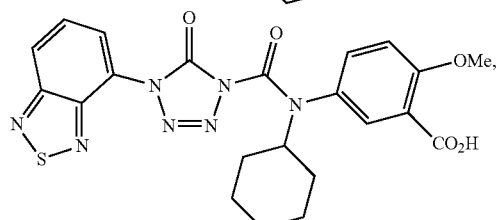
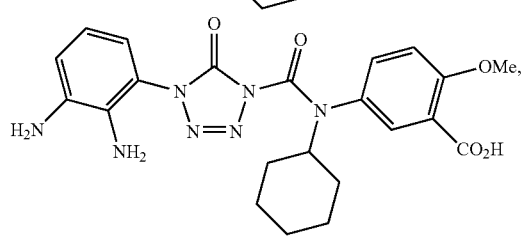
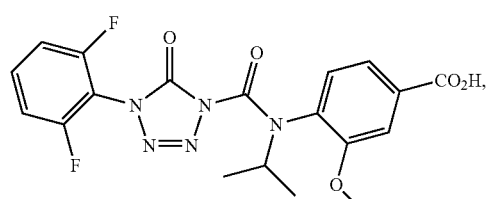
or a pharmaceutically acceptable form thereof.
In other embodiments, the compound of formula (I) is a compound selected from the group consisting of:
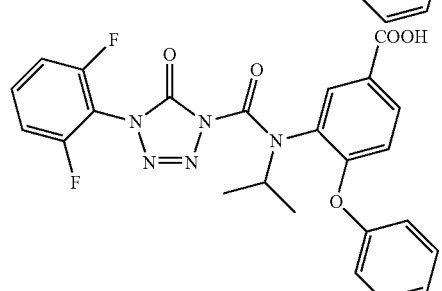
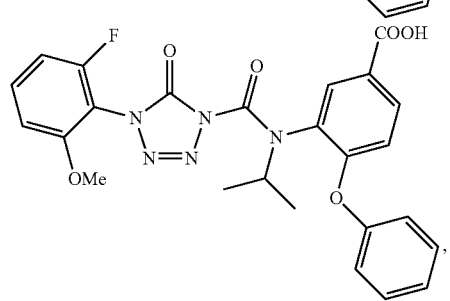
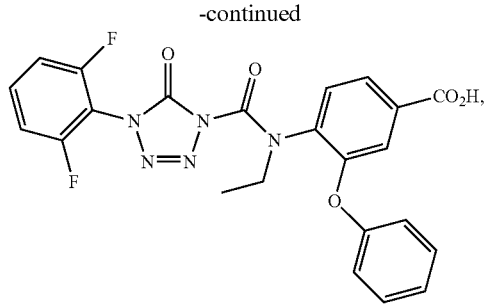
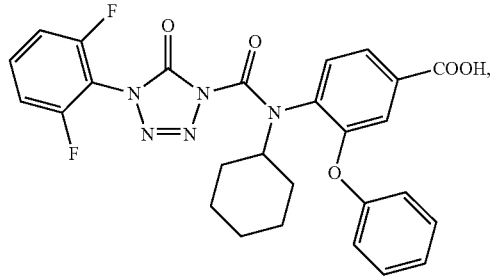
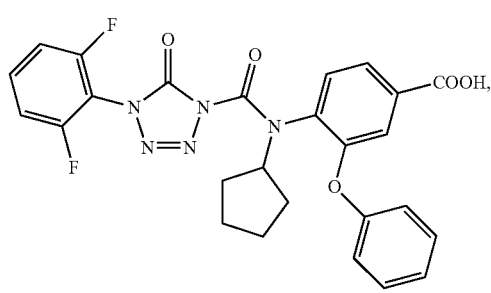
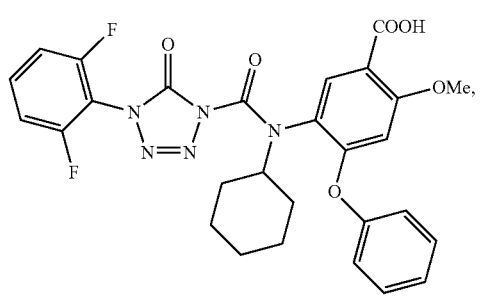
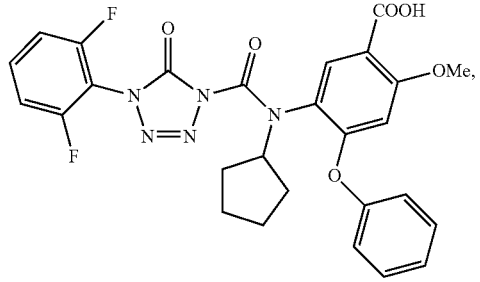
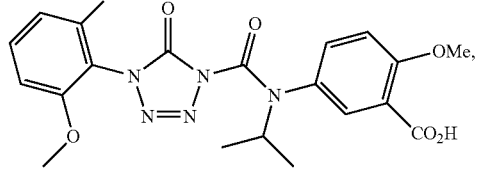

-continued

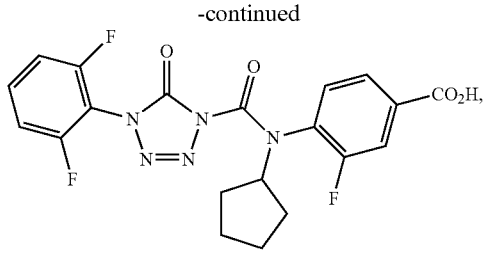
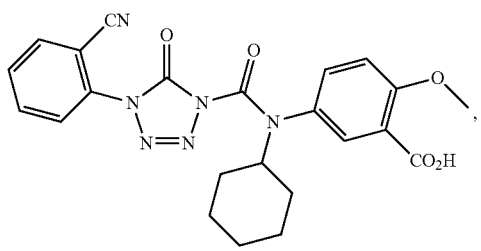
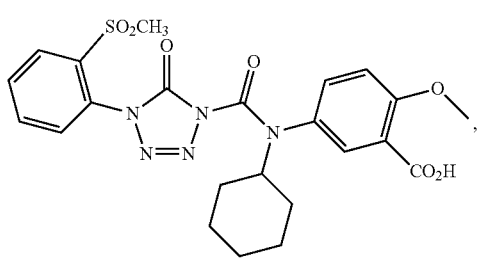
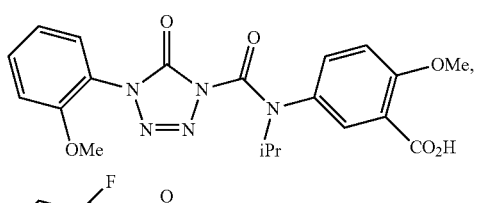
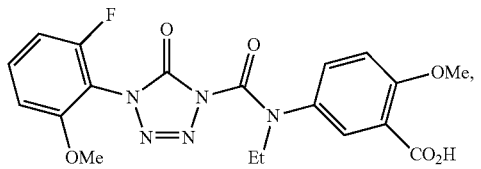
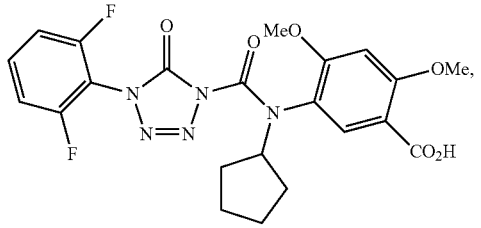
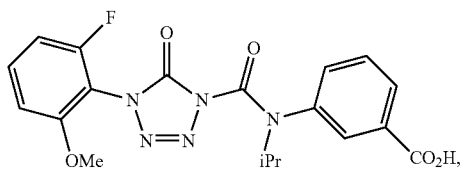
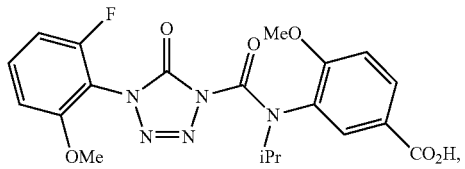

-continued

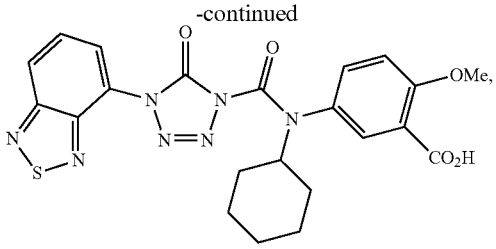

or a pharmaceutically acceptable form thereof.

3. Pharmaceutical Compositions and Formulations

In certain embodiments, provided herein is a pharmaceutical composition comprising at least one compound of formula (I) or a pharmaceutically acceptable form thereof, and one or more pharmaceutically acceptable excipients.

In some embodiments, provided herein is a pharmaceutical composition comprising at least one compound of formula (I) or a pharmaceutically acceptable form thereof, as provided in Tables 1, 2, 3, or 4 and one or more pharmaceutically acceptable excipients. In other embodiments, provided herein is a pharmaceutical composition comprising at least one compound of formula (I) or a pharmaceutically acceptable form thereof, as provided in Tables 1, 2, or 3 having an activity of "A", "A*", "B" or "B*" and one or more pharmaceutically acceptable excipients. In other embodiments, provided herein is a pharmaceutical composition comprising at least one compound of formula (I) or a pharmaceutically acceptable form thereof, as provided in Tables 1, 2 or 3 having an activity of "A" or "A*" and one or more pharmaceutically acceptable excipients.

As described above, the pharmaceutical compositions provided herein can comprise a "pharmaceutically acceptable excipient", which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences,* 16th Ed., E. W. Martin (Mack Publishing Co., Easton, Pa., 1980) discloses various pharmaceutically acceptable excipients used in formulating pharmaceutically acceptable compositions and known techniques for the preparation thereof. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure. Some examples of materials which can serve as pharmaceutically acceptable excipients include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil;

corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the pharmaceutically acceptable composition, according to the judgment of the formulator.

In some embodiments, a compound of formula (I) is administered at about 0.01 mg/kg to about 200 mg/kg, such as at about 0.1 mg/kg to about 100 mg/kg, further such as at about 0.5 mg/kg to about 50 mg/kg.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

The formulations of the pharmaceutically acceptable compositions described herein can be prepared by any method known or hereafter developed in the art of pharmacology. In general, such preparatory methods include the step of bringing the compound of formula (I) into association with one or more pharmaceutically acceptable excipients and then, if necessary and/or desirable, shaping and/or packaging the product into a desired single- or multi-dose unit.

A pharmaceutical composition provided herein can be prepared, packaged, and/or sold in bulk, as a single unit dose, and/or as a plurality of single unit doses. As used herein, a "unit dose" is a discrete amount of the pharmaceutical composition comprising a predetermined amount of at least one compound of formula (I). The amount of the compound of formula (I) is generally equal to the dosage of the compound of formula (I) which would be administered to a subject and/or a convenient fraction of such a dosage such as, for example, one-half or one-third of such a dosage.

The relative amounts of the compound of formula (I), the pharmaceutically acceptable excipient, and/or any additional ingredients in a pharmaceutical composition provided herein will vary, depending upon the identity, size, and/or condition of the subject treated and further depending upon the route by which the composition is to be administered. By way of example, the composition can comprise between 0.1% and 100% (w/w) of the compound of formula (I).

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient has been approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutically acceptable compositions include, but are not limited to, inert diluents, dispersing and/or granulating agents, surface active agents and/or emulsifiers, disintegrating agents, binding agents, preservatives, buffering agents, lubricating agents, and/or oils. One or more such excipients can optionally be included in the formulations. Excipients such as cocoa butter and suppository waxes, coloring agents, coating agents, sweetening, flavoring, and perfuming agents can be present in the pharmaceutically acceptable composition, according to the judgment of the formulator.

Exemplary pharmaceutically acceptable excipients include, but are not limited to, diluents such as calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the compound of formula (I), the liquid dosage forms can comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates provided herein are mixed with solubilizing agents such as Cremophor, alcohols, oils, modified oils, glycols, polysorbates, cyclodextrins, polymers, and combinations thereof. For example, in certain embodiments, the oral suspension can comprise at least one compound of formula (I) and carboxymethylcellulose. In some embodiments, the oral suspension can comprise at least one compound of formula (I), carboxymethylcellulose, and DMSO. In one embodiment, the oral suspension can comprise a compound of formula (I) and 0.5% carboxymethylcellulose/5% DMSO/0.5% Tween (PKPD#5). In another embodiment, the oral suspension can comprise a compound of formula (I) and between about 0.1 and 2% carboxymethylcellulose.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of the compound of formula (I).

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form can be accomplished by dissolving or suspending the drug in an oil vehicle.

Compositions for rectal or vaginal administration are typically suppositories which can be prepared by mixing the conjugates provided herein with suitable non-irritating excipients such as cocoa butter, polyethylene glycol or a suppository wax which are solid at ambient temperature but liquid at body temperature and therefore melt in the rectum or vaginal cavity and release the compound of formula (I).

Solid dosage forms for oral administration include capsules, tablets, pills, powders, and granules. In such solid dosage forms, the compound of formula (I) is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can comprise buffering agents. The unit dose formulation, for example, a tablet, can contain from about 0.05% to about 95% by weight of the compound of formula (I).

Solid compositions of a similar type can be employed as fillers in soft and hard-filled gelatin capsules using such pharmaceutically acceptable excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally comprise opacifying agents and can be of a composition that they release the compound of formula (I) only. In some embodiments, the compound of formula (I) can be released in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The compound of formula (I) can be in micro-encapsulated form with one or more pharmaceutically acceptable excipients as noted above. In such solid dosage forms, the compound of formula (I) can be admixed with at least one inert diluent such as sucrose, lactose or starch. Such dosage forms can comprise, as is normal practice, additional substances other than inert diluents, e.g., tableting lubricants and other tableting aids such a magnesium stearate and microcrystalline cellulose. In the case of capsules, tablets and pills, the dosage forms can comprise buffering agents.

Dosage forms for topical and/or transdermal administration of a compound of formula (I) provided herein can include ointments, pastes, creams, lotions, gels, powders, solutions, sprays, inhalants and/or patches. Generally, the compound of formula (I) is admixed under sterile conditions with one or more pharmaceutically acceptable excipients and/or any needed preservatives and/or buffers as may be required. Additionally, the use of transdermal patches, which often have the added advantage of providing controlled delivery of a compound of formula (I) to the body, is contemplated herein. Such dosage forms can be prepared, for example, by dissolving and/or dispensing the compound of formula (I) in the proper medium. Alternatively or additionally, the rate can be controlled by either providing a rate controlling membrane and/or by dispersing the compound of formula (I) in a polymer matrix and/or gel.

Suitable devices for use in delivering intradermal pharmaceutically acceptable compositions described herein include short needle devices such as those described in U.S. Pat. Nos. 4,886,499; 5,190,521; 5,328.483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790.824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations can, for example, comprise from about 1% to about 10% (w/w) compound of formula (I), although the concentration of the compound of formula (I) can be as high as the solubility limit of the compound of formula (I) in the solvent. In some embodiments, topically-administrable formulations can, for example, comprise from about 1% to about 9% (w/w) compound of formula (I), such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) compound of formula (I). Formulations for topical administration can further comprise one or more of the additional pharmaceutically acceptable excipients described herein.

A pharmaceutical composition provided herein can be prepared, packaged, and/or sold in a formulation suitable for pulmonary administration via the buccal cavity. Such a formulation can comprise dry particles which comprise the compound of formula (I) and which have a diameter in the range from about 0.5 to about 7 nanometers, such as from about 1 to about 6 nanometers, further such as from about 2 to about 5 nanometers, and further such as from about 3 to about 4 nanometers. Such pharmaceutical compositions are conveniently in the form of dry powders for administration using a device comprising a dry powder reservoir to which a stream of propellant can be directed to disperse the powder and/or using a self propelling solvent/powder dispensing container such as a device comprising the compound of formula (I) dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions can include a solid fine powder diluent such as sugar and can be provided in a unit dose form.

Low boiling propellants generally include liquid propellants having a boiling point of below 65° F. at atmospheric pressure. Generally, the propellant can constitute 50% to 99.9% (w/w) of the pharmaceutical composition, and the active ingredient can constitute 0.1% to 20% (w/w) of the pharmaceutical composition. The propellant can further comprise additional excipients such as a liquid non-ionic and/or solid anionic surfactant and/or a solid diluent (which may have a particle size of the same order as particles comprising the compound of formula (I)).

Pharmaceutical compositions provided herein formulated for pulmonary delivery can provide the compound of formula (I) in the form of droplets of a solution and/or suspension. Such formulations can be prepared, packaged, and/or sold as aqueous and/or dilute alcoholic solutions and/or suspensions, optionally sterile, comprising the compound of formula (I), and can be administered using any nebulization and/or atomization device. Such formulations can further comprise one or more additional excipients including, but not limited to, a flavoring agent such as saccharin sodium, a volatile oil, a buffering agent, a surface active agent, and/or a preservative such as methylhydroxybenzoate. The droplets provided by this route of administration can have an average diameter in the range from about 0.1 to about 200 nanometers.

The formulations described herein as being useful for pulmonary delivery are useful for intranasal delivery of a pharmaceutical composition provided herein. Another formulation suitable for intranasal administration is a coarse powder comprising the compound of formula (I) and having an average particle from about 0.2 to 500 micrometers. Such a formulation is administered, for example, by rapid inhalation through the nasal passage from a container of the powder held close to the nostrils.

Formulations suitable for nasal administration can, for example, comprise from about as little as 0.1% (w/w) and as much as 100% (w/w) of the compound of formula (I), and can comprise one or more of the additional excipients described herein. A pharmaceutical composition provided herein can be prepared, packaged, and/or sold in a formulation suitable for buccal administration. Such formulations can, for example, be in the form of tablets and/or lozenges made using conventional methods, and can, for example, comprise 0.1 to 20% (w/w) of the compound of formula (I), the balance comprising an orally dissolvable and/or degradable composition and, optionally, one or more of the additional pharmaceutically acceptable excipients described herein. In some embodiments, formulations suitable for buccal administration can comprise a powder and/or an aerosolized and/or atomized solution and/or suspension comprising the compound of formula (I). Such powdered, aerosolized, and/or aerosolized formulations, when dispersed, can have an average particle and/or droplet size in the range from about 0.1 to about 200 nanometers, and can further comprise one or more of the additional pharmaceutically acceptable excipients described herein.

A pharmaceutical composition provided herein can be prepared, packaged, and/or sold in a formulation suitable for ophthalmic administration. Such formulations can, for example, be in the form of eye drops including, for example, a 0.1/1.0% (w/w) solution and/or suspension of the compound of formula (I) in an aqueous or oily liquid carrier. Such drops can further comprise buffering agents, salts, and/or one or more other of the additional pharmaceutically acceptable excipients described herein. Other opthalmically-administrable formulations which are useful include those which comprise the compound of formula (I) in microcrystalline form and/or in a liposomal preparation. Ear drops and/or eye drops are contemplated as being within the scope of this disclosure.

General considerations in the formulation and/or manufacture of pharmaceutical compositions can be found, for example, in Remington: The Science and Practice of Pharmacy $21^{st}$ Ed., (Lippincott Williams & Wilkins, 2005).

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Further provided herein are kits comprising one or more compounds of formula (I) (or pharmaceutically acceptable forms thereof), and/or an pharmaceutical composition as described above. Kits are typically provided in a suitable container (e.g., for example, a foil, plastic, or cardboard package). In certain embodiments, a kit can include one or more pharmaceutically acceptable excipients, pharmaceutical additives, therapeutically active agents, and the like, as described herein. In certain embodiments, a kit can include means for proper administration, such as, for example, graduated cups, syringes, needles, cleaning aids, and the like. In certain embodiments, a kit can include instructions for proper administration and/or preparation for proper administration.

The instructions would direct the consumer or medical personnel to administer the dosage form according to administration modes known to those skilled in the art. Such kits could be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

It can be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week. Monday, Tuesday, . . . " etc. Other variations of memory aids will be readily apparent. A "daily dose" can be a single tablet or capsule or several pills or capsules to be taken on a given day.

4. Uses and Methods of Treatment 4.1 Definitions

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition.

As used herein, unless otherwise specified, the terms "prevent," "preventing" and "prevention" contemplate an action that occurs before a subject begins to suffer from the specified disease, disorder or condition, which inhibits or reduces the severity of the disease, disorder or condition.

As used herein, and unless otherwise specified, the terms "manage," "managing" and "management" encompass preventing the recurrence of the specified disease, disorder or condition in a subject who has already suffered from the disease, disorder or condition, and/or lengthening the time that a subject who has suffered from the disease, disorder or condition remains in remission. The terms encompass modulating the threshold, development and/or duration of the disease, disorder or condition, or changing the way that a subject responds to the disease, disorder or condition.

As used herein "inhibition", "inhibiting", "inhibit" and "inhibitor", and the like, refer to the ability of a compound to reduce, slow, halt or prevent activity of a particular biological process (e.g., FASN activity) in a cell relative to vehicle. In certain embodiments, the inhibition results in reduction of the activity by 5%, 10%, 15%, 20%, 25%, 30%, 35%, 40%, 45%, 50%, 60%, 70%, 80%, 90% or more of the activity without such inhibition.

As used herein, and unless otherwise specified, a "therapeutically effective amount" of a compound is an amount sufficient to provide a therapeutic benefit in the treatment or management of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment or management of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

4.2 Embodiments

In one embodiment, provided herein are methods for treating, preventing and/or managing a FASN-mediated disorder, disease or condition comprising administering to a subject in need thereof a therapeutically or prophylactically effective amount of at least one compound of formula (I) or a pharmaceutically acceptable form thereof, or a pharmaceutical composition comprising at least one compound of formula (I) or a pharmaceutically acceptable form thereof.

In another embodiment, provided herein are methods for inhibiting FASN in a subject comprising administering to a subject in need thereof a therapeutically effective amount of at least one compound of formula (I) or a pharmaceutically acceptable form thereof, or a pharmaceutical composition comprising at least one compound of formula (I) or a pharmaceutically acceptable form thereof.

In another embodiment, provided herein is a method of inhibiting activation of the FASN pathway in vitro or ex vivo, comprising contacting a FASN protein with at least one compound of formula (I) or a pharmaceutically acceptable form thereof, or a pharmaceutical composition comprising at least one compound of formula (I) or a pharmaceutically acceptable form thereof, in an amount sufficient to reduce the activation of the FASN pathway.

In another embodiment, provided herein is the use of at least one compound of formula (I) or a pharmaceutically acceptable form thereof, or a pharmaceutical composition comprising at least one compound of formula (I) or a pharmaceutically acceptable form thereof, for the treatment of a FASN-mediated disorder, disease or condition in a subject.

In another embodiment, provided herein is the use of at least one compound of formula (I) or a pharmaceutically acceptable form thereof, or a pharmaceutical composition comprising at least one compound of formula (I) or a pharmaceutically acceptable form thereof, in the manufacture of a medicament. In certain embodiments, the medicament is useful for treating a FASN-mediated disorder in a subject.

Compounds of formula (I) provided herein can be inhibitors of FASN. A "FASN-mediated disorder" as used herein, refers to a disease, disorder or condition which is treatable by inhibition of FASN activity. FASN-mediated disorders include, but are not limited to, hyperproliferative disorders; inflammatory disorders; obesity related disorders, such as, but not limited to. Type II diabetes mellitus and fatty liver disease; microbial infections, such as, but not limited to, viral, bacterial, fungal, parasitic, and protozoal infections; and complications thereof.

In certain embodiments, the FASN-mediated disorder is a hyperproliferative disorder. In certain embodiments, the hyperproliferative disorder is cancer. To date, aberrant FASN activity has been observed in a variety of hyperproliferative disorders which include, but are not limited to:

(i) bladder cancer (see Visca et al., *Anticancer Res.* (2003) 23:335-339);

(ii) brain cancer (e.g., meningioma, see: Haase et al., *Neuro-Oncology* (2010) Advance Access published Feb. 5, 2010, 1-11; e.g., glioma: see Zhao et al., *Br. J. Cancer* (2006) 95:869-878; e.g., meduloblastoma: see Slade et al., *Anticancer Res.* (2003) 23:1235-1243);

(iii) breast cancer (see Alo et al., *Cancer* (1996) 77:474-482; Pizer et al., *Cancer Res.* (1996) 56:2745-2747; Pizer et al., *Cancer Res.* (2000) 60:213-218; Milgraum et al., *Clin. Cancer Res.* (1997) 3:2115-2120; Lupu and Menendez, *Endocrinology* (2006) 147:4056-4066; Alo et al. *Oncol. Rep.* (2000) 7:1383-1388; Wang et al., *Cancer Lett.* (2001) 167: 99-104; Liu et al., *Mol. Cancer Ther.* (2008) 7:263-270; and Kuhajda et al., *PNAS* (2000) 97:3450-3454; e.g., mammary cancer: see Hennigar et al., *Biochim. Biophys. Acta* (1998) 1392:85-100 and Alli et al., *Oncogene* (2005) 24:39-46):

(iv) colorectal cancer (see Rashid et al., *Am. J. Pathol.* (1997) 150:201-208; Huang et al., *World J. Gastroenterol.* (2000) 6:295-297; Zhan et al., *Clin. Cancer Res.* (2008) 14:5735-5742);

(v) esophageal cancer (see Nemoto et al., *Pathobiology* (2001) 69:297-303);

(vi) endometrial cancer (see Pizer et al., *Cancer* (1998) 83:528-537: Pizer et al., *Int. J. Gynecol. Pathol.* (1997) 16:45-51; Lupu and Menendez, *Endocrinology* (2006) 147:4056-406; and Sebastiani et al., *Gynecologic Oncology* (2004) 92:101-105);

(viii) gastric cancer (see Kusakabe et al., *Histopathology* (2002) 40:71-79);

(ix) gastrointestinal stromal tumor (see Rossi et al., *J. Pathol.* (2006) 209:369-375);

(x) kidney cancer (e.g., nephroblastoma/Wilms' tumor: see Camassei et al., *Med. Pediatr. Oncol.* (2003) 40:302-308);

(xi) liver cancer (see Evert et al., *Lab. Invest.* (2005) 85:99-108);

(xii) lung cancer (see Piyathilake et al., *Human Pathol.* (2000) 31:1068-1073 and Visca et al., *Anticancer Res.* (2004) 24:4169-4173);

(xiii) mesothelioma (see Gabrielson et al., *Clin. Cancer Research* (2001) 7:153-157);

(xiv) multiple myeloma (see Wang et al., *J. Zhejiang Univ. Sci B* (2008) 9:441-447);

(xv) neuroblastoma (see Slade et al., *Anticancer Res.* (2003) 23:1235-1243);

(xvi) oral cancer (see Krontiras et al., *Head Neck* (1999) 21:325-329; and Agostini et al., *Oral Oncol.* (2004) 40:728-735; see also e.g., oral squamous cell carcinoma (OSCC): Silva et al., *Oral Diseases* (2007) 14:376-382);

(xvii) ovarian cancer (see Pizer et al., *Cancer Res.* (1996) 56:1189-1193; Alo et al., *Oncol. Rep.* (2000) 7:1383-1388; Wang et al., *Oncogene* (2005) 24:3574-3582; Gansler et al., *Hum. Pathol.* (1997) 28:686-692; and Zhou et al., *Cancer Res.* (2007) 2964-2971);

(xviii) pancreatic cancer (e.g., pancreatic adenocarcinoma, intraductal papillary mucinous neoplasm (IPMN): see Walter et al., *Cancer Epidemiol. Biomarkers Prev.* (2009) 18:2380-2385);

(xix) Pagets disease of the vulva (see Alo et al., *Int. J. Gynecol. Pathol.* (2005) 24:404-408);

(xx) prostate cancer (see Pizer et al., *Proc Am. Assoc. Cancer Res.* (2000) 41:655; Swinnen et al., *Int. J. Cancer* (2002) 98:19-22; Epstein et al., *Urology* (1995) 45:81-86; De Schrijver et al., *Cancer Res.* (2003) 63:3799-3804; Pizer et al., *Prostate* (2001) 47:102-110; Furuya et al., *Anticancer Res.* (1997) 17:4589-4593; Shurbaji et al., *Hum. Pathol.* (1996) 27:917-921; Migita et al., *J. Nat. Cancer Inst.* (2009) 101:519-532; Rossi et al., *Mol. Cancer Res.* (2003) 1:707-715; and Shah et al., *Hum. Pathol.* (2006) 37:401-409);

(xxi) retinoblastoma (see Camassei et al., *Investig. Opthalmol. Vis. Sci.* (2003) 44:2399-2403; and Slade et al., *Anticancer Res.* (2003) 23:1235-1243);

(xxii) soft tissue sarcoma (e.g., malignant fibrous histiocytoma (MFH), liposarcoma, malignant peripheral nerve sheath tumor (MPNST), chondrosarcoma: see Takahiro et al., *Clin. Cancer Res.* (2003) 9:2204-2212);

(xxiii) skin cancer (e.g., melanoma: see Innocenzi et al., *J. Culan. Pathol.* (2003) 30:23-28; Kapur et al., *Modern Pathology* (2005) 18:1107-1112 and Carvalho et al., *Int. J. Cancer* (2008) 123:2557-2565); and (xxiv) thyroid cancer (see Vald et al., *Mod. Path.* (1999) 12:70 A; Sekiguchi et al., *Biomed. Pharmacother.* (2001) 55:466-474; e.g., papillary thyroid carcinoma (PTC): see Uddin et al., *J. Clin. Endocrinol. Metab.* (2008) 93:4088-4097).

It is envisioned that aberrant FASN activity plays a role in other hyperproliferative disorders. Exemplary hyperproliferative diseases, disorders, conditions or cancers include, but are not limited to acoustic neuroma, adenocarcinoma, adrenal gland cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer (e.g., bronchogenic carcinoma), cervical cancer (e.g., cervical adenocarcinoma), choriocarcinoma, chordoma, craniopharyngioma, colorectal cancer (e.g., colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer, heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC) such as hepatocellular carcinoma, malignant hepatoma), lung cancer (e.g., small cell lung cancer (SCLC), non-small cell lung cancer (NSCLC), adenocarcinoma of the lung), leukemia (e.g., acute lymphocytic leukemia (ALL), acute myelocytic leukemia (AML), chronic myelocytic leukemia (CML), chronic lymphocytic leukemia (CLL)), lymphoma (e.g., Hodgkin lymphoma, non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, oral cancer (e.g., oral squamous cell carcinoma (OSCC)), ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenström's macroglobulinemia.

In certain embodiments, the hyperproliferative disorder is selected from bladder cancer, brain cancer, breast cancer, colorectal cancer, esophageal cancer, endometrial cancer, gastric cancer, gastrointestinal stromal tumor, kidney cancer, liver cancer, lung cancer, mesothelioma, multiple myeloma, neuroblastoma, oral cancer, ovarian cancer, pancreatic cancer, prostate cancer, Paget's disease of the vulva, retinoblastoma, soft tissue sarcoma, skin cancer or thyroid cancer.

In certain embodiments, the cancer is selected from mesothelioma, multiple myeloma, neuroblastoma, Paget's disease, retinoblastoma, leukemia, myelodisplastic syndrome, or soft tissue sarcoma.

In certain embodiments, the brain cancer is meningioma, glioma or meduloblastoma.

In certain embodiments, the oral cancer is oral squamous cell carcinoma.

In certain embodiments, the pancreatic cancer is pancreatic andenocarcinoma or intraductal papillary mucinous neoplasm.

In certain embodiments, the soft tissue carcinoma is malignant fibrous histiocytoma, liposarcoma, malignant peripheral nerve sheath tumor, or chondrosarcoma.

In certain embodiments, the skin cancer is melanoma.

In certain embodiments, the thyroid cancer is papillary thyroid carcinoma.

In certain embodiments, the FASN-mediated disorder is an inflammatory disorder. The term "inflammatory disorder" refers to a disease or condition characterized by one or more symptoms of pain, heat, redness, swelling, and loss of function. Inflammatory disorders are meant to encompass inflammation associated with immune system disorders as well as inflammation associated with non-immune system disorders. Inflammatory disorders are meant to encompass acute inflammation and chronic inflammation. To date, aberrant FASN activity has been observed in inflammatory bowel diseases such as ulcerative colitis (see Consolazio et al., *Anatomic Pathology* (2006) 126:113-118; Rashid et al., *Am. J. Pathol.* (1997) 150:201-208). It is envisioned that aberrant FASN activity plays a role in other inflammatory disorders.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, Alzheimer's disease, atherosclerosis, bronchitis, bursitis, cancer, chronic prostatitis, conjunctivitis, Chagas disease, chronic obstructive pulmonary disease, cermatomyositis, diverticulitis, diabetes (e.g., type I diabetes mellitus, type 2 diabetes mellitus), dermatitis, eosinophilic gastrointestinal disorders (e.g., eosinophilic esophagitis, eosinophilic gastritis, eosinophilic gastroenteritis, eosinophilic colitis), eczema, endometriosis, gastrointestinal bleeding, gastritis, gastroesophageal reflux disease (GORD, or its synonym GERD), Guillain-Barre syndrome, infection, ischaemic heart disease. Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis, inflammatory bowel disease (IBD) (e.g., Crohn's disease, ulcerative colitis, collagenous colitis, lymphocytic colitis, ischaemic colitis, diversion colitis, Behcet's syndrome, indeterminate colitis), inflammatory bowel syndrome (IBS), lupus, multiple sclerosis, morphea, myeasthenia gravis, myocardial ischemia, nephrotic syndrome, pemphigus vulgaris, pernicious aneaemia, peptic ulcers, psoriasis, polymyositis, primary biliary cirrhosis, Parkinson's disease, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In some embodiment, the inflammatory disorder is selected from anemia, asthma, arteritis, arthritis, chronic obstructive pulmpnary disease, dermatitis, gastroesophageal reflux disease, Crohn's disease, inflammatory bowel syndrome, multiple sclerosis, psoriasis and an autoimmune disease.

Inhibition of FASN activity has also been observed to reduce body weight (e.g., by blocking the body's ability to convert carbohydrates to fat) and to suppress appetite (see Loftus et al., *Science* (2000) 288:2379-2381). Reduction of storage fat is expected to provide various primary and/or secondary benefits in a subject (e.g., in a subject diagnosed with a complication associated with obesity) such as, for example, an increased insulin responsiveness (e.g., in a subject diagnosed with Type II diabetes mellitus); a reduction in elevated blood pressure; a reduction in elevated cholesterol levels; and/or a reduction (or a reduced risk or progression) of ischemic heart disease, arterial vascular disease, angina, myocardial infarction, stroke, migraines, congestive heart failure, deep vein thrombosis, pulmonary embolism, gall stones, gastroesophagael reflux disease, obstructive sleep apnea, obesity hypoventilation syndrome, asthma, gout, poor mobility, back pain, erectile dysfunction, urinary incontinence, liver injury (e.g., fatty liver disease, liver cirrhosis, alcoholic cirrhosis, endotoxin mediated liver injury) or chronic renal failure. Thus, In some embodiments, disclosed methods are applicable to obese subjects, diabetic subjects, and alcoholic subjects, and are generally useful as part of a program to treat an obesity-related disorder or a complication thereof.

An "obesity-related disorder" as used herein, includes, but is not limited to, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" as used herein, refers to class I obesity, class II obesity, class III obesity or pre-obesity (e.g., being "overweight") as defined by the World Health Organization.

In some embodiments, obesity-related disorder include, but are not limited to, Type II diabetes mellitus, elevated blood pressure, elevated cholesterol levels, ischemic heart disease, arterial vascular disease, angina, myocardial infarction, stroke, migraines, congestive heart failure, deep vein thrombosis, pulmonary embolism, gall stones, gastroesophagael reflux disease, obstructive sleep apnea, obesity hypoventilation syndrome, asthma, gout, poor mobility, back pain, erectile dysfunction, urinary incontinence, liver injury, fatty liver, and chronic renal failure.

In some embodiments, treatment of an obesity-related disorder or complication thereof involves reduction of body weight in the subject. In some embodiments, treatment of an obesity-related disorder or complication thereof involves appetite control in the subject.

In other embodiments, provided herein are methods for treating, preventing and/or managing a microbial infection (e.g., such as a bacterial infection, viral infection, fungal infection, or parasitic or protozoal infection) comprising administering to a subject a therapeutically or prophylactically effective amount of at least one compound of formula (I) or a pharmaceutically acceptable form thereof or a pharmaceutical composition comprising at least one compound of formula (I) or a pharmaceutically acceptable form thereof.

Also provided herein is the use of at least one compound of formula (I), or a pharmaceutically acceptable form thereof, or a pharmaceutical composition comprising at least one compound of formula (I) or a pharmaceutically acceptable form thereof for the treatment, prevention and/or management of a microbial infection in a subject.

Also provided herein is the use of at least one compound of formula (I), or a pharmaceutically acceptable form thereof, or a pharmaceutical composition comprising at least one compound of formula (I) or a pharmaceutically acceptable form thereof, in the manufacture of a medicament useful for treating, preventing and/or managing a microbial infection.

FASN has been identified as a target for treatment of microbial infections, e.g., such as a viral infection, for example, infection with an enveloped virus such as the herpes virus (e.g., human cytomegalomous virus (HCMV), herpes simplex virus 1 (HSV-1), herpes simplex virus 2 (HSV-2), varicella zoster virus (VZV), Epstein-Barr virus), influenza A virus and Hepatitis C virus (HCV) (see Munger et al., *Nature Biotechnology* (2008) 26: 1179-1186; Syed et al., *Trends in Endocrinology and Metabolism* (2009) 21:33-40; Sakamoto et al., *Nature Chemical Biology* (2005) 1:333-337; Yang et al., *Hepatology* (2008) 48:1396-1403) or a picornavirus such as Coxsackievirus B3 (CVB3) (see Rassmann et al., *Anti-viral Research* (2007) 76:150-158). Other exemplary viruses include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, and filovirus.

In some embodiments, the virus infects humans. In other embodiments, the virus infects non-human animals. In another embodiment, the virus infects primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

In certain embodiments, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma-associated herpes virus (KSHV). B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus.

In some embodiments, the virus is a non-enveloped virus, i.e., the virus does not have an envelope and is naked. Examples include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2. BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses A1-22, 24 (CA1-22 and CA24, CA23 (echovirus 9)), human coxsackieviruses (B1-6 (CB1-6)), human echoviruses 1-7, 9, 11-27, 29-33, vilyuish virus, simian enteroviruses 1-18 (SEV1-18), porcine enteroviruses 1-11 (PEV1-11), bovine enteroviruses 1-2 (BEV1-2), hepatitis A virus, rhinoviruses, hepatoviruses, cardioviruses, aphthoviruses and echoviruses.

In certain embodiments, the virus is a herpes virus, e.g., HSV-I, HSV-2, and CMV. In another embodiment, the virus is HCMV. In another embodiment, the virus is a liver trophic virus. In another embodiment, the virus is an influenza virus. In some embodiments, the virus is HIV. In certain embodiments, the virus is a hepatitis B virus. In a specific embodiment, the virus is EBV. In some embodiments, the virus is Kaposi's sarcoma-associated herpes virus (KSHV). In certain embodiments the virus is a variola virus. In one embodiment, the virus is a Dengue virus. In other embodiments, the virus is a SARS virus. In one embodiment, the virus is an Ebola virus. In some embodiments the virus is a Marburg virus. In certain embodiments, the virus is a measles virus. In particular embodiments, the virus is a vaccinia virus. In some embodiments, the virus is varicella-zoster virus (VZV). In some embodiments, the virus is a picornavirus. In certain embodiments the virus is a rhinovirus. In certain embodiments the virus is not a rhinovirus. In some embodiments, the virus is an adenovirus. In particular embodiments, the virus is a coxsackievirus (e.g., coxsackievirus B3). In some embodiments, the virus is a rhinovirus. In certain embodiments, the virus is a human papillomavirus (HPV).

In certain embodiments, the virus is a DNA virus. In other embodiments, the virus is an RNA virus. In one embodiment, the virus is a DNA or a RNA virus with a single-stranded genome. In another embodiment, the virus is a DNA or a RNA virus with a double-stranded genome.

In some embodiments, the virus has a linear genome. In other embodiments, the virus has a circular genome. In some embodiments, the virus has a segmented genome. In other embodiments, the virus has a non-segmented genome.

In some embodiments, the virus is a positive-stranded RNA virus.

In other embodiments, the virus is a negative-stranded RNA virus. In one embodiment, the virus is a segmented, negative-stranded RNA virus. In another embodiment, the virus is a non-segmented negative-stranded RNA virus.

In some embodiments, the virus is an icosahedral virus. In other embodiments, the virus is a helical virus. In yet other embodiments, the virus is a complex virus.

In some embodiments, the virus is a hepatitis C virus.

In certain embodiments, the virus is selected from: a herpes virus such as HSV-1, HSV-2, VZV, EBV, CMV (HCMV, MCMV, GPCMV), HMCV, CVB3, HHV-6 and HHV-8; an influenza virus such as influenza type A and influenza type B; respiratory viruses such as RSV, PIV (types 1, 2 and 3), measles virus, rhinovirus, adenovirus, HMPV and SARS virus: orthopoxviruses such as vaccinia virus, cowpox virus, ectromelia virus, monkeypox virus and rabbitpox virus; a hepatitis virus such as HBV and HCV; a papova virus such as papillomavirus (e.g., cotton tail rabbit papillomavirus and human papillomavirus) and BK virus; or other viruses such as VEE virus, Rift Valley fever virus, Tacaribe virus, Yellow fever virus, West Nile virus, dengue virus, PTV and Pichinde virus.

In one embodiment, the virus is HSV-1. In another embodiment, the virus is HSV-2. In another embodiment, the virus is VZV. In another embodiment, the virus is EBV. In another embodiment, the virus is HCMV. In another embodiment, the virus is MCMV. In another embodiment, the virus is GPCMV. In another embodiment, the virus is HHV-6. In another embodiment, the virus is HHV-8.

In one embodiment, the virus is influenza type A virus. In another embodiment, the virus is influenza type B virus.

In one embodiment, the virus is RSV. In another embodiment, the virus is PIV-3.

In another embodiment, the virus is measles virus. In another embodiment, the virus is rhinovirus. In another embodiment, the virus is adenovirus. In another embodiment, the virus is HMPV. In another embodiment, the virus is SARS virus.

In one embodiment, the virus is vaccinia virus. In another embodiment, the virus is cowpox virus. In another embodiment, the virus is ectromelia virus. In another embodiment, the virus is monkeypox virus. In another embodiment, the virus is rabbitpox virus.

In one embodiment, the virus is HBV. In another embodiment, the virus is HCV.

In one embodiment, the virus is cotton tail rabbit papillomavirus. In another embodiment, the virus is human papillomavirus. In another embodiment, the virus is BK virus.

In one embodiment, the virus is VEE virus. In another embodiment, the virus is Rift Valley fever virus. In another embodiment, the virus is Tacaribe virus. In another embodiment, the virus is Yellow fever virus. In another embodiment, the virus is West Nile virus. In another embodiment, the virus is dengue virus. In another embodiment, the virus is PTV. In another embodiment, the virus is Pichinde virus.

In certain embodiments, at least one compound of formula (I) or a pharmaceutically acceptable form thereof, or a pharmaceutical composition comprising at least one compound of formula (I) or a pharmaceutically acceptable form thereof provided herein can treat an infection caused by one type of virus. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by two or more types of viruses at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by three or more types of viruses at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by four or more types of viruses at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by five or more types of viruses at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by six, seven, eight, nine, ten, fifteen, twenty or more types of viruses at the same time.

In certain embodiments, the microbial infections can encompass the disease related to infection by prions, e.g., scrapie, madcow disease, and any modified forms thereof. In certain embodiments, the microbial infections encompass those prion diseases that affect humans.

It is envisioned that a compound of formula (I) or a pharmaceutically acceptable form thereof, or a pharmaceutical composition comprising at least one compound of formula (I) or a pharmaceutically acceptable form thereof provided herein will also be useful in the treatment of other microbial infections, such as bacterial infections, fungal infections, and parasitic infections.

In certain embodiments, the microbial infection is a bacterial infection. Examples of bacterial infections include, but are not limited to, infections by mycobacteria (e.g., *Mycobacteria tuberculosis, M. bovis, M. avium, M. leprae*, and *M. africanum*), rickettsia, mycoplasma, chlamydia, and *legionella*. Other examples of bacterial infections include, but are not limited to, infections caused by Gram positive *bacillus* (e.g., *Listeria, Bacillus* such as *Bacillus anthracis, Erysipelothrix* species), Gram negative *bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species.

Specific examples of infectious bacteria include, but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia*, and *Actinomyces israelli*.

In one embodiment, the bacterial infection is an infection caused by *Mycobacteria tuberculosis*.

In certain embodiments, at least one compound of formula (I) or a pharmaceutically acceptable form thereof, or a pharmaceutical composition comprising at least one compound of formula (I) or a pharmaceutically acceptable form thereof provided herein can treat an infection caused by one type of bacteria. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by two or more types of bacteria at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by three or more types of bacteria at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by four or more types of bacteria at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by five or more types of bacteria at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by six, seven, eight, nine, ten, fifteen, twenty or more types of bacteria at the same time.

In certain embodiments, provided herein are methods of treating, preventing and/or managing diseases, disorders, or conditions caused by fungal infection. Examples include, but are not limited to, aspergilliosis, crytococcosis, sporotrichosis, coccidioidomycosis, paracoccidioidomycosis, histoplasmosis, blastomycosis, zygomycosis, and candidiasis.

In certain embodiments, at least one compound of formula (I) or a pharmaceutically acceptable form thereof, or a pharmaceutical composition comprising at least one compound of formula (I) or a pharmaceutically acceptable form thereof provided herein can treat an infection caused by one type of fungi. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by two or more types of fungi at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by three or more types of fungi at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by four or more types of fungi at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by five or more types of fungi at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by six, seven, eight, nine, ten, fifteen, twenty or more types of fungi at the same time.

In certain embodiments, provided herein are methods of treating, preventing and/or managing diseases, disorders, or conditions caused by parasitic or protozoal infection. Examples of parasitic or protozoal diseases and disorders include, but are not limited to, diseases, disorders and conditions caused by parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, B. hominis, C. parvum, C. cayetanensis, D. fragilis, E. histolytica, I. belli, S. mansonii, S. haematobium, Trypanosoma* ssp., *Toxoplasma* ssp., and *O. volvulus*. Other diseases, disorders and conditions include, but are not limited to, those caused by *Babesia bovis, Babesia canis, Banesia Gibsoni, Besnoitia darlingi, Cytauxzoon felis, Eimeria* ssp., *Hammondia* ssp., *T. canis, Cestoda* (i.e., tapeworms) and *Theileria* ssp. Specific diseases, disorders and conditions include, but are not limited to, malaria, babesiosis, trypanosomiasis, American trypanosomiasis (i.e., Chagas disease), leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis, and dermatitis caused by animal schistosomes.

In one embodiment, the parasitic or protozoal disease is malaria. In another embodiment, the parasitic or protozoal disease is leishmaniasis. In another embodiment, the parasitic or protozoal disease is babesiosis. In another embodiment, the parasitic or protozoal disease is toxoplasmosis. In another embodiment, the parasitic or protozoal disease is trypanosomiasis.

In certain embodiments, at least one compound of formula (I) or a pharmaceutically acceptable form thereof, or a pharmaceutical composition comprising at least one compound of formula (I) or a pharmaceutically acceptable form thereof provided herein can treat an infection caused by one type of parasite. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by two or more types of parasite at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by three or more types of parasite at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by four or more types of parasite at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by five or more types of parasite at the same time. In other embodiments, at least one compound of formula (I) or a pharmaceutically acceptable form thereof, or a pharmaceutical composition comprising at least one compound of formula (I) or a pharmaceutically acceptable form thereof provided herein can treat one or more infections caused by six, seven, eight, nine, ten, fifteen, twenty or more types of parasite at the same time.

In some embodiments, compounds provided herein can treat infection by any combination of viruses, bacteria, fungi and parasites at the same time. For example, in certain embodiments, compounds provided herein can treat the infection by one or more viruses and one or more fungi. In other embodiments, compounds provided herein can treat the infection by one or more viruses and one or more bacteria. In other embodiments, compounds provided herein can treat the infection by one or more fungi and one or more bacteria. In other embodiments, compounds provided herein can treat the infection by one or more viruses and one or more parasites. In other embodiments, compounds provided herein can treat the infection by one or more fungi and one or more parasites. In other embodiments, compounds provided herein can treat the infection by one or more bacteria and one or more prasites. In other embodiments, compounds provided herein can treat the infection by one or more viruses, one or more fungi and one or more bacteria. In other embodiments, compounds provided herein can treat the infection by one or more bacteria, one or more fungi and one or more parasites. In other embodiments, compounds provided herein can treat the infection by one or more viruses, one or more fungi and one or more parasites. In other embodiments, compounds provided herein can treat the infection by one or more viruses, one or more bacteria and one or more parasites.

Compounds provided herein are inhibitors of FASN. Thus, in certain embodiments, the compounds provided herein can be used to treat and/or manage other FASN-related disorders, examples of which include, but are not limited to, diabetes and general wellness of liver such as treatment, prevention and/or management of fatty liver.

In certain embodiments, the compound is an inhibitor of palmitate synthesis. As used herein "inhibition", "inhibiting", "inhibit" and "inhibitor", and the like, refer to the ability of a compound to reduce, halt or prevent activity of a particular biological process (e.g., FASN activity, palmitate synthesis) in a cell relative to vehicle.

In other embodiments, provided herein are methods for inhibiting ELOVL in a subject comprising administering to a subject in need thereof a therapeutically effective amount of at least one compound of formula (I) or a pharmaceutically acceptable form thereof.

In another embodiment, provided herein is use of at least one compound of formula (I) for the treatment of a ELOVL-mediated disorder in a subject.

In another embodiment, provided herein is use of at least one compound of formula (I) in the manufacture of a medicament. In certain embodiments, the medicament is useful for treating a ELOVL-mediated disorder.

"ELOVL-mediated disorder" as used herein, refers to a disease, disorder or condition which is treatable by inhibition of ELOVL activity. Typically, ELOVL-mediated disorders are substantially similar to those mediated by FASN. Thus, ELOVL-mediated disorders include the FASN-mediated disorders described herein above. Examples include, but are not limited to hyperproliferative disorders, inflammatory disorders, obesity-related disorders and complications thereof, diabetes and general wellness of liver such as treatment, prevention and/or management of fatty liver.

In one embodiment, the ELOVL-mediated disorder is a hyperproliferative disorder. In another embodiment, the ELOVL-mediated disorder is an inflammatory disorder. In another embodiment, the ELOVL-mediated disorder is obesity. In another embodiment, the ELOVL-mediated disorder is diabetes mellitus. In another embodiment, the ELOVL-mediated disorder is fatty liver.

In one embodiment, the ELOVL-mediated disorder is ELOVL6-mediated disorder.

5. Administration

The compound of formula (I) or a pharmaceutically acceptable form thereof, or a pharmaceutical composition comprising at least one compound of formula (I) or a pharmaceutically acceptable form thereof can be administered using any amount and any route of administration effective for treatment. The compounds provided herein are typically formulated in dosage unit form for ease of administration and uniformity of dosage. It will be understood, however, that the total daily usage of the compounds provided herein will be decided by the attending physician within the scope of sound medical judgment. The specific therapeutically effective dose level for any particular subject will depend upon a variety of factors including the disease, disorder, or condition being treated and its severity; the activity of the specific compound employed; the specific composition employed; the species, age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

A therapeutically effective amount of at least one compound of formula (I) or a pharmaceutically acceptable form thereof, or a pharmaceutical composition comprising at least one compound of formula (I) or a pharmaceutically acceptable form thereof disclosed herein can be measured by the therapeutic effectiveness of the compound. Compounds of formula (I) can be administered in a dose of about 1 μg/kg to about 200 mg/kg daily; such as from about 1 μg/kg to about 150 mg/kg, from about 1 mg/kg to about 200 mg/kg, from about 1 μg/kg to about 100 mg/kg, from about 1 μg/kg to about 1 mg/kg, from about 50 μg/kg to about 200 mg/kg, from about 10 μg/kg to about 1 mg/kg, from about 10 μg/kg to about 100 μg/kg, from about 100 μg to about 10 mg/kg, and from about 500 μg/kg to about 50 mg/kg.

In certain embodiments, a therapeutically effective amount of at least one compound of formula (I) or a pharmaceutically acceptable form thereof, or a pharmaceutical composition comprising at least one compound of formula (I) or a pharmaceutically acceptable form thereof for administration one or more times a day to a 70 kg adult human can comprise about 0.0001 mg to about 1000 mg of an compound per unit dosage form. It will be appreciated that dose ranges as described herein provide guidance for the administration of pharmaceutical compositions to an adult. The amount to be administered to, for example, a child or an adolescent can be determined by a medical practitioner or person skilled in the art and can be lower or the same as that administered to an adult.

The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In one embodiment, the therapeutically effective amount of a disclosed compound of formula (I) or a pharmaceutically acceptable form thereof, or a pharmaceutical composition comprising at least one compound of formula (I) or a pharmaceutically acceptable form thereof is sufficient to establish a maximal plasma concentration ranging from about 0.001 μM to about 100 μM, e.g., from about 1 μM to about 20 μM. Preliminary doses as, for example, determined according to animal tests, and the scaling of dosages for human administration is performed according to art-accepted practices.

The therapeutically effective dose can be estimated initially from cell culture assays. A dose can be formulated in animal models to achieve a circulating plasma concentration range that includes the $IC_{50}$ (i.e., the concentration of the therapeutic which achieves a half-maximal inhibition of symptoms) as determined in cell culture assays or animal models. Levels in plasma can be measured, for example, by high performance liquid chromatography. The effects of any particular dosage can be monitored by a suitable bioassay.

Examples of dosages are: about $0.1 \times IC_{50}$, about $0.5 \times IC_{50}$, about $1 \times IC_{50}$, about $5 \times IC_{50}$, $10 \times IC_{50}$, about $50 \times IC_{50}$, and about $100 \times IC_{50}$.

Therapeutically effective dosages achieved in one animal model can be converted for use in another animal, including humans, using conversion factors known in the art (see, e.g., Freireich et al., *Cancer Chemother. Reports* 50(4):219-244 (1966) and Table A for Equivalent Surface Area Dosage Factors).

TABLE A

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

In some embodiments, the compound of formula (I) or a pharmaceutically acceptable form thereof, or a pharmaceutical composition comprising at least one compound of formula (I) or a pharmaceutically acceptable form thereof is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the delivery of the pharmaceutical composition by any appropriate route, taking into consideration likely advances in the sciences of drug delivery, is also encompassed herein.

It will be also appreciated that at least one compound of formula (I) or a pharmaceutically acceptable form thereof, or a pharmaceutical composition comprising at least one compound of formula (I) or a pharmaceutically acceptable form thereof, as described above and herein, can be administered in combination with one or more additional therapeutically active agents.

By "in combination with," it is not intended to imply that the agents must be administered at the same time and/or formulated for delivery together, although these methods of delivery are certainly within the scope of this disclosure. The compound of formula (I) or a pharmaceutically acceptable form thereof, or a pharmaceutical composition comprising at least one compound of formula (I) or a pharmaceutically acceptable form thereof can be administered concurrently with, prior to, or subsequent to, one or more other additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the compound of formula (I) with the additional therapeutically active agent and/or the desired therapeutic effect to be achieved.

In some embodiments, additional therapeutically active agents utilized in combination with at least one compound of formula (I) or a pharmaceutically acceptable form thereof, or a pharmaceutical composition comprising at least one compound of formula (I) or a pharmaceutically acceptable form thereof will be administered at levels that do not exceed the levels at which they are utilized individually. In some embodiments, the levels utilized in combination will be lower than those utilized individually.

By a "therapeutically active agent", "therapeutic agent", "agent" or "active agent" refers to any substance that is useful for therapy, including prophylactic and therapeutic treatment.

Also encompassed herein is the delivery of the pharmaceutical compositions in combination with agents that can improve their bioavailability, reduce and/or modify their metabolism, inhibit their excretion, and/or modify their distribution within the body. It will also be appreciated that the therapy employed can achieve a desired effect for the same disorder (for example, at least one compound of formula (I) or a pharmaceutically acceptable form thereof, or a pharmaceutical composition comprising at least one compound of formula (I) or a pharmaceutically acceptable form thereof can be administered in combination with an anti-inflammatory, anti-anxiety and/or anti-depressive agent, etc.), and/or they can achieve different effects (e.g., control of any adverse side-effects).

Exemplary therapeutically active agents include, but are not limited to, anti-cancer agents, antibiotics, anti-obesity drugs, anti-viral agents, anesthetics, anti-coagulants, inhibitors of an enzyme, steroidal agents, anti-inflammatory agents, antihistamine, immunosuppressant agents, anti-neoplastic agents, antigens, vaccines, antibodies, decongestants, sedatives, opioids, pain-relieving agents, analgesics, anti-pyretics, enhancing agents, hormones, prostaglandins, progestational agents, anti-glaucoma agents, ophthalmic agents, anticholinergics, anti-depressants, anti-psychotics, hypnotics, tranquilizers, anti-convulsants, muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), or inhibitors/intercalators of DNA, RNA, protein-protein interactions, protein-receptor interactions, etc. Active agents include small organic molecules such as drug compounds (e.g., compounds approved by the Food and Drugs Administration as provided in the Code of Federal Regulations (CFR)), antibodies, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, antibodies, vitamins and cells, and combinations thereof.

In certain embodiments, the therapeutically active agent is an anti-cancer agent. Exemplary anti-cancer agents, include, but are not limited to, radiation therapy, interferon (e.g., interferon α, interferon γ), antibodies (e.g., HERCEPTIN (trastuzumab), T-DM1, AVASTIN (bevacizumab), ERBITUX (cetuximab), VECTIBIX (panitumumab), RITUXAN (rituximab) BEXXAR (tositumomab)), anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel, albumin-bound paclitaxel (ABRAXANE), nab-paclitaxel, docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase Inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), Ca2+ ATPase inhibitors (e.g., thapsigargin), imatinib, thalidomide, lenalidomide, tyrosine kinase inhibitors tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®). ENMD-2076, PCI-32765, AC220, dovitinib lactate (TKI258, CHIR-258), BIBW 2992 (TOVOKTM), SGX523, PF-04217903, PF-02341066, PF-299804, BMS-777607, ABT-869, MP470. BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

Exemplary combinations of therapeutically active agents useful for the treatment of cancer (a.k.a. an "anti-cancer treatment regimen") which can be used in combination with at least one compound of formula (I) or a pharmaceutically acceptable form thereof, or a pharmaceutical composition comprising at least one compound of formula (I) or a pharmaceutically acceptable form thereof includes, but is not limited to:

ABVD Adriamycin (doxorubicin), bleomycin, vinblastine, dacarbazine
AC Adriamycin (doxorubicin), cyclophosphamide
BEACOPP Bleomycin, etoposide, Adriamycin (doxorubicin), cyclophosphamide, Oncovin (vincristine), procarbazine, prednisone
BEP Bleomycin, etoposide, platinum agent (cisplatin)
CA Cyclophosphamide, Adriamycin (doxorubicin) (same as AC)
CAF Cyclophosphamide, Adriamycin (doxorubicin), fluorouracil (5-FU)
CAV Cyclophosphamide, Adriamycin (doxorubicin), vincristine
CBV Cyclophosphamide, BCNU (carmustine), VP-16 (etoposide)
ChlVPP/EVA Chlorambucil, vincristine (Oncovin), procarbazine, prednisone, etoposide, vinblastine, Adriamycin (doxorubicin)
CHOP Cyclophosphamide, hydroxydoxorubicin (doxorubicin), vincristine (Oncovin), prednisone
CHOP-R or R-CHOP CHOP+rituximab
COP or CVP Cyclophosphamide, Oncovin (vincristine), prednisone
CMF Cyclophosphamide, methotrexate, fluorouracil (5-FU)
COPP Cyclophosphamide, Oncovin (vincristine), procarbazine, prednisone
EC Epirubicin, cyclophosphamide
ECF Epirubicin, cisplatin, fluorouracil (5-FU)
EP Etoposide, platinum agent (cisplatin)
EPOCH Etoposide, prednisone, Oncovin, cyclophosphamide, and hydroxydaunorubicin
FEC Fluorouracil (5-FU), epirubicin, cyclophosphamide
FL (Also known as Mayo) Fluorouracil (5-FU), leucovorin (folinic acid)
FOLFOX Fluorouracil (5-FU), leucovorin (folinic acid), oxaliplatin
FOLFIRI Fluorouracil (5-FU), leucovorin (folinic acid), irinotecan
ICE Ifosfamide, carboplatin, etoposide (VP-16)
ICE-R ICE+rituximab
m-BACOD Methotrexate, bleomycin, Adriamycin (doxorubicin), cyclophosphamide, Oncovin (vincristine), dexamethasone
MACOP-B Methotrexate, leucovorin (folinic acid), Adriamycin (doxorubicin), cyclophosphamide, Oncovin (vincristine), prednisone, bleomycin
MOPP Mechlorethamine, Oncovin (vincristine), procarbazine, prednisone
PCV Procarbazine, CCNU (lomustine), vincristine
ProMACE-MOPP Methotrexate, Adriamycin (doxorubicin), cyclophosphamide, etoposide+MOPP
ProMACE-CytaBOM Prednisone, doxorubicin (adriamycin), cyclophosphamide, etoposide, cytarabine, bleomycin, Oncovin (vincristine), methotrexate, leucovorin
R-FCM Rituximab, fludarabine, cyclophosphamide, mitoxantrone
Stanford V Doxorubicin, mechlorethamine, bleomycin, vinblastine, vincristine, etoposide, prednisone
Thal/Dex Thalidomide, dexamethasone
TIP Paclitaxel, ifosfamide, platinum agent cisplatin
VAC Vincristine, Actinomycin, Cyclophosphamide
VAD Vincristine. Adriamycin (doxorubicin), dexamethasone
VAPEC-B Vincristine, Adriamycin (doxorubicin), prednisone, etoposide, cyclophosphamide, bleomycin
VIP Etoposide, ifosfamide, platinum agent cisplatin In other embodiments, the therapeutically effective agent is an anti-vial agent. Exemplary anti-viral agents include, but are not limited to, Abacavir. Aciclovir, Acyclovir, Adefovir, Amantadine, Amprenavir, Ampligen, Arbidol, Atazanavir, Atripla, BI1201335, Boceprevir, BMS-858 (see, e.g., Gao et al., Nature, 465(6): 96-102 (2010)), BMS-790052 ((see, e.g., Gao et al., Nature, 465(6): 96-102 (2010)), Cidofovir, Combivir, Danoprivir (ITMN-191; RG-7227), Darunavir, Delavirdine, Didanosine, Docosanol, Edoxudine, EI-1 to EI-12 (see, e.g., Baldick et al., PLoS Pathogens, 6(9) e1001086: 1-14 (2010)), Elvitegravir, Efavirenz, Emtricitabine, Enfuvirtide, Entecavir, Etravirine, Famciclovir, Fosamprenavir, Foscarnet, Fosfonet, Ganciclovir, GSK-572, Ibacitabine, Immunovir, Idoxuridine, Imiquimod, Indinavir. Inosine, Interferon (e.g., Interferon type III, Interferon type II, Interferon type I, Peginterferon alfa-2a, Peginterferon alpha-2b, standard interferon alfa-2a, standard interferon alfa-2b, consensus interferon, interferon alfacon-1, ALBUFERON, omega interferon, interferon gamma-1b, lymphoblastoid interferon tau), Lamivudine, Lopinavir, Loviride, Maraviroc, Moroxydine, Methisazon, MK-2048, Nelfinavir, Nevirapine, Nexavir, Oseltamivir (Tamiflu), Penciclovir, Peramivir, Pleconaril, Podophyllotoxin, Raltegravir, Ribavirin, Rimantadine, Ritonavir, Pyramidine, Saquinavir, Stavudine, Tenofovir (e.g., Tenofovir disoproxil), Telaprivir, Tipranavir, Trifluridine, Trizivir, Tromantadine, Truvada, Valaciclovir (Valtrex), Valganciclovir, vaccines (e.g., VZV vaccines such as Varivax and Zostavax), Vicriviroc, Vidarabine, Viramidine, Zalcitabine, Zanamivir (Relenza), Zidovudine, and other small molecule anti-viral agents described, for example, in Herker et al., Nature Medicine, Advance Online Publication doi:10.1038/nm2238: 1-4 (Oct. 10, 2010), and combinations thereof.

Examples of additional anti-viral agents include, but are not limited to, interleukin 2, interleukin 6, inteleukin 12, a compound that enhances the development of a type 1 helper T cell response, interfering RNA, anti-sense RNA, Imiqimod, an inosine 5'-phosphate dehydrogenase inhibitor, amantadine and rimantadine.

Other examples include, but are not limited to, those described in WO 2009/023059, the entirety of which is incorporated herein by reference.

In one embodiment, the anti-viral agent is interferon. In another embodiment, the anti-viral agent is telaprivir. In one embodiment, combinations of two or more anti-viral agents are used in further combination with a compound provided herein.

In certain embodiments, the anti-viral agent is a protease inhibitor. Exemplary protease inhibitors include, but are not limited to, Saquinavir, Ritonavir, Indinavir, Nelfinavir, Amprenavir, Lopinavir, Atazanavir, Fosamprenavir, Tipranavir and Darunavir.

In certain embodiments, the anti-viral agent is an integrase inhibitor. Exemplary integrase inhibitors include, but are not limited to, Raltegravir, Elvitegravir and MK-2048, GSK-572.

In certain embodiments, the anti-viral agent is a reverse transcriptase inhibitor (e.g., a nucleoside analog reverse trascriptase inhibitor (NRTI), a nucleotide analog reverse trascriptase inhibitor (NtRTI), a non-nucleoside reverse transcripase inhibitor (NNRTI)).

Exemplary nucleoside analog reverse trascriptase inhibitors (NRTIs) include, but are not limited to, Zidovudine, Didanosine, Zalcitabine, Stavudine, Lamivudine, Abacavir, Emtricitabine, Entecavir and Aciclovir (partial nucleoside structure).

Exemplary nucleotide analog reverse trascriptase inhibitors (NtRTIs) include, but are not limited to, Tenofovir and Adefovir.

Exemplary non-nucleoside reverse transcripase inhibitors (NNRTIs) include, but are not limited to, Efavirenz, Nevirapine, Delavirdine and Etravirine. In certain embodiments, the compound of formula (I) or a pharmaceutically acceptable form thereof, or a pharmaceutical composition comprising at least one compound of formula (I) or a pharmaceutically acceptable form thereof provided herein and/or the anti-viral agent is further used in combination with an enhancing agent. An "enhancing agent", used in this context, is an agent which, when used in combination with a compound provided herein and/or an anti-viral agent, improves treatment, prevention or management of the microbial infection relative to treatment with the compound of formula (I) or a pharmaceutically acceptable form thereof, or a pharmaceutical composition comprising at least one compound of formula (I) or a pharmaceutically acceptable form thereof provided herein and/or an anti-viral agent without the enhancing agent. Exemplary enhancing agents include, but are not limited to, chloroquine, a quinoline antimalarial, grapefruit juice, hydroxyurea, leflunomide, myucophenolic acid, resveratrol and Ritonavir.

In one embodiment, the anti-viral agent is an anti-viral agent described in U.S. Pub. No. 2011/0064698, which is incorporated herein by reference in its entirety. Exemplary anti-viral agents include, but are not limited to, IP-501, Merimebodib VX-497. IDN-6556, XTL-002, HCV/MF59, CIVACIR, ZADAXIN, CEPLENE, VX 950/LY 570310, ISIS 14803, JTK 003, Tarvacin, HCV-796, CH-6, ANA971, ANA245, CPG 10101, Rituximab, NM 283, HepX™-C, IC41, Medusa interferon, E-1, multiferon, BILN 2061, TMC435350, Telaprevir, Boceprevir, ACH-1625, ABT-450. BI-201335, PHIX-1766, VX-500, MK-7009, R7227, Narlaprevir, Alinia, ABT-072, ABT-333, Filibuvir, VCH-916, R7128, IDX 184, R7128, R1626. MK-3281, PSI-7851, ANA 598, BI-207127, GS9190, VCH-759, Clemizole, A-832, BMS-790052, ITX 5061, GS-9450, ANA773, CYT 107, SPC3649, Debio 25, SCY-635 and a combination thereof.

Other examples include, but are not limited to, AZD-7295, BI207127, BIT225, BM824383, BMS65032, BMS791325, GS-9256, IDX 375, INX-189, PPI-461, PSI-938, PSI-7977. TMC435, TMC649128, VX-222, VX-759, VX-916 and a combination thereof. These agents are currently in various stages of clinical trials and information is readily available to those in the art.

In one embodiment, provided herein is a method of treating, preventing and/or managing hepatitis C virus (HCV) infection comprising administering a therapeutically or prophylactically effective amount of at least one compound of formula (I) or a pharmaceutically acceptable form thereof, or a pharmaceutical composition comprising at least one compound of formula (I) or a pharmaceutically acceptable form thereof provided herein in combination with one or more other therapeutic agents provided herein.

Examples of such therapeutic agents include compounds having anti-HCV activity, for example, by inhibiting the function of a target such as, but not limited to, HCV metalloprotease, HCV serine protease, HCV polymerase, HCV helicase, SCV NS4B protein, HCV entry, HCV assembly, HCV egress, HCV NS5A protein and IMPDH.

In other embodiments, at least one compound of formula (I) or a pharmaceutically acceptable form thereof, or a pharmaceutical composition comprising at least one compound of formula (I) or a pharmaceutically acceptable form thereof provided herein can be used in combination with at least one additional therapeutic agent having anti-HCV activity, including, but not limited to, Alinia (Nitazoxanide), Bavituximab, Belerofon, Chronvac-C, Civacir, Clemizole. Fluvastatin, Glycoferon, Hepavaxx C, HuMax-HepC, Lenocta (sodium stibogluconate SSG), Locteron, peginterferon, Ribavirin, Suvus, Telaprevir (VX-950), Zadaxin-thymalfasin, ZALBIN (Albuferon albinterferon alfa-2b), A-837093, ABT-072, ABT-333, ABT-450, ACH-1095, ACH-1625, ACH-2684, ACH-2928, AN 025-1, ANA598, ANA773, ATI-0810 (formerly PG301029), AVL-181. AVL-192, AZD7295, BI 201335, BI 207127, BIT225, BMS-650032, BMS-790052, BMS-791325, BMS-824393, CB5300, CB-183872 (formerly IB657), CF102, CSL123, CTS-1027, CYT107. Debio 025, ECH18, EDP-239, GEA007.1, GI 5005, GNI-103, GNI-104, GS 9190, GS 9256, GSK625433, IC41, ID-12, IDX184, IDX320, IDX375, IMO-2125, IMMU 105. ITMN-191 R7227 (RO5190591), ITX2155, ITX4520, ITX5061NS5A inhibitors, JKB-122, KPE02001003, KPE00001113, MBL-HCV1, MDX-1106 (ONO-4538), Mito-Q, MK-0608, MX3235 Celgosivir, NOV-205, PF-868554, PF-4878691, PHX1766, PYN17, PYN18, PPI-461, PPI-1301, PRO-206, PSI-7977, PSI-9381NX08189, R7128 (RO5024048), REP 9C, RG7348, SCV-07, SCY-635, SD-101, SIRNA-034, SP-30, SPC3649, TG4040, TT033, VCH-759, VX-222, VX-500, VX-813, and VX-985.

In one embodiment, the other therapeutic agent is an interferon. In one embodiment, the interferon is Interferon type III, Interferon type II, Interferon type I, Peginterferon alfa-2a, Peginterferon alpha-2b, standard interferon alfa-2a, standard interferon alfa-2b, consensus interferon, interferon alfacon-1, ALBUFERON, omega interferon, interferon gamma-1b, lymphoblastoid interferon tau or a combination thereof. In another embodiment, the interferon is interferon alfa-2a, interferon alfa-2b, peginterferon alfa-2a, peginterferon alpha-2b, consensus interferon or lymphoblastoid interferon tau.

In another embodiment, the other therapeutic agent is ribavirin.

In another embodiment, at least one compound of formula (I) or a pharmaceutically acceptable form thereof, or a pharmaceutical composition comprising at least one compound of formula (I) or a pharmaceutically acceptable form thereof provided herein can be used in combination with ribavirin and an interferon. In one embodiment, the interferon is Interferon type III, Interferon type II, Interferon type I, Peginterferon alfa-2a, Peginterferon alpha-2b, standard interferon alfa-2a, standard interferon alfa-2b, consensus interferon, interferon alfacon-1, ALBUFERON, omega interferon, interferon gamma-1b, lymphoblastoid interferon tau or a combination thereof. In another embodiment, the interferon is interferon alfa-2a, interferon alfa-2b, peginterferon alfa-2a, peginterferon alpha-2b, consensus interferon or lymphoblastoid interferon tau.

6. Anti-viral Assays

Anti-viral assays used to screen compounds having efficacy for a specific virus are well-known in the art and described, for example, in WO 2009/023059, the entirety of which is incorporated herein by reference. Exemplary anti-viral assays are provided herein below.

6.1 Herpes Simplex Virus (HSV)

Mouse models of herpes simplex virus type 1 or type 2 (HSV-1 or HSV-2) can be employed to assess the anti-viral activity of test compounds in vivo. BALB/c mice are commonly used, but other suitable mouse strains that are susceptible can also be used. Mice are inoculated by various routes with an appropriate multiplicity of infection of HSV, followed by administration of test compounds and placebo. For i.p. inoculation, HSV-1 replicates in the gut, liver, and spleen and spreads to the CNS. For i.n. inoculation, HSV-1 replicates in the nasopharynx and spreads to the CNS. Any appropriate route of administration (e.g., oral, topical, systemic and nasal), frequency and dose of administration can be tested to determine the optimal dosages and treatment regimens using test compounds, optionally in combination with other therapies.

In a mouse model of HSV-2 genital disease, intravaginal inoculation of female Swiss Webster mice with HSV-1 or HSV-2 is carried out, and vaginal swabs are obtained to evaluate the effect of therapy on viral replication. (See, e.g., Crute et al., *Nature Medicine*, 2002, 8:386-391). For example, viral titers by plaque assays are determined from the vaginal swabs. A mouse model of HSV-1 using SKH-1 mice, a strain of immunocompetent hairless mice, to study cutaneous lesions is also described in the art. (See, e.g., Crute et al., *Nature Medicine*, 2002, 8:386-391 and Bolger et al., *Antiviral Res.*, 1997, 35:157-165). Guinea pig models of HSV have also been described. (See, e.g., Chen et al., *Virol. J.*, 2004 Nov. 23, 1:11). Statistical analysis is typically carried out to calculate significance of the anti-viral activity.

6.2 Human Cytomegalovirus (HCMV)

Since HCMV does not generally infect laboratory animals, mouse models of infection with murine CMV (MCMV) can be used to assay anti-viral activity of test compounds in vivo. For example, a MCMV mouse model with BALB/c mice can be used to assay the anti-viral activities of test compounds in vivo when administered to infected mice, which is described, for example, in Kern et al., *Antimicrob. Agents Chemother.*, 2004, 48:4745-4753. Tissue homogenates isolated from infected mice treated or untreated with test compounds are tested using standard plaque assays with mouse embryonic fibroblasts (MEFs). Statistical analysis is then typically carried out to calculate significance of the anti-viral activity.

Alternatively, human tissue (i.e., retinal tissue or fetal thymus and liver tissue) is implanted into SCID mice, and the mice are subsequently infected with HCMV, preferably at the site of the tissue graft. (See, e.g., Kern et al., *Antimicrob. Agents Chemother.*, 2004, 48:4745-4753). The pfu of HCMV used for inoculation can vary depending on the experiment and virus strain. Any appropriate routes of administration (e.g., oral, topical, systemic and nasal), frequency and dose of administration can be tested to determine the optimal dosages and treatment regimens using test compounds, optionally in combination with other therapies. Implant tissue homogenates isolated from infected mice treated or untreated with test compounds at various time points are tested using standard plaque assays with human foreskin fibroblasts (HFFs). Statistical analysis is then typically carried out to calculate significance of the anti-viral activity.

Guinea pig models of CMV to study anti-viral agents have also been described, for example, in Bourne et al., *Antiviral Res.*, 2000, 47:103-109; Bravo et al., *Antiviral Res.*, 2003, 60:41-49; and Bravo et al, *J. Infectious Diseases*, 2006, 193: 591-597.

6.3 Influenza Virus

Animal models, such as ferret, mouse and chicken, developed for use to test anti-viral agents against influenza virus have been described, for example, in Sidwell et al., *Antiviral Res.* 2000, 48: 1-16 and McCauley et al., *Antiviral Res.*, 1995, 27: 179-186. For mouse models of influenza, non-limiting examples of parameters that can be used to assay anti-viral activity of test compounds administered to the influenza-infected mice include pneumonia-associated death, serum $\alpha$1-acid glycoprotein increase, animal weight, lung virus assayed by hemagglutinin, lung virus assayed by plaque assays, and histopathological change in the lung. Statistical analysis is typically carried out to calculate significance of the anti-viral activity.

Nasal turbinates and trachea can be examined for epithelial changes and subepithelial inflammation. The lungs can be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); and 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); and 2.5+ (diffuse squamous metaplasia with very few cilia evident).

Virus immunohistochemistry is performed using a viral-specific monoclonal antibody (e.g., NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); and 3+ (numerous infected cells, affecting most of the epithelial layer in bronchioles, or widespread in large sublobular foci in alveoli).

6.4 Hepatitis Type B Virus (HBV)

A HBV transgenic mouse model, lineage 1.3.46 (official designation, Tg[HBV 1.3 genome] Chi46) has been described previously and can be used to test the in vivo anti-viral activities of test compounds as well as the dosing and administration regimen. (See, e.g., Cavanaugh et al., *J. Virol.*, 1997, 71:3236-3243; and Guidotti et al., *J. Virol.*, 1995, 69:6158-6169). In these HBV transgenic mice, a high level of viral replication occurs in liver parenchymal cells and in the proximal convoluted tubules in the kidneys of these transgenic mice at levels comparable to those observed in the infected liver of patients with chronic HBV hepatitis. HBV transgenic mice that have been matched for age (i.e., 6-10 weeks), sex (i.e., male), and levels of hepatitis B surface antigen (HBsAg) in serum can be treated with test compounds or placebo followed by anti-viral activity analysis to assess the activity of test compounds. Non-limiting examples of assays that can be performed on these mice treated and untreated with test compounds include southern analysis to measure HBV DNA in the liver, quantitative reverse transcriptase PCR (qRT-PCR) to measure HBV RNA in the liver, immunoassays to measure hepatitis e antigen (HBeAg) and HBV surface antigen (HBsAg) in the serum, immunohistochemistry to measure HBV antigens in the liver, and quantitative PCR (qPCR) to measure serum HBV DNA. Gross and microscopic pathological examinations can be performed as needed.

6.5 Human Immunodeficiency Virus (HIV)

The safety and efficacy of test compounds against HIV can be assessed in vivo with established animal models well-known in the art. For example, a Trimera mouse model of HIV-1 infection has been developed by reconstituting irradiated normal BALB/c mice with murine SCID bone marrow and engrafted human peripheral blood mononuclear cells. (See Ayash-Rashkovsky et al., *FASEB J.*, 2005, 19:1149-1151). These mice are injected intraperitoneally with T- and M-tropic HIV-1 laboratory strains. After HIV infection, rapid loss of human CD4.sup.+ T cells, decrease in CD4/CD8 ratio, and increased T cell activation can be observed. A test compound can be administered to these mice and standard assays known in the art can be used to determine the viral replication capacity in animals treated or untreated with the compound. Non-limiting examples of such assays include the COBAS AMPLICOR™ RT-PCR assay (Roche Diagnostics, Branchberg, N.J.) to determine plasma viral load (HIV-1 RNA copies/ml); active HIV-1 virus replication assay where human lymphocytes recovered from infected Trimera mice were cocultured with target T cells (MT-2 cells) and HIV-dependent syncytia formation was examined; and human lymphocytes recovered from infected Trimera mice were cocultured with cMAGI indicator cells, where HIV-1 LTR driven trans-activation of β-galactosidase was measured. Levels of anti-HIV-1 antibodies produced in these mice can also be measured by ELISA. Other established mouse models described in the art can also be used to test the anti-viral activity of test compounds in vivo. (See, e.g., Mosier et al., *Semin. Immunol.*, 1996, 8:255-262; Mosier et al., *Hosp. Pract.* (Off Ed)., 1996, 31:41-48, 53-55, 59-60; Bonyhadi et al., *Mol. Med. Today*, 1997, 3:246-253; Jolicoeur et al., *Leukemia*, 1999, 13:S78-S80; Browning et al., *Proc. Natl. Acad. Sci. USA*, 1997, 94:14637-14641; and Sawada et al., *J. Exp. Med.*, 1998, 187:1439-1449). A simian immunodeficiency virus (SIV) nonhuman primate model has also been described, for example, in Schito et al., *Curr. HIV Res.*, 2006, 4:379-386.

6.6 In Vitro Screening Assays 6.6.1 General Procedures for Assays for Herpes Viruses To quickly screen out samples that do not have activity against any of the herpes viruses, or are too toxic to evaluate, an inexpensive, rapid assay such as a CPE-inhibition assay that is semi-automated is commonly used initially to screen out the negatives. Typically, all screening assays are conducted in low passage human cells, and each assay system contains a positive control (ACV, GCV, CDV) and a negative control (AZT). Efficacy is demonstrated by at least two different assay systems that detect functional biologic activity and should be confirmed using low passaged clinical isolates and drug resistant mutants whenever available. In the case of EBV, efficacy against EBV is confirmed using a hybridization assay that quantifies DNA synthesis. Toxicity is determined using both resting and proliferating human fibroblast cells and proliferating lymphoblastic cells, and for selected compounds, toxicity in human myeloid and erythroid progenitor cells is assessed.

6.6.1.1 HSV-1, HSV-2, CMV and VZV

All the screening assay systems utilized are selected to show specific inhibition of a biologic function, i.e., cytopathic effect (CPE) in susceptible human cells. In the CPE-inhibition assay, a test compound is added 1 hour prior to infection so the assay system will have maximum sensitivity and detect inhibitors of early replicative steps, such as adsorption or penetration, as well as later events. To rule out non-specific inhibition of virus binding to cells, all compounds that show reasonable activity in the CPE assay are confirmed using a classical plaque reduction assay in which the compound is added 1 hour after infection. In the case where a compound blocks attachment, a positive result will appear in the CPE assay, but may be negative by plaque assay. In this case, the plaque assay is repeated with compound being added prior to viral infection. These assay systems also can be manipulated by increasing the pretreatment time in order to demonstrate anti-viral activity with oligodeoxynucleotides and/or peptides and by delaying addition of drug after infection. Information regarding which step in the virus life cycle is inhibited (i.e., early vs. late functions) can be gained.

In all the assays used for primary screening, a minimum of six compound concentrations is contemplated to cover a range of, e.g., 100 µg/ml to 0.03 µg/ml, in 5-fold increments to determine efficacy. Dose response curves are obtained from these data. The dose that inhibits viral replication by 50% (effective concentration 50; $EC_{50}$) is typically calculated using a computer software program, for example, MacSynergy II by M. N. Prichard, K. R. Asaltine, and C. Shipman, Jr., University of Michigan, Ann Arbor, Mich.

The same compound concentrations used to determine efficacy are also used on uninfected cells in each assay to determine toxicity of each experimental compound. The compound concentration that is cytotoxic to cells as determined by their failure to take up a vital stain, neutral red (cytotoxic concentration 50; $CC_{50}$), is determined as described above.

In some embodiments, compounds to treat herpes virus infections are for systemic diseases, such as neonatal herpes, CMV, and disseminated VZV, and may need to be given parenterally. Therefore, the toxicity of test compounds on dividing cells is determined at a very early stage of testing. In this regard, a cell proliferation assay using HFF cells can be a very sensitive assay for detecting compound toxicity to dividing cells, and the compound concentration that inhibits cell growth by 50% ($IC_{50}$) can be calculated as described above. In comparison with four human diploid cell lines and vero cells, HFF cells are the most sensitive and predictive of toxicity for bone marrow cells.

To determine if each compound has sufficient anti-viral activity that exceeds its level of toxicity, a selectivity index (SI) is calculated according to $CC_{50}/EC_{50}$. This index, also referred to as a therapeutic index, is used to determine if a compound warrants further study. Typically, a compound that had an SI of 10 or greater is evaluated in additional assay systems.

For HSV-1 and HSV-2, compounds that show activity in the CPE-inhibition assay are confirmed using the plaque reduction assay. Susceptibility of additional virus strains, including both lab passaged and clinical isolates, is determined for selected compounds. A battery of ACV resistant HSV strains can be also utilized. For CMV, compounds that show activity in the CPE-inhibition assay are confirmed using the plaque reduction assay in HFF cells. A variety of laboratory, clinical, and GCV resistant isolates are also available for testing. For VZV, compounds with activity in a CPE assay are evaluated further in a plaque reduction assay.

6.6.1.2 Epstein-Barr Virus (EBV)

The initial system to be used to determine anti-viral activity against EBV can be VCA production in Daudi cells using an ELISA assay. Six concentrations of drug covering a range of, e.g., 50 µg/ml to 0.03 µg/ml are utilized. Using the results obtained from untreated and drug treated cells, an $EC_{50}$ can be calculated. Selected compounds that have good activity against EBV VCA production without toxicity are tested for their ability to inhibit EBV DNA synthesis.

In each assay system utilized, drug treatment of uninfected cells is incorporated to obtain as much toxicity data as possible. In some embodiments, for calculation of the SI, the data on toxicity is at least as reliable as the results for efficacy. An example of a toxicity assay is a colormetric method using MTS.

All compounds that have an SI of, for example, greater than 10 in the screening assay are confirmed in a hybridization assay that measures the amount of EBV DNA produced by P3HR-1 infected cells. A wide range of compound concentrations can be utilized so an accurate $EC_{50}$ can be calculated. Uninfected control cells treated with compound are also utilized as another measure of drug toxicity. In some cases, it is possible that results obtained using assays for VCA production and DNA synthesis may not correlate since the two events may be independent.

6.6.1.3 Human Herpes Virus HHV-6 and HHV-8

Cord Blood Lymphocytes (CBL) and the Human T cell lymphoblastoid lines, HSB-2 and SupT-1, are used in screening assays for HHV-6. CBL are isolated from fresh heparinized umbilical cord blood and are infected with the Z29 strain of HHV-6. The body cavity based B-cell lymphoma cell line, BCBL-1, are used for screening against HHV-8.

There are two variants of HHV-6 known as type A variants or type B variants. The HHV-6 type A variant is, for example, the GS strain which is propagated in HSB-2 or SupT-I cells. The HHV-6 type B variant is, for example, Z29 (ATCC, Rockville, Md.) which is grown as a stock in CBL. The HHV-8 is propagated in a latent state in the BCBL-1 cell line. Lytic growth of the HHV-8 can be induced by the addition of the phorbol ester, TPA.

Six concentrations of each drug ranging from, e.g., 100 µg/ml to 0.03 µg/ml drug are tested to obtain the $EC_{50}$, $EC_{90}$, $CC_{50}$, and $IC_{50}$ values. The initial assay for HHV-6 is a flow cytometric analysis of HHV-6 antigens in either HSB-2 cells (HHV-6A), CBL (HHV-6B), or SupT-1 (6A or 6B). For HHV-8, yytic infection of virus in BCBL-1 cells will be carried out as described above. The initial assay for HHV-8 is a flow cytometric analysis of HHV-8 antigens in BCBL-1 cells. As with the other herpes virus assays, these assays contain the positive (infected and untreated cells) and negative (uninfected or uninduced and compound treated cells) controls needed for effective analysis and cytotoxicity determinations.

6.6.2 In Vitro Laboratory Procedures for Assays for Herpes Viruses

6.6.2.1 Efficacy Screening for HSV-1, HSV-2, CMV and VZV

Preparation of Human Foreskin Fibroblast Cells: Newborn human foreskins can be obtained from the University of Alabama School of Medicine (UAB) or Brookwood Hospital, Birmingham, Ala., as soon as possible after circumcisions are performed and placed in minimal essential medium (MEM) containing vancomycin, fungizone, penicillin, and gentamicin, at the usual concentrations, for four hours at room temperature. The medium is then removed, the foreskin minced into small pieces and washed repeatedly until red cells are no longer present. The tissue is then trypsinized using trypsin at 0.25% with continuous stirring for 15 minutes at 37° C. in a $CO_2$ incubator. At the end of each 15 minute period, the tissue is allowed to settle to the bottom of the flask. The supernatant containing cells is poured through sterile cheesecloth into a flask containing MEM and 10% fetal bovine serum (FBS). The flask containing the medium is kept on ice throughout the trypsinizing procedure. After each decanting of cells, the cheese cloth is washed with a small amount of MEM containing serum. Fresh trypsin is added each time to the foreskin pieces and the procedure repeated until no more cells become available. The cell-containing medium is then centrifuged at 1000 RPM at 4° C. for 10 minutes. The supernatant liquid is discarded and the cells are resuspended in a small amount of MEM with 10% FBS. The cells are counted using a Coulter Counter and then placed in an appropriate number of 25 $cm^2$ tissue culture flasks. As cells become confluent and need trypsinization, they are gradually expanded into 175 $cm^2$ flasks. The cells are maintained on vancomycin and fungizone to passage three. Cell lines are tested periodically for the presence of mycoplasma contamination using the Hoechst fluorescent stain for mycoplasma DNA. Cells are utilized usually only until passage 10.

Cytopathic Effect Inhibition Assay: Low passage (3-10) human foreskin fibroblast (HFF) cells are trypsinized, counted, and seeded into 96 well tissue culture plates at a cell concentration of 2.5×104 cells in 0.1 ml of MEM supplemented with 10% FBS. The cells are then incubated for 24 hours at 37° C. in a 5% $CO_2$—95% air, 90% humidified atmosphere. The media is then removed and 100 µl of MEM containing 2% FBS is added to all but the first row. In the first row, 125 µl of media containing the experimental compound is added in triplicate wells. Media alone is added to both cell and virus control wells. The compound in the first row of wells is then diluted serially 1:5 throughout the remaining wells by transferring 25 µl using a Beckman Bio-Mek Liquid Handling Machine. The plates are then incubated for 60 minutes and 100 µl of an appropriate virus concentration added to each well, excluding cell control wells which received 100 µl of MEM. For HSV-1 and HSV-2 assays, the virus concentration utilized is 1000 Plaque Forming Units (PFU) per well. For CMV and VZV assays, the virus concentration added is 2500 and 1000 PFU per well, respectively. The plates are then incubated at 37° C. in a $CO_2$ incubator for three days for HSV-1 and HSV-2, 10 days for VZV, or 14 days for CMV. After the incubation period, the media is aspirated and the cells are stained with a 0.1% crystal violet in formalin solution for 4 hours. The stain is then removed and the plates rinsed using tap water until all excess stain is removed. The plates are allowed to dry for 24 hours and the amount of CPE in each row determined using a BioTek Multiplate Autoreader. $EC_{50}$ and $IC_{50}$ values are determined by comparing compound treated and untreated cells using a computer program.

Plaque Production Assay for HSV-1 and HSV-2: Two days prior to use, HFF cells are trypsinized, counted, and plated into six well plates and incubated at 37° C. with 5% $CO_2$ and 90% humidity. On the date of assay, the compound is made up at twice the desired concentration in 2×MEM and then serially diluted 1:5 in 2×MEM to give six concentrations of compound. The compound concentrations utilized are usually 200 µg/ml down to 0.06 µg/ml. The virus to be used is diluted in MEM containing 10% FBS to a desired concentration which will give 20-30 plaques per well. The media is then aspirated from the wells and 0.2 ml of virus is added to each well in triplicate with 0.2 ml of media being added to drug toxicity wells. The plates are then incubated for 1 hour with shaking every 15 minutes. After the incubation period, an equal amount of 1% agarose is added to an equal volume of each compound dilution. This provides final compound concentrations beginning with 100 µg/ml and ending with 0.03 µg/ml and a final agarose overlay concentration of 0.5%. The compound agarose mixture is applied to each well in a 2 ml volume and the plates are incubated for three days, after which the cells are stained with a 1.5% solution of neutral red. At the end of the 4-6 hours incubation period, the stain is aspirated, and plaques counted using a stereomicroscope at 100× magnification.

Plaque Production Assay for CMV: The procedures are nearly identical to those provided for HSV with a few minor changes. The agarose used for both the initial overlay and the two subsequent overlays is 0.8% rather than 1%. The assay is incubated for 14 days with the additional 1 ml overlays being applied on days 4 and 8.

Plaque Production Assay for VZV: The procedures are essentially identical to those described for the HSV plaque assay with the following possible exceptions: after addition of the compound, the plates are incubated for ten days; on days 3 and 6, an additional 1 ml overlay with equal amounts of 2×MEM and 1% agarose are added.

Plaque Reduction Assay: In certain cases, some large or highly charged molecules that are active in the CPE inhibition assay may be inactive in the plaque assay because the compound failed to diffuse through the agarose overlay. Therefore, a modified plaque assay can be used for confirmation, wherein the overlay medium is liquid rather than semi-solid. The procedure for the liquid overlay plaque assay is similar to that using the agarose overlay. The procedure for adding the virus is the same as for the regular plaque assay. The compounds are made up at the desired concentrations in MEM with 2% FBS. For HSV-1 and HSV-2 assays, an antibody preparation obtained from, e.g., Baxter Health Care Corporation is diluted 1:500 and added to the media that the compound is diluted in to limit extracellular spread of virus through the media. For VZV and CMV, no antibody in the overlay is necessary. For the CMV and VZV assays, additional medium without the new compound is added on day five and allowed to incubate for a total of 8 and 10 days, respectively. At the end of the incubation period for all of the assays, 2 ml of a 6.0% neutral red solution is added to each well and incubated for 6 hours. The liquid is then aspirated off and plaques enumerated using a stereomicroscope.

6.6.2.2 Efficacy Screening for EBV

Cells: The two lymphoid cell lines, Raji and Daudi derived from Burkitt's lymphoma, are used. The Raji cell line is a non-producer of viral gene products associated with the productive viral cycle. The Daudi cell line is a low level producer, i.e., fewer than 1% of the cells express EA spontaneously. These cells are equally susceptible to superinfection by the P3HR-1 virus as determined by EBV VCA expression. The cells are maintained at 37° C. in a humidified atmosphere with 5% $CO_2$, in culture with RPMI-1640 medium containing 10% heat inactivated FBS, 100 u/ml Penicillin, 25 µg/ml gentamicin and 2 mM L-glutamine. The cells are passaged twice weekly and the cell concentration adjusted to $2 \times 10^6$/ml for use.

Virus: The following prototypes of infectious EBV can be used: (1) one derived from supernatant fluids of the P3HR-1 cell line, which produces non-transforming virus that induces the production of VCA after primary infection or superinfection of B cell lines; and (2) B95-8 virus, which immortalizes cord blood lymphocytes and induces tumors in marmosets, but does not induce an abortive productive infection even in cell lines harboring EBV genome copies. As an example, for virus production, P3HR-1 cells are cultured at a concentration of $2 \times 10^5$/ml for two weeks in medium containing 2% FCS at 34° C. in a humidified atmosphere with 5% $CO_2$. Concentrated virus then is prepared from the supernatant of the culture by centrifugation at 12,000 g for 90 minutes in a Sorvall Centrifuge. The pellets are resuspended in RPMI-1640 medium at $\frac{1}{100}$ of the original volume and stored at $-70°$ C.

Antibodies: Murine monoclonal antibody to EBV VCA (Chemicon International, Inc. Temecula, Calif.), is used in immunofluorescence assays and ELISA. Optimal monoclonal antibody concentration is determined by antibody titration for each assay system. For single fluorochrome analyses FITC-labelled goat anti-mouse total IgG (Southern Biotechnology Associates, Birmingham, Ala.) is used as the second antibody.

EBV Superinfection and Compound Treatment: Superinfection is initiated by the incubation of 0.5 ml of an appropriate concentration of EBV with 106 cells/tube in a total of 1 ml/tube. In most cases, this amounts to a multiplicity of infection (MOI) of 0.1-0.2 based on VCA induction in Daudi cells. After adsorption at 37° C. for 1 hour, 3 ml of RPMI-1640 medium is added. The cells are pelleted by centrifugation and supernatants discarded. Compound concentrations (0.08, 0.4, 2, 10, 50 µg/ml) in 4 ml of RPMI-1640 are added to the appropriate tubes. RPMI-1640 is added to positive and negative control tubes and each compound concentration is added to Daudi cells without virus for toxicity controls. After incubation, the cells in each tube are counted using a Coulter Counter and washed three times with phosphate buffered saline solution (PBS) (without Ca and Mg). Each cell suspension is adjusted to a concentration of $4.0 \times 10^6$ cells/ml in PBS. For EBV IFA and DNA hybridization assays, two sets of slides are prepared with $4 \times 10^4$ cells/spot for each cell suspension, and air-dried overnight.

Immunofluorescence Assay: The infected and compound treated cells are counted and washed three times with PBS. Cells, $4 \times 10^4$ in PBS, are spotted on multiwell slides and air dried. The cells are then fixed for 10 minutes in acetone, washed in PBS and stained for immunofluorescence with the mouse monoclonal antibodies and FITC-labeled goat anti-mouse IgG. EBV VCA specific antibodies are used in the immunofluorescence assays. FITC-labeled goat anti-mouse IgG (Southern Biotechnology Associates, Birmingham, Ala.) is used as the second antibody. The slides are counterstained with 0.1% Evan's blue for 5 minutes and mounted with 10% glycerin in PBS. The number of FITC-positive cells on each smear is determined using a Nikon fluorescence microscope. Five hundred cells are counted in each spot. The number of cells expressing EBV VCA is calculated by multiplying the fraction of antigen positive cells by the number of cells/ml in the culture at the time of harvest. The compound concentration is plotted against the number of antigen positive cells/ml using a computer program, and $EC_{50}$ and $EC_{90}$ values are calculated.

ELISA: Daudi cells infected with P3HR-1 virus and treated with drug are harvested by centrifugation and washed three times with PBS. The cells are pelleted and suspended to a concentration of $4 \times 10^6$ cells/ml in PBS. One hundred µl of each suspension is dispensed in triplicate into a 96-well plate, air-dried and fixed with 95% ethanol and 5% acetic acid. Uninfected cells are prepared in the same manner and used as controls. After washing the plate, primary and secondary antibodies diluted in 1% bovine serum albumin containing 0.05% Tween-20 are added sequentially to each well and incubated at room temperature. Antibody additions are separated by 3 washes with PBS containing 0.005% Tween-20. O-phenyldiamine (OPD) substrate is added and the reaction stopped with 3N $H_2SO_4$ after about 10 minutes. The optical density is measured at 492 nm and the $EC_{50}$ extrapolated using the computer software program described herein.

Evaluation of Anti-Viral Agents Against EBV DNA Replication: The Enzo Simply Sensitive Horseradish Peroxidase-AEC In Situ Detection System for EBV (Enzo Diagnostics, Farmingdale, N.Y.) is used to determine anti-viral activity against DNA synthesis. Detection and staining are performed according to the manufacturer's instructions. Three days after superinfection and compound treatment, slides are prepared with $4 \times 10^4$ cells/spot for each cell suspension, and air-dried overnight. The slides are fixed in acetone for 10 minutes. A biotin labelled EBV probe is added to each spot of fixed cells and the slide is covered with a glass coverslip. The slide is then heated on a hot plate at 95° C. for 5 minutes. After heating, the slide is placed at 37° C. on a slide warmer for 30-60 minutes for the DNAs to anneal. The coverslips are then removed and the Post Hybridization Reagent is added to each spot. After incubation for 10 minutes and rinsing with washing buffer, Detection Reagent is applied. The Detection Reagent is left on the slide for 30-60 minutes on a slide warmer and then washed off with washing buffer. Chromogen Substrate Solution is added and incubated for 20 minutes on a slide warmer. The slides are washed and counter stained with Blue Counterstain. The slides are then rinsed with deionized water and mounted with water. The slides are viewed in a light microscope under a magnification of 400×. Positive cells appear as red spots. All the cells are counted in several fields. The fraction of red spots in the total number of cells counted multiplied by 100 reflects the percent hybridization.

Primary Infection Assay: The primary infection of umbilical cord blood lymphocytes with the transforming strain B95-8 of EBV induces the expression of the virus-associated nuclear antigen (EBNA) in the cell. It is also known that B95-8 virus induces cellular DNA synthesis after infection of CBL. The availability of EBNA virus-infected cells in culture allows for the identification and quantitation of EBV-positive cell antigens by indirect IFA staining and FACS. Cord blood lymphocytes separated by ficoll-hypaque gradient are cultured in complete RPMI-1640. The EBV-B95-8 is produced by incubating the B95-8 cell line in RPMI-1640 plus 10% fetal calf serum for 10-14 days. The supernatant is collected and stored at 0-4° C. One million CBL are infected by incubation with 1 ml of the B95-8 supernant for 1 hour. The virus is removed by centrifugation. After one wash with RPMI-1640, the infected cells are treated with anti-viral compounds as described earlier for P3HR-1 superinfection. The cell cultures are incubated for 4-6 days. Cell harvesting and immunofluorescent staining is the same as described above.

6.6.2.3 Efficacy Screening for HHV-6 and HHV-8

Cord Blood Lymphocytes (CBL) Cells: Fresh heparinized umbilical cord blood can be obtained, e.g., from the University of Alabama at Birmingham Hospital, and diluted 1:1 with Hank's balanced salt solution and layered on a Histopaque 1077 (Sigma Chemical Co., St. Louis, Mo.) gradient. The tubes are centrifuged at 1600 rpm for 30 minutes at room temperature and serum is carefully aspirated off. The lymphocytes are removed, washed with Hank's balanced salt solution and centrifuged at 1200 rpm for 10 minutes. The supernatant is aspirated, and the cells are resuspended in RPMI 1640 containing 10% heat-inactivated FBS, 2 mM L-glutamine, 100 U/ml penicillin, 0.25 g/ml fungizone, 25 g/ml gentamicin, 0.1 U/ml Interleukin-2 (Sigma, St. Louis, Mo.) and 0.5 µg/ml *Phaseolus Vulagaris* agglutinin protein (PHAP). CBLs are used in the HHV-6, Z-29 (Variant B) assays.

Human T Cell Lymphoblastoid Line HSB-2: The HSB-2 cells can be obtained through, e.g., the NIH AIDS Research and Reference Reagent Program (Rockville, Md.), and are propagated in RPMI 1640 containing 10% heat-inactivated FBS, 100 U/ml penicillin, 25 µg/ml gentamicin and 2 mM L-glutamine. The cells are split 1:5 in a 175 $cm^2$ flask every 3-4 days and used in the HHV-6, GS (Variant A) assays.

Body Cavity-Based Lymphoma (BCBL-1) Cells: BCBL-1 cells (NIH AIDS Research and Reference Program, Rockville, Md.) propagated in RPMI 1640 media containing 10% FBS, 2 mM L-Glutamine, 10 µM (3-Mercaptoethanol 100 µ/l penicillin, and 25 µg/ml gentamicin are utilized in the HHV-8 assay.

Viruses: There are two variants of HHV-6 known as type A variants or type B variants. An example of HHV-6 type A variant is the GS strain which is propagated in the HSB-2 cells and can be obtained through, e.g., the AIDS Research and Reference Reagent Program, Division of AIDS, NIAID, NIH. These cells, referred to as HSB-2/HHV-6GS, are maintained at $5 \times 10^5$ cells/ml under the same conditions and in the same media as the uninfected HSB-2 cells. The cells are split every 3-4 days by addition of uninfected cells at 9 parts to 1 part infected cells. Stock titers of this virus of $1 \times 10^5$ both in cell-associated and cell-free virus can be obtained by growth for 5 days. An example of HHV-6 type B variant is Z29 (ATCC, Rockville, Md.) which is grown as a stock in CBL by incubation for 10 days followed by collection, centrifugation and freezing of the supernatant. HHV-8, latently expressed in the primary effusion lymphoma derived BCBL-1 cell line (NIH AIDS Research and Reference Program, Rockville, Md.) is induced into lytic HHV-8 expression by addition of 100 ng/ml phorbol 12-myristate 13-acetate. BCBL-1 cells are cultured in RPMI 1640 media containing 10% FBS, 2 mM L-glutamine, 10 µM β-mercaptoethanol 100 U/ml penicillin and 25 g/ml gentamicin.

Primary Antibodies: The primary antibodies used for the indirect IFA and FACS are selected for their antigen specificity, low cross-reactivity with other herpes viruses and fluorescence intensity as monitored by FACS. Monoclonal antibodies selected for use in the HHV-6 assay systems are screened for variant specificity and demonstrated no A or B variant cross-reactivity in the assay systems. Monoclonal antibody 8532 (Chemicon, Temecula, Calif.) targets HHV-6 induced early nuclear proteins and is used as a primary antibody in the HHV-6GS assay systems at a 5 µg/ml concentration. Monoclonal antibody 8535 (Chemicon, Temecula, Calif.) which targets a B variant 101 kDa virion protein is used as a primary antibody in the HHV-6Z-29 assay system at a 5 µg/ml concentration. The HHV-8 monoclonal antibody KS8.1 (Bala Chandran, University of Kansas Department of Microbiology, Molecular Genetics and Immunology) targets the HHV-8 viral envelope associated glycoprotein 8.1 expressed in the late lytic phase of HHV-8 replication (Zoeteweij et al., 1999) and is used at approximately 5 µg/ml. Monoclonal antibody to the EBV VCA glycoprotein 125 (Chemicon, Temecula, Calif.) is used at a concentration of 2.5 µg/ml for ELISA and 5 µg/ml for IFA.

Efficacy Against HHV-6: Serial 5-fold dilutions of drug starting at 50 µg/ml are prepared in media. CDV is used as a positive control. Samples for determining anti-viral efficacy are prepared by incubating $1 \times 10^6$ cells for one hour with sufficient virus to infect approximately 35% of the cells. After infection, the appropriate dilution of compound is added and cells incubated for 4 to 6 days at 37° C. Virus free controls are prepared by incubating $1\times10^6$ cells in compound-free media for the designated period and virus controls are prepared by incubating $1\times10^6$ cells for one hour with sufficient virus to infect 35% of the cells followed by incubation in compound-free media for the designated period. After incubation, the cells are rinsed with PBS and permeabilized overnight in methanol at −80 C for use in FACS.

FACS Assay: Cells are rinsed thoroughly with PBS and a blocking solution containing 5% FBS, 4% Normal goat serum (NGS) and 0.5% DMSO. Cells are then incubated with the appropriate monoclonal antibody (HHV-6 early nuclear proteins (Chemicon, Temecula, Calif.) for HHV-6, GS variant A, a 101 kDa virion protein (Chemicon, Temecula, Calif.) for HHV-6, Z-29 variant B, and KS8.1 for HHV-8 (Bala Chandran, University of Kansas, Department of Microbiology, Molecular Genetics and Immunology).

6.6.2.4 Toxicity Screening for Herpes Viruses

Neutral Red Uptake Assay—HFF Cells: Twenty-four hours prior to assay, HFF cells are plated into 96 well plates at a concentration of $2.5\times10^4$ cells per well. After 24 hours, the media is aspirated and 125 µl of each compound concentration is added to the first row of wells and then diluted serially 1:5 using the automated Bio-Mek Liquid Handling System in a manner similar to that used in the CPE assay. The plates are then incubated in a $CO_2$ incubator at 37° C. for seven days. At this time the media/compound is aspirated and 200 µl/well of 0.01% neutral red in DPBS is added. This mixture is incubated in the CO, incubator for 1 hour. The compound is aspirated and the cells are washed using a Nunc Plate Washer. After removing the DPBS wash, 200 µl/well of 50% ETOH/1% glacial acetic acid (in $H_2O$) is added. The plates are rotated for 15 minutes and the optical densities are read at 550 nm on a plate reader. $CC_{50}$ values are calculated using a computer program.

Cell Proliferation Assay—HFF Cells: Twenty-four hours prior to assay, HFF cells are seeded in 6-well plates at a concentration of $2.5\times10^4$ cells per well in MEM containing 10% FBS. On the day of the assay, test compounds are diluted serially in MEM containing 10% FBS at increments of 1:5 covering a range from 100 µg/ml to 0.03 µg/ml. For compounds that have to be solubilized in DMSO, control wells receive MEM containing 1.0% DMSO. The media from the wells is then aspirated and 2 ml of each compound concentration is then added to each well. The cells are then incubated in a $CO_2$ incubator at 37° C. for 72 hours. At the end of this time, the media-compound solution is removed and the cells are washed. One ml of 0.25% trypsin is added to each well and incubated until the cells start to come off of the plate. The cell-media mixture is then pipetted up and down vigorously to break up the cell suspension, and 0.2 ml of the mixture is added to 9.8 ml of Isoton III and counted using a Coulter Counter. Each sample is counted 3 times with 2 replicate wells per sample.

MTS Tetrazolium Cytotoxicity Assay: Serial 5-fold dilutions of test compound starting at 50 µg/ml are prepared in media and added to $1\times10^6$ cells. Controls are prepared by incubating $1\times10^6$ cells in compound-free media. After an incubation period of 3-6 days depending on the assay system, 200 µl is transferred to a 96 well plate in duplicate, 20 µl of MTS is added, and the plate is wrapped in foil and incubated at 37° C. for 4 hours. MTS is bioreduced by dehydrogenase enzymes found in metabolically active cells into an aqueous soluble formazan. The quantity of formazan product as measured by the amount of 490 nm absorbance is directly proportional to the number of living cells in culture. Compound concentration is plotted against the optical density of each sample and $CC_{50}$ values were calculated using MacSynergy II.

Cell Proliferation Assay—HSB-2 and Daudi Cells: Serial 5-fold dilutions of compound starting at 50 g/ml are prepared in media and added to $1\times10^6$ cells. Controls are prepared by incubating $1\times10^6$ cells in compound-free media. After an incubation period of 3-4 days depending on the assay system, a Coulter Counter is used to determine the total number of cells for each sample (HSB-2 and Daudi cell lines). Compound concentration is plotted against the total concentration of cells for each sample and $IC_{50}$ values are calculated using MacSynergy II.

Bone Marrow Assay: In vitro toxicity can be determined by inhibition of myeloid [colony-forming units granulocyte/macrophage (CFU-GM)] and erythroid [burst-forming unit-erythroid (BFU-E)] colony formation in soft agar clonal assays. Using a 21-23 gauge needle attached to a syringe, rodent bone marrow cells are collected from the leg bone of rats or mice by flushing with Isocoves' Modified Dulbecco's medium (IMDM). A single cell suspension is obtained by repeated aspiration through the needle. Nucleated cells are enumerated with a hemacytometer and adjusted to the desired cell concentration in IMDM. Murine CFU-GM assays are prepared with $2.5\times10^5$ nucleated cells/ml, 20% FBS, 10 ng/ml rmGM-CSF, and 0.2% agarose. BFU-E cultures include 30% FBS, 1% deionized BSA, 0.1 mM 2-ME, 4 U/ml rhEpo, 10 ng/ml rmIL-3, $2.5\times10$ nucleated cells/ml and 0.2% agarose (140). Triplicate wells (in 6 well plates) containing 0.1 ml of compound (10×) receive 1 ml of either culture mixture for each concentration group and slowly mixed. The cultures are allowed to gel at 4° C. and then incubated for 7 (CFU-GM) or 9 (BFU-E) days at 37° C. in a humidified atmosphere of 5% $CO_2$ in air. Colonies are counted using an inverted microscope. CFU-GM colonies are identified as cell clones containing at least 40 cells. BFU-E cultures are stained with dianisidine, and aggregates of greater than 60 hemoglobin-containing cells are counted as erythroid colonies. The median inhibitory concentration ($IC_{50}$) and the 90% inhibitory concentration ($IC_{90}$) are derived from linear regression analysis of the logarithm of compound concentration versus CFU-GM or BFU-E survival fraction.

6.6.3 In Vitro Laboratory Procedures for Assays for Influenza, Respiratory and Other Viruses 6.6.3.1 Screening Efficacy for RSV, PIV and Flu, Measles, Rhino, Adeno, SARS, VEE, Yellow Fever, West Nile, Pichinde, Punta Toro and Dengue Viruses Rapid Screening Assay: When relatively large numbers (10 or more) of test compounds are available, the compounds are evaluated in a 2-concentration test. In this procedure, two concentrations (e.g., 200 and 20 µg/ml) are tested. Compounds are diluted 1:2 when virus is added, making final concentrations 100 and 10 µg/ml. The standard CPE test uses an 18 hour monolayer (80-100% confluent) of the appropriate cells, medium is drained and each of the concentrations of test compound or placebo are added, followed within 15 minutes by virus or virus diluent. Two wells are used for each concentration of compound for both anti-viral and cytotoxicity testing. The plate is sealed and incubated the standard time period required to induce near-maximal viral CPE. The plate is then stained with neutral red by the method described below, and the percentage of uptake indicating viable cells read on a microplate autoreader at dual wavelengths of 405 and 540 nm, with the difference taken to eliminate background. An approximated virus-inhibitory concentration, 50% endpoint ($EC_{50}$) and cell-inhibitory concentration, 50% endpoint ($IC_{50}$) are determined from which a general selectivity index is calculated: SI=(IC$_{50}$)/(EC$_{50}$). An SI of 3 or greater typically indicates confirmatory testing is needed.

Inhibition of Cytopathic Effect (CPE): This test, run in 96 well flat-bottomed microplates, is used for the initial anti-viral evaluation of all new test compounds. In this CPE inhibition test, four log$_{10}$ dilutions of each test compound (e.g., 1000, 100, 10, 1 g/ml) are added to 3 cups containing the cell monolayer; within 5 minutes, the virus is then added and the plate sealed, incubated at 37° C. and CPE read microscopically when untreated infected controls develop a 3 to 4+CPE (approximately 72 to 120 hours). A known positive control compound is evaluated in parallel with test compounds in each test. The positive control compound, for example, is: ribavirin for dengue, influenza, measles, RSV, PIV, Pichinde, Punta Toro and VEE viruses; cidofovir for adenovirus; pirodovir for rhinovirus; 6-azauridine for West Nile and yellow fever viruses; and alferon (interferon alfa-n3) for SARS virus. Follow-up testing with compounds that are found active in initial screening tests are run in the same manner except 8 one-half log$_{10}$ dilutions of each compound are used in 4 cups containing the cell monolayer per dilution. The data are expressed as 50% effective concentrations (EC$_{50}$).

Increase in Neutral Red (NR) Dye Uptake: This test is run to validate the CPE inhibition seen in the initial test, and utilizes the same 96-well micro plates after the CPE has been read. Neutral red is added to the medium; cells not damaged by virus take up a greater amount of dye, which is read on a computerized micro plate autoreader. For example, the method as described by McManus, *Appl. Environment. Microbiol.* 1976, 31:35-38, can be used. An EC$_{50}$ is determined from this dye uptake.

Decrease in Virus Yield: Compounds considered active by CPE inhibition and by NR dye uptake are re-tested if additional, fresh material is available, using both CPE inhibition and, using the same plate, the effect on reduction of virus yield by assaying frozen and thawed eluates from each cup for virus titer by serial dilution onto monolayers of susceptible cells. Development of CPE in these cells is the indication of presence of infectious virus. As in the initial tests, a known active compound is run in parallel as a positive control. The 90% effective concentration (EC$_{90}$), which is that test compound concentration that inhibits virus yield by 1 log 10, is determined from these data.

6.6.3.2 Screening Toxocity for RSV, PIV and Flu, Measles, Rhino, Adeno, SARS, VEE, Yellow Fever, West Nile, Pichinde, Punta Toro and Dengue Viruses Visual Observation: In the CPE inhibition tests, two wells of uninfected cells treated with each concentration of test compound are run in parallel with the infected, treated wells. At the time CPE is determined microscopically, the toxicity control cells are also examined microscopically for any changes in cell appearance compared to normal control cells run in the same plate. These changes can be enlargement, granularity, cells with ragged edges, a filmy appearance, rounding, detachment from the surface of the well, or other changes. These changes are given a designation of T (100% toxic), PVH (partially toxic-very heavy—80%), PH (partially toxic-heavy—60%), P (partially toxic—40%), Ps (partially toxic-slight—20%), or 0 (no toxicity—0%), conforming to the degree of cytotoxicity seen. A 50% cell inhibitory (cytotoxic) concentration (IC$_{50}$) is determined by regression analysis of these data.

Neutral Red Uptake: In the neutral red dye uptake phase of the anti-viral test described above, the two toxicity control wells also receive neutral red and the degree of color intensity is determined spectrophotometrically. A neutral red IC$_{50}$ (NR IC$_{50}$) is subsequently determined.

Viable Cell Count: Compounds considered to have significant anti-viral activity in the initial CPE and NR tests are re-tested for their effects on cell growth. In this test, 96-well tissue culture plates are seeded with cells (sufficient to be approximately 20% confluent in the well) and exposed to varying concentrations of the test drug while the cells are dividing rapidly. The plates are then incubated in a CO$_2$ incubator at 37° C. for 72 hours, at which time neutral red is added and the degree of color intensity indicating viable cell number is determined spectrophotometrically; an IC$_{50}$ is determined by regression analysis.

Data Analysis: Each test compound's anti-viral activity is expressed as a selectivity index (SI), which is the IC$_{50}$ or IC$_{90}$ divided by the EC$_{50}$. Generally, an SI of 10 or greater is indicative of positive anti-viral activity, although other factors, such as a low SI for the positive control, are also taken into consideration. Compounds having SI values of 10 or greater can be evaluated against additional strains of the original virus inhibited in order to more fully determine the spectrum of anti-viral activity of the compound.

6.6.4 General Procedures for Assays for Orthopoxviruses

To quickly screen out compounds that do not have activity against any of the herpes viruses, or are too toxic to evaluate, an assay such as a CPE-inhibition assay that is semi-automated is commonly used initially to screen out the negative compounds. Typically, all screening assays are conducted in low passage human cells, and each assay system contains a positive control (CDV) and a negative control (ACV). Efficacy is demonstrated by at least two different assay systems that detect functional biologic activity and should be confirmed using low passaged clinical isolates and drug resistant mutants whenever available. In the case of Vaccinia virus (VV) and Cowpox virus (CV), efficacy against VV and CV is confirmed using other isolates. Toxicity is determined using both resting and proliferating human fibroblast cells and proliferating lymphoblastic cells, and for selected compounds, toxicity in rodent myeloid and erythroid progenitor cells is assessed.

6.6.4.1 Screening Assays for VV and CV

Compounds are initially screened for activity using the CPE assay in HFF cells. Further testing in two other cells lines, Vero and MRC-5, and against other strains of virus is possible for compounds that demonstrate activity in other assay systems. The screening assay systems utilized are selected to show specific inhibition of a biologic function, i.e., cytopathic effect (CPE) in susceptible human cells. In the CPE-inhibition assay, test compound is added 1 hour prior to infection so the assay system will have maximum sensitivity and detect inhibitors of early replicative steps such as adsorption or penetration as well as later events. To rule out non-specific inhibition of virus binding to cells, all compounds that show reasonable activity in the CPE assay are confirmed using a classical plaque reduction assay in which the drug is added 1 hour after infection. These assay systems also can be manipulated by increasing the pre-treatment time in order to demonstrate anti-viral activity with oligodeoxynucleotides and/or peptides. By delaying the time of addition of compound after infection, information regarding which step in the virus life cycle is inhibited (i.e., early vs. late functions) can be gained. A direct inactivation assay can be employed to determine the virucidal activity of selected compounds.

Efficacy: In the assays used for primary screening, a minimum of six compound concentrations is typically used, covering a range of, e.g., 100 mg/ml to 0.03 mg/ml, in 5-fold increments. These data allow for creating dose response curves. From these data, the dose that inhibited viral replication by 50% (effective concentration 50; EC$_{50}$) is usually calculated using a computer software program, for example, MacSynergy II by M. N. Prichard, K. R. Asaltine, and C. Shipman, Jr., University of Michigan, Ann Arbor, Mich.

Toxicity: The same compound concentrations used to determine efficacy are also used on uninfected cells in each assay to determine toxicity of each experimental compound. The compound concentration that is cytotoxic to cells as determined by their failure to take up a vital stain, neutral red (cytotoxic concentration 50; $CC_{50}$), is determined as described above. A neutral red uptake assay can be used. The assay is reproducible and allows quantitation of toxicity based on the number of viable cells rather than cellular metabolic activity. In some cases, the toxicity of new compounds on dividing cells is determined at a very early stage of testing. A cell proliferation assay using HFF cells is a sensitive assay for detecting compound toxicity to dividing cells. The compound concentration that inhibits cell growth by 50% ($IC_{50}$) is calculated as described above. In comparison with four human diploid cell lines and Vero cells, HFF cells are known to be very sensitive and predictive of toxicity for bone marrow cells.

6.6.4.2 Confirmation Assays for VV and CV

Anti-viral Activity: Compounds that show activity in the CPE-inhibition assay are confirmed using the plaque reduction assay. Susceptibility of additional virus strains of VV, CV and activity in other cell types can also be determined for selected compounds.

Toxicity: In addition to the toxicity component incorporated into each assay system, a standardized cell cytotoxicity assay using a vital stain uptake (Neutral Red) is performed using 7 days of compound exposure to confluent non-dividing cells. This assay measures direct cell cytotoxicity ($CC_{50}$). In this regard, a neutral red uptake assay is reproducible and allows for quantitation of toxicity based on the number of viable cells rather than cellular metabolic activity. In some cases, the toxicity of new compounds on dividing cells is determined at a very early stage of testing. A cell proliferation assay using HFF cells is a sensitive assay for detecting compound toxicity to dividing cells, and the compound concentration that inhibits cell growth by 50% ($IC_{50}$) is calculated as described above.

6.6.5 In Vitro Laboratory Procedures for Assays for Orthopoxviruses

6.6.5.1 Efficacy Screening for VV and CV

Preparation of Human Foreskin Fibroblast (HFF) Cells: Newborn human foreskins are obtained as soon as possible after circumcision and placed in minimal essential medium (MEM) containing vancomycin, fungizone, penicillin, and gentamicin at the usual concentrations, for 4 hours. The medium is then removed, the foreskin minced into small pieces and washed repeatedly with phosphate buffered saline (PBS) deficient in calcium and magnesium (PD) until red cells are no longer present. The tissue is then trypsinized using trypsin at 0.25% with continuous stirring for 15 minutes at 37° C. in a $CO_2$ incubator. At the end of each 15-minute period, the tissue is allowed to settle to the bottom of the flask. The supernatant containing cells is poured through sterile cheesecloth into a flask containing MEM and 10% fetal bovine serum. The flask containing the medium is kept on ice throughout the trypsinizing procedure. After each addition of cells, the cheesecloth is washed with a small amount of MEM containing serum. Fresh trypsin is added each time to the foreskin pieces and the procedure repeated until all the tissue is digested. The cell-containing medium is then centrifuged at 1000 RPM at 4° C. for 10 minutes. The supernatant liquid is discarded and the cells are resuspended in a small amount of MEM with 10% FBS. The cells are then placed in an appropriate number of 25 $cm^2$ tissue culture flasks. As cells become confluent and need trypsinization, they are expanded into larger flasks. The cells are kept on vancomycin and fungizone to passage four, and maintained on penicillin and gentamicin. Typically, cells are used only through passage 10.

Cytopathic Effect Inhibition Assay: Low passage HFF cells are seeded into 96 well tissue culture plates 24 hours prior to use at a cell concentration of $2.5 \times 10^5$ cells per ml in 0.1 ml of MEM supplemented with 10% FBS. The cells are then incubated for 24 hours at 37° C. in a $CO_2$ incubator. After incubation, the medium is removed and 125 ml of experimental compound is added to the first row in triplicate wells, all other wells having 100 ml of MEM containing 2% FBS. The compound in the first row of wells is then diluted serially 1:5 throughout the remaining wells by transferring 25 ml using the BioMek 2000 Laboratory Automation Workstation. After dilution of the compound, 100 ml of the appropriate virus concentration is added to each well, excluding cell control wells, which received 100 ml of MEM. The virus concentration utilized is 1000 PFU's per well. The plates are then incubated at 37° C. in a $CO_2$ incubator for 7 days. After the incubation period, media is aspirated and the cells stained with a 0.1% crystal violet in 3% formalin solution for 4 hours. The stain is removed and the plates rinsed using tap water until all excess stain is removed. The plates are allowed to dry for 24 hours and then read on a BioTek Multiplate Autoreader at 620 nm. The $EC_{50}$ values are determined by comparing compound treated and untreated cells using a computer program.

Plaque Reduction Assay: Two days prior to use, HFF cells are plated into 6 well plates and incubated at 37° C. with 5% $CO_2$ and 90% humidity. On the date of assay, the compound is made up at twice the desired concentration in 2×MEM and then serially diluted 1:5 in 2×MEM using 6 concentrations of compound. The initial starting concentration is usually 200 mg/ml down to 0.06 mg/ml. The virus to be used is diluted in MEM containing 10% FBS to a desired concentration which will give 20-30 plaques per well. The media is then aspirated from the wells, and 0.2 ml of virus is added to each well in duplicate with 0.2 ml of media being added to drug toxicity wells. The plates are then incubated for 1 hour with shaking every 15 minutes. After the incubation period, an equal amount of 1% agarose is added to an equal volume of each compound dilution. This addition gives final compound concentrations beginning with 100 mg/ml and ending with 0.03 mg/ml and a final agarose overlay concentration of 0.5%. The compound/agarose mixture is applied to each well in 2 ml volume and the plates are incubated for 3 days, after which the cells are stained with a 0.01% solution of neutral red in phosphate buffered saline. After a 5-6 hours incubation period, the stain is aspirated, and plaques counted using a stereomicroscope at 10× magnification.

6.6.5.2 Toxicity Screening for VV and CV

Neutral Red Uptake Assay: Twenty-four hours prior to assay, HFF cells are plated into 96 well plates at a concentration of $2.5 \times 10^4$ cells per well. After 24 hours, the media is aspirated and 125 ml of compound is added to the first row of wells and then diluted serially 1:5 using the BioMek 2000 Laboratory Automation Workstation in a manner similar to that used in the CPE assay. After compound addition, the plates are incubated for 7 days in a $CO_2$ incubator at 37° C. At this time, the media/compound mixture is aspirated and 200 ul/well of 0.01% neutral red in PBS is added. This mixture is incubated in the $CO_2$ incubator for 1 hour. The dye is aspirated and the cells are washed using a Nunc Plate Washer. After removing the PBS, 200 mg/well of 50% ETOH/1% glacial acetic acid (in $H_2O$) is added. The plates are rotated for 15 minutes and the optical densities read at 540 nm on a plate reader. The $EC_{50}$ values are determined by comparing compound treated and untreated cells using a computer program.

Cell Proliferation Assay: Twenty-four hours prior to assay, HFF cells are seeded in 6-well plates at a concentration of $2.5 \times 10^4$ cells per well in MEM containing 10% FBS. On the day of the assay, compounds are diluted serially in MEM containing 10% FBS at increments of 1:5 covering a range from 100 mg/ml to 0.03 mg/ml. For drugs that have to be solubilized in DMSO, control wells receive MEM containing 1% DMSO. The media from the wells is aspirated, and 2 ml of each drug concentration is then added to each well. The cells are incubated in a $CO_2$ incubator at 37° C. for 72 hours. At the end of this time, the media-compound solution is removed and the cells washed. One ml of 0.25% trypsin is added to each well and incubated until the cells start to come off of the plate. The cell-media mixture is then pipetted up and down vigorously to break up the cell suspension and 0.2 ml of the mixture is added to 9.8 ml of Isoton III and counted using a Coulter Counter. Each sample is counted 3 times with 2 replicate wells per sample.

Bone Marrow Clonogenic Assay: In vitro toxicity to bone marrow progenitor cells can be determined by inhibition of myeloid [colony-forming units granulocyte/macrophage (CFU-GM)] and erythroid [burst-forming unit-erythroid (BFU-E)] colony formation in soft agar clonal assays. Using a 21-23 gauge needle attached to a syringe, rodent bone marrow cells are collected from the leg bone of rats or mice by flushing with Isocoves' Modified Dulbecco's medium (IMDM). A single cell suspension is obtained by repeated aspiration through the needle. Nucleated cells are enumerated with a hemacytometer and adjusted to the desired cell concentration in IMDM. Murine CFU-GM assays are prepared with $2.5 \times 10^5$ nucleated cells/ml, 20% FBS, 10 ng/ml rmGM-CSF, and 0.2% agarose. BFU-E cultures include 30% FBS, 1% deionized BSA, 0.1 mM 2-ME, 4 U/ml rhEpo, 10 ng/ml rmIL-3, $2.5 \times 10^5$ nucleated cells/ml and 0.2% agarose. Triplicate wells (in 6 well plates) containing 0.1 ml of compound (10×) receive 1 ml of either culture mixture for each concentration group and slowly mixed. The cultures are allowed to gel at 4° C. and then incubated for 7 (CFU-GM) or 9 (BFU-E) days at 37° C. in a humidified atmosphere of 5% $CO_2$ in air. Colonies are counted using an inverted microscope. CFU-GM colonies are identified as cell clones containing at least 40 cells. BFU-E cultures are stained with dianisidine, and aggregates of greater than 60 hemoglobin-containing cells are counted as erythroid colonies. The median inhibitory concentration ($IC_{50}$) and the 90% inhibitory concentration ($IC_{90}$) are derived from linear regression analysis of the logarithm of compound concentration versus CFU-GM or BFU-E survival fraction.

6.6.6 Assays for Hepatitis Viruses 6.6.6.1 Hepatitis B Virus (HBV)

A variety of cell-culture based anti-HBV analyses are available. Candidate compounds are initially assayed in a primary screening assay. Compounds demonstrating reasonable anti-viral and cytotoxicity profiles are then candidates for several additional follow-up analyses. For the primary screening assay, routinely 2-3 mg are required for compounds with molecular weights in the range of standard nucleosides (e.g., 300-500). Additional compound may be required for follow-up analyses. Molecular weights and solubility information are provided if available. If no preferred solvent is specified, 100% tissue culture DMSO will be used. Compounds are typically solubilized in aqueous solutions (normal pH range) at a minimum of a 10× final testing concentration or in DMSO at a minimum 50× test concentration. EtOH is generally not well tolerated by the cell lines used for these studies, but final concentrations of EtOH of less than 0.03% are usually acceptable. Compounds which need to be tested in other solvents should be accompanied by a small amount of solvent (under a separate accession number) to control for cytotoxicity. For compounds in solution, approximately 0.25 ml of a 100× stock is minimally required.

Primary Assay: HBV anti-viral assays (Korba & Gerin, Antivir. Res. 1992, 19:55) are conducted using confluent cultures of 2.2.15 cells maintained on 96-well flat-bottomed tissue culture plates (confluence in this culture system is required for active, high levels of HBV replication equivalent to that observed in chronically-infected individuals (Sells et al., J. Virol. 1988, 62:2836; Korba and Gerin, Antivir. Res. 1992, 19:55). HepG2-2.2.15 is a stable cell line containing the hepatitis B virus (HBV) ayw strain genome. Anti-viral compounds blocking any late step of viral replication such as transcription, translation, pregenome encapsidation, reverse transcription, particle assembly and release can be identified and characterized using this cell line.

Cultures are treated with nine consecutive daily aliquots of the test compounds. Typically, 4 doses (10-fold or 3-fold steps), in triplicate are used. HBV DNA levels in the culture medium (representing HBV virion production) are assessed by quantitative blot hybridization 24 hours after the last treatment. Alternatively, whether a compound reduces the production of secreted HBV from cells can be initially assessed utilizing real time quantitative PCR (TaqMan) assay to directly and accurately measure HBV DNA copies. Cytotoxicity is assessed by uptake of neutral red dye 24 hours following the last treatment. Lamivudine (LMV) is used as the standard assay control, but other control compounds are also available.

$EC_{50}$, $EC_{90}$ and $CC_{50}$ values are calculated by linear regression analysis (MS EXCEL®, QuattroPro®) using data combined from all treated cultures (Korba & Gerin, Antivir. Res. 1992, 19:55; Okuse et al., Antivir. Res. 2005, 65:23). Standard deviations for $EC_{50}$ and $EC_{90}$ values are calculated from the standard errors generated by the regression analyses. $EC_{50}$ and $EC_{90}$ are compound concentrations at which a 2-fold, or a 10-fold depression of HBV DNA (relative to the average levels in untreated cultures), respectively, is observed. $CC_{50}$ is the compound concentration at which a 2-fold lower level of neutral red dye uptake (relative to the average levels in untreated cultures) is observed. The Selectivity index (S.I.) is calculated as $CC_{50}/EC_{90}$ since at least a 3-fold depression of HBV DNA levels is typically required to achieve statistical significance in this assay system (Korba & Gerin, Antivir. Res. 1992, 19:55).

Secondary Assay: Confluent cultures of 2.2.15 cells maintained on 48-well flat-bottomed tissue culture plates are treated as described for the primary assay. HBV virion DNA levels in the culture medium and cytotoxicity are assessed as described for the primary assay. In addition, intracellular HBV DNA replication is measured by quantitative Southern blot hybridization analysis (Korba & Gerin, Antivir. Res. 1992, 19:55). $EC_{50}$, $EC_{90}$ and S.I. values are calculated for both virion DNA and intracellular HBV DNA replication intermediates. In certain cases, additional assays (tertiary assays) can be conducted.

Combination Studies: Compounds are mixed at approximately equipotent concentrations and this molar ratio is maintained during serial dilution (Korba, Antivir. Res. 1996, 29:49; Iyer et al. 2004). To compensate for potential unforeseen interactions (e.g., changes in uptake, metabolism, etc.), the concentration of one compound is altered approximately 3-fold higher of lower relative to the second compound so that three different ratios are used in one experiment. Cultures are treated with 6-8 serial dilutions of the mixtures, as with the corresponding monotherapies, as described for the primary assay. Evaluation of compound interactions in the combination treatments is conducted against the corresponding monotherapies in the same experiments using the Combostat® (Biosoft, Inc.) analysis software. For combination treatments, $EC_{50}$, $EC_{90}$, $CC_{50}$ and S.I. ($CC_{50}/EC_{90}$) are presented for the first compound listed. The molar ratio of the compounds in each combination is also indicated.

Alternatively, after the anti-viral activity of test compounds against HBV is confirmed, the interactions of the compounds with 3TC, IFNα and other compounds in terms of efficacy (synergy, additivity, antagonism) and toxicity (combination toxicity) can be evaluated with the 2.2.15 cells using the quantitative HBV TaqMan PCR assay.

Drug Resistant HBV: Activity against recombinant HBV carrying clinically relevant mutations that confer resistance to licensed drugs is performed using transient transfection of HBV DNA (Tatti et al., *Antivi. Res.* 2002, 55:27; Iyer et al., *AAC* 2004, 48:2199). Cultures are transfected in 48-well culture plates with Lipofectamine 2000™ (Gibco, Inc) following the manufacturer's procedure. Beginning three days post-transfection, cultures are treated for 5 days with anti-viral compounds. Anti-viral activity is determined by quantitative Southern Blot hybridization of intracellular HBV DNA replication intermediates. Currently, the following mutants are available: lamviudine (LMV)-resistant, polM204V, polM204I, polL180M, polM204V/L180M (Allen et al., *Hepatology* 1998, 27:1670); adefovir dipovoxil (ADV)-resistant, polN236T (Angus et al., *Gastroenterology* 2003. 125: 292). Standardized nomenclature is used for HBV polymerase assignment (Stuyver et al., *Hepatology* 2001, 33:751). Additional mutants (TNFR, ETVR) are under construction.

Other tests can be conducted in order to evaluate the ability of compounds to inhibit the known 3TC- and penciclovir-resistant mutants of HBV. Stable cell lines with control wild-type HBV and the following mutations known to be associated with resistance of HBV to these agents can be used: (1) L526M (rtL180M) of Domain B & YMDD M550V (rtM204V) of Domain C (the most common mutation pattern observed during HBV breakthrough viremia); (2) L526M alone (the most common mutation associated with penciclovir resistance; also associated with some resistance against 3TC); and control wild-type HBV.

HBV Protein Production and RNA Transcription: Semi-quantitative ELISA-based analysis of HBV proteins is performed (Korba & Gerin, *Antivir. Res.* 1995, 28:225; Korba et al., *Antivir. Res.* 2008, 77:56) using samples diluted (2 to 10-fold) to bring levels into the dynamic response ranges of the assays. Qualitative analysis of HBV proteins is also performed using standard Western blot techniques (Muller et al., *J. Infect. Dis.* 1992, 165:929). HBV surface (HBsAg) and HBV e (HBeAg) antigens are analyzed from culture medium samples, and HBV core (HBcAg) is analyzed from intracellular lysates (normalized for total cell protein content in each culture sample). Intracellular HBV RNA (normalized to the level of cellular B-actin RNA in each culture sample) is assessed by quantitative northern blot hybridization (Korba & Gerin, *Antivir. Res.* 1995, 28:225).

HBV Mechanism of Action Studies: A variety of assays can be used to pinpoint the mechanism of action of anti-viral compounds. Examples include the following:

Extracellular HBV virions: In addition to the quantitative PCR analysis, a Southern blot of the HBV particles secreted from compound-treated cells can be performed;

Intracellular HBV particles: HBV particles can be isolated from the treated 2.2.15 cells and the pregenomic RNA examined by Southern blot analysis. This can be helpful in identifying the site of action of a late-acting compound;

Intracellular HBV replicative intermediates: Nucleic acids isolated from the cells can be examined by Southern blots to assess the distribution of circular partially double-stranded HBV DNA, linear partially double-stranded DNA and single stranded HBV DNA;

HBV transcription: Effects on HBV genomic and subgenomic viral RNA synthesis are studied by Northern blot and primer extension analysis;

HBsAg and HBeAg release assay: ELISAs are used to quantify the amounts of the HBV envelope protein, surface antigen (HBsAg), and of secreted e-antigen (HBeAg) released from cultures;

Western blot analysis: Western blots are conducted to study HBV core and envelope protein expression;

Novel mechanism of action studies: Specific effects on HBV transcription and replication may arise from alterations in DNA-protein interactions, sometimes affected by cellular growth factors, at the HBV enhancers, promoters or through the transcriptional transactivator X-protein; and Endogenous Polymerase Assay: Extracellular HBV virions contain partially double-stranded circular DNA genomes. Purified virions are used to assay the ability of anti-viral drugs to inhibit the endogenous polymerase activity of HBV. Normally, this activity functions to complete (+) strand synthesis following the infection of new cells by HBV virions.

6.6.6.2 Hepatitis C Virus (HCV) Protocol I

Cell line Huh7 ET (luc-ubi-neo/ET), which contains a new HCV RNA replicon with a stable luciferase (LUC) reporter, is used. It is similar to the cell line 5-2 (Krieger et al., *J. Virol.* 2001, 75:4614-4624.), but contains additional modifications that make the cell line more robust and provide stable LUC expression for anti-viral screening. The composition of the replicon is shown diagrammatically below:

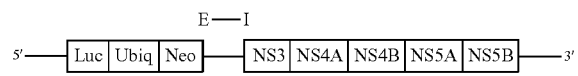

The HCV RNA replicon ET contains the 5' NTR (IRES) of HCV 5' which drives the production of a firefly luciferase (Luc), ubiquitin (Ubiq), and neomycin phosphotransferase (Neo) fusion protein. Ubiquitin cleavage releases the LUC and Neo genes. The EMCV IRES element (E-I) controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV.

The LUC reporter is used as an indirect measure of HCV replication. The activity of the LUC reporter is directly proportional to HCV RNA levels and positive control anti-viral compounds behave comparably using either LUC or RNA endpoints. The use of the LUC endpoint is more economical than HCV RNA and can be used for high-throughput applications to screen libraries of compounds.

Primary HCV RNA Replicon Assay: First, the effect of compounds added in triplicate at a single high-test concentration of 20 mM on HCV RNA-derived LUC activity and cytotoxicity is examined. Human interferon alpha-2b is included in each run as a positive control compound. Subconfluent cultures of the ET line are plated out into 96-well plates that are dedicated for the analysis of cell numbers (cytotoxicity) or anti-viral activity, and test compounds are added to the appropriate wells the next day. Cells are processed 72 hours later when the cells are still subconfluent. Compounds that reduced the LUC signal by 50% or more relative to the untreated cell controls move forward to the next screening steps. A compound's cytotoxicity is assessed as the percent viable cells relative to the untreated cell controls.

HCV RNA Replicon Confirmation Assay: The HCV RNA replicon confirmatory assay is then used to examine the effects of compounds at, for example, five half-log concentrations each. Human interferon alpha-2b is included in each run as a positive control compound. Subconfluent cultures of the ET line are plated out into 96-well plates that are dedicated for the analysis of cell numbers (cytotoxicity) or anti-viral activity and the next day test compounds are added to the appropriate wells. Cells are processed 72 hours later when the cells are still subconfluent. Compound $EC_{50}$ and $EC_{90}$ values (anti-viral activity) are derived from HCV RNA levels assessed as either HCV RNA replicon-derived LUC activity or as HCV RNA using TaqMan RT-PCR. Compound $IC_{50}$ and $IC_{90}$ values (cytotoxicity) are calculated using CytoTox-1 (Promega), a colorimetric assay used as an indicator of cell numbers and cytotoxicity when the LUC assay system is employed, while ribosomal (rRNA) levels determined via TaqMan RT-PCR are used as an indication of cell numbers in the RNA-based assay. Compound selectivity indices $SI_{50}$ and $SI_{90}$ values are also calculated.

6.6.6.3 Hepatitis C Virus (HCV) Protocol II

A variety of cell-culture based anti-HCV analyses are available. Candidate compounds are initially assayed in a primary screening assay. Compounds demonstrating reasonable anti-viral and cytotoxicity profiles are then candidates for several additional follow-up analyses. For the primary screening assay, routinely 2-3 mg are required for compounds with molecular weights in the range of standard nucleosides (e.g., 300-500). Additional compound may be required for follow-up analyses. Molecular weights and solubility information are provided if available. If no preferred solvent is specified, 100% tissue culture DMSO is used. Compounds are solubilized in aqueous solutions (normal pH range) at a minimum of a 10× final testing concentration or in DMSO at a minimum 50× test concentration. EtOH is generally not well tolerated by the cell lines used for these studies, but final concentrations of EtOH of less than 0.03% are acceptable. Compounds which need to be tested in other solvents should be accompanied by a small amount of solvent (under a separate accession number) to control for cytotoxicity. For compounds in solution, approximately 0.25 ml of a 100× stock is minimally required.

Primary Assay: Anti-viral activity against HCV is assessed in a 3-day assay (Okuse et al., *Antivir. Res.* 2005, 65:23; Korba et al., *Antivir. Res.* 2008, 77:56) using the stably-expressing HCV replicon cell line, AVA5 (sub-genomic (CON1), genotype 1b) (Blight et al., *Science* 2000, 290:1972) maintained as sub-confluent cultures on 96-well plates. Anti-viral activity is determined by blot hybridization analysis of intracellular HCV RNA (normalized to the level of cellular B-actin RNA in each culture sample). Cytotoxicity is assessed by neutral red dye uptake in cultures maintained in parallel plates.

$EC_{50}$, $EC_{90}$ and $CC_{50}$ values are calculated by linear regression analysis (MS EXCEL®, QuattroPro®) using data combined from all treated cultures (Korba & Gerin, *Antivir. Res.* 1992, 19:55; Okuse et al., *Antivir. Res.* 2005, 65:23). Standard deviations for $EC_{50}$ and $EC_{90}$ values are calculated from the standard errors generated by the regression analyses. $EC_{50}$ and $EC_{90}$ are compound concentrations at which a 2-fold, or a 10-fold depression of intracellular HCV RNA (relative to the average levels in untreated cultures), respectively, is observed. $CC_{50}$ is the compound concentration at which a 2-fold lower level of neutral red dye uptake (relative to the average levels in untreated cultures) is observed. The Selectivity index (S.I.) is calculated as $CC_{50}/EC_{90}$. Recombinant human interferon 2b (PBL laboratories, Inc.) is used as an assay control. Compounds currently in clinical trials that are directed against NS3 and NS5B can also be used.

Secondary Assay: This assay assesses activity against additional genotypes using the format described for the primary assay. Activity against the genotype 1b HCV is included for comparison. One exemplary replicon cell line contains H/FL-Neo (genotype 1a (H77), full length construct) (Blight et al., *J. Virol.* 2003, 77:3181). A genotype 2a construct (J6/JFH-1, full length) can be used to assess for future inclusion. $EC_{50}$, $EC_{90}$, $CC_{50}$ and S.I. values are calculated for each replicon cell line. In some instances, additional assays (tertiary assays) may also be conducted.

Combination Studies: Compounds are mixed at approximately equipotent concentrations and this molar ratio is maintained during serial dilution (Korba, *Antivir. Res.* 1996, 29:49; Iyer et al., 2004). Usually, three different ratios are used in one experiment. Cultures are treated with 6-8 serial dilutions of the mixtures, as with the corresponding monotherapies, as described for the primary assay. Evaluation of compound interactions in the combination treatments is conducted against the corresponding monotherapies in the same experiments using the Combostat® (Biosoft, Inc.) analysis software. For combination treatments, $EC_{50}$, $EC_{90}$, $CC_{50}$ and S.I. ($CC_{50}/EC_{90}$) are presented for the first compound listed. The molar ratio of the compounds in each combination is also indicated.

Drug-Resistant HCV: Since no licensed anti-HCV drugs for which resistance mutations have yet been identified, a panel of mutants conferring resistance to compounds in mid to late phase clinical trials is compiled. Some available stable replicon-containing cell lines (Korba et al., *Antivir. Res.* 2008, 77:56) are genotype 1 B NS5B S282T (Perra et al., *Nucleosides Nucleotides Nucleic Acids* 2005, 24:767), and NS3 A156S and NS3 A156V (Courcambeck et al., *Antivir. Ther.* 2006, 11:847) drug-resistant mutants. The genetic background is the same as that in the BB7 replicon (AVA5 cells) used in the primary assay. Activity against these mutants is assessed as described in the primary assay, except that semi-quantitative real-time PCR is used for the analysis of HCV RNA due to reduced replication levels.

The genotype 1b mutants can also be assessed in this manner. For this assay, Huh7.5 cells are transfected with HCV RNA using Liofectamine 2000™ (Gibco, Inc.) in 6-well culture plates. Three days post-transfection, cultures are exposed to 125 µg/mL G418 and test compounds. After 10-14 days, surviving colonies are fixed, stained, and counted. $EC_{50}$ and $EC_{90}$ values are calculated for each transfected RNA.

6.6.7 Assays for Papilloma Viruses

Assays for Human Papilloma Virus (HPV) 11 and 40: A431 cells are plated $2 \times 10^5$ cells/well in 6-well cluster dishes. Replicate aliquots of HPV-11 (or HPV-40) are added to each well representing an MOI of 150 particles per cell. Dilutions of compound are added to triplicate cultures. Control wells without virus are included and receive media alone. Positive control compound can be, e.g., HPMPC (cidofovir) at 300 µg/ml. Cell cultures are harvested, lysed with Trizol reagent (GIBCO/BRL) and RNA prepared. QRT-PCR is conducted to quantitate the proportion of viral E1-E4 transcripts and a cellular reference RNA for the TATA-binding protein (TBP). Anti-viral effects of compounds are assessed as an $EC_{50}$ value representing a 50% reduction in the amount of E1-E4 viral transcript when compared with cultures infected with HPV-11 (or HPV-40) alone. $CC_{50}$ toxicity is calculated as the compound dose at which 50% of total cellular RNA is recovered. From these two values, the Selectivity Index (SI) is determined from $CC_{50}/EC_{50}$. Usually, SI>5 would be significant for the detection of an anti-viral activity.

The assay procedure can be modified to test compounds with microbicidal activity if necessary. This modification is represented by drug addition to A431 cells at the same time as infectious virus.

Assays for Bovine Papilloma Virus (BPV) 1: C127 cells are plated $3 \times 10^3$ cells/well into wells of a 96-well filat-bottomed microculture plate. Replicate aliquots of BPV-1 are added to each well, representing approximately 100 focus-forming units. Control wells without virus are included. Dilutions of drug are added to triplicate cultures of both BPV-1-infected and uninfected cultures. Control wells receive media without compound. Positive control compound can be, e.g., cidofovir at 5 µg/ml. Cell cultures are fed with medium and compound every 3-4 days. Cell numbers and viability are assessed using the MTS assay. Anti-viral effects of compounds are calculated using the following formula to obtain % anti-viral activity:

$$B \& A/B \& C \times 100\% = \% \text{ Anti-viral activity}$$

A=O.D. of BPV-1-containing, compound-treated cultures
B=O.D. of BPV-1 containing cell cultures
C=O.D. of cultures of cells alone.

The $EC_{50}$ value represents a 50% reduction in the amount of O.D. values (MTS signal) of compound-treated virus-infected cultures when compared with cultures containing BPV-1 alone and cultures containing cells alone. The Selectivity Index (SI) is determined from $CC_{50}/EC_{50}$. Usually, SI>5 would be significant for the detection of an anti-viral activity.

The assay procedure can be modified to test compounds with microbicidal activity if necessary. This modification is represented by drug addition to C127 cells at the same time as infectious virus.

Assays for Human Papilloma Virus (HPV) 31b: Cultures of CIN612, clone 9E cells are prepared from known protocols. Individual rafts are developed containing multi-layers of 9E cells growing on a collagen matrix impregnated with mitomycin C-treated fibroblast cells. Rafts are treated with compound delivered into the cell culture media that can diffuse into the 9E multilayer. Treatments are continuous for the culture duration, which is typically a period of 10 days. After 10 days culture, the 9E rafts are harvested and assayed for HPV-31b DNA (measure of viral DNA replication) and E1-E4 viral transcription (viral function) using the QRT-PCR assay described for the HPV-11 monolayer assay system. Primers are prepared to quantitate HPV-31B DNA and RNA (E1-E4) and the quantitation compared to TBP. Anti-viral activity is measured quantitatively as either or both a reduction in viral DNA and RNA when compared to placebo-treated 9E rafts. A portion of each raft is removed for histology (H&E, immunostaining for specific marker keratins [keratin 10, involucrin]). Viral DNA and RNA levels are plotted against compound concentrations to determine $EC_{50}$ (50% reduction in viral DNA and/or RNA), $CC_{50}$ (50% reduction in yield of total RNA/DNA). The Selectivity Index (SI) is determined from $CC_{50}/EC_{50}$. Usually, SI>5 would be significant for the detection of an anti-viral activity.

6.6.8 Assays for BK Virus (BKV)

Assays for BK virus (BKV) can be conducted by following the procedures described in, e.g., Farasati et al., *Transplantation*, 2005, 79(1): 116-118. Generally, the principle of the assay is to measure the effect of test compounds on the rate of viral replication by quantitative real-time PCR for BKV viral capsid protein 1 DNA. Simultaneous quantification of a housekeeping gene such as aspartoacylase (ACY) DNA permits monitoring of host-cell replication. Regression analysis of dose-response curve allows for determination of $EC_{50}$, which is defined as the compound concentration that reduces the yield of BKV DNA by 50%. The ratio of $IC_{50}$ to $EC_{50}$ (selectivity index) is used to compare the anti-viral effect of different test compounds in relation to their safety.

For example, anti-viral testing can be performed using BKV, Gardner strain (available from ATCC). The cells are expanded, e.g., in human embryonic lung fibroblasts (WI-38 cells), using DMEM medium supplemented by 10% fetal bovine serum and L-glutamine, incubated at 37° C. under 5% $CO_2$. Each test compound is typically tested at least three times using a broad range of concentrations covering 4-5 orders of magnitude. Experiments usually include a negative control consisting of cells exposed only to the diluents.

Each compound sensitivity experiment requires inoculation of 50,000 log-phase WI-38 cells in six-well culture plates. After plating the cells, viral infection is achieved by the addition of $2 \times 10^3$ to $2 \times 10^6$ BKV particles to each culture well in a volume of 0.5 mL. After a 2 hours of 37° C. incubation, unbound virus is washed off with tissue culture medium. The cultures are maintained in DMEM medium, supplemented by 10% fetal bovine serum and L-Glutamine, at 37° C., under 5% $CO_2$, for 7 days. Cells are harvested by 0.25% trypsin-1 mM Na-EDTA digestion at 37° C. for 10 minutes and viability assessed by Trypan blue dye exclusion test. DNA extraction on the cell lysates is performed with a commercially available kit (QIAampu DNA Mini kit, Qiagen, Valencia, Calif.). BKV VP-1 DNA is amplified from the total DNA by a TaqMan quantitative PCR reaction performed in an ABI Prism 7700 Sequence Detector (ABI, Foster City, Calif.). To keep track of variable input of cellular DNA in different cell-culture experiments, each cell lysate is subjected to simultaneous TaqMan PCR for ACY.

6.6.9 Assays for Dengue Virus (DENV)

In vitro assays for DENV can be conducted using procedures substantially similar to those described, for example, in Heaton et al., *Proc. Natl. Acad. Sci.*, 2010, 107(40): 17345-17350. Huh-7.5 cells (a subline derived from the hepatocyte Huh7 cell line) are maintained in DMEM-high glucose supplemented with 0.1 mM nonessential aminid acids, 5% v/v FBS, and penicillin-streptomycin. In certain cases, DENV-luciferase replicon RNAs are introduced in Huh-7.5 cells by electroporation. At 24 hour post-electroporation, the cells are treated with varying concentrations of test compounds, maintained for another 24 hours, and assayed for luciferase activity.

In other cases, Huh-7.5 cells are infected with DENV (multiplicity of infection=1) for 4 hours and then treated with test compounds at varying concentrations. Twenty four hours post-infection, viral RNA levels or released virus are quantified along with cellular ATP levels.

Three types of in vitro assays for DENV include those described in Chen et al., *Antimicrobial Agents and Chemotherapy*, 2010, 54(8):3255-3261.

Type 1: The assays measure viral titer reduction in the presence of test compounds. Vero cells are seeded in a 12-well plate ($4 \times 10^5$ cells per well). At 24 hours post-seeding, the cells are infected with DENV at a multiplicity of infection of 0.1 and treated immediately with the test compounds. Culture medium are collected at an appropriate time, and viral titers are determined using plaque assays.

Type 2: Cell-based flavivirus immunodetection (CFI) is used to measure the amount of viral E protein in infected cells. A549 cells are seeded to a 96-well plate ($2\times10^4$ cells per well). The cells are infected with DENV on the following day. During the infection, the cells are incubated with a test compound/virus mixture for 1 hour, with shaking every 10 to 15 minutes. The culture fluid is then replenished with fresh medium containing test compounds. On day 2 post-infection, the cells are washed with PBS, fixed with 100% methanol at 4° C. for 10 minutes, and detected for intracellular viral E protein by ELISA. The ELISA uses mouse monoclonal antibody 4G2 against the DENV E protein and goat anti-mouse IgG conjugated with horseradish peroxidase as the primary and secondary antibodies, respectively.

Type 3: The assay uses Huh-7 cells and luciferase-reporting replicon of DENV. The procedures are similar to those described above.

6.7 In Vivo Assays
6.7.1 In Vivo Assays for Herpes Viruses
6.7.1.1 HSV-1 and HSV-2

| Animal Models of Herpes Encephalitis: | | | |
| --- | --- | --- | --- |
| Virus | Species | Route | Disease |
| HSV-1 | BALB/c Mice | i.p. | Encephalitis |
|  |  | i.n. | Encephalitis |
| HSV-2 | BALB/c Mice | i.p. | Encephalitis |
|  |  | i.n. | Disseminated infection of newborns and encephalitis |
| HSV-1 | Rat | i.n. | Encephalitis |
| HSV-1 | SKH-1 Mice | i.cut. | Herpes labialis |

New compounds are screened initially for HSV activity in BALB/c mice (Charles River Laboratories) inoculated i.p. with HSV-1 or HSV-2. Following i.p. inoculation with HSV-1 or HSV-2, virus replicates in the gut, liver, and spleen and spreads to the CNS by viremia and likely peripheral nerves as well. Virus is detected first in the brain around day five, thus allowing time for compounds to demonstrate anti-viral effects. This model system one of the most sensitive for determining efficacy of a new anti-viral compound. Although it does not simulate a natural route of infection, it allows for screening new compounds to determine optimal dosages and treatment regimens. This screening is followed by testing in mice inoculated i.n. which more closely simulates human infections. If the experimental compound exhibits activity in mice inoculated i.p., it is next evaluated in mice inoculated by the i.n. route.

I.n. inoculation of three-week-old BALB/c mice with HSV-1 provides a model for herpes encephalitis of humans utilizing a natural route of infection. After inoculation of approximately 105 pfu of HSV-1, strain E-377, virus replicates in the nasopharynx and spreads to the CNS by way of olfactory and trigeminal nerves. Untreated animals generally die by days 6-10. The use of i.n. inoculation is known as a natural route of infection for herpes encephalitis. I.n. inoculation of three-week-old BALB/c mice with about $4\times10^4$ pfu of HSV-2, strain MS, provides a model of disseminated neonatal herpes with CNS involvement. After viral inoculation, virus replicates in nasopharyngeal and lung tissue, and disseminates to the liver, spleen, and kidney. In addition, virus spreads to the CNS via olfactory and trigeminal nerves. Acy-clovir, ACV, given parenterally or orally is effective in all the experimental infections mentioned above and is utilized as a positive control.

The SKH-1 strain of immunocompetent hairless mice is used to facilitate scoring of cutaneous lesions. Orofacial inoculation of HSV-1 in these mice provides an appropriate model for testing new anti-viral therapies. In this model, mice are anesthetized with a ketamine/xylazine mixture and injected subcutaneously with an electronic microchip for individual identification. Prior to inoculation, the snout, composed of the triangular shaped area over the nasal bones from the nose bridge to the eyes, is lightly abraded with a #113 tungsten-carbide engraving bit Dremmel tool. This procedure is performed carefully to prevent bleeding. This area is then swabbed for 10 seconds with a dacron swab soaked with HSV-1. Following this procedure, animals are returned to their cages and observed until recovery.

Animals infected with HSV-1 in the orofacial area exhibit lesions that begin to appear on days 4-6 and are usually cleared by day 15. To determine the effect of treatment on cutaneous viral replication, severity of lesions is scored from days 4-21 and swabs of the snout area are taken on days 3-10. The samples are placed in 2.0 mls of media and frozen at −70° C. until titrated for HSV-1 on rabbit kidney fibroblast cells in a CPE microtiter plate assay. All experimental drug efficacy studies are placebo or vehicle controlled and also the positive control, Zovirax, is administered topically.

Mouse Model of Primary HSV-1/HSV-2 Challenge: The primary screening model provides a rapid initial evaluation of anti-viral efficacy against HSV primary infection with both clinical and virological endpoints. This model utilizes intravaginal inoculation of female Swiss Webster mice (25 g) with HSV-1 or HSV-2 to evaluate potential anti-viral therapies as well as vaccine/adjuvant candidates. Animals are followed daily for signs and systems of herpes disease and vaginal swabs are obtained to evaluate the effect of therapy on viral replication. Single or combined anti-viral therapies can be administered topically, orally or systemically and can be given at varying intervals begun before or after viral challenge. Dose range studies can also be performed. Dose and route of administration are individualized for each experimental compound. Treatment group size is typically 12-16 mice.

Microbicide Screening Model of Primary HSV-2 Challenge in Mice: This model is designed to evaluate the protection afforded by a microbicide candidate against infection with HSV-2. The model utilizes intravaginal inoculation of female Swiss Webster mice for evaluation. The initial trial is usually performed by applying compound 5 minutes prior to challenge with HSV-2. Further evaluation of microbicides in this model either extend the time between microbicide administration and challenge or examine dose range. Compounds can be advanced to a secondary species evaluation in the guinea pig model of genital infection. Evaluation includes daily evaluation for signs and symptoms of genital herpes and viral examination of vaginal secretions. Treatment group size is typically 12-16 mice.

Guinea Pig Model of Primary Genital HSV-2 Infection: Because genital herpes disease in the guinea pig more closely resembles human disease, this animal is used as a second species for therapies with demonstrated efficacy against HSV in mice. As with humans, genital HSV infection in guinea pigs is a self limited vesiculoulcerative disease which is followed by healing, the establishment of latency, and then both spontaneous and inducible symptomatic and asymptomatic recurrences. An exemplary model utilizes intravaginal inoculation of female Hartley guinea pigs and provides both clinical and virologic indices to asses both the effect of treatment on primary disease as well as on the frequency or severity of subsequent recurrent infections. Anti-viral therapy can be administered orally, topically or systemically and can be given at varying intervals beginning before or after virus challenge. Following intravaginal inoculation, animals are followed daily for the development of genital herpes using a validated genital herpes scoring system. Vaginal swabs are also obtained to evaluate the effect against viral replication. Because this is a non lethal model, animals can be sacrificed at the conclusion of the experiment to evaluate the effects of treatment on latency. This model can be adapted to evaluate anti-viral activity against available drug resistant strains (ACV and Foscarnet). Dose, route of administration and duration of treatment are individualized for each experimental agent. Treatment group size is typically 10-15 animals.

Guinea Pig Model of Recurrent Genital HSV-2 Infection: The guinea pig model of genital herpes is unique in that after recovery from primary genital infection, animals experience spontaneous recurrent genital lesions as well as viral shedding in the absence of lesions. This allows a candidate compound to be evaluated for efficacy in controlling recurrent disease. Female Hartley guinea pigs who have recovered from symptomatic primary genital infection are randomized into treatment groups for anti-viral treatments beginning on day 21 PI and continued for 21 days after. Treatments can be given orally, topically or systemically. The indices for these studies include quantification and severity assessment of recurrent episodes during treatment and for 21 days following cessation of treatment. Additionally, vaginal swabs are collected to evaluate any impact on shedding. Dose, route of administration are individualized for each experimental agent. Treatment group size is typically 10-15 animals, and duration of treatment is typically 21 days.

Model of Neonatal HSV-2 Infection in Guinea Pigs: An exemplary model of neonatal HSV infection mimics the natural history of infection in the human newborn. This model is available to evaluate candidate anti-viral compounds and combined therapeutic approaches including combination of anti-virals or anti-virals and immune modulators. Additionally, this model can be used to evaluate the efficacy of candidate vaccines by measuring the protection afforded by transplacental antibody. In this model, newborn Hartley guinea pigs are inoculated intranasally with HSV-2 within 48 hours of delivery. Newborn animals are then randomized to receive experimental compound, placebo or ACV (control). A positive control of ACV (60 mg/kg/day) BID is typically used. Animals are evaluated daily for evidence of cutaneous herpetic disease and weight gain as well as pulmonary, CNS symptoms and death. Surviving animal are followed for 45 days to assess the effectiveness of therapy on the incidence and frequency of cutaneous herpetic recurrences. Dose and route of administration are individualized for each experimental agent. Duration of treatment is typically 10 days or more.

6.7.1.2 Cytomegaloviruses

Animal Models for Cytomegalovirus Infections:

| Virus | Species | Route | Disease |
| --- | --- | --- | --- |
| MCMV | BALB/c mice | i.p. | Disseminated CMV acute, chronic |
|  | SCID-mice | i.p. | Disseminated CMV acute |
| HCMV | SCID-hu-Ret | i.oc. | HCMV replication in Retinal tissue |
|  | SCID-hu-thy/liv | i.im. | HCMV replication in thymus/liver tissue |

Human CMV does not generally infect laboratory animals. For this reason, it is necessary to use surrogate models, that is, a similar but different virus in its natural host. While there are cytomegalovirus strains in a number of animal species, two that have been studied include the murine and guinea pig CMVs. The murine model is predictive of efficacy for anti-viral drugs, such as Foscarnet (PFA), ganciclovir (GCV), and cidofovir (CDV) that have been evaluated in humans.

I.p. inoculation of three-week-old BALB/c mice with approximately $2.0 \times 10^5$ pfu of MCMV results in an acute, lethal infection with rapid virus replication in the lung, liver, spleen, kidney, intestine, salivary gland, and other visceral and glandular tissue. Animals die on approximately days 5-7. Since this is a lethal infection, the model can be used for rapid identification of potential anti-viral compounds. Reduction of the virus inoculum to $10^4$ pfu of MCMV results in a non-lethal, chronic, generalized infection, which has many similarities to human CMV infections. At various times after inoculation, virus can be readily isolated from blood, lung, liver, spleen, kidney, urine, intestine, and salivary gland. Virus replication persists in these target organs for 45-60 days and in the salivary gland for months. The nature of the chronic infection allows for evaluating long term or maintenance therapy.

Severe combined immunodeficient (SCID) mice, which lack functional T and B cells, are extremely sensitive to infection with MCMV and are utilized as models for CMV infections in an immunocompromised host. SCID mice that are inoculated with a range of $1.0$-$10^5$ pfu of MCMV, and are left untreated, eventually die in a dose dependent manner. Animals that receive $10^5$ pfu have a mean day of death of about 14 days, whereas, those inoculated with 10 pfu survive an average of 25 days. With each log 10 increase in virus inoculum, survival time is decreased by about three days. To determine the pathogenesis of MCMV in SCID mice, mice are inoculated with 10 pfu. On each of various days post infection, three mice are euthanized, their tissues removed, homogenized, and assayed for MCMV. Virus is first detected in salivary gland by day six followed by lung, spleen, kidney, adrenals, and pancreas on days 9-12. Liver, which is one of the most permissive organs in normal mice, does not exhibit detectable virus until day 18. In addition, brain is infected by day 18. These data indicate that inoculation of SCID mice with low concentrations of MCMV results in a disseminated infection with viral replication in the same target organs as observed in immunodeficient humans. These animals demonstrate high levels of virus in their tissues for 2-3 weeks, thus allowing adequate time to document an anti-viral response in treated animals compared with placebo animals.

Human CMV infections can cause a wide range of clinical manifestations, especially in the immunocompromised host. Few models exist to study HCMV infection since the virus is host-specific, and infection and replication are limited to human cells. In this regard, a model that involves HCMV infection of fetal human retinal tissue implanted in the eyes of severe combined immunodeficient (SCID) mice can be utilized. Small fragments of fetal human retinas are implanted into the anterior chamber, and four to six weeks after transplantation are inoculated with 2,000 to 10,000 pfu of HCMV. Animals are euthanized and eyes enucleated at various time points after infection. Eyes are prepared for microscopy by sectioning fixed tissue, or are homogenized for detection of infectious HCMV by plaque assay. The model has been validated using GCV. CDV, and other anti-viral therapies. In addition, this model can also be utilized to study and identify the virulence characteristics of HCMV by examining the growth of various HCMV mutants.

The SCID-hu thy/liv implant model can also be used in compound efficacy studies. In this model, small fragments of human fetal thymus and liver are implanted under the kidney capsule in the SCID mouse. Approximately 12-16 weeks later, implants that are fully vascularized and quite large (10-50% the size of the kidney) are inoculated with $10^3$-$10^4$ pfu of HCMV. At various time points after infection, implants are biopsied and homogenized, and HCMV replication is quantified by plaque assay. As with the SCID-hu mouse ocular model, this model can be useful in determining the efficacy of various anti-viral therapies.

Immunocompromised GPCMV Model: This guinea pig model mimics CMV infection of the immunocompromised host, a common target population of cytomegalovirus infections. Young Hartley guinea pigs are immunossuppressed with cylcophosphamide administered 1 and 7 days prior to viral inoculation with ~$10^5$ pfu salivary gland passaged guinea pig cytomegalovirus (GPCMV). In a typical experiment, two groups of 12 animals each receive the experimental compound or placebo beginning 24 hours after infection. Animals are followed daily for evidence of disease and death which usually occurs by day 14 as described in Bourne et al., *Antiviral Research* 2000, 47:103-09. Effects on viral replication are measured by sacrificing animals and quantitating virus in specific organs and blood by Real-Time PCR and/or culture. The amount of compound is typically based on an average guinea pig weight of 350-500 g.

Neonatal GPCMV Model: CMV infection of premature newborns may be life-threatening disease if untreated. The neonatal guinea pig model resembles perinatal CMV infection and allows systematic evaluation of anti-viral compounds in a relatively immature host. In this model, newborn Hartley guinea pigs are infected with ~$10^6$ pfu of salivary gland derived GPCMV 24-48 hours after birth. Anti-viral or placebo treatments, administered orally or by intraperitoneal injection are begun at 0-24 hours after infection. Infection results in decreased weight gain and mortality as high as 70% due to dissemination to target organs such as the liver, spleen and brain by day 10 post-infection (Bravo et al., *Antiviral Research* 2003, 60:41-49). Animals are followed daily for signs of disease and death. The effects on viral replication are assessed by sacrificing animals and comparing viral titers in various target organs and blood by Real-Time PCR and/or culture. Dosing is typically based on an average newborn guinea pig weight of 100 g.

Congenital GPCMV Model: CMV is the most common congenital infection. The guinea pig is a small mammal in which virus crosses the placenta to cause fetal infection and disease, thus allowing the study of new anti-virals and unique therapies that may target placental and congenital infection. In this model, Hartley pregnant guinea pigs are infected with ~$10^5$ pfu GPCMV at approximately 45 to 55 days of a 70 day gestation. Animals can be treated by systemic or oral routes. Endpoints include prevention of premature delivery, survival of the offspring and PCR analysis of placenta, and other maternal tissues (blood, liver and spleen) and pup organs (liver and spleen) harvested 3, 5 or 10 days post infection (Bravo et al., *Journal of Infectious Diseases* 2006, 193:591-7). The dose is typically based on a pregnant guinea pig weight of about 1200 g.

CMV Model of Hearing Loss: Hearing loss is the most common manifestation of congenital CMV infection. Using direct inoculation of GPCMV (~$10^5$ pfu) into the cochlea through the round window, hearing loss can be induced in guinea pigs as measured by ABR. Animals can then be treated to prevent the hearing loss. Test compounds can be administered either systemically, orally and possibly direct intratympanic administration. Dose is typically based on the weight of the animals, approximately 350 g.

Murine CMV Model: The murine CMV model is used to study CMV pathogenesis and to evaluate new anti-CMV compounds. In this model, 5-week old female mice are infected with $1 \times 10^6$ pfu of MCMV by intraperitoneal injection. Treatment can begin before or following infection and lasts 3-5 days. Animals are sacrificed at 3 to 5 days after infection and viral titers of the spleen and liver are determined by plaque assay. Other tissues such as salivary gland and lungs can be analyzed as well. Ganciclovir (50 mg/kg, twice daily) serves as a control drug and inhibits MCMV replication in this model. Dosing depends on the weight of the animals, typically about 25 g.

6.7.2 In Vivo Assays for Influenza Viruses

Efficacy: The influenza animal model consists of an infection of laboratory mice with various strains of influenza A (H1N1, H3N2, H5N1) and B viruses, with the employment of several parameters to measure disease severity. The parameters which can be used include the following: (a) monitoring of blood oxygen saturation ($SaO_2$) levels in live animals at frequent intervals utilizing pulse oximetry; (b) measuring of infectious pulmonary virus titers using in vitro endpoint dilution assay of homogenates of lungs taken at designated intervals during the infection; (c) assay of the degree of pulmonary consolidation using lungs taken in as determined both by score of lung discoloration and by weight of the lung; (d) death of the animal due to viral pneumonia; (e) mean survival time of the animals; and (f) selected histopathological analysis of lung sections. Where appropriate, studies are conducted to determine the development of viruses resistant to significant anti-viral drugs.

Toxocity: One or more toxicity determinations are performed on the test compounds under evaluation. These determinations include: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as an indicator of possible renal impairment; and (c) increase in circulating creatinine phosphokinase (CK) levels as indicator of general tissue damage.

6.7.3 In Vivo Assays for Respiratory Viruses 6.7.3.1 RSV, PIV-3, MV and hMPV

Respiratory syncytial virus (RSV), parainfluenza virus type 3 (PIV-3), measles virus (MV) and human metapneumovirus (hMPV) are human pathogens where there is a lack of licensed vaccines for preventing illnesses caused by RSV, PIV-3, or hMPV, although efficacious MV vaccines are available. Ribavirin, immune serum globulins and the humanized monoclonal antibody have been approved for use against some of these paramyxoviruses. However, all of these agents have limitations and can be expensive. Thus, the elucidation and development of new compounds, reagents or vaccines with activity against these viruses are needed. Potential anti-virals and vaccines that can be effective against RSV, PIV-3, MV or hMPV are evaluated in cotton rats. In addition, studies are performed to characterize, enhance or further develop the different paramyxovirus-cotton rat models. Evidence obtained in numerous studies support the usefulness of the different paramyxovirus-cotton rat models for preclinical evaluation of potential paramyxovirus anti-virals and vaccines.

6.7.3.2 SARS Virus

Efficacy: The SARS virus animal model utilizes weanling mice infected intranasally with the virus. A moderate lung infection is manifested by occasional lung hemorrhaging but primarily by infectious virus recovered from the lungs. Inhibition of development of virus in the lungs of the mice is used as parameters for evaluation of test agents.

Toxicity: One or more toxicity determinations are performed on the test compounds under evaluation. These determinations are: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as indicator of possible renal impairment; and (c) increase in circulating creatinine phosphokinase (CK) levels as indicator of general tissue damage.

6.7.4 In Vivo Assays for Orthopoxviruses 6.7.4.1 Vaccinia and Cowpox Viruses (Smallpox Assay)

The smallpox animal model is an intranasal infection of laboratory mice by the cowpox and vaccinia viruses, which induce an infection of the nose and lungs resulting in a smallpox-like toxemia-associated death. Parameters used in evaluating test compounds in this model include: (a) death of the animal; (b) mean survival time of the animals; (c) lung and nose virus titers; and (d) host weight loss. Other parameters can include: (a) monitoring $SaO_2$ levels; (b) assay of degree of pulmonary consolidation both by lung score and lung weight increase; and (c) histopathological analysis of lungs and other organs.

Also utilized is a cutaneous infection in immunocompromised hairless mice that can be induced by vaccinia virus. This infection is progressive and leads to the death of the mice. It is now also being used in selected anti-viral experiments. Parameters used in evaluating test agents in this cutaneous infection model include: (a) death of the animal; (b) severity score in initially induced lesions; (c) size of initially induced lesions; (d) number of spontaneous "satellite" lesions; and (e) virus titer in various organs in the animal.

| Animal Models for Vaccinia and Cowpox Virus Infections: | | | |
|---|---|---|---|
| Virus | Species | Route | Disease |
| Cowpox Virus (BR) | BALB/c Mice | i.p. | Death - Rapid Liver-Visceral Involvement |
|  | BALB/c Mice | i.n. | Death - Slower Lung-respiratory involvement |
| Vaccinia Virus (WR) | SKH-1 mice | i.d. | Skin lesions |
|  | SCID Mice | i.p. | Disseminated disease |
|  | BALB/c Mice | i.n. | Death Disseminated Disease |
| Vaccinia Virus (IHD) | BALB/c Mice | i.n. | Death Disseminated Disease |
| Vaccinia Virus (WR) | SCID Mice | i.p. | Death Disseminated Disease |
| Vaccinia Virus (NYC) | SCID Mice | i.p. | Death |

The causative agent of smallpox, variola virus, cannot be utilized outside a BSL-4 containment area and does not cause disease in adult mice. Various orthopoxviruses can be utilized as surrogate viruses for smallpox including VV and CV. They can be inoculated i.p. or i.n. into SCID mice with an endpoint of death. In normal mice, CV, VV-WR, or VV-IHD, but not VV-Copenhagen Strain, will produce mortality when inoculated by variety of routes. Intranasal inoculation of mice with CV produced an infection with features similar to systemic or disseminated smallpox. Other routes of inoculation such as i.p. or i.v. with VV or CV result in less bronchial involvement and more skin lesions. The IHD strain of VV is less virulent in BALB/c mice than the WR strain. The WR strain of VV produces mortality in BALB/c mice by i.n. inoculation and SCID mice by i.p. inoculation. SKH-1 hairless mice can also be inoculated with VV and CV by inoculation of abraded orofacial areas, similar to the HSV techniques. Mice can be treated systemically or topically with anti-viral compounds for evaluation of efficacy against disease (lesion scores) or viral replication (viral titers).

6.7.4.2 Ectromelia (Mousepox Assay)

Ectromelia virus is the causative agent of mousepox, an acute exanthematous disease of mouse colonies in Europe, Japan, China, and the USA. Laboratory studies have shown ECTV to have a very narrow host range, infecting only certain mouse species. A number of different strains of ECTV have been isolated which have been shown to differ in their virulence for the mouse. The Moscow, Hampstead, and NIH79 strains have been studied, with the Moscow strain being one of the most infectious and virulent for the mouse. Studies in the last five decades have resulted in a detailed description of the virologic and pathologic disease course in genetically susceptible (A, BALB/c, DBA/2, and C3H/He; death ~7 days post-infection) and resistant (C57BL/6 and AKR) inbred and out-bred mice; identification and characterization of the important cell-mediated and innate responses for recovery from infection; and the discovery of rmp-1, rmp-2, nnp-3 and rmp-4 loci which govern resistance to severe mousepox. Varying mouse genotype, virus strain, and dose of virus result in distinct disease patterns for a given route of infection.

Mousepox differs from smallpox in at least two features following a respiratory tract infection. First, the disease course in mousepox is shorter as compared to smallpox. The eclipse period in mousepox and smallpox are 6 and 10 days, respectively. Fatal cases of mousepox usually occur 7 to 14 days post-infection (p.i.), whereas deaths in ordinary smallpox occur from ~18 to 22 days p.i. Second, the major lesions in mousepox are observed in the liver and spleen, whereas these organs are relatively uninvolved in smallpox. A feature of mousepox that is similar to smallpox is the relatively small dose of virus that is required to initiate disease in the upper and lower respiratory tract. Another similarity is the detection of virus in respiratory gases during the preexanthem period. Additionally, both diseases present with a characteristic exanthematous rash. In the case of mousepox, the development of rash is dependent on a number of parameters including mouse strain, virus strain, route of inoculation and virus dose.

Efficacy: An important use of the mousepox model is the evaluation of orthopoxvirus compounds and vaccines. The ECTV aerosol model provides a broad dynamic range for evaluating compounds. An aerosol lethal dose of 100 PFU can be used, which is ~3-fold greater that the $LD_{50}$ value of 32 PFU, and is likely in the range of the infectious dose for aerosolized smallpox. Alternatively, a dose 1000 to 10,000 times the $LD_{50}$ can be used to fully examine the robustness of the test compound.

6.7.4.3 Monkeypox Virus (MPXV)

Animal assays for monkeypox virus (MPXV) can be performed by following the procedures described in, e.g., Americo et al., *Journal of Virology*, 2010, 84(16): 8172-8180. Generally, the assay is based on an intranasal or intraperitonial infection of CAST/EiJ mice with MPXV, for example, an isolate of Congo Basin clade of MPXV or West African clade of MPXV. Upon infection, the animals exhibit loss of weight, morbidity and death in a dose dependent manner. In addition, MPX replication is observed in the lung, spleen and liver of the tested animals.

Consequently, anti-viral efficacy of the test compounds can be assessed by following the criteria such as weight loss, morbidity and death in the presence and absence of the test compounds upon infection with MPXV. Further, replication in organs such as lung, spleen and liver of the animals in the presence and absence of the test compounds upon infection can also be examined to assess the anti-viral efficacy.

6.7.4.4 Rabbitpox Virus (RPV)

Animal assays for rabbitpox virus (RPV) can be performed by following the procedures described in, e.g., Rice et al., *Viruses*, 2011, 3:63-82, and Adams et al., *J. Virol.*, 2007, 81:11084-11095 ( ). Generally, the model is based on bilateral, intradermal infection of New Zealand White rabbits with 100-1000 pfu of RPV. Upon infection, the animals exhibit weight loss, elevated body temperature (fever), severe respiratory distress, swelling of primary and secondary lesions, eye and nasal discharge and inoculation site necrosis. In addition, viral replication is observed in the respiratory tract. If untreated, the animals are eventually subjected to death (euthanasia) according to euthanasia guidelines.

Consequently, anti-viral efficacy of the test compounds can be assessed by following the criteria described above, including length of survival upon injection and viral replication. In addition, an overall clinical score can be examined to assess the anti-viral efficacy.

Alternatively, animal assays can be based on the procedures described, e.g., in Roy et al., *Viruses*. 2010, 2:2096-2107, in which similar clinical criteria are examined following an infection through aerosol containing RPV. In this model, experimental infection with RPV initiates with exposure to aerosols with a particle size distribution that is preferential for penetration to the tracheobronchial and pulmonary regions of the lung, with emphasis on the lower respiratory tract.

6.7.5 In Vivo Assays for Papillomaviruses 6.7.5.1 Cottontail Rabbit Papillomavirus (CRPV) Model The procedures substantially similar to those described, for example, in Christensen, *Antiviral Chemistry & Chemotherapy*, 2005, 16:283-294 are followed in connection with cottontail rabbit papillomavirus (CRPV) model. In short, topical formulations of the test compound are tested at three doses in groups of 5 rabbits at 4 sites per rabbit. One additional rabbit group includes a placebo treatment. Alternative deliveries include interalesional and systemic treatments depending on the nature of the compound to be tested (e.g., anti-viral, immunomodulator).

Adult New Zealand White rabbits can be purchased from, for example, CoVance, Inc. Rabbits are of both genders. Rabbits are quarantined and cleared (14 days). Each rabbit is inoculated with $10^{-2}$ wtCRPV (4 sites: 2 on the left side of the back (L1 and L2) and 2 on the right side of the back (R1 and R2)) CRPV stock. Combinations of L1, R1, L2 and R2 sites receive treatments. Exemplary treatment schemes are provided below.

Group A: all 4 sites=placebo ointment;
Group B: L and L2=GS327422 (0.1%); R1 and R2=GS327422 (0.03%) Treatments are once/week (Monday) for 8 weeks;
Group C: L1 and L2=GS327422 (0.1%); R1 and R2=GS327422 (0.03%) Treatments are three times/week (MWF) for 8 weeks; and
Group D: L1 and L2=GS327422 (0.1%); R1 and R2=GS327422 (0.03%) Treatments are five times/week (MTWTF) for 8 weeks.

The experiment contains 20 rabbits. Most experiments include 4-5 groups of rabbits (Groups A-E). A placebo group serves as controls to assess local effects of treatment in treated Groups B to D. Vehicle consists of placebo. Groups B-D represents test compound comparisons vs placebo negative control. Doses of compounds are chosen based on various criteria including the past experience. Treatments (topical) begin at a time when the papillomas are visible but not greater than a GMD of 5.0 mm. This time point allows effects on visible papillomas to be assessed, and is a clinically relevant situation. Treatment is once weekly (Group B), 3 times weekly (group C—MWF), and 5 times weekly (MTWTF), for eight weeks with a dose of 0.1 ml per site. Alternatively, treatments may begin 14 days after infection at a time when there are no visible papillomas to maximize the effectiveness of the treatments. Body weights are taken weekly, and sera collected at the end of the treatment period for blood chemistries as needed. Papillomas are measured weekly in 3 axes (length×width×height) in mm. Data are entered into a spread sheet and calculations conducted of the geometric mean diameter of each papilloma, mean±SEM for each group, t-test between each paired groups and plots made of papilloma size vs time. Plots of weight changes are also conducted. At termination, kidney and liver samples are retrieved for histology and toxicity assessment. Skin/papilloma sites are monitored photographically and biopsies assessed for histology at experiment/treatment termination. Serum samples can be collected to conduct blood chemistries to assess any toxicities of the compound under treatment.

6.7.5.2 Mouse Xenograft Model

Figure 2:
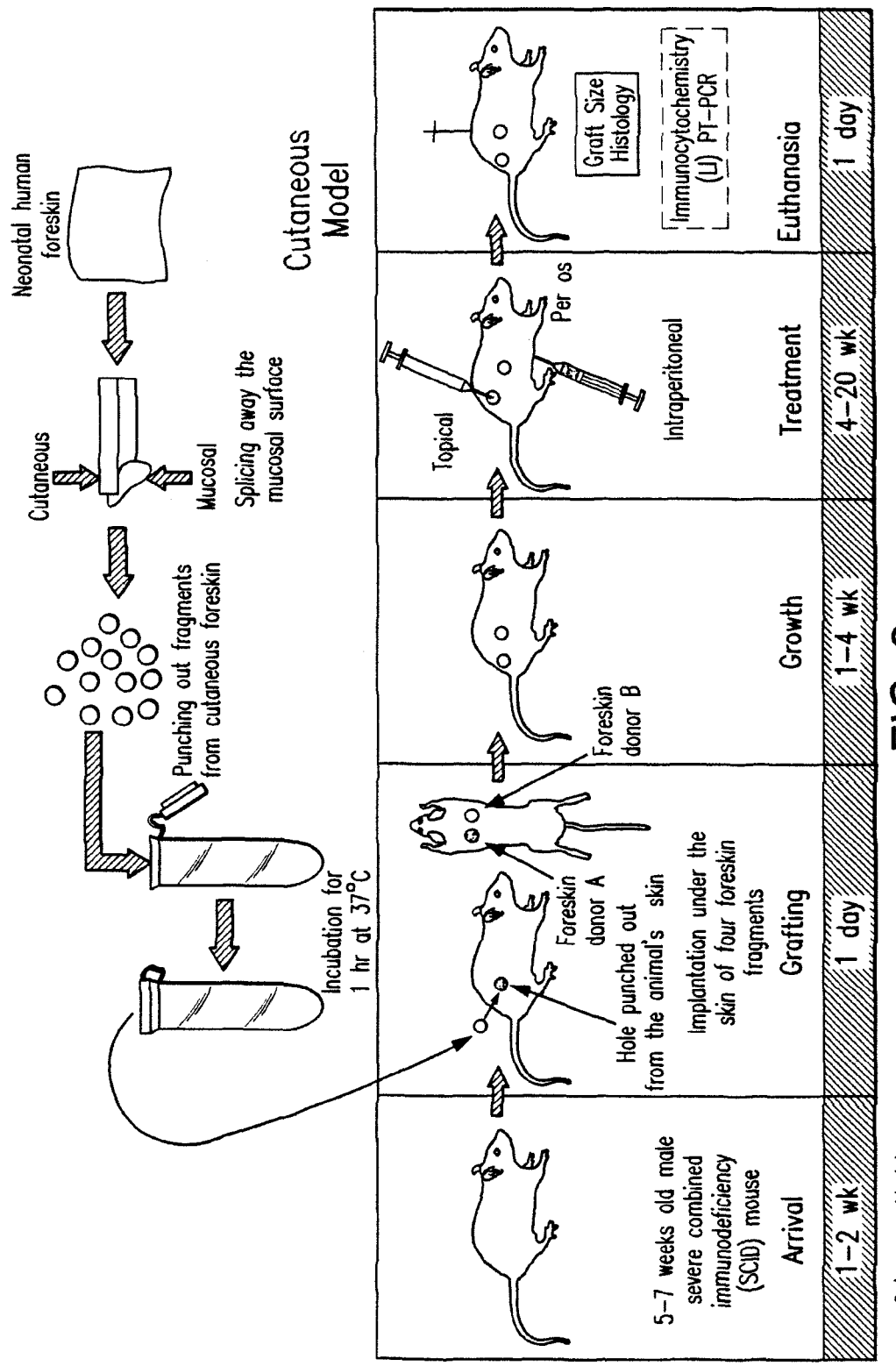
FIG. 2 illustrates a schematic diagram of cutaneous mouse xenograft model for assaying papillomaviruses.

Subcutaneous and cutaneous mouse xenograft models are schematically described in FIGS. 1 and 2.

6.7.6 In Vivo Assays for Other Viruses 6.7.6.1 Punta Toro Virus

Efficacy: The Punta Toro virus infection is achieved in C57BL/6 mice and in Syrian golden hamsters, with a generalized disease resembling that induced by Rift Valley fever. Parameters used for anti-viral testing include: (a) death of the animal; (b) hepatic icterus, seen as yellowed liver; (c) elevated ALT levels in serum; (d) virus titers in liver and serum; and (e) host weight loss.

Toxicity: One or more toxicity determinations are performed on the test compounds under evaluation. These determinations are: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as indicator of possible renal impairment; and (c) increase in circulating creatinine phosphokinase (CK) levels as indicator of general tissue damage.

6.7.6.2 Pichinude Virus

Efficacy: The Pichinde virus model utilizes Syrian golden hamsters. Parameters used for anti-viral testing include: (a) death of the animal; (b) virus titers in brain, liver, spleen and serum; and (c) elevated ALT levels in serum.

Toxicity: One or more toxicity determinations are performed on the test substances under evaluation. These determinations are: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as indicator of possible renal impairment; and (c) increase in circulating creatinine phosphokinase (CK) levels as indicator of general tissue damage.

6.7.6.3 VEE Virus

Efficacy: The VEE virus animal model utilizes the TC-83 vaccine strain of virus administered intranasally to C3H/Hen mice; the virus progresses to the central nervous system causing high virus titers in the brain and death of the animal. The Semliki Forest virus model is very similar to that for the Banzi virus, with the same disease parameters. The Semliki Forest virus is a BSL-3-rated pathogen which requires special handling. Parameters for evaluation include: (a) death of the animal; (b) prolongation in mean day to death; (c) virus titers in the brains; and (d) host weight loss.

Toxicity: One or more toxicity determinations are performed on the test substances under evaluation. These determinations are: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as indicator of possible renal impairment; and (c) increase in circulating creatinine phosphokinase (CK) levels as indicator of general tissue damage.

6.7.6.4 West Nile Virus

Efficacy: The West Nile virus animal model currently utilizes both mice and hamsters. In each, neurological signs are produced, leading to eventual death of the animals. This virus is a BSL-3-rated pathogen which is recovered from various tissues. Other parameters such as functional abilities are also reviewed. Disease parameters used for anti-viral evaluation include: (a) death of the animal; (b) prolongation on mean day to death; (c) virus titers in brain and other tissues; and (d) host weight loss.

Toxicity: One or more toxicity determinations are performed on the test substances under evaluation. These determinations are: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as indicator of possible renal impairment; and (c) increase in circulating creatinine phosphokinase (CK) levels as indicator of general tissue damage.

6.7.6.5 Dengue Virus

In vivo assays for DENV can be conducted using procedures substantially similar to those described, for example, in Guabiraba et al., *PLoS ONE,* 2010, 5(12):e15680 and Souza et al., *Proc. Natl. Acad. Sci.,* 2009, 106(33):14138-14143. DENV virus stock solutions are diluted in endotoxin-free PBS or DPBS to appropriate concentrations. The virus is injected i.p. into mice. Test compounds are given via appropriate routes at appropriate dosing frequency (e.g., twice a day oral administration). Lethality rates are evaluated every 12 hours and other parameters (body weight loss, inflammation, etc.) are checked as appropriate. For tests using knockout mice, the control typically includes the same test on the wild-type mice. Negative control usually involves the administration of vehicle instead of test compound.

In the case of evaluation of vaccines for DENV virus, assays can be conducted using procedures similar to those described, for example, in Johnson et al., *Journal of Virology,* 1999, 73(1):783-786. The assay uses IFN deficient mice (e.g., A129 mice, which lack alpha/beta IFN and gamma IFN receptor genes) and involves intraperitoneal administration of DENV into such mice. Typically, IFN deficient mice are universally lethal upon administration of DENV regardless of age. Based on this, criteria such as changes in survival time and rate can be monitored in IFN deficient mice immunized with test vaccine to assess the efficacy of a test vaccine in vivo.

6.7.7 In Vivo Assays for Prion Diseases

Efficacy: The prion transgenic mouse model utilizes knockout mice for endogenous mouse PrP-sen. These mice express high levels of hamster PrP-sen in a wide range of tissues, including the brain. The animals infected with hamster scrapie agent replace the Syrian hamster model. The latter animals require approximately 120 days to die of the scrapie infection, whereas the prion transgenic mice die in approximately 82 days when infected with the same agent. Death is used as the parameter for anti-prion evaluation.

Toxicity: One or more toxicity determinations are performed on the test substances under evaluation. These determinations are: (a) lethality; and (b) host weight loss or failure to gain weight. As needed and where applicable, the following additional parameters can also be investigated: (a) increase in circulating serum levels of glutamic oxalic acid transaminase (SGOT) and pyruvic acid transaminase (SGPT) in the serum as markers for possible liver damage; (b) increase in circulating creatinine (CT) level as indicator of possible renal impairment; and (c) increase in circulating creatinine phosphokinase (CK) levels as indicator of general tissue damage.

6.7.8 Other Follow-up Tests

Follow-up determinations of promising anti-virals seen in the original animal studies can include effect of the administered test compounds on key immunologic components in infected and in uninfected (toxicity control) mice. The immunologic effects studied include: (a) cytotoxic T lymphocyte activity; (b) natural killer cell activity; (c) total T, T-helper, T-suppressor/cytotoxic and B cell enymeration; (d) response to the T-cell mitogen phytohemagglutinin (PHA); (e) production of interferon; and (f) production of neutralizing antibody. Where appropriate, studies are conducted to determine the development of viruses resistant to significant anti-viral drugs.

7. Assays for ELOVL

ELOVL assays can be conducted in vitro using procedures substantially similar to those described in, for example, Shimamura et al., *European Journal of Pharmacology*, 2010, 630: 34-41.

7.1 In Vitro Assays 7.1.1 Elongation Enzyme Assay

Elongation is carried out using 30 μl of substrate reaction mixture containing 100 mM potassium phosphate buffer (pH 6.5), 200 μM BSA (fatty acid free), 500 μM NADPH, 1 μM rotenone, 20 μM malonyl-CoA, 833 kBq/ml [$^{14}$C]malonyl-CoA (GH Healthcare Science. Little Chalfont, UK) and acyl-CoA. The following long chain acyl-CoAs are used as a preferential substrate for each ELOVL: ELOVL1, 10 μM stearoyl-CoA; ELOVL2, 10 μM arachidonoyl-CoA; ELOVL3, 10 μM stearoyl-CoA; ELOVL5, 40 μM arachidonoyl-CoA; and ELOVL6, 40 μM palmitoyl-CoA. To start the reaction, 20 μl of the ELOVL microsomal fraction is added to the substrate mixture, and then incubated for 1 hour at 37° C. with gentle shaking in a 96-well plate. After 1 h incubation, 100 μl of 5 M HCl is added to hydrolyze acyl-CoA, and then the reaction mixture is filtered through a Unifilter-96. GF/C plate (PerkinElmer. Waltham, Mass.) using a FilterMate cell harvester (PerkinElmer, Waltham. Mass.). The 96-well GF/C filter plate is subsequently washed with distilled water to remove excess [$^{14}$C]malonyl-CoA and dried, after which 25 μl of MICROSCINT 0 is added to each well and radioactivity determined.

7.1.2 Fatty Acid Elongation Assay in Mouse Hepatocytes

Mouse hepatoma 112.35 cells are grown on 24-well plates in Dulbecco's modified Eagle's medium (DMEM) (Invitrogen, Carlsbad, Calif.) supplemented with 200 nM dexamethason and 4% heat-inactivated fetal bovine serum (FBS) at 33° C. under 5% $CO_2$ in a humidified incubator. The test compound is dissolved in medium and incubated with subconfluent H2.35 cells for 1 hour at 33° C. [$1$-$^{14}$C]palmitic acid (PerkinElmer Japan, Kanagawa, Japan) is added to each well to a final concentration of 0.8 μCi/ml to detect elongase activity. After 4 hours of incubation at 33° C., the culture medium is removed, and the labeled cells are washed with chilled PBS (3×0.5 ml) and dissolved in 250 μl of 2 M sodium hydroxide. The cell lysate is incubated at 70° C. for 1 hour to hydrolyze radiolabeled cellular lipids. After acidification with 100 μl of 5M HCl, fatty acids are extracted with 300 μl of acetonitrile. Radiolabeled palmitic acid (16:0), palmitoleic acid (16:1), stearic acid (18:0), and vaccenic acid:oleic acid (18:1) are quantified by reversed-phase radio-HPLC (RI-HPLC). The identity of the labeled fatty acids is determined by comparing the retention times with known fatty acid standards. Elongation activity was monitored as the elongation index (EI) which was the ratio of radiolabeled C18 (C18:0+C18:1) to C16 (C16:0+C16:1) estimated from each peak area measured by RI-HPLC.

7.2 In Vivo Assays 7.2.1 [$^{14}$C]Palmitate Assay in Mouse Liver

The in vivo efficacy of ELOVL6 inhibitor is determined by following the conversion of radiolabeled 16:0 to 16:1, 18:0), and 18:1 in mice. Male C57BL 6J mice are orally administrated with ELOVL6 inhibitor and 1 hour later, the radioactive tracer, [$1$-$^{14}$C]palmitic acid, is interperitoneally administered at 10 μCi/body. For time-course study of the pharmacodynamic effect, [$1$-$^{14}$C]palmitic acid is administered 1, 8 or 12 hours after administration of test compounds. At 1 hour post-dosing of the radioactive precursor, animals are anesthetized with isoflurane (4%) and sacrificed for blood collection from the vena cava. Liver (50 mg) is harvested and incubated in potassium hydroxide/ethanol (2 ml/1.4 ml) at 70° C. or 1 hour. The nonacid-lipid is extracted by 4 ml of petroleum ether and discarded. Fatty acids are extracted by 2 ml of petroleum ether following saponification by 2 ml of 6 M HCl. The ether phase containing the fatty acid fraction is evaporated under nitrogen gas and reconstituted in methanol to measure the radioactivity by RI-HPLC. The radioactivity corresponding to each fatty acid is quantified to calculate the EI.

7.2.2 In Vivo Efficacy in Diet-Induced Obesity (DIO) Mice

Male C57BL 6J mice are maintained on a high-fat diet with ad libitum access to water (D12492, Research Diets, Inc. NJ) for 7 months. Mice are orally administered ELOVL6 inhibitor (dissolved in 0.5% methylcellulose) twice daily (09:30 and 18:30) for 14 days at 30 mg/kg dose. At day 13, body composition is determined and an intraperitoneal glucose tolerance test (0.5 kg/g glucose) is performed. At day 14, mice are sacrificed. At 4 hour post-final dosing of ELOVL6 inhibitor, mice are anestheized and the liver tissues are immediately isolated, weighed, frozen in liquid nitrogen and stored at −80° C. until use. Plasma is prepared and glucose insulin and leptin are measured using commercially available assay kits (Glucose, KyowaMedex, Tokyo. Japan: leptin and insulin, Morinaga, Tokyo, Japan). Liver tissues are isolated for the measurement of triglyceride contents and fatty acid composition. For hepatic triglyceride contents, isolated tissues are homogenized in 2 ml distilled water, followed by the addition of 6 ml chloroform methanol (2:1). After centrifugation the chloroform phase is transferred to a new glass tube containing 1 ml of distilled water and then 3 ml chloroform is added. The lower phase is collected after centrifugation and evaporated to dryness. Extracts are dissolved in 2-propanol and the triglyceride concentration is measured enzymatically (Determiner TGII, Kyowa Medex Tokyo Japan). For hepatic fatty acid composition, the liver samples are incubated in 100-fold volume (w/v) of 5 M NaOH/ethanol (1:1) at 60° C.

After 2 hour incubation, 500 µl of 5 MC17:0 (internal standard) are added to all hydrolysates. The fatty acid compositions are analyzed as following. The fatty acids in the tissue hyrolysate are derivatized with 2-nitrophenylhydrazine (2-NPH), and these derivatives are purified using an Oasis HLB column. An aliquot (10 µl) of the eluate is injected into the HPLC apparatus for analysis. HPLC analysis is performed with a Shimazu 10Avp system (Kyoto. Japan, equipped with a UV detector (SPD-10Avp), two pumps (LC-10ADvp), an auto-sampler (SIL-10ADvp) and a column oven (CTO-10ACvp). The mobile phase consist of $CH_3CN$-water (80:20, flow rate: 0.6 ml/min). The separation is performed with a CAPCELL PAK C18 MGII (2.0 mm i.d.×150 mm, 5 µm) at 35° C. and the UV absorbance is subsequently measured at 400 nm. The elongation index represents the ratio of C18 (C18:0+C18:1) to C16 (C16:0+C16:1) which is quantified from each fatty acid amount.

7.2.3 In Vivo Efficacy in KKAy Mice

Male KKAy mice given a regular diet (CE2, CLEA Japan) are orally administered ELOVL6 inhibitor (dissolved in 0.5% methylcellulose) twice daily (09:30, 18:30) for 28 days at 30 mg/kg dose. At day 21, an intraperitoneal glucose tolerance test (0.5 kg/g glucose) is performed. At day 28, body composition is determined and mice are sacrificed. Plasma parameters, hepatic triglyceride contents, and fatty acid composition are measured as described above.

7.2.4 Pharmacokinetic Studies in Mice

Single doses of test compound at 10 mg/kg body weight are administered orally to C57BL/6J mice by gavage in a vehicle of 0.5% methylcellulose aqueous suspension. Blood samples from the abdominal vein and liver samples are obtained 2 hours after administration. In the case of an in diet regimen, mice are dosed with 100 mg/kg at 17:00 and fed a diet containing 0.13% test compound overnight. Then mice are sacrificed the next morning. Blood samples are centrifuged to separate the plasma. Liver samples are homogenized with phosphate-buffered saline (pH 7.4). Each sample is deproteinized with ethanol containing an internal standard. Test compound and the internal standard are detected by liquid chromatography mass spectrometry/mass spectrometry (Quattro Ultima mass spectrometer, Waters, Milford, Mass.) in positive ionization mode using an electrospray ionization probe, and their precursor to production combinations are monitored using the Multiple Reaction Monitoring mode.

EXEMPLIFICATION

The disclosed compounds can be prepared in a number of ways well known to one skilled in the art of organic synthesis.

More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Synthetic Methods

General Synthesis (i) Synthesis of Tetrazolone Intermediate

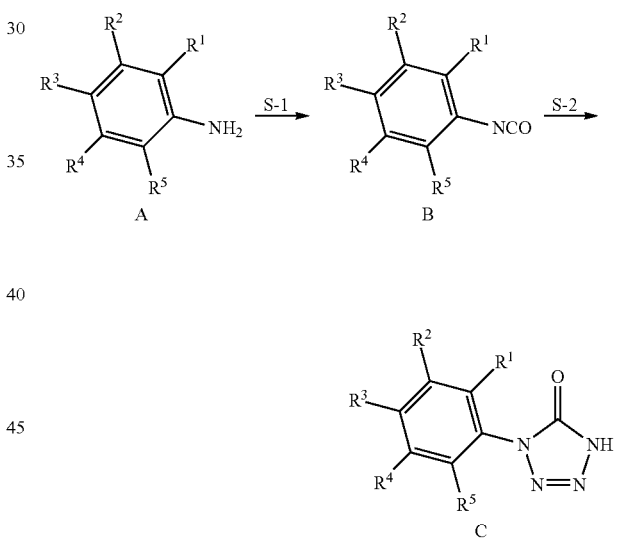

Step S-1: A solution of aniline (A) (1.0 equiv) and triethylamine (1.0 equiv) in dry dichloroethane (DCE) (0.2 M) under argon is treated with triphosgene (0.4 equiv) and heated to reflux for 2 hours, or until the reaction is determined to be complete by LCMS or TLC. The reaction is then cooled to room temperature, diluted with dichloromethane, washed with 1N HCl (aq) and brine, dried over $MgSO_4$, and then filtered and concentrated in vacuo. The desired isocyanate (B) is used in the next step without purification.

Step S-2: A mixture of the isocyanate (B) (1.0 equiv) and trimethylsilyl azide (2.0 equiv) is heated to reflux for 24 hours, or until the reaction is determined to be complete by LCMS or TLC. The excess of azide is removed in vacuo and the residue is crystallized from toluene or methanol to provide the desired tetrazolone intermediate (C) as a white solid.

(ii) Synthesis of the Amine Intermediate

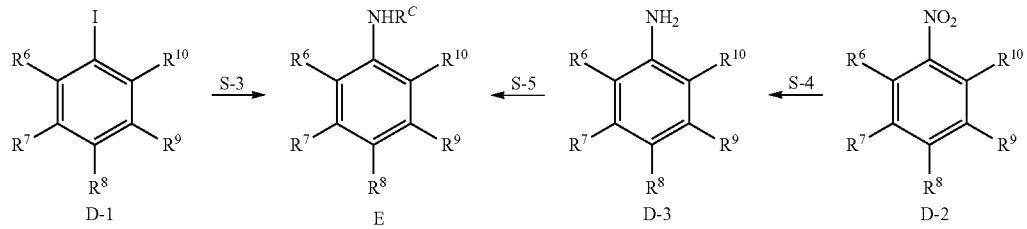

Step S-3: Copper iodide (1 equiv) and cesium carbonate (2.0 equiv) are added to a microwave vial, and the vial is evacuated and filled with argon three times. An aryl iodide (D-1) in dry dimethylformamide (0.6 M), an alkyl amine ($R^{11}NH_2$) (2.0 equiv) and 2-isobutyrylcyclohexanone (0.2 equiv) are then added to the vial, the vial is sealed and the resulting mixture is heated to 100° C. under microwave irradiation for 2 hours, or until the reaction is determined complete by LCMS or TLC. At that time, the vial is cooled to room temperature, and the reaction mixture is diluted with ethyl acetate and filtered through a pad of Celite with the aid of ethyl acetate. The filtrate is washed with brine (3×), dried over $MgSO_4$, filtered and concentrated in vacuo. The residue is purified by flash chromatography on silica gel (ethyl acetate/hexanes as eluant) to provide the desired amine intermediate (E).

Step S-4: To a mixture of nitro compound (D-2) (1.0 equiv) and iron (15.0 equiv) in 1:1 absolute ethanol/dry tetrahydrofuran solution (0.8 mL/mmol of ester) is added water (10 uL/ml of solvent). The mixture is then cooled to 0° C. and a solution of concentrated sulfuric acid (4.0 equiv) in water (1.2 ml/mmol of ester) is added dropwise to the mixture. The reaction is warmed to room temperature and stirred for 1 hour, or until the reaction is determined complete by LCMS or TLC. The reaction is then filtered through a pad of Celite® with the aid of ethyl acetate. The filtrate is diluted with brine, saturated aqueous sodium bicarbonate solution and additional ethyl acetate, the organic and aqueous layers are separated, and the organic layer is washed with saturated sodium bicarbonate solution, brine, dried over $MgSO_4$, filtered and concentrated in vacuo. The residue is purified by flash chromatography on silica gel (ethyl acetate/hexanes as eluant) to provide D-3.

Step S-5: To a stirred solution of D-3 (1.0 equiv) in acetic acid (0.2 M) is added a carbonyl compound (10.0 equiv of a ketone or aldehyde) and sodium borohydride (10.0 equiv), and the resulting mixture is stirred at room temperature for 1 hour, or until the reaction is determined complete by LCMS or TLC. The reaction is then diluted with ethyl acetate, and washed with saturated aqueous sodium bicarbonate solution (5×) and brine (2×), and the organic layer is dried over $MgSO_4$, filtered and concentrated in vacuo. The residue is purified by flash chromatography on silica gel (ethyl acetate/hexanes) to provide the desired amine intermediate (E).

(iii) Coupling of Tetrazolone Intermediate and Amine Intermediate

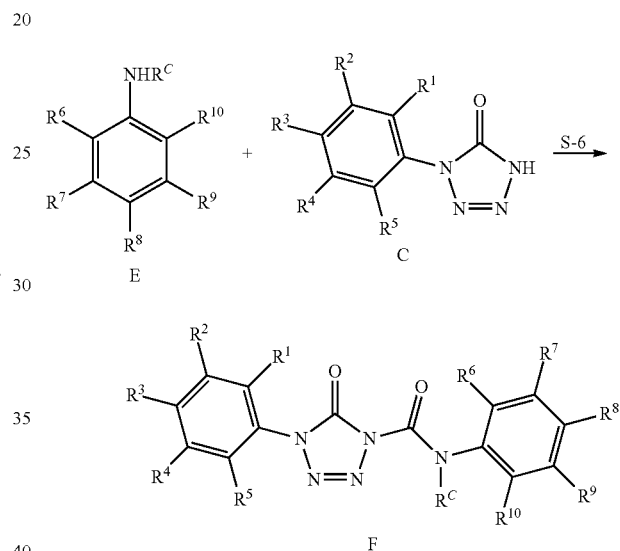

Step S-6: To a solution of amine intermediate (E) (1.3 equiv) in dry tetrahydrofuran (0.5 M) under argon is added triethylamine (1.3 equiv) followed by triphosgene (0.7 equiv). The resulting heterogeneous mixture is stirred at room temperature for 15 minutes, treated with dimethylaminopyridine (DMAP) (1.0 equiv) and the tetrazolone intermediate (C) (1.0 equiv), diluted with dry tetrahydrofuran (to 0.25 M final concentration with respect to amine) and heated to reflux for 1 hour, or until the reaction is determined to be complete by LCMS or TLC. The reaction mixture is cooled to room temperature and diluted with ethyl acetate and brine, and the aqueous and organic layers are separated. The organic layer is washed with brine, 10% aqueous HCl, then brine, and dried over $MgSO_4$, filtered and concentrated in vacuo. The residue is purified by flash chromatography on silica gel (ethyl acetate/hexanes) to provide the desired tetrazolone product (F).

(iv) Scope of the General Synthetic Method

The general synthetic method is not intended to be limited to the coupling of amine intermediates such as (E) with phenyl tetrazolone intermediates such as (C) in the formation of compounds provided herein. For example, other amines and tetrazolones have been coupled using the general methods described above to provide a wide variety of tetrazolone compounds, e.g., such as the tetrazolone compounds provided in Tables 1-4.

Exemplary Syntheses of Compounds
  (i) Synthesis of Tetrazolone Compounds 7 and 8

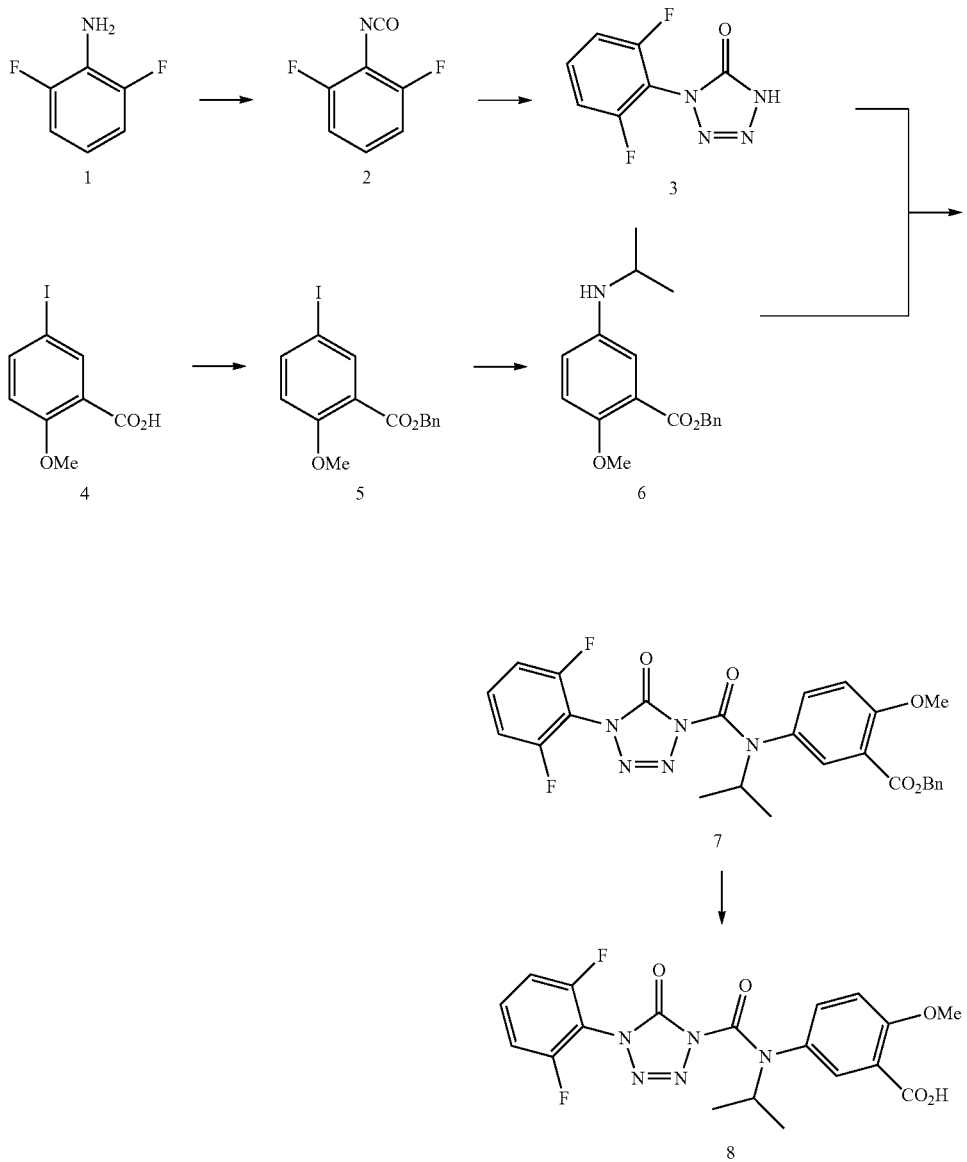

Compound 3: A mixture of commercially available 2,6-difluorophenyl isocyanate (2) (1.0 equiv) and trimethylsilyl azide (2.0 equiv) was heated to reflux for 12 hours. The excess of azide was removed in vacuo and the residue was crystallized from toluene to provide compound (3) as white needles.

Compound 5: To a solution of commercially available 5-iodo-2-methoxybenzoic acid (4) (1.0 equiv) in dry dimethylformamide (DMF) (0.5 M) under argon was added solid potassium carbonate (1.5 equiv) followed by benzyl bromide (1.1 equiv), and the resulting mixture was stirred at room temperature for 4 hours, acidified with 10% HCl, and diluted with brine and ethyl acetate. The aqueous and organic layers were separated and the organic layer was washed with brine (5×), dried over MgSO$_4$, filtered and concentrated in vacuo to afford an oil, compound (5), which was used without further purification.

Compound 6: Copper iodide (1 equiv) and cesium carbonate (2.0 equiv) were added to a microwave vial and the vial was evacuated and filled with argon three times. Compound (5) in dry dimethylformamide (0.6 M), isopropylamine (2.0 equiv) and 2-isobutyrylcyclohexanone (0.2 equiv) were then added to the vial, the vial was sealed and the resulting mixture was heated to 100° C. under microwave irradiation for 2 hours. At that time, the vial was cooled to room temperature and the reaction mixture was diluted with ethyl acetate and filtered through a pad of Celite® with the aid of ethyl acetate. The filtrate was washed with brine (3×), dried over MgSO$_4$, filtered and concentrated in vacuo. The residue was purified by flash chromatography on silica gel (ethyl acetate/hexanes) to provide compound (6).

Compound 7: To a solution of compound (6) (1.5 equiv) in dry dichloromethane (0.5 M) under argon was added triethylamine (3.0 equiv) followed by triphosgene (1.5 equiv). The resulting heterogeneous mixture was stirred at room temperature for 15 minutes, concentrated in vacuo, and the residue was taken up in dry toluene (0.25 M with respect to amine) and treated with dimethylaminopyridine (DMAP) (1.0 equiv)

and the compound (3) (1.0 equiv). The resulting mixture was heated to reflux for 1 hour, cooled to room temperature and diluted with ethyl acetate and brine, and the aqueous and organic layers were separated. The organic layer was washed with brine, 10% aqueous HCl, then brine, and dried over MgSO$_4$, filtered and concentrated in vacuo. The residue was purified by flash chromatography on silica gel (ethyl acetate/hexanes) to provide compound (7) as a white foam.

Compound 8: To a solution of compound 7 (1.0 equiv) in 2:1 methanol/THF (0.1 M) under argon was added 5% Pd/C (0.1 equiv) and the inert atmosphere was replaced with hydrogen. The resulting mixture was stirred at room temperature for 30 minutes, filtered through a pad of Celite with the aid of methanol and the resulting filtrate was concentrated in vacuo. The residue was purified by preparative HPLC (0.1% formic acid in acetonitrile/water) to provide compound (8) as a white solid.

(ii) Synthesis of Tetrazolone Compounds 15 and 16 ration to provide compound (10) which was advanced without purification.

Compound 11: To a stirred solution of (10) (1.0 equiv) in 20:1 acetone:DMF (0.2 M) under nitrogen was added potassium carbonate (1.5 equiv), p-methoxybenzyl chloride (1.0 equiv), and sodium iodide (catalytic) at room temperature. The resulting mixture was heated to 70° C. for six hours. The resulting solution was cooled to room temperature and the volume was reduced by rotary evaporation. The resulting solution was diluted with hexanes and ethyl acetate, washed with water, dried with sodium sulfate and concentrated via rotary evaporation. The resulting oil was purified by silica gel column chromatography (hexanes to 25% ethyl acetate/hexanes) to afford compound (11) as an oil.

Compound 12: To a stirred solution of compound (11) (1.0 equiv) in DMF (0.12M) at room temperature in a microwave vial was added cesium carbonate (2.00 equiv), copper iodide

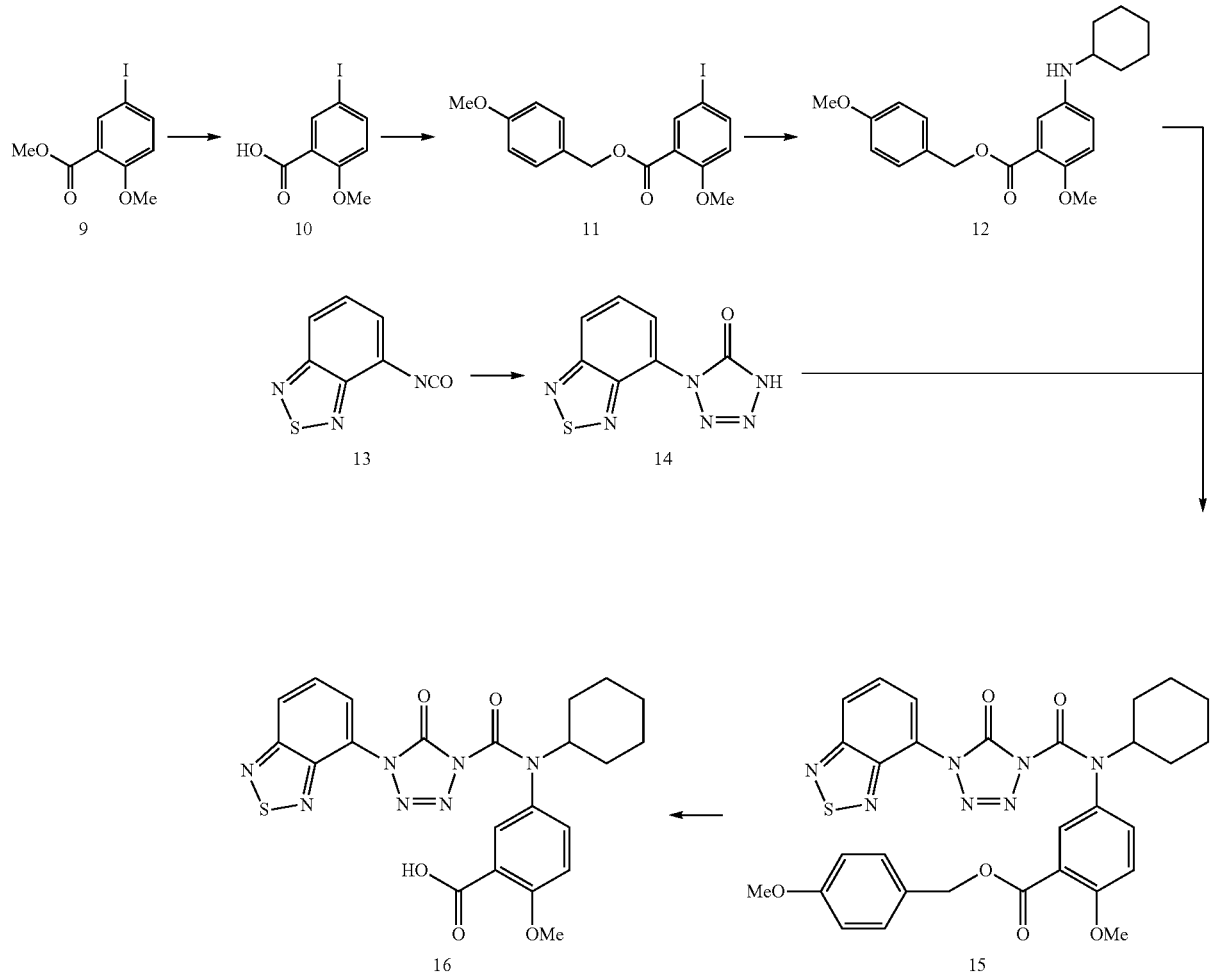

Compound 10: To a stirred solution of commercially available compound (9) (1.0 equiv) in 1:1 THF:H$_2$O (0.6 M) under nitrogen was added LiOH (5.0 equiv) at room temperature. The reaction was heated to 80° C. for two hours. The resulting solution was cooled to room temperature and the volume was reduced by rotary evaporation. The resulting solution was acidified with 2N HCl to pH=1, extracted with ethyl acetate, dried with sodium sulfate, and concentrated via rotary evapo- (0.1 equiv), 2-isobutyrylcyclohexanone (0.2 equiv), and cyclohexylamine (3.0 equiv). The resulting suspension was heated in the microwave at 100° C. for 1 hr. The resulting suspension was cooled to room temperature, diluted with ethyl acetate, washed with dilute aqueous lithium chloride, and washed with water. The organic layer was dried with sodium sulfate and concentrated via rotary evaporation to afford a green oil which was purified by silica gel column chromatography (hexanes to 1:2 ethyl acetate/hexanes) to afford compound (12) as an oil.

Compound 14: To a stirred solution of commercially available compound (13) (1.00 equiv) was added azidotrimethylsilane (4.00 equiv). The resulting suspension was heated at 90° C. for six hours. The hot reaction solution was poured directly into a beaker containing toluene:ice (1:1). The resulting yellow precipitate was collected via vacuum filtration and washed with cold toluene to afford compound (14) as a yellow solid.

Compound 15: To a stirred solution of compound (12) (1.2 equiv) in dichloromethane (0.5M) at 0° C. was added triethylamine (3.0 equiv) and triphosgene (1.0 equiv). The ice bath was removed and the solution was stirred at room temperature for 15 minutes followed by concentrated by rotary evaporation. The resulting foam was dissolved in toluene (0.4M) followed by addition of compound (14) (1.0 equiv) and dimethylaminopyridine (1.0 equiv). The resulting suspension was heated at 70° C. for sixteen hours. The solution was cooled to room temperature, diluted with ethyl acetate, and washed with water. The organic layer was dried with sodium sulfate and concentrated via rotary evaporation. The resulting oil was purified by silica gel column chromatography (ethyl acetate/hexanes) to afford compound (15) as a white solid.

Compound 16: To a stirred solution of compound (15) (1.0 equiv) in $CH_2Cl_2$ (0.1 M) under nitrogen was added trifluoroacetic acid (10.0 equiv) followed by anisole (1.0 equiv) at room temperature. The reaction was run at room temperature for ten minutes. The reaction was diluted with dichloromethane and neutralized with aqueous sodium bicarbonate solution. The organic layer was dried with sodium sulfate and concentrated via rotary evaporation. The resulting oil was purified by preparative HPLC (0.1% formic acid in acetonitrile/water) and lyophilized to give compound (16) as a white powder.

(iii) Synthesis of Tetrazolone Compounds 17 and 18

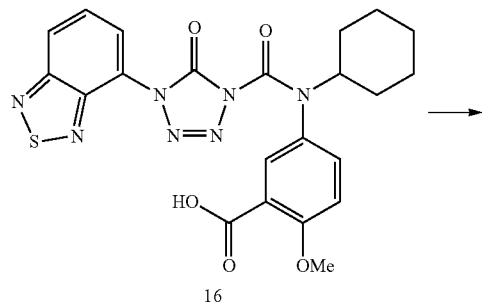

16

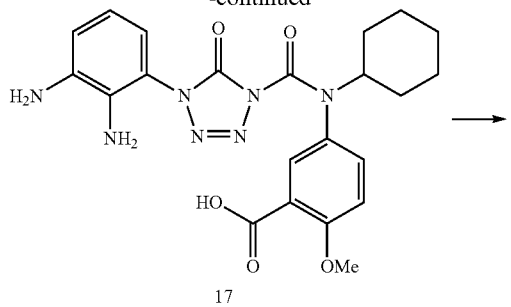

17

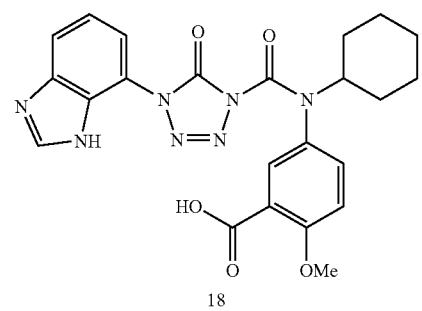

18

Compound 17: To a stirred solution of compound (16) (1.0 equiv) in MeOH (0.02 M) under nitrogen was added palladium hydroxide on carbon (0.2 equiv) followed by vacuum evacuation and exposure to hydrogen gas (1 atm, balloon). The reaction was run at room temperature overnight. The resulting solution was filtered thru celite, washed with dichloromethane and concentrated via rotary evaporation. The resulting oil was purified by preparative HPLC (0.1% formic acid in acetonitrile/water) and lyophilized to afford compound (17) as a white solid.

Compound 18: To a stirred solution of compound (17) was added formic acid (500 equiv). The reaction was heated at 100° C. for 1 hour. After cooling to room temperature, the reaction was diluted with ethyl acetate and the organic layer was washed with water, dried with sodium sulfate, and concentrated via rotary evaporation. The resulting oil was purified by preparative HPLC (0.1% formic acid in acetonitrile/water) and lyophilized to afford compound (18) as a white solid. Compound (18) is depicted above as one compound, but it exists in equilibrium as a mixture of tautomers as shown below.

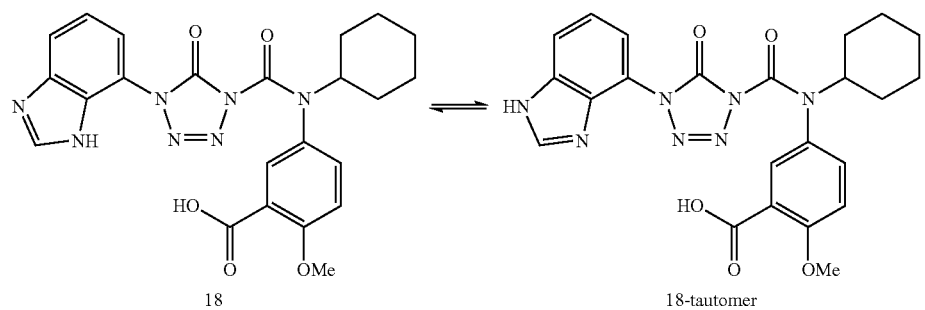 [SMILES: COc1ccc(N(C(=O)n2nnn(-c3cccc4nc[nH]c34)c2=O)C2CCCCC2)cc1C(=O)O ; COc1ccc(N(C(=O)n2nnn(-c3cccc4[nH]cnc34)c2=O)C2CCCCC2)cc1C(=O)O]

18   18-tautomer (iv) Synthesis of Tetrazolone Compounds 24 and 25

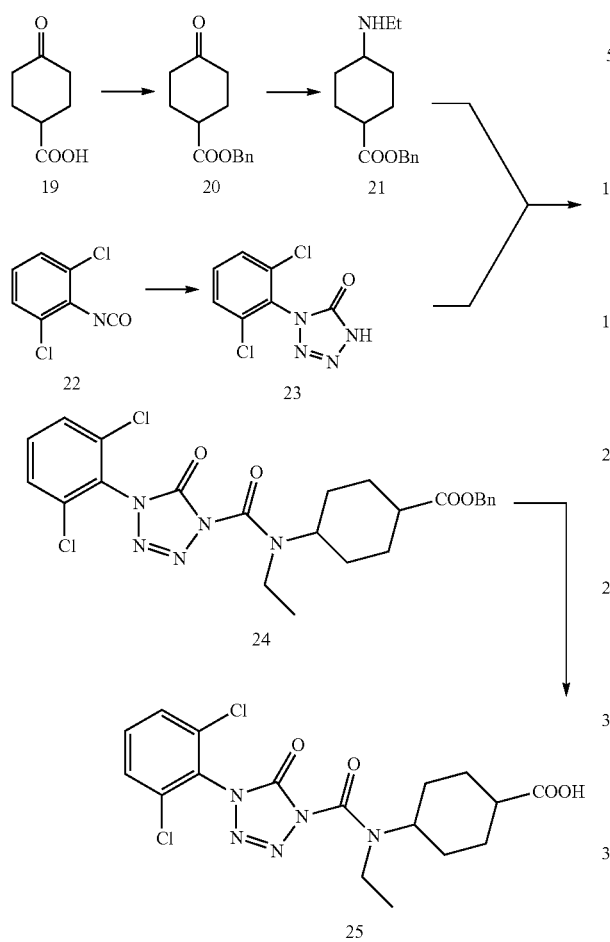

Compound 20: To a solution of commercially available 4-oxocyclohexanecarboxylic acid (19) (1.0 equiv) in dry DMF (0.5 M) under argon was added solid potassium carbonate (1.5 equiv) followed by benzyl bromide (1.1 equiv). The resulting mixture was stirred at room temperature for 4 hours, acidified with 10% HCl, diluted with brine and ethyl acetate, and the layers were separated. The organic layer was washed with brine (5×), dried (MgSO$_4$), filtered and concentrated in vacuo to afford a solid which was used without further purification.

Compound 21: A solution of benzyl 4-oxocyclohexanecarboxylate (20) (1.0 equiv) and a 2M ethylamine solution in THF (2.0 equiv) in dry DCE (1.4 M) under argon was treated with sodium triacetoxyborohydride (1.5 equiv) and the resulting mixture was stirred at rt for 1 h, and quenched with saturated aqueous sodium bicarbonate solution. The layers were separated and the aqueous one extracted with DCM (3×). The combined organic layers were washed with brine, dried (MgSO$_4$), filtered and concentrated in vacuo. The residue was purified by flash chromatography on silica gel (ethyl acetate/hexanes) to provide compound (21) as an oil.

Compound 23: A mixture of commercially available 2,6-dichlorophenyl isocyanate (22) (1.0 equiv) and trimethylsilyl azide (2.0 equiv) was heated to reflux for 12 hours. The excess of azide was removed in vacuo and the residue was crystallized from methanol to provide compound (23) as white needles.

Compound 24: To a solution of compound (21) (1.3 equiv) in dry tetrahydrofuran (0.5 M) under argon was added triethylamine (1.3 equiv) followed by triphosgene (1.3 equiv). The resulting heterogeneous mixture was stirred at room temperature for 15 minutes diluted with dry tetrahydrofuran (0.25 M with respect to amine) and treated with DMAP (1.0 equiv) and compound (23) (1.0 equiv). The resulting mixture was heated to reflux for 1 hour, cooled to room temperature and diluted with ethyl acetate and brine, and the aqueous and organic layers were separated. The organic layer was washed with brine, 10% aqueous HCl, then brine, and dried over MgSO$_4$, filtered and concentrated in vacuo. The residue was purified by flash chromatography on silica gel (ethyl acetate/hexanes) to provide compound (24) as a white solid.

Compound 25: To a solution of compound (24) (1.0 equiv) in methanol (0.1 M) under argon was added 10% Pd(OH)$_2$ on carbon (0.1 equiv) and the inert atmosphere was replaced with hydrogen. The resulting mixture was stirred at room temperature for 2 h, filtered through a pad of Celite with the aid of methanol, and the resulting filtrate concentrated in vacuo. The residue was purified by preparative HPLC (0.1% formic acid in acetonitrile/water) to provide compound (25) as a white solid.

(v) Synthesis of Tetrazolone Compounds 27 and 28

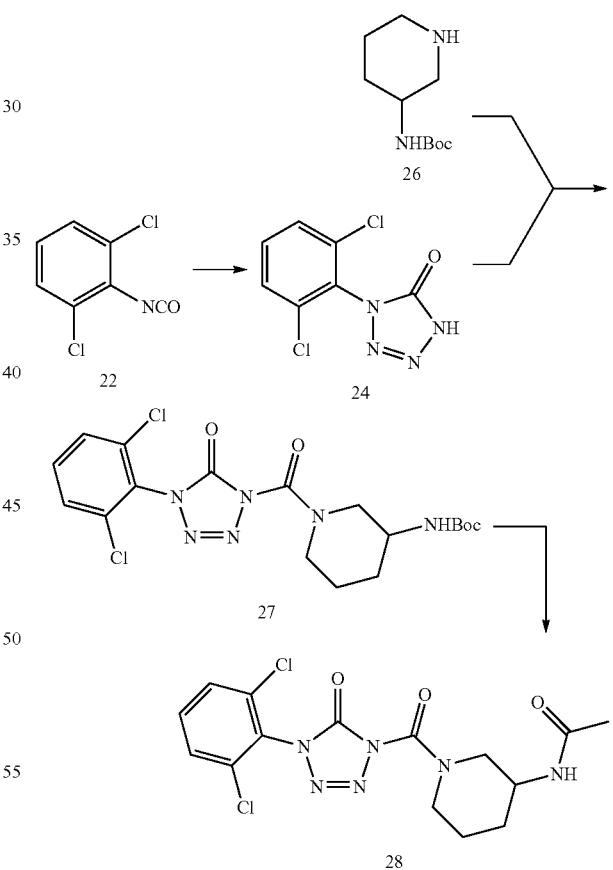

Compound 27: Commercially available tert-butyl piperidin-3-ylcarbamate (26) (1.3 equiv) in dry tetrahydrofuran (0.5 M) under argon was added triethylamine (1.3 equiv) followed by triphosgene (1.3 equiv). The resulting heterogeneous mixture was stirred at room temperature for 15 minutes, diluted with dry tetrahydrofuran (0.25 M with respect to amine) and treated with DMAP (1.0 equiv) and compound

(23) (1.0 equiv). The resulting mixture was heated to reflux for 1 hour, cooled to room temperature and diluted with ethyl acetate and brine, and the aqueous and organic layers are separated. The organic layer was washed with brine, 10% aqueous HCl, then brine, and dried over MgSO$_4$, filtered and concentrated in vacuo. The residue was used without further purification. An analytical sample was obtained by preparative HPLC (0.1% formic acid in acetonitrile/water) to provide compound (27) as a white solid.

Compound 28: Compound (27) (1.0 equiv) was dissolved in dry dichloromethane (0.2 M) at 0° C. and was treated dropwise with TFA (3:1 DCM/TFA). The resulting solution was stirred at room temperature for 1 h and was concentrated in vacuo. The amine salt was then taken up in dry dichloromethane, cooled to 0° C. and treated with excess of acetyl chloride (10.0 equiv) and triethylamine (1.0 equiv). The resulting mixture was stirred at 0° C. for 15 min, quenched with 10% HCl and extracted with DCM (2×). The combined organic extracts were washed with brine, dried (MgSO$_4$), filtered and concentrated in vacuo. The residue was purified by preparative HPLC (0.1% formic acid in acetonitrile/water) to provide compound (28) as a white solid.

(vi) Synthesis of Tetrazolone Compounds 32 and 33

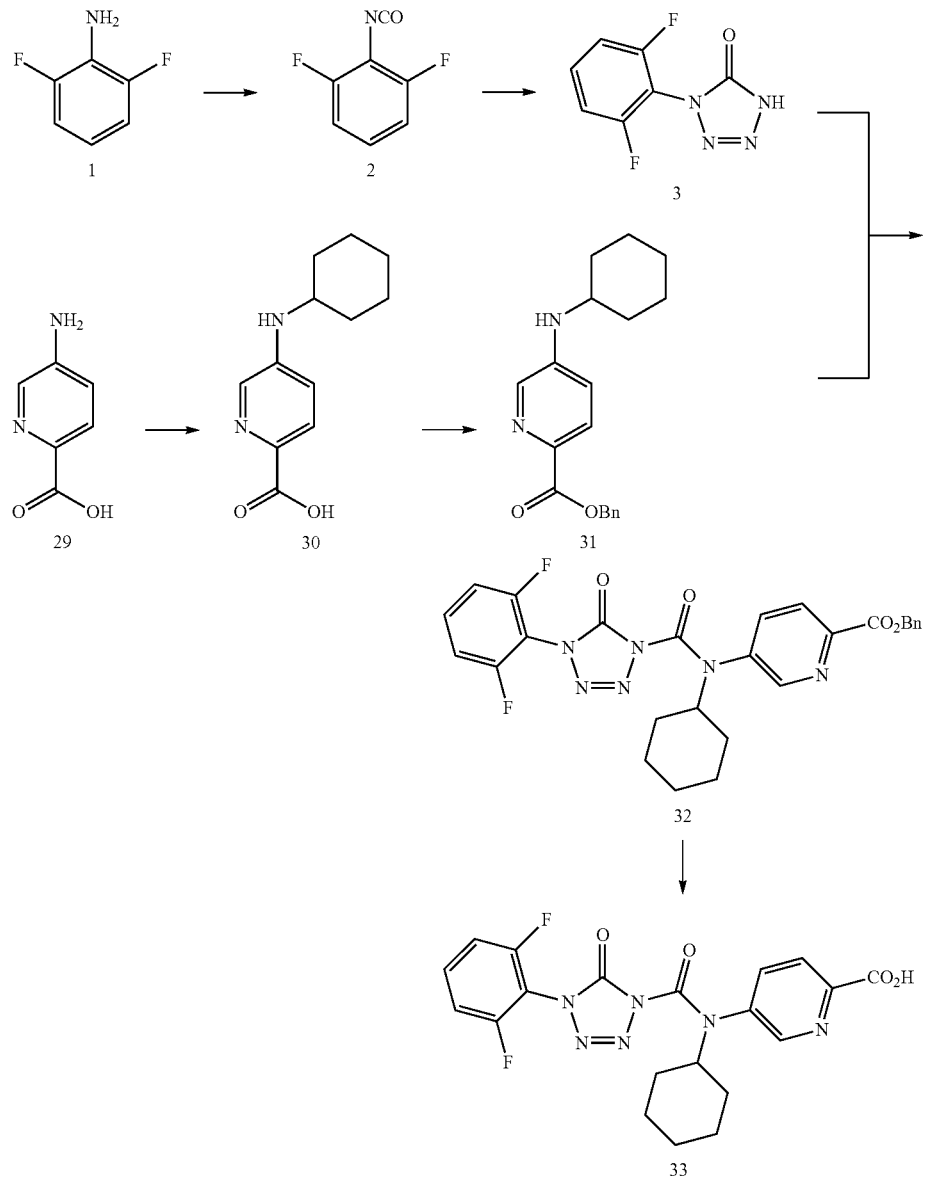

Compound 30: To a stirred solution of 5-amino-2-pyridinecarboxylic acid (29) (1.0 equiv) in AcOH (0.9 M) under nitrogen was added cyclohexanone (1.1 equiv) and sodium triacetoxyborohydride (1.1 equiv) at room temperature. The resulting mixture was stirred at room temperature for 72 hours. Methanol was added and the resulting solution was concentrated by rotary evaporation. The resulting oil was dissolved in CHCl$_3$:IPA (4:1) and water, and the organic layer was concentrated in vacuo to provide compound (30) which was advanced without purification.

Compound 31: To a stirred solution of compound (30) (1.0 equiv) in 2:1 CH$_2$Cl$_2$:DMSO (0.13M) was added AgO (3.0 equiv) followed by benzyl bromide (1.1 equiv). The reaction was run at room temperature overnight. The resulting solution was filtered through a celite pad, diluted with $CH_2Cl_2$, washed with water, dried with sodium sulfate, and concentrated by rotary evaporation. The resulting oil was purified by silica gel chromatography (hexanes to 50% ethyl acetate/hexanes) to afford compound (31) as an off-white foam.

Compound 32: To a stirred solution of compound (31) (0.9 equiv) in dichloromethane (0.5M) at 0 C was added triethylamine (3.0 equiv) and triphosgene (1.0 equiv). The ice bath was removed and the solution was stirred at room temperature for 15 minutes followed by concentrated by rotary evaporation. The resulting foam was dissolved in toluene (0.4M) followed by addition of compound (3) (1.0 equiv) and dimethylaminopyridine (1.0 equiv). The resulting suspension was heated at 90° C. for two hours. The solution was cooled to room temperature, diluted with ethyl acetate, and washed with water. The organic layer was dried with sodium sulfate and concentrated via rotary evaporation. The resulting oil was purified by silica gel column chromatography (hexanes to 50% ethyl acetate/hexanes) to afford compound (32).

Compound 33: To a stirred solution of (32) (1.00 equiv) in methanol (0.1M) at room temperature was added 20% palladium hydroxide on carbon (~0.2 equiv). The reaction was evacuated and flushed with nitrogen followed by charging with hydrogen gas. After stirring for one hour, the reaction was filtered through celite, washed with dichloromethane, and concentrated by rotary evaporation. The resulting oil was purified by silica gel column chromatography (dichloromethane to 9:1 dichloromethane:methanol) to afford 33 as a clear oil.

(vii) Synthesis of Tetrazolone Compounds 40 and 41 was stirred for 19 hours, additional potassium carbonate (1.5 equiv) was added followed by phenol (1.2 equiv) and stirring was continued for 24 h. The resulting suspension was filtered through a pad of Celite with aid of AcOEt, the filtrate was diluted with additional AcOEt and was washed with brine and 10% HCl. The aqueous layer was back-extracted with AcOEt and the combined organic layers were washed with brine (3×), dried ($MgSO_4$), filtered and concentrated in vacuo. An orange oil was obtained, which was purified by flash chromatography (Hexane/AcOEt 9:1) to render compound 36 as a thick yellow oil (90% yield).

Compound 37: To a stirred solution of (36) (1.0 equiv) and iron powder (15.3 equiv) in 1:6 absolute EtOH/THF (0.3 M) cooled to 0° C. was dropwise added a solution of $H_2SO_4$ (0.6 ml/mmol) in $H_2O$ (1.8 ml/mmol). The resulting mixture was stirred at rt for 1 h, filtered through a pad of Celite with the aid of AcOEt, and the filtrate diluted with brine and additional AcOEt. The layers were separated, the organic one was washed with brine, saturated sodium bicarbonate solution, brine, dried ($MgSO_4$), filtered and concentrated in vacuum. Compound (37) was obtained as a pale yellow oil which crystallized upon standing.

Compound 38: To an stirred suspension of aniline (37) in glacial AcOH (0.3M) was added acetone (5 equiv) followed by sodium borohydride (2 equiv). The resulting mixture was stirred at rt for 1 h, diluted with AcOEt and washed with brine (3×), saturated sodium bicarbonate solution (6×, until basic pH) and brine (2×). The organic layer was dried ($MgSO_4$), filtered and concentrated in vacuo. Compound (38) was obtained as an oil after purification by flash chromatography (Hexane/AcOEt 91 to 3:1) (80% yield over 2 steps).

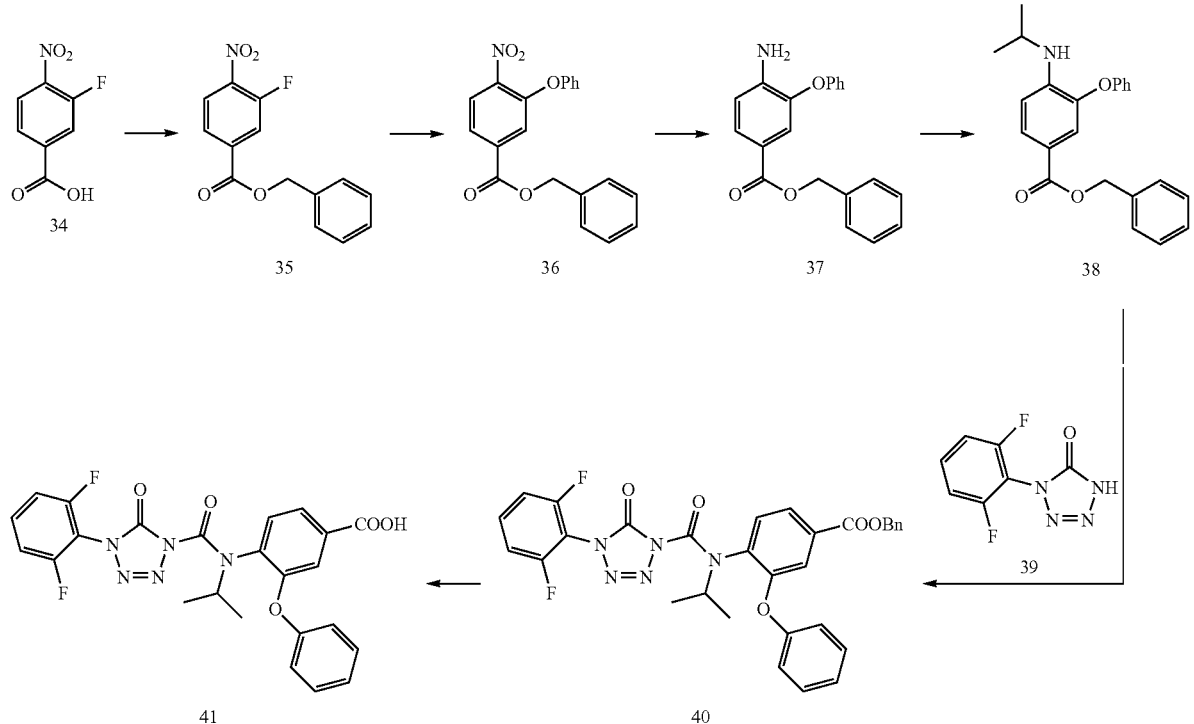

Compound 36: To a stirred suspension of commercially available compound (34) (1.0 equiv) and potassium carbonate (1.5 equiv) in dry DMF (0.3 M) under nitrogen was added benzyl bromide (1.2 equiv) at room temperature. The reaction Compound 40: To a stirred solution of compound (38) (1.0 equiv) in dichloromethane (0.3 M) at 0° C. was added triethylamine (2.0 equiv) and triphosgene (0.7 equiv). The ice bath was removed and the solution was stirred at room temperature for 15 minutes and was concentrated in vacuo. The resulting foam was dissolved in toluene (0.3 M) followed by addition of compound (39) (1.1 equiv) and dimethylaminopyridine (1.0 equiv). The resulting suspension was heated to reflux for 3 h, was then cooled to room temperature, diluted with ethyl acetate, and washed with water, 10% hydrochloric acid solution and brine. The organic layer was dried (MgSO$_4$), filtered and concentrated in vacuo. The resulting crude was purified by flash chromatography (Hexane/AcOEt 5:1 to 2:1) to afford compound (40) as a pale yellow foam (66% yield).

Compound 41: To a solution of compound (40) (1.0 equiv) in 1:1 methanol/AcOEt (0.3 M) under argon was added 10% Pd/C (0.15 equiv) and the inert atmosphere was replaced with hydrogen. The resulting mixture was stirred at room temperature for 30 minutes, filtered through a pad of Celite with the aid of methanol and the resulting filtrate was concentrated in vacuo. The residue was purified by flash chromatography (Hexane/AcOEt 2:1 to 1:4 and DCM/MeOH 9:1) to provide compound (41) as a white foam (58% yield) [M+1]$^+$=495.1.

(viii) Synthesis of Tetarzolone Compounds 51 and 52

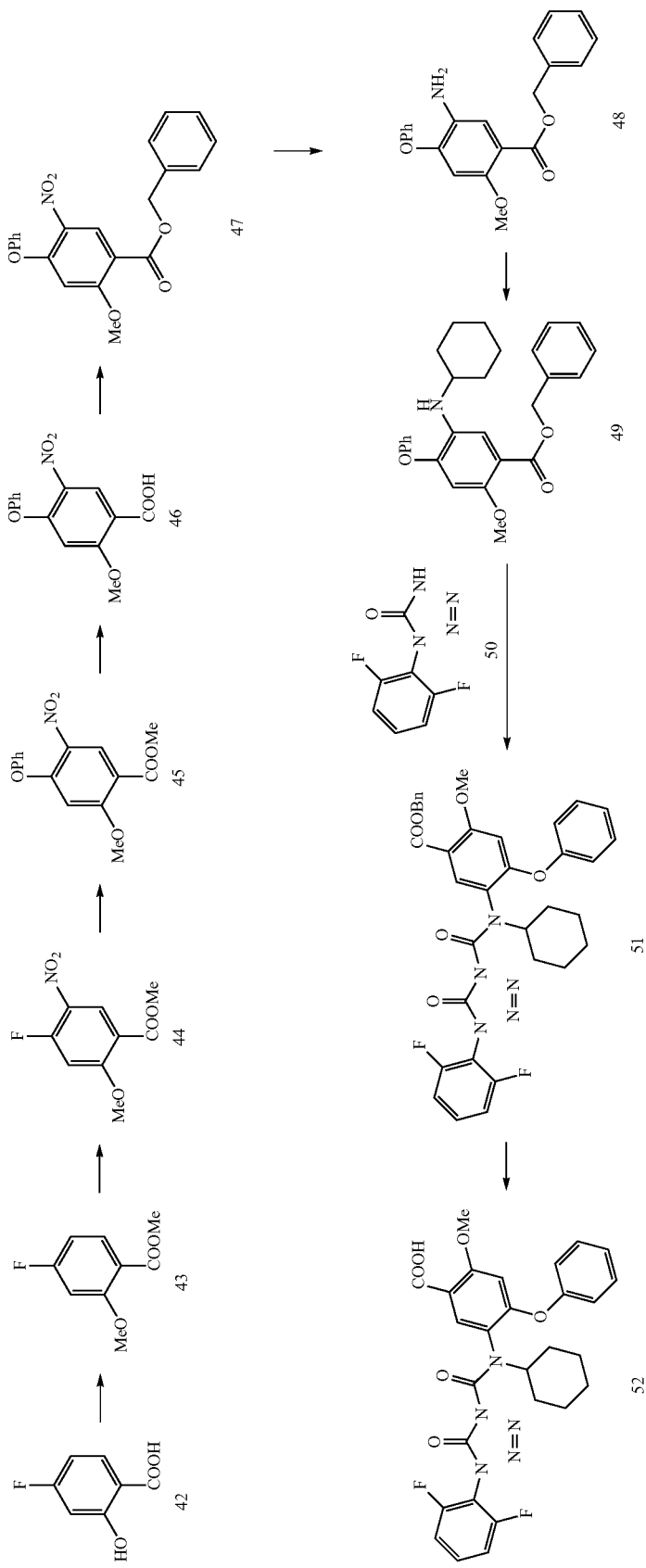

Compound 44: Compound (44) was prepared in 64% yield via methylation of commercially available 4-fluorosalicilic acid (42) followed by nitration as described in the literature (Del Corona. L.; Signorelli, G.; Pinzetta, A.; Coppi. G. *Eur. J. Med. Chem.* 1993, 28: 419-425).

Compound 45: To a solution of compound (44) (1.0 equiv) in dry DMF (0.9 M) was added phenol (1.1 equiv) and potassium carbonate (1.5 equiv) and the resulting mixture was stirred at rt for 1 h, the solid filtered and washed with AcOEt, the filtrate further diluted with AcOEt and washed with 10% HCl and brine (5×). The aqueous layer was back-extracted with AcOEt, which was washed with brine. The combined organic layers were dried ($MgSO_4$), filtered and concentrated in vacuo. Compound (45) was obtained as an oil, which was used directly.

Compound 46: A solution of methyl ester (45) (1.0 equiv) in 2:2:5 MeOH/THF/$H_2O$ (0.3 M) was added LiOH (1.5 equiv). The suspension was stirred at 60° C. for 1.5 h. The reaction mixture was allowed to cool to rt, diluted with brine and extracted with diethyl ether. The aqueous layer was acidified with 10% HCl and extracted with AcOEt (3×). The combined AcOEt layers were washed with brine, dried ($MgSO_4$), filtered and concentrated in vacuo. Compound 46 was obtained as a pale yellow foam, which was used directly.

Compound 47: To a stirred solution of acid (46) (1.0 equiv) and potassium carbonate (1.5 equiv) in dry DMF (0.6 M) under nitrogen was added benzyl bromide (1.1 equiv) at room temperature. The reaction was stirred for 19 hours, filtered through a pad of Celite with aid of AcOEt, the filtrate was acidified with 10% HCl, diluted with brine and extracted with AcOEt (3×). The combined organic extracts were washed with brine, dried ($MgSO_4$), filtered and concentrated in vacuo. The residue (oil) was used directly.

Compound 48: To a stirred solution of (47) (1.0 equiv) in 2:1 THF/AcOH (0.6 M) cooled to 0° C., was portionwise added zinc powder (10.0 equiv). The resulting mixture was stirred at 0° C. for 1 h, filtered through a pad of Celite with the aid of AcOEt and the filtrate was diluted with brine and additional AcOEt. The layers were separated, the organic one was washed with brine, saturated sodium bicarbonate solution, brine, dried ($MgSO_4$), filtered and concentrated in vacuo. Compound (48) was obtained as a pale yellow oil which crystallized upon standing.

Compound 49: To an stirred suspension of aniline (48) in glacial AcOH (0.3 M) was added cyclohexanone (4.0 equiv) followed by sodium borohydride (2.5 equiv). The resulting mixture was stirred at rt for 1 h, diluted with AcOEt and washed with brine (3×), saturated sodium bicarbonate solution (6×, until basic pH) and brine (2×). The organic layer was dried ($MgSO_4$), filtered and concentrated in vacuo. The residue was purified by flash chromatography (Hexane/AcOEt 9:1) to give compound (49) as an oil (46% yield over 5 steps).

Compound 51: To a stirred solution of compound (49) (1.0 equiv) in dichloromethane (0.2 M) at 0° C. was added triethylamine (2.0 equiv) and triphosgene (0.7 equiv). The ice bath was removed and the solution was stirred at room temperature for 15 minutes and was concentrated in vacuo. The resulting foam was dissolved in toluene (0.2 M) followed by addition of compound (50) (1.1 equiv) and dimethylaminopyridine (1.0 equiv). The resulting suspension was heated to reflux for 2 h, was then cooled to room temperature, diluted with ethyl acetate, and washed with water, 10% hydrochloric acid solution, and brine. The organic layer was dried ($MgSO_4$), filtered and concentrated in vacuo. The resulting product was purified by flash chromatography (Hexane/AcOEt 9:1 to 2:1) to afford compound (51) as a crystalline solid (22% yield).

Compound 52: To a solution of compound (51) (1.0 equiv) in 1:1 methanol/THF (0.1 M) under argon was added 10% Pd/C (0.15 equiv) and the inert atmosphere was replaced with hydrogen. The resulting mixture was stirred at room temperature for 1 h, filtered through a pad of Celite with the aid of methanol and the resulting filtrate was concentrated in vacuo. Compound (52) was obtained as a crystalline solid (99% yield).

Biological Assays

Preparation of Human FASN Protein

Human FASN protein (SEQ ID NO. 1) was purified from SKBR3 cells using procedures modified from those in Jayakumar et al. *PNAS* 1995, 92:8695-8699. SKBR3 cells were obtained from ATCC and grown in DMEM high glucose medium supplemented with 10% FBS, 1 μg/mL bovine pancreas insulin, 100 U/mL penicillin and 100 g/mL streptomycin. The confluent cells were trypsinized and washed three times with PBS buffer before frozen in liquid $N_2$ and stored at −80° C. Frozen cells were thawed on ice and resuspended in lysis buffer (25 mM Tris-HCl, pH 7.0, 15 mM NaCl, 1 mM EDTA, and 1 mM DTT) with protease inhibitors. The cells were lysed by sonication, and the cell debris was removed by centrifugation at 20,000 rpm for 30 min. To the supernatant, neutralized saturated ammonium sulfate solution was added to a final concentration of 35%. The solution was left on ice for 1 hr, and the precipitated proteins were harvested by centrifugation at 20,000 rpm for 30 min. The proteins were redissolved in lysis buffer without NaCl and loaded on a mono Q column. Bound proteins were eluted with a linear gradient of NaCl in lysis buffer. Each fraction was analyzed by SDS-PAGE and FASN NADPH consumption assay. The fractions containing FASN were pooled and concentrated to 2-3 mg/mL. Glycerol was added to 20%, and the protein was frozen in liquid $N_2$ and stored at −80° C.

FASN NADPH Consumption Assay

All chemicals were purchased from Sigma (St. Louis, Mo.). The procedures of NADPH consumption assay were similar to those described in Cox et al., *PNAS* 1983, 80:4233-4237. On a 96-well polypropylene microplate, dilution series (typical concentrations 60 nM-1.0 mM) of test compounds were prepared in DMSO, of which 4.0 μL each was transferred to a black polystyrene assay microplate and mixed with 36 μL FASN assay buffer (50 mM potassium phosphate, pH 7.0, 1.0 mM EDTA, 0.01% NP-40) plus 5.0 mM fresh DTT. FASN protein (40 μL 150 nM FASN) was added per well, and the microplate was incubated at 37° C. for 30 min. Enzyme activity measurement was initiated by addition of 20 μL 5× substrate mixture to final concentrations of 60 nM FASN, 2.4 nM-40 μM compound, 0.2 mM NADPH, 50 μM butyryl-CoA, 0.5 mM malonyl-CoA in 100 μL assay buffer plus 5.0 mM DTT and 4.0% DMSO. NADPH consumption was monitored kinetically by fluorescence ($\lambda_{Ex}$=340 nm, $\lambda_{Em}$=460 nm) on an EnVision 2100 multilabel plate reader (Perkin Elmer, Waltham, Mass.). FASN enzyme activity (slope) in the presence of 4% DMSO was used as maximum control, whereas background (minimum control) was measured by omission of malonyl-CoA in the substrate mixture. Inhibition curves were fitted by a logistic function to yield $IC_{50}$ values:

$$\% \text{ Inhibition} = \left[1 - \frac{(\text{Slope} - \text{Min})}{(\text{Max} - \text{Min})}\right] \times 100\%$$

-continued $$\% \text{ Inhibition} = \frac{100}{1 + (IC_{50}/[I]_{total})^{Hill\ coefficient}}$$

Compounds provided herein were found to inhibit FASN activity using this assay.

Activities obtained by the above-described FASN NADPH Consumption Assay are designated in Tables 1, 2, 3 and 4 with a star (*), wherein "A*" refers to compounds having an $IC_{50}$ of less than 60 nM; "B*" refers to compounds having an $IC_{50}$ of 60 nM to 250 nM, inclusive; "C*" refers to compounds having an $IC_{50}$ of greater than 250 nM to 1000 nM, inclusive; "D*" refers to compounds having an $IC_{50}$ of greater than 1000 nM to 10,000 nM, inclusive; and "E*" refers to compounds having an $IC_{50}$ of greater than 10,000 nM.

FASN Scintillation Proximity Flaslhplate Assay

Acetyl-coenzyme A, malonyl-coenzyme A, NADPH, bovine gamma globulin, and ORLISTAT were purchased from Sigma (St. Louis, Mo.). Tris(2-carboxyethyl) phosphine hydrochloride (TCEP) was purchased from Pierce Biotechnologies (Rockford, Ill.). [$^3$H]-acetyl-coenzyme A was purchased from Moravek Biochemicals (Brea, CA). FlashPlate™ PLUS phospholipid 96-well scintillant coated microplates were purchased from Perkin Elmer Life and Analytical Sciences (Shelton, CT). The method of the FASN Scintillation Proximity FlashPlate assay is similar to that described in Weiss and Glickman Assay Drug Dev Technol 2003, 1:161-6. In a 96-well polypropylene microplate, a dilution series (typical concentrations 60 nM-1.0 mM) of test compounds were prepared in DMSO followed by a 20-fold dilution into FASN assay buffer (50 mM potassium phosphate, pH 7.0, 1.0 mM EDTA, 0.01% NP-40), of which 5.0 μL each was transferred to a FlashPlate® PLUS 96-well plate and mixed with 35 μL FASN assay buffer plus 0.5 mg/mL bovine gamma globulin and 1 mM TCEP. FASN protein (10 μL, 10 nM) was added per well, and the microplate was incubated at 37° C. for 30 min. 10 μL of 20 mM NADPH was added, and the reaction was initiated by addition of 40 L substrate mixture to final concentrations of 1 nM FASN, 100 μM acetyl-coenzyme A, 6 μCi [$^3$H]-acetyl-coenzyme A, 300 μM malonyl-coenzyme A, 2 mM NADPH, 0.5 mg/mL bovine gamma globulin, and 1 mM TCEP in a volume of 100 μL per well. Assay plates were incubated for 2 hr at 37° C. and the reaction was stopped with 2 μL of 2.5 mM stock solution of ORLISTAT in DMSO to ~50 μM. The plates were read in a Wallac 1450 Microbeta Plus liquid scintillation counter (Perkin Elmer, Waltham, Mass.), and counts per minute (CPM) were collected over 2 min. Each inhibitor well CPM was compared to the maximum FASN enzyme activity (Max) CPM and the background (Min) CPM, as measured by omission of FASN enzyme in the background well. % Inhibition values were calculated, and curves were fitted by a four-parameter logistic function to yield $IC_{50}$ values:

$$\% \text{ Inhibition} = \left[1 - \frac{(\text{Inhibitor} - \text{Min})}{(\text{Max} - \text{Min})}\right] \times 100\%$$

Compounds provided herein were found to inhibit FASN activity using this assay.

Activities obtained by the above-described FASN Scintillation Proximity Flashplate Assay are provided in Tables 1, 2, 3 and 4 wherein "A" refers to compounds having an $IC_{50}$ of less than 15 nM; "B" refers to compounds having an $IC_{50}$ of 15 nM to 100 nM, inclusive; "C" refers to compounds having an $IC_{50}$ of greater than 100 nM to 200 nM, inclusive; "D" refers to compounds having an $IC_{50}$ of greater than 200 nM to 5000 nM, inclusive; and "E" refers to compounds having an $IC_{50}$ of greater than 5000 nM.

FASN Cellular Flashplate Assay

Compound was added to HCT116 cells 24 hours post-plating (1×10^6 cells per well, 6-well plates) and incubated for 24 hours (37C, 5% CO2). Cell pellets were harvested and washed with PBS. 30 uL FAS buffer minus BGG (50 mM KPB, pH 7.0, 1.0 mM EDTA, 0.01% NP-40, 1 mM TCEP) was added to the cell pellet, and the cells were lysed by freeze/thaw (3×, liquid nitrogen/42C water bath) before pelleting debris (20,000 rcf, 15 minutes, 4 C). Total protein concentration of the lysates were determined (Pierce BCA Total Protein assay, BSA standard) and samples were normalized to 1 mg/mL total protein in assay buffer.

Assay setup: 50 uL assay buffer was added to each well of the FlashPlate (PerkinElmer, FlashPlate Plus Phospholipid 96-well scintillant coated microplate). To the wells 10 uL of each of the following were added; 1 mM Acetyl-CoA, 3 mM Malonyl-CoA, 0.05 mCi/mL [$^3$H]Acetyl-CoA and 20 mM NADPH for final concentrations of 10 uM Acetyl-CoA, 300 uM Malonyl-CoA, 0.5 uCi/well [$^3$H]Acetyl-CoA and 2000 uM NADPH. Finally, 10 uL of FAS enzyme was added to the wells either in the form of HCT116 cell lysate or purified FAS for a standard curve. The FlashPlate was incubated at 37° C. for 120 min then read on the MicroBeta instrument.

Compounds provided herein were found to inhibit FASN activity using this assay.

HCV-Replicon Luciferase Assay

DMEM complete medium (Life Technologies) was supplemented with 10% FCS, 2 mM glutamin, penicillin and streptomycin, and 1× nonessential amino acids and pre-warmed in a 37° C. thermostat water bath for use as a growth medium.

A dish containing HCV-replicon reporter cells, which were kept in a 37° C. CO$_2$ incubator, was removed from the incubator. The medium was aspirated, and cells were rinsed with 1 ml PBS. The solution was discarded, and 1 ml of 1.25% trypsin/0.02% EDTA was added to additionally rinse the cells. The trypsin/EDTA solution was removed with a vacuum pump, and the cells were incubated at 37° C. for 3 to 5 minutes. Cell morphology was examined under an inverted microscope until a single cell suspension was clearly visible, then the cell was suspended with 3 ml of complete medium by gentle pipetting.

Upon suspension, cell numbers were counted with a hematometer, and cell density was adjusted to 100K/ml by adding appropriate volume of the complete medium. One hundred microliters (100 μl) of cell suspension was added to each well of a 96-well white plate to provided cell density of each of the wells to be 10K/well. The 96-well assay plate was placed in a 37° C. 5% CO$_2$ incubator for 24 hours.

At the end of the incubation, the plate was removed and test compound was added at various desired concentrations using a serial dilution. The plate was placed back into the 37° C. CO$_2$ incubator for 48 hours. After the incubation, 30 μl of Stead-Glo Luciferase System® (Promega) reagent was added to each well and mixed by gentle shaking for 5 minutes to allow thorough cell lysis. Luminescence was measured with Envision® (Perkin-Elmer) with an integration time of 2 seconds.

The tests were conducted using the following compounds:
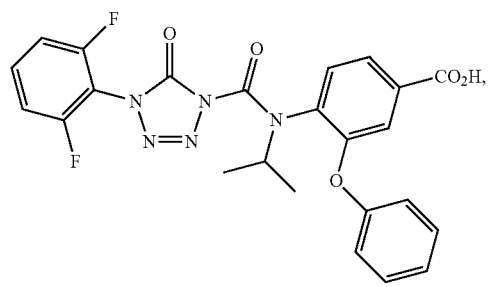
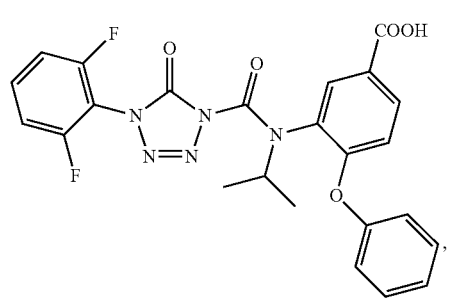
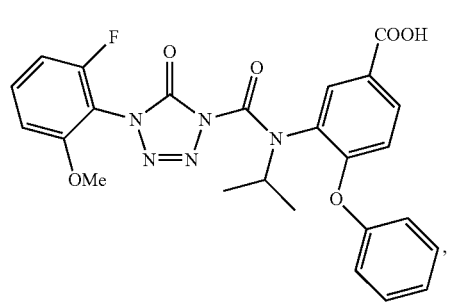
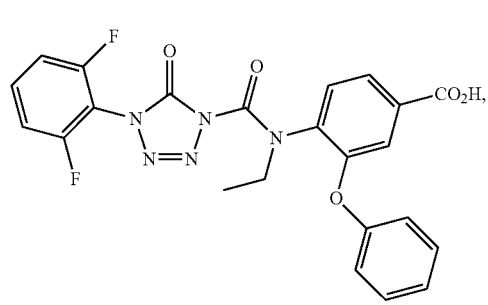
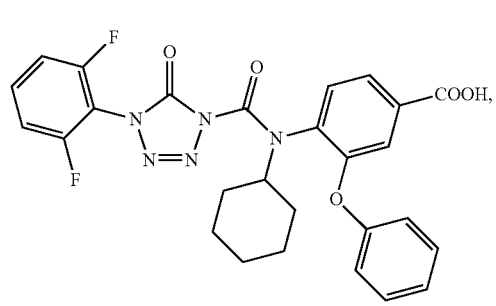
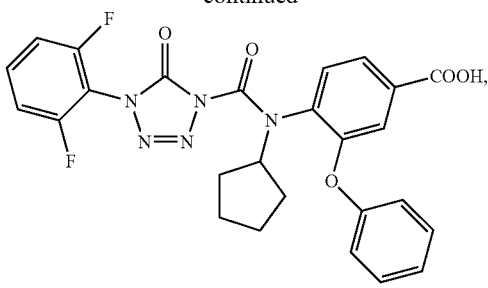
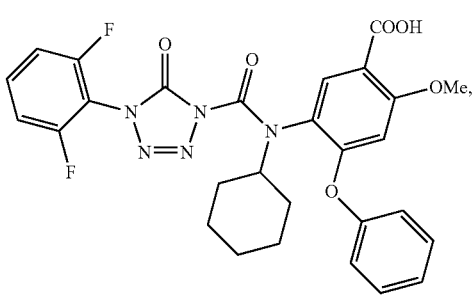
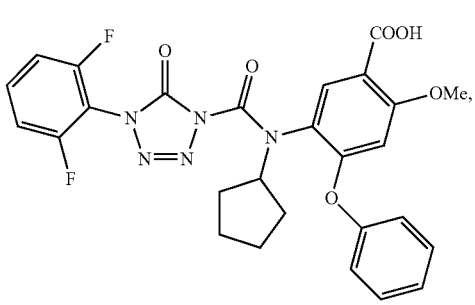
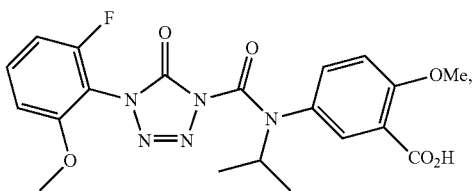
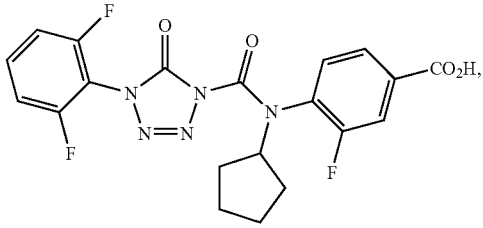
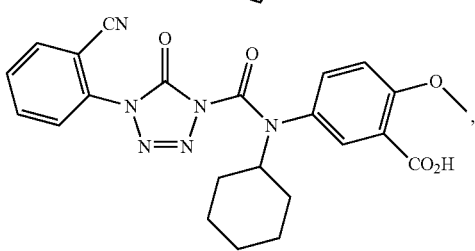

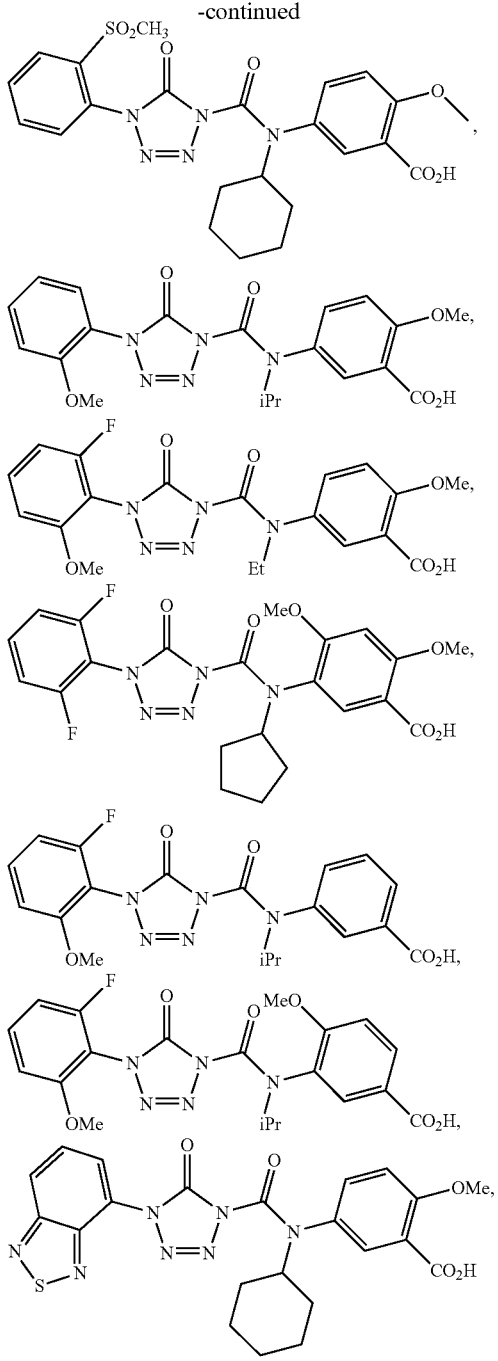

From this test, it was found that IC$_{50}$ values for HCV-replicon of the tested compounds range from about 4 nM to about 7.3 M. These results indicate that compounds provided herein are effective inhibitors of HCV.

MTT Assay

DMEM complete medium (Life Technologies) was supplemented with 10% FCS, 2 mM glutamin, penicillin and streptomycin, and 1× nonessential amino acids and pre-warmed in a 37° C. thermostat water bath for use as a growth medium.

A dish containing HCV-replicon cells, which were kept in a 37° C. CO$_2$ incubator, was removed from the incubator. The medium was aspirated, and the cells were rinsed with 1 ml PBS. The solution was discarded, and 1 ml of 1.25% trypsin/ 0.02% EDTA was added to additionally rinse the cells. The trypsin/EDTA solution was removed with a vacuum pump, and the cells were incubated at 37° C. for 3 to 5 minutes. Cell morphology was examined under an inverted microscope until single cell suspension was clearly visible, then the cell was suspended with 3 ml of complete medium by gentle pipetting.

Upon suspension, cell numbers were counted with a hematometer, and cell density was adjusted to 100K/ml by adding appropriate volume of the complete medium. One hundred microliters (100 μl) of cell suspension was added to each well of a 96-well white plate to provided cell density of each of the wells to be 10K/well. The 96-well assay plate was placed in a 37° C. 5% CO$_2$ incubator for 24 hours.

At the end of the incubation, the plate was removed and test compound was added at various desired concentrations using a serial dilution. The plate was placed back into the 37° C. CO$_2$ incubator for 48 hours. After the incubation, 10 μl of 5 mg/ml 3-(4,5-dimethylthiazol-2-yl)-2,5-diphenyltetrazolium bromide (MTT) was added to each well, and the mixture was incubated in the 37° C. CO$_2$ incubator for 4 hours. One hundred microliters (100 μl) of testing solution (10% SDS+5% isobutyl alcohol+10 mmol/l HCl) was added directly to each well, and the mixture was incubated in the 37° C. 5% CO$_2$ incubator overnight. Absorbance at 580/680 nm was measured on SpectraMax Plus 384® (MDC).

C$^{13}$ Palmitate Assay

HCT-116 tumor cells (ATCC) were labeled for 24 hours in Dulbecco's minimum Eagle's medium supplemented with 0.5 g/liter [U-$^{13}$C]glucose (Cambridge Isotope Laboratories) and 2.0 g/liter unlabeled glucose (Sigma). Cells were concurrently treated with test compounds at 0.2% DMSO. After 24 hours, cells were harvested with trypsin/EDTA, counted by hemacytometer, washed with PBS, and centrifuged at 2000 rpm for 5 minutes. Pellets of 5M cells were stored at −80° C.

The cell pellet was saponified in strong base overnight at 70° C. The media was acidified and the palmitic acid extracted with hexanes. After drying the hexane layer, the palmitic acid was reconstituted in methanol that had been made slightly acidic. The palmitic acid was then monitored for C$^{13}$ incorporation via GCMS. Palmitic acid synthesis was deemed to have been halted if no C$^{13}$ was incorporated into the palmitate. Unhindered palmitate synthesis was determined by the amount of C$^{13}$ incorporated in absence of test compound.

Compounds provided herein were found to inhibit palmitate synthesis using this assay.

Pharmacokinetic Studies

Distribution Upon Oral Administration

Prior to the beginning of the tests, a study was conducted to determine if perfusion of the livers is necessary for an accurate quantification of levels of test compounds in the liver. If necessary, animals were perfused prior to liver collection. Additionally, a single dose 24-hour tolerability study was conducted on a few animals to verify that a given level of test compound is tolerated.

To the animals, single oral (PO) dose was administered at a volume of 10 ml/kg based on most recent body weight. Twenty milligrams per milliliter (20 mg/ml) of test compound in 0.5% Carboxymethylcellulose/5% DMSO/0.5% Tween was used. Vehicle control was also included.

At 0, 15, 30, 60, 120, 240, 360, 480 & 1440 minutes after dose administration, 3 animals from each group were anesthetized by carbon dioxide inhalation and euthanized by cardiac puncture. Blood was collected into lithium heparin vacutainers, placed on wet ice and centrifuged at 4° C. within 15 minutes of collection at 10,200 rpm for 5 minutes. Plasma was collected into a fresh eppendorf tube, frozen on dry ice and stored at −80° C. until PK analysis. Livers were harvested and bisected. Half of each tumor was snap-frozen in liquid nitrogen in pre-weighed Genogrinder tubes, placed on dry ice and stored at −80° C. until pharmacokinetic analysis, and the other half was snap-frozen in liquid nitrogen in pre-weighed Genogrinder tubes, placed on dry ice, and stored at −80° C. until PD analysis.

Inhibition of Human FASN

Scintillation Proximity Flashplate Assay and NADPH Consumption Assay

Compounds prepared following the above described synthetic methods are provided in Tables 1-4 below. Substituent abbreviations used in Tables 1-4 are given in Table 5. Compounds were assayed as inhibitors of human FASN using the above-described FASN Scintillation Proximity Flashplate Assay ($IC_{50}$; nM) or FASN NADPH Consumption Assay (*) ($IC_{50}$; nM). The corresponding activity of the isolated compound is also provided along with the measured mass ($ES^+$).

TABLE 1

| STRUCTURE | ACTIVITY | $(M + H)^+$ |
|---|---|---|
| 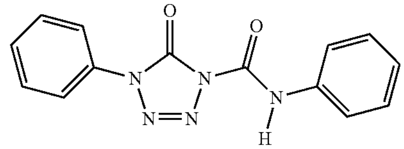 [SMILES: O=C(Nc1ccccc1)n1nnn(-c2ccccc2)c1=O] | E* | 282.1 |
| | B* | 384.1 |
| 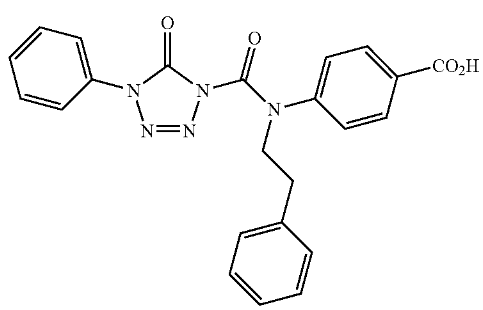 [SMILES: O=C(O)c1ccc(N(CCc2ccccc2)C(=O)n2nnn(-c3ccccc3)c2=O)cc1] | C* | 430.1 |
| | B* | 384.1 |
| 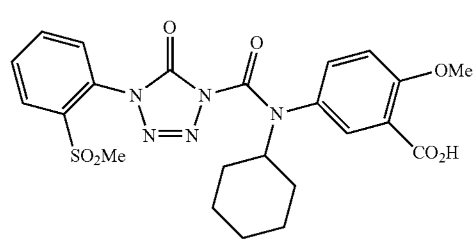 [SMILES: COc1ccc(N(C(=O)n2nnn(-c3ccccc3S(C)(=O)=O)c2=O)C2CCCCC2)cc1C(=O)O] | A | 560.2 |

TABLE 1-continued

| STRUCTURE | ACTIVITY | (M + H)+ |
|---|---|---|
| | C | 463.2 |
| | B* | 420.1 |
| 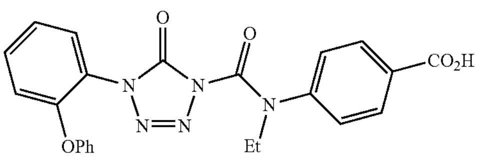 [SMILES: CCN(C(=O)n1nnn(-c2ccccc2Oc2ccccc2)c1=O)c1ccc(C(=O)O)cc1] | A | 446.1 |
| | B* | 450.2 |
| | B* | 404.1 |
| | C* | 414.1 |
| 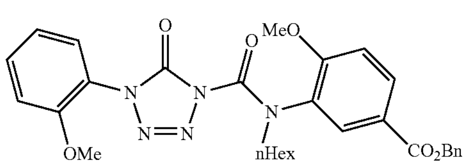 | D* | 560.2 |
| | B* | 384.1 |

TABLE 1-continued

| STRUCTURE | ACTIVITY | (M + H)+ |
|---|---|---|
| 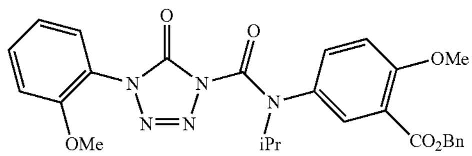 [SMILES: COc1ccc(N(C(=O)n2nnn(-c3ccccc3OC)c2=O)C(C)C)cc1C(=O)OCc1ccccc1] | A | 518.2 |
| | B* | 414.1 |
| 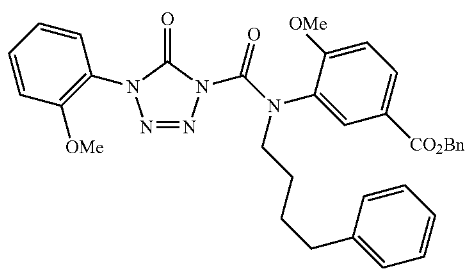 [SMILES: COc1ccc(C(=O)OCc2ccccc2)cc1N(CCCCc1ccccc1)C(=O)n1nnn(-c2ccccc2OC)c1=O] | D* | 608.2 |
| 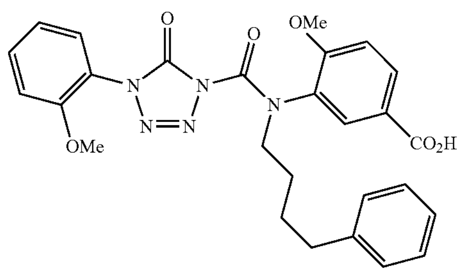 [SMILES: COc1ccc(C(=O)O)cc1N(CCCCc1ccccc1)C(=O)n1nnn(-c2ccccc2OC)c1=O] | C* | 518.2 |
| | B | 474.2 |
| | B* | 504.2 |
| | B* | 414.1 |

TABLE 1-continued

| STRUCTURE | ACTIVITY | (M + H)+ |
|---|---|---|
| | A | 504.2 |
| 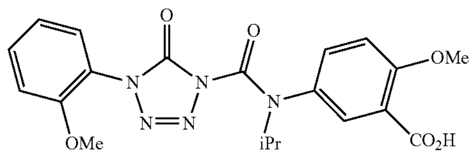 [SMILES: CCN(C(=O)n1nnn(-c2ccccc2OC)c1=O)c1ccc(OC)cc1] | D | 428.2 |
| | A | 504.2 |
| | C | 370.1 |
| 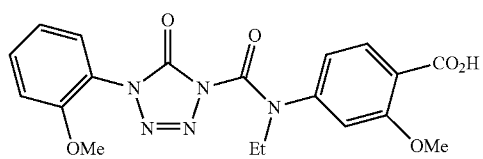 [SMILES: CCN(C(=O)n1nnn(-c2ccccc2OC)c1=O)c1ccc(C(=O)O)c(OC)c1] | B* | 414.1 |
| | C* | 414.1 |
| | A* | 432.1 |
| | C* | 442.2 |

TABLE 1-continued

| STRUCTURE | ACTIVITY | (M + H)+ |
|---|---|---|
| | C* | 470.2 |
| | A* | 418.1 |
| | C* | 504.2 |
| | A | 510.0 |
| 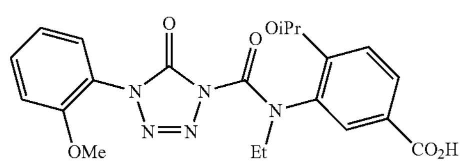 [SMILES: CCN(C(=O)n1nnn(-c2ccccc2OC)c1=O)c1cc(C(=O)O)ccc1OC(C)C] | D* | 442.2 |
| | A | 456.2 |
| | C* | 330.1 |

TABLE 1-continued

| STRUCTURE | ACTIVITY | (M + H)+ |
|---|---|---|
| [2-chlorophenyl-tetrazolone, N-phenyl-N-iPr carboxamide] | C* | 358.1 |
| [2-chlorophenyl-tetrazolone, N-(4-bromophenyl)-N-Me carboxamide] | B* | 408.0 |
| [2-chlorophenyl-tetrazolone, N-phenyl-N-allyl carboxamide] | B* | 356.1 |
| [2-chlorophenyl-tetrazolone, N-(3-fluorophenyl)-N-Me carboxamide] | C* | 348.1 |
| [2-chlorophenyl-tetrazolone, N-(4-(but-2-en-2-yl)phenyl)-N-Me carboxamide] | C* | 384.1 |
| [2-chlorophenyl-tetrazolone, N-(2-fluorophenyl)-N-Me carboxamide] | B* | 348.1 |
| [2-chlorophenyl-tetrazolone, N-phenyl-N-Et carboxamide] | B* | 344.1 |
| [2-bromophenyl-tetrazolone, N-phenyl-N-Me carboxamide] | C* | 374.0 |
| [2-fluorophenyl-tetrazolone, N-phenyl-N-Me carboxamide] | C* | 314.1 |

TABLE 1-continued

| STRUCTURE | ACTIVITY | (M + H)+ |
|---|---|---|
| 2,6-difluorophenyl tetrazolinone-C(O)-N(Et)-(2-F,4-NO2-phenyl) | B* | 409.1 |
| 2,6-difluorophenyl tetrazolinone-C(O)-N(Et)-(4-Br-phenyl) | A* | 424.0 |
| 2,6-difluorophenyl tetrazolinone-C(O)-N(CH2CH2OH)-phenyl | D* | 362.1 |
| 2,6-difluorophenyl tetrazolinone-C(O)-N(iPr)-(4-OMe,3-CO2H-phenyl) | A | 434.1 |
| 2,6-difluorophenyl tetrazolinone-C(O)-N(N(Me)2)-phenyl | B* | 360.1 |
| 2,6-difluorophenyl tetrazolinone-C(O)-N(Et)-(2,4-F-phenyl) | A | 382.1 |
| 2,6-difluorophenyl tetrazolinone-C(O)-N(Me)-(3-OMe-phenyl) | B* | 362.1 |
| 2,6-difluorophenyl tetrazolinone-C(O)-N(Et)-(3-OiPr,5-CO2H-phenyl) | B | 448.1 |

TABLE 1-continued

| STRUCTURE | ACTIVITY | (M + H)+ |
|---|---|---|
| [structure: 1-(2,6-difluorophenyl)-tetrazolinone with N-iPr, N-(2-methoxy-5-CO2Bn-phenyl) carboxamide] | A | 524.2 |
| [structure: 1-(2,6-difluorophenyl)-tetrazolinone with N,N-diphenyl carboxamide] | B* | 394.1 |
| [structure: 1-(2,6-difluorophenyl)-tetrazolinone with N-Et, N-(4-chlorophenyl) carboxamide] | B* | 380.1 |
| [structure: 1-(2,6-difluorophenyl)-tetrazolinone with N-Et, N-(3-fluoro-4-(NHC(=O)NHEt)phenyl) carboxamide] | A | 450.1 |
| [structure: 1-(2,6-difluorophenyl)-tetrazolinone with N-Me, N-(2-bromophenyl) carboxamide] | B* | 410.0 |
| [structure: 1-(2,6-difluorophenyl)-tetrazolinone with N-Et, N-(2-chloro-6-fluorophenyl) carboxamide] | B* | 398.1 |
| [structure: 1-(2,6-difluorophenyl)-tetrazolinone with N-Et, N-(2-fluoro-4-amino-phenyl) carboxamide] | A | 379.1 |

TABLE 1-continued

| STRUCTURE | ACTIVITY | (M + H)+ |
|---|---|---|
| | B* | 350.1 |
| | B* | 410.0 |
| | A* | 382.1 |
| | A | 421.1 |
| | A | 474.2 |
| | B* | 360.1 |
| | A* | 358.1 |

TABLE 1-continued

| STRUCTURE | ACTIVITY | (M + H)+ |
|---|---|---|
| | A* | 382.1 |
| | B* | 360.1 |
| 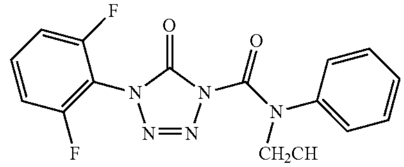 | C* | 357.1 |
| | B* | 480.1 |
| | A | 513.2 |
| | B* | 368.1 |
| | A | 510.2 |
| | B* | 360.1 |

TABLE 1-continued

| STRUCTURE | ACTIVITY | (M + H)+ |
|---|---|---|
| | A* | 346.1 |
| | B* | 396.1 |
| | B* | 391.1 |
| | B* | 332.1 |
| | B* | 444.2 |
| | A* | 494.2 |
| | B* | 510.2 |
| | A | 382.1 |

TABLE 1-continued

| STRUCTURE | ACTIVITY | (M + H)+ |
|---|---|---|
| | A* | 390.1 |
| | B* | 524.2 |
| | A* | 449.2 |
| | B* | 464.1 |
| | B* | 510.2 |
| | A* | 535.1 |

TABLE 1-continued

| STRUCTURE | ACTIVITY | (M + H)+ |
|---|---|---|
| [structure: 1-(2,6-difluorophenyl)-5-oxo-tetrazole-N-methyl-N-(4-bromophenyl)carboxamide] | B* | 410.0 |
| [structure: 1-(2,6-difluorophenyl)-5-oxo-tetrazole-N-isopropyl-N-phenylcarboxamide] | B* | 360.1 |
| [structure: 1-(2,6-difluorophenyl)-5-oxo-tetrazole-N-methyl-N-(3-fluorophenyl)carboxamide] | B* | 350.1 |
| [structure: 1-(2,6-difluorophenyl)-5-oxo-tetrazole-N-ethyl-N-aryl carboxamide with biotin tag] | A | 718.3 |
| [structure: 1-(2,6-difluorophenyl)-5-oxo-tetrazole-N-methyl-N-(2-trifluoromethylphenyl)carboxamide] | B* | 400.1 |
| [structure: 1-(2,6-difluorophenyl)-5-oxo-tetrazole-N-ethyl-N-(2-fluoro-4-(tBu-ethynyl)phenyl)carboxamide] | B* | 444.2 |
| [structure: 1-(2,6-difluorophenyl)-5-oxo-tetrazole-N-ethyl-N-(2,4-dichlorophenyl)carboxamide] | B* | 414.0 |

TABLE 1-continued

| STRUCTURE | ACTIVITY | (M + H)+ |
|---|---|---|
| | B* | 350.1 |
| | A | 462.2 |
| | B* | 468.2 |
| | B* | 430.1 |
| | A | 364.1 |
| 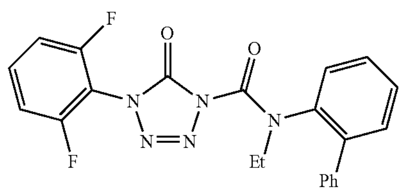 [SMILES: CCN(C(=O)n1nnn(-c2c(F)cccc2F)c1=O)c1ccccc1-c1ccccc1] | D* | 422.1 |
| 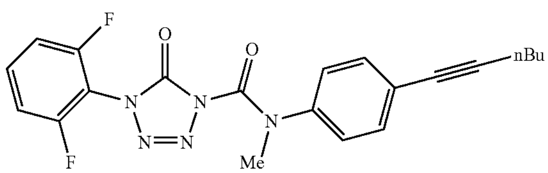 | C* | 412.2 |
| | B* | 432.1 |

TABLE 1-continued

| STRUCTURE | ACTIVITY | (M + H)⁺ |
|---|---|---|
| [structure: 1-(2,6-difluorophenyl)-5-oxo-tetrazole-N-Et-N-(2-fluoro-4-NHSO₂Me-phenyl)carboxamide] | A | 457.1 |
| [structure: 1-(2,6-difluorophenyl)-5-oxo-tetrazole-N-(3-phenylpropyl)-N-(2-MeO-5-CO₂Bn-phenyl)carboxamide] | A | 600.2 |
| [structure: 1-(2,6-difluorophenyl)-5-oxo-tetrazole-N-Et-N-(3-Me-phenyl)carboxamide] | A* | 360.1 |
| [structure: 1-(2,6-difluorophenyl)-5-oxo-tetrazole-N-N(Me)₂-N-(4-CO₂Et-phenyl)carboxamide] | B* | 433.1 |
| [structure: 1-(2,6-difluorophenyl)-5-oxo-tetrazole-N-Me-N-(2-MeO-phenyl)carboxamide] | C* | 362.1 |
| [structure: 1-(2,6-difluorophenyl)-5-oxo-tetrazole-N-Et-N-(3-PhO-4-CO₂H-phenyl)carboxamide] | A | 482.1 |
| [structure: 1-(2,6-difluorophenyl)-5-oxo-tetrazole-N-Et-N-(2-PhO-phenyl)carboxamide] | A | 438.1 |

TABLE 1-continued

| STRUCTURE | ACTIVITY | (M + H)+ |
|---|---|---|
| | B* | 484.2 |
| | B | 420.1 |
| | A* | 391.1 |
| | B* | 442.0 |
| | A | 420.1 |
| | A* | 366.0 |
| | A | 400.2 |

TABLE 1-continued

| STRUCTURE | ACTIVITY | (M + H)+ |
|---|---|---|
| | A | 599.2 |
| | A | 600.2 |
| | A | 596.2 |
| | A | 686.2 |
| | A | 573.2 |

TABLE 1-continued
| STRUCTURE | ACTIVITY | (M + H)+ |
|---|---|---|
| 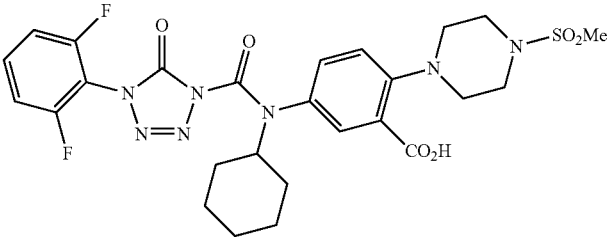 [SMILES: CS(=O)(=O)N1CCN(c2ccc(N(C(=O)n3nnn(-c4c(F)cccc4F)c3=O)C3CCCCC3)cc2C(=O)O)CC1] | A | 606.2 |
| 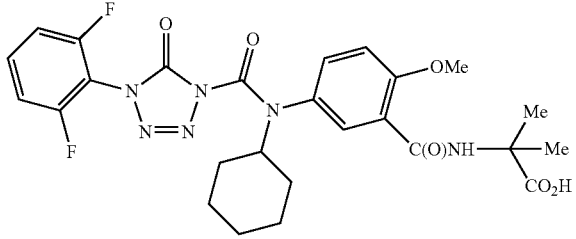 | A | 559.2 |
| 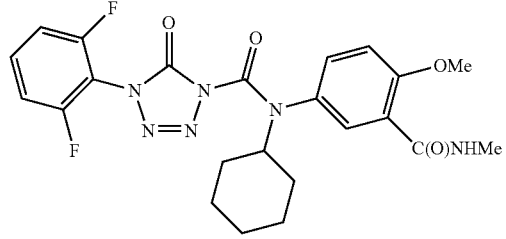 | A | 487.2 |
| 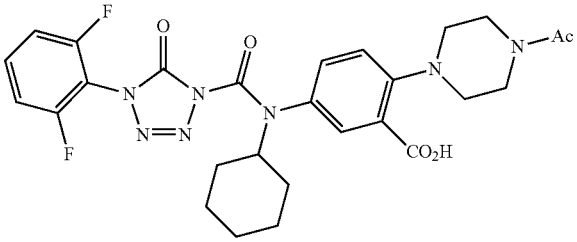 [SMILES: CC(=O)N1CCN(c2ccc(N(C(=O)n3nnn(-c4c(F)cccc4F)c3=O)C3CCCCC3)cc2C(=O)O)CC1] | A | 570.2 |
| 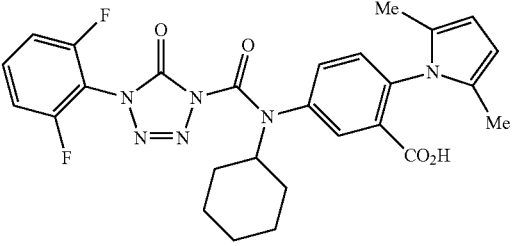 [SMILES: Cc1ccc(C)n1-c1ccc(N(C(=O)n2nnn(-c3c(F)cccc3F)c2=O)C2CCCCC2)cc1C(=O)O] | A | 537.2 |
| 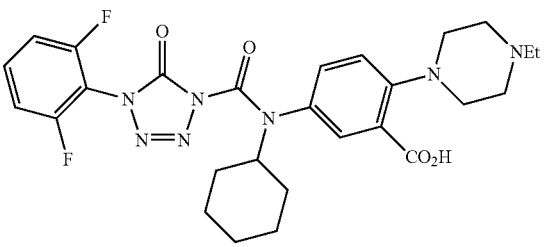 | B | 556.2 |

TABLE 1-continued

| STRUCTURE | ACTIVITY | (M + H)+ |
|---|---|---|
| | A | 488.2 |
| | A | 518.2 |
| | A | 501.2 |
| | A | 473.2 |
| | A | 628.3 |
| | A | 718.3 |

TABLE 1-continued

| STRUCTURE | ACTIVITY | (M + H)+ |
|---|---|---|
| 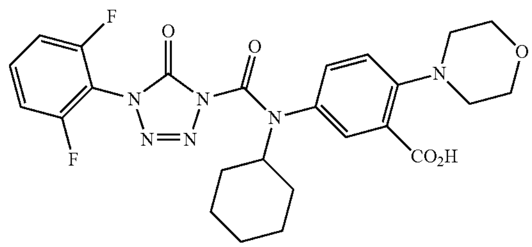 [SMILES: O=C(O)c1cc(N(C(=O)n2nnn(-c3c(F)cccc3F)c2=O)C2CCCCC2)ccc1N1CCOCC1] | B | 529.2 |
| | A | 504.2 |
| | A | 487.2 |
| | A | 490.1 |
| | A | 486.2 |
| | A | 639.2 |

TABLE 1-continued

| STRUCTURE | ACTIVITY | (M + H)+ |
|---|---|---|
| 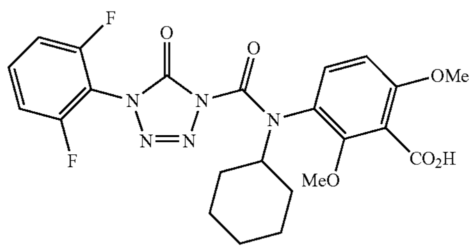 [SMILES: COc1ccc(N(C(=O)n2nnn(-c3c(F)cccc3F)c2=O)C2CCCCC2)c(OC)c1C(=O)O] | B | 504.2 |
| | A | 548.2 |
| | A | 594.2 |
| | A | 360.1 |
| | A | 638.2 |
| | A | 459.2 |

TABLE 1-continued
| STRUCTURE | ACTIVITY | (M + H)+ |
|---|---|---|
| 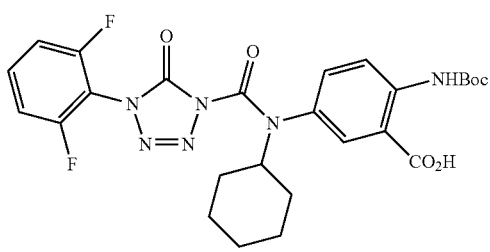 [SMILES: CC(C)(C)OC(=O)Nc1ccc(N(C(=O)n2nnn(-c3c(F)cccc3F)c2=O)C2CCCCC2)cc1C(=O)O] | A | 559.2 |
| 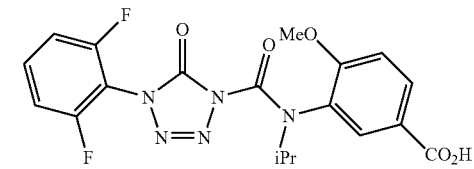 [SMILES: COc1ccc(C(=O)O)cc1N(C(=O)n1nnn(-c2c(F)cccc2F)c1=O)C(C)C] | A | 391.1 |
| 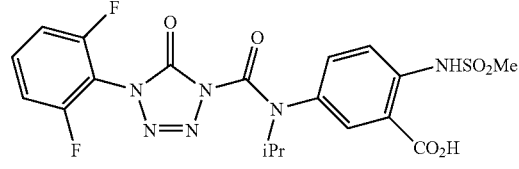 | A | 454.0 |
| 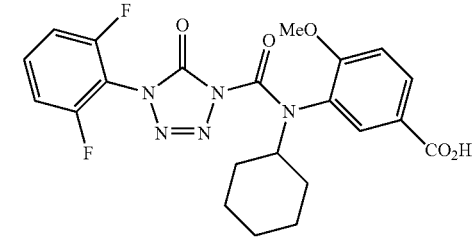 [SMILES: COc1ccc(C(=O)O)cc1N(C(=O)n1nnn(-c2c(F)cccc2F)c1=O)C1CCCCC1] | A | 474.2 |
| 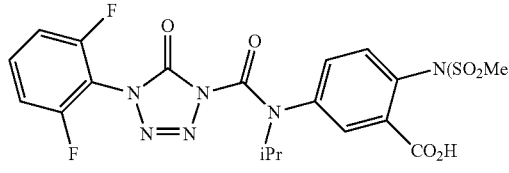 | A | 532.0 |
| 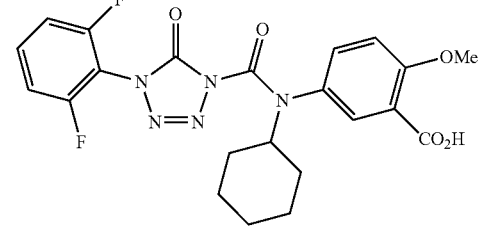 | A | 474.2 |
| 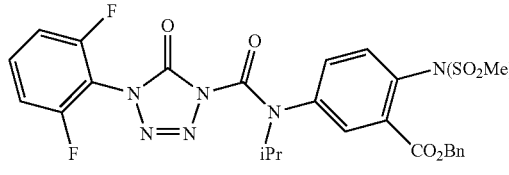 | A | 622.1 |

TABLE 1-continued

| STRUCTURE | ACTIVITY | (M + H)+ |
|---|---|---|
| (2,6-difluorophenyl-tetrazolone)-C(O)-N(cyclohexyl)-(4-CO2H, 3-OH phenyl) | A | 460.1 |
| (2,6-difluorophenyl-tetrazolone)-C(O)-N(iPr)-(4-NH2, 3-CO2H phenyl) | A | 376.1 |
| (2,6-difluorophenyl-tetrazolone)-C(O)-N(iPr)-(3-CO2H phenyl) | B | 361.1 |
| (2,6-difluorophenyl-tetrazolone)-C(O)-N(iPr)-(4-NH2, 3-CO2Bn phenyl) | A | 466.1 |
| (2,6-difluorophenyl-tetrazolone)-C(O)-N(iPr)-(4-NHBoc, 3-CO2H phenyl) | A | 476.1 |
| (2,6-difluorophenyl-tetrazolone)-C(O)-N(cyclohexyl)-(4-OH, 3-CO2H phenyl) | A | 460.1 |
| (2,6-difluorophenyl-tetrazolone)-C(O)-N(iPr)-(4-NHBoc, 3-CO2Bn phenyl) | A | 566.2 |

TABLE 1-continued

| STRUCTURE | ACTIVITY | (M + H)+ |
|---|---|---|
| | A | 467.1 |
| | A | 379.0 |
| | A | 391.1 |
| | A | 543.1 |
| 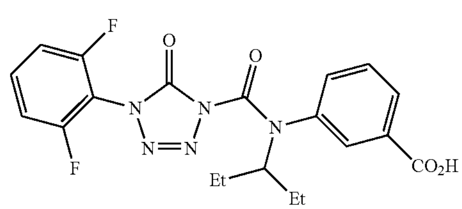 [SMILES: CCC(CC)N(C(=O)n1nnn(-c2c(F)cccc2F)c1=O)c1cccc(C(=O)O)c1] | B | 432.1 |
| | A | 469.1 |
| | A | 395.0 |

TABLE 1-continued

| STRUCTURE | ACTIVITY | (M + H)+ |
|---|---|---|
| | A | 522.2 |
| | A | 443.1 |
| | A | 474.2 |
| | A | 391.1 |
| | A | 485.1 |
| 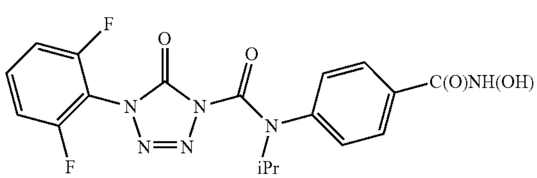 | B | 376.1 |
| | A | 533.2 |

TABLE 1-continued
| STRUCTURE | ACTIVITY | (M + H)+ |
|---|---|---|
| 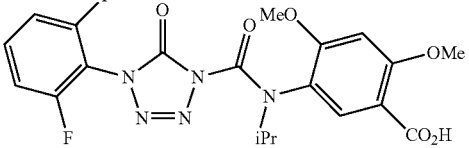 | B | 421.1 |
| 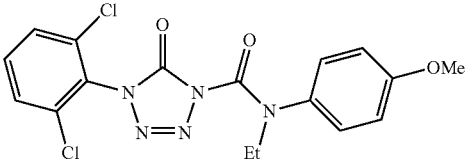 [SMILES: CCN(C(=O)n1nnn(-c2c(Cl)cccc2Cl)c1=O)c1ccc(OC)cc1] | B | 408.1 |
| 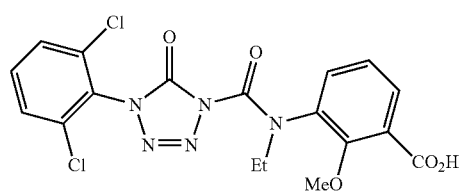 [SMILES: CCN(C(=O)n1nnn(-c2c(Cl)cccc2Cl)c1=O)c1cccc(C(=O)O)c1OC] | D* | 452.0 |
| 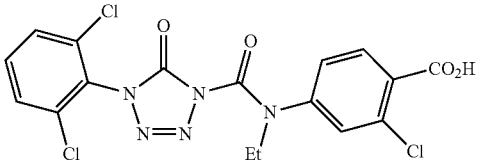 [SMILES: CCN(C(=O)n1nnn(-c2c(Cl)cccc2Cl)c1=O)c1ccc(C(=O)O)c(Cl)c1] | A | 456 |
| 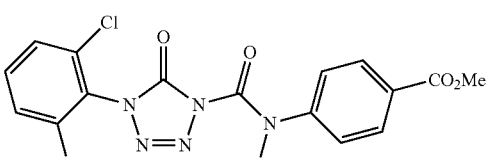 | B | 436.1 |
| 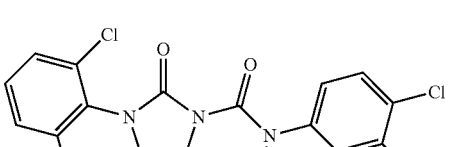 | A | 576.1 |
| 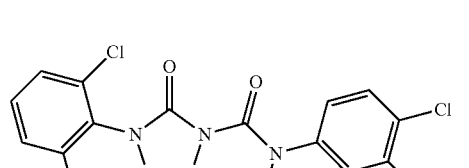 | B* | 456.0 |
| 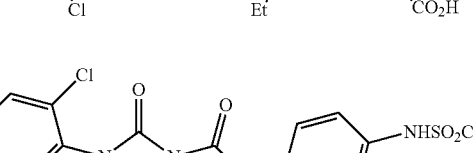 | B* | 525.0 |

TABLE 1-continued

| STRUCTURE | ACTIVITY | (M + H)+ |
|---|---|---|
| | B* | 546.0 |
| | B* | 576.1 |
| | B* | 396.0 |
| 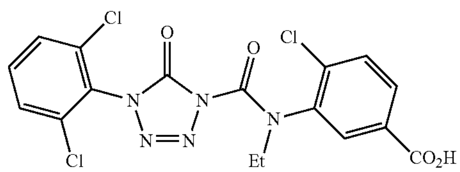 [SMILES: CCN(C(=O)n1nnn(-c2c(Cl)cccc2Cl)c1=O)c1cc(C(=O)O)ccc1Cl] | A* | 456.0 |
| 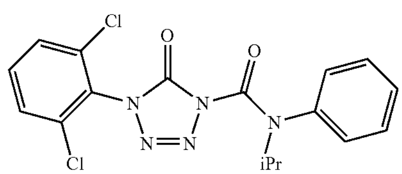 [SMILES: CC(C)N(C(=O)n1nnn(-c2c(Cl)cccc2Cl)c1=O)c1ccccc1] | C* | 349.0 |
| | B* | 403.0 |
| | B* | 452.0 |
| | B* | 546.0 |

TABLE 1-continued

| STRUCTURE | ACTIVITY | (M + H)+ |
|---|---|---|
| 2,6-dichlorophenyl-tetrazolinone-C(O)-N(Et)-(4-C(=O)NHSO₂Ph-phenyl) | B* | 561.0 |
| 2,6-dichlorophenyl-tetrazolinone-C(O)-N(Et)-(2-Cl-4-CO₂H-phenyl) | A | 456.0 |
| 2,6-dichlorophenyl-tetrazolinone-C(O)-N(Et)-(3-NH₂-phenyl) | B* | 393.1 |
| 2,6-dichlorophenyl-tetrazolinone-C(O)-N(Et)-(4-NO₂-phenyl) | B* | 423.0 |
| 2,6-dichlorophenyl-tetrazolinone-C(O)-N(Et)-(3-NO₂-phenyl) | B* | 423.0 |
| 2,6-dichlorophenyl-tetrazolinone-C(O)-N(Et)-(3-CO₂H-phenyl) | B | 422.0 |
| 2,6-dichlorophenyl-tetrazolinone-C(O)-N((CH₂)₃NHSO₂CH₃)-(4-CO₂H-phenyl) | D* | 529.0 |
| 2,6-dichlorophenyl-tetrazolinone-C(O)-N(Et)-(2-OMe-4-CO₂Bn-phenyl) | B* | 542.1 |

TABLE 1-continued
| STRUCTURE | ACTIVITY | (M + H)+ |
|---|---|---|
| 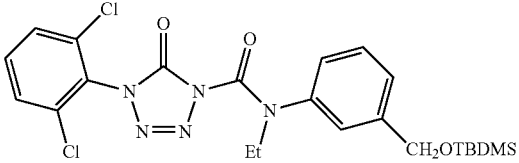 | B* | 522.1 |
| 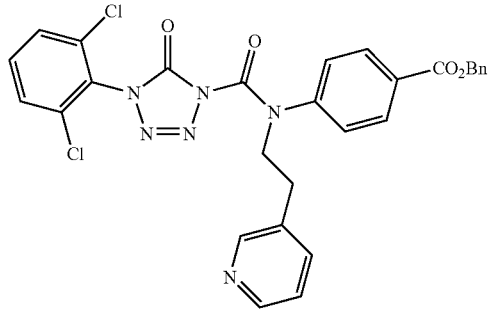 [SMILES: O=C(OCc1ccccc1)c1ccc(N(CCc2cccnc2)C(=O)n2nnn(-c3c(Cl)cccc3Cl)c2=O)cc1] | C* | 589.1 |
| 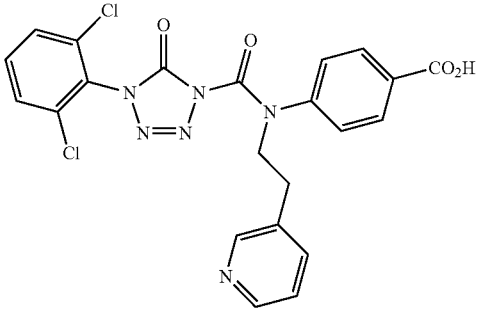 [SMILES: O=C(O)c1ccc(N(CCc2cccnc2)C(=O)n2nnn(-c3c(Cl)cccc3Cl)c2=O)cc1] | D* | 499.1 |
| 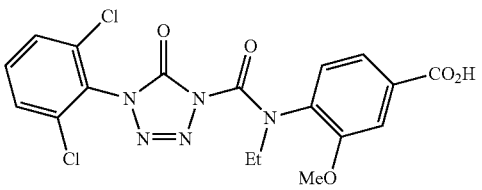 [SMILES: CCN(C(=O)n1nnn(-c2c(Cl)cccc2Cl)c1=O)c1ccc(C(=O)O)cc1OC] | B* | 452.0 |
| 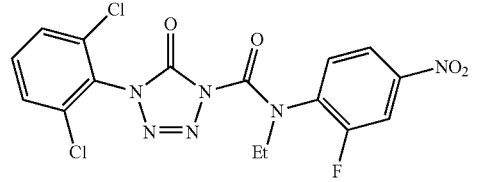 [SMILES: CCN(C(=O)n1nnn(-c2c(Cl)cccc2Cl)c1=O)c1ccc([N+](=O)[O-])cc1F] | C* | 441.0 |
| 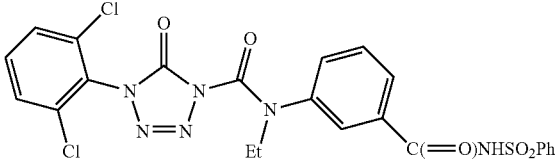 | A* | 561.0 |

TABLE 1-continued

| STRUCTURE | ACTIVITY | (M + H)+ |
|---|---|---|
| | C* | 408.1 |
| | B* | 393.1 |
| | C* | 378.0 |
| 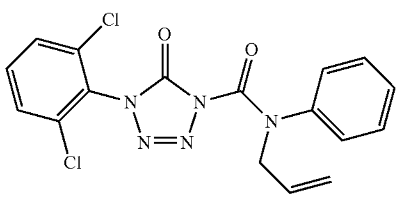 [SMILES: C=CCN(C(=O)n1nnn(-c2c(Cl)cccc2Cl)c1=O)c1ccccc1] | D* | 390.0 |
| | B* | 576.1 |
| | B* | 364.0 |
| 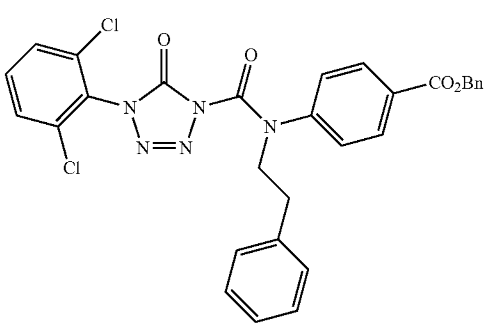 [SMILES: O=C(OCc1ccccc1)c1ccc(N(CCc2ccccc2)C(=O)n2nnn(-c3c(Cl)cccc3Cl)c2=O)cc1] | E* | 588.1 |

TABLE 1-continued

| STRUCTURE | ACTIVITY | (M + H)+ |
|---|---|---|
| | A | 422.0 |
| | B* | 525.0 |
| | C* | 444.1 |
| | C* | 534.2 |
| | B | 450.2 |
| | A | 430.1 |
| | A | 472.2 |
| | B | 432.1 |

TABLE 1-continued

| STRUCTURE | ACTIVITY | (M + H)+ |
|---|---|---|
| | A | 562.2 |
| | B | 412.2 |
| | A | 478.2 |
| | B | 432.1 |
| | A | 656.2 |
| 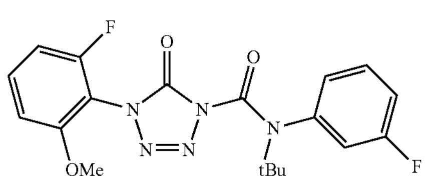 [SMILES: COc1cccc(F)c1-n1nnn(C(=O)N(c2cccc(F)c2)C(C)(C)C)c1=O] | D | 404.2 |
| | A | 486.2 |

TABLE 1-continued

| STRUCTURE | ACTIVITY | (M + H)+ |
|---|---|---|
| | B | 416.1 |
| | A* | 522.2 |
| | B | 536.2 |
| | A | 446.1 |
| 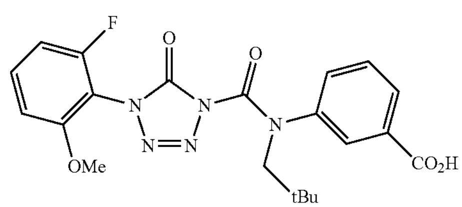 [SMILES: COc1cccc(F)c1-n1nnn(C(=O)N(CC(C)(C)C)c2cccc(C(=O)O)c2)c1=O] | D | 444.2 |
| | A | 398.2 |
| | B | 536.2 |
| | B | 460.2 |

TABLE 1-continued

| STRUCTURE | ACTIVITY | (M + H)+ |
|---|---|---|
| [structure: 1-(2-fluoro-6-methoxyphenyl)-tetrazolone with N-ethyl-N-(2-methyl-5-(4-benzyloxycarbonylphenoxy)phenyl)carboxamide] | D | 598.2 |
| [structure: 1-(2-fluoro-6-methoxyphenyl)-tetrazolone with N-ethyl-N-(3-(3-carboxyphenoxy)phenyl)carboxamide] | A | 494.1 |
| [structure: 1-(2-fluoro-6-methoxyphenyl)-tetrazolone with N-cyclopropyl-N-(3-carboxyphenyl)carboxamide] | B* | 414.1 |
| [structure: 1-(2-fluoro-6-methoxyphenyl)-tetrazolone with N-tBu-N-(3-carboxyphenyl)carboxamide] | D | 430.1 |
| [structure: 1-(2-fluoro-6-methoxyphenyl)-tetrazolone with N-ethyl-N-(2-methyl-5-(4-carboxyphenoxy)phenyl)carboxamide] | B | 508.2 |
| [structure: 1-(2-fluoro-6-methoxyphenyl)-tetrazolone with N-iPr-N-(4-methoxy-3-benzyloxycarbonylphenyl)carboxamide] | A | 536.2 |
| [structure: 1-(2-fluoro-6-methoxyphenyl)-tetrazolone with N-iPr-N-(4-methoxy-3-carboxyphenyl)carboxamide] | B | 446.1 |

TABLE 1-continued

| STRUCTURE | ACTIVITY | (M + H)+ |
|---|---|---|
| | A | 504.2 |
| 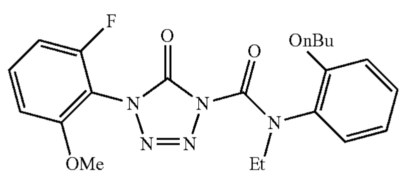 | C* | 430.2 |
| | A | 522.2 |
| | B | 414.2 |
| | A | 474.2 |
| | B | 534.2 |
| 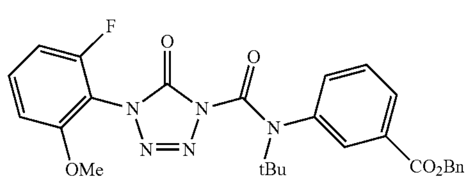 | D | 520.2 |

TABLE 1-continued

| STRUCTURE | ACTIVITY | (M + H)⁺ |
|---|---|---|
| | A | 358.1 |
| 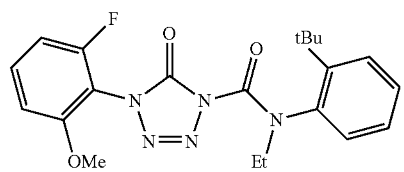 [SMILES: CCN(C(=O)n1nnn(-c2c(F)cccc2OC)c1=O)c1ccccc1C(C)(C)C] | D* | 414.2 |
| | A | 520.2 |
| | A | 487.2 |
| | A | 486.2 |
| 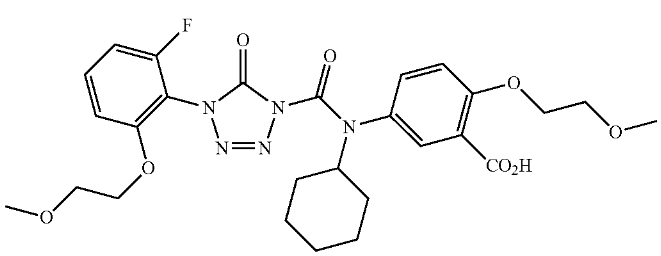 | B | 574.2 |
| | A | 530.2 |

TABLE 1-continued

| STRUCTURE | ACTIVITY | (M + H)+ |
|---|---|---|
| | A | 560.2 |
| | A | 514.2 |
| | B | 514.2 |
| | B | 604.3 |
| | B | 550.2 |
| 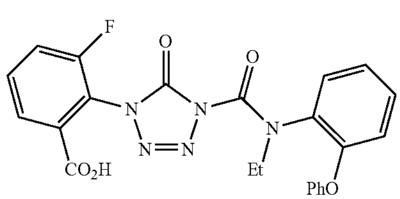 [SMILES: CCN(C(=O)n1nnn(-c2c(F)cccc2C(=O)O)c1=O)c1ccccc1Oc1ccccc1] | D* | 464.1 |

TABLE 1-continued
| STRUCTURE | ACTIVITY | (M + H)+ |
|---|---|---|
| 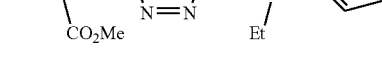 | B* | 386.1 |
| 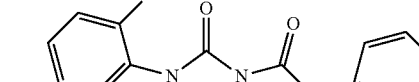 | D | 533.2 |
| 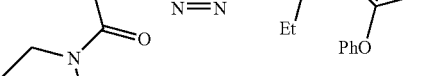 | A | 619.2 |
|  | D | 529.2 |
| 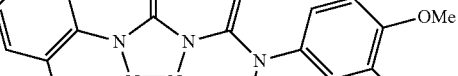 | A | 617.2 |
|  | B | 527.2 |

TABLE 1-continued

| STRUCTURE | ACTIVITY | (M + H)+ |
|---|---|---|
| 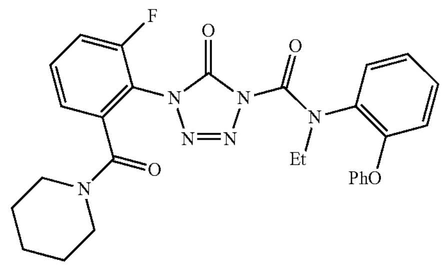 [SMILES: CCN(C(=O)n1nnn(-c2c(F)cccc2C(=O)N2CCCCC2)c1=O)c1ccccc1Oc1ccccc1] | C | 531.2 |
| | A | 461.2 |
| | B | 553.2 |
| | A | 563.2 |
| | A | 653.2 |
| | A | 539.2 |
| | B | 549.2 |

TABLE 1-continued

| STRUCTURE | ACTIVITY | (M + H)+ |
|---|---|---|
| 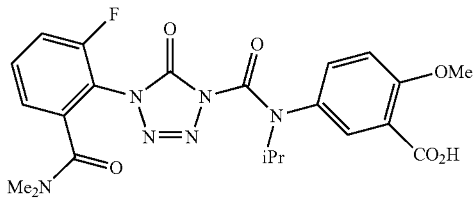 [SMILES: COc1ccc(N(C(=O)n2nnn(-c3c(F)cccc3C(=O)N(C)C)c2=O)C(C)C)cc1C(=O)O] | D | 487.2 |
| 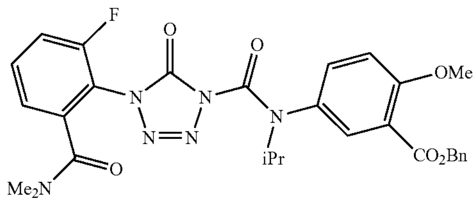 [SMILES: COc1ccc(N(C(=O)n2nnn(-c3c(F)cccc3C(=O)N(C)C)c2=O)C(C)C)cc1C(=O)OCc1ccccc1] | A | 577.2 |
| | B* | 428.1 |
| | B* | 442.2 |
| | B* | 432.2 |

TABLE 1-continued

| STRUCTURE | ACTIVITY | (M + H)+ |
|---|---|---|
| | B* | 446.2 |
| | B | 541.2 |
| | B* | 406.0 |
| | B* | 424.0 |
| 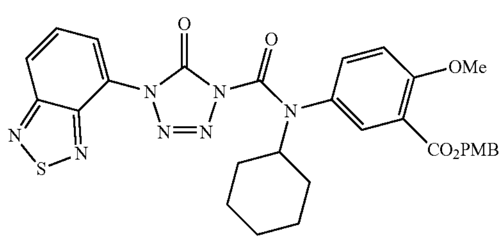 | A | 616.2 |
| | B | 496.1 |

TABLE 1-continued

| STRUCTURE | ACTIVITY | (M + H)+ |
|---|---|---|
| 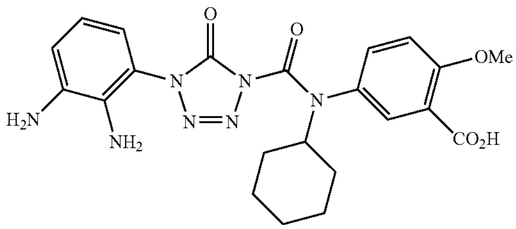 [SMILES: COc1ccc(N(C(=O)n2nnn(-c3cccc(N)c3N)c2=O)C2CCCCC2)cc1C(=O)O] | B | 468.2 |
| | C | 478.2 |
| | D* | 331.1 |
| | C* | 333.1 |
| 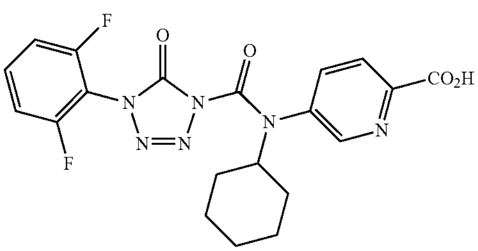 [SMILES: O=C(O)c1ccc(N(C(=O)n2nnn(-c3c(F)cccc3F)c2=O)C2CCCCC2)cn1] | A | 445.1 |
| | D* | 344.1 |
| 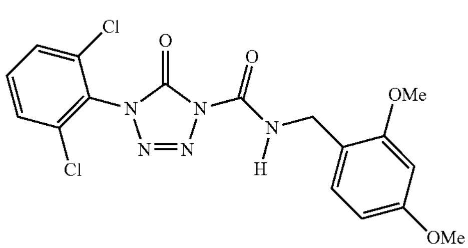 [SMILES: COc1ccc(CNC(=O)n2nnn(-c3c(Cl)cccc3Cl)c2=O)c(OC)c1] | E* | 424.1 |

TABLE 1-continued

| STRUCTURE | ACTIVITY | (M + H)+ |
|---|---|---|
| 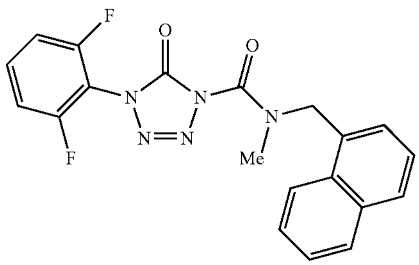 [SMILES: CN(Cc1cccc2ccccc12)C(=O)n1nnn(-c2c(F)cccc2F)c1=O] | C | 396.1 |
| 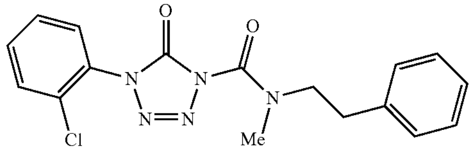 [SMILES: CN(CCc1ccccc1)C(=O)n1nnn(-c2ccccc2Cl)c1=O] | E* | 358.1 |
| | A | 496.1 |
| | A | 508.2 |
| | A | 536.2 |

TABLE 1-continued

| STRUCTURE | ACTIVITY | (M + H)+ |
|---|---|---|
| *[structure]* | A | 522.2 |
| *[structure]* | A | 566.2 |
| *[structure]* | A | 552.2 |
| *[structure]* | A | 448.12 |

TABLE 2

| STRUCTURE | ACTIVITY | (M + H)+ |
|---|---|---|
| *[structure]* | D* | 443.1 |

TABLE 2-continued

| STRUCTURE | ACTIVITY | (M + H)⁺ |
|---|---|---|
| | E* | 443.1 |
| | E* | 328.0 |
| | E* | 385.1 |
| | E* | 385.1 |
| | E* | 399.1 |
| | E* | 385.1 |
| 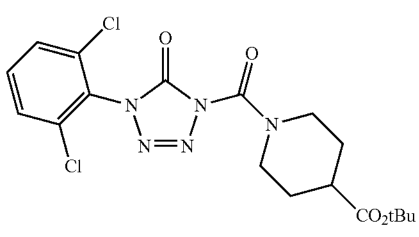 [SMILES: CC(C)(C)OC(=O)C1CCN(C(=O)n2nnn(-c3c(Cl)cccc3Cl)c2=O)CC1] | D* | 442.1 |
| | E* | 439.1 |

TABLE 2-continued
| STRUCTURE | ACTIVITY | (M + H)+ |
|---|---|---|
| 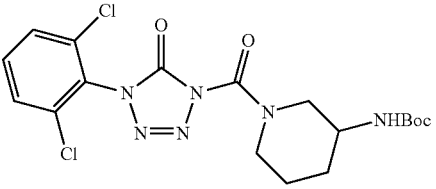 [SMILES: CC(C)(C)OC(=O)NC1CCCN(C(=O)n2nnn(-c3c(Cl)cccc3Cl)c2=O)C1] | D* | 457.1 |
| 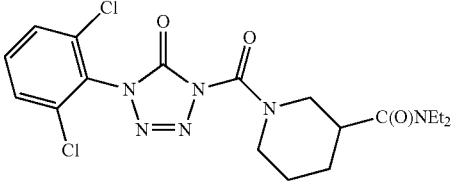 | D* | 441.1 |
| 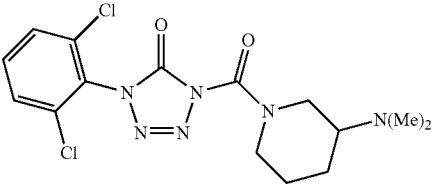 | D* | 385.1 |
| 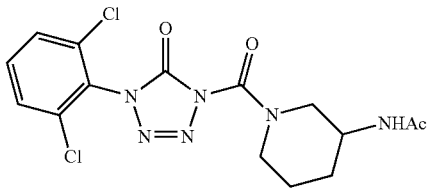 [SMILES: CC(=O)NC1CCCN(C(=O)n2nnn(-c3c(Cl)cccc3Cl)c2=O)C1] | E* | 399.1 |
| 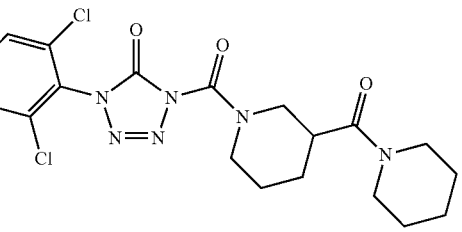 | D* | 453.1 |
| 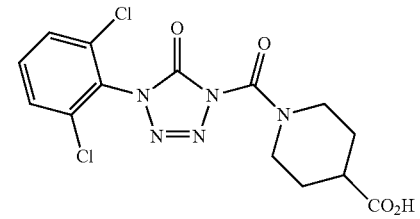 [SMILES: O=C(O)C1CCN(C(=O)n2nnn(-c3c(Cl)cccc3Cl)c2=O)CC1] | E* | 386.0 |
| 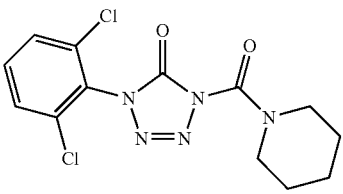 [SMILES: O=C(N1CCCCC1)n1nnn(-c2c(Cl)cccc2Cl)c1=O] | D* | 342.0 |

TABLE 2-continued

| STRUCTURE | ACTIVITY | (M + H)+ |
|---|---|---|
| (2,6-dichlorophenyl tetrazolinone piperidine-NHSO₂Me) | E* | 435.0 |
| (2,6-dichlorophenyl tetrazolinone piperidine-NHC(=O)NHEt) | E* | 428.1 |
| (2-chlorophenyl tetrazolinone morpholine) | E* | 310.1 |
| (2-F,6-(2-methylphenylethynyl)phenyl tetrazolinone decahydroquinoline) | B* | 460.2 |
| (2-Br,6-F-phenyl tetrazolinone decahydroquinoline) | B* | 424.1 |
| (2,6-difluorophenyl tetrazolinone decahydroquinoline) | B* | 364.2 |
| (2-OPh-phenyl tetrazolinone decahydroquinoline) | C* | 420.2 |

TABLE 2-continued

| STRUCTURE | ACTIVITY | (M + H)+ |
|---|---|---|
| (2,6-dichlorophenyl-tetrazolone-carbonyl-decahydroquinoline) | C* | 396.1 |
| (2,6-difluorophenyl-tetrazolone-carbonyl-decahydroquinoline with Ph, OH substituents) | D* | 456.2 |
| (2,6-difluorophenyl-tetrazolone-carbonyl-decahydroquinoline with Me and ketone) | D* | 392.2 |
| (2,6-difluorophenyl-tetrazolone-carbonyl-tetrahydroisoquinoline) | C* | 358.1 |
| (2,6-difluorophenyl-tetrazolone-carbonyl-benzo-fused isoquinoline) | B | 394.1 |
| (phenyl-tetrazolone-carbonyl-tetrahydroquinoline-CO2H) | B* | 366.1 |
| (2-phenoxyphenyl-tetrazolone-carbonyl-tetrahydroquinoline) | B* | 414.2 |

TABLE 2-continued

| STRUCTURE | ACTIVITY | (M + H)+ |
|---|---|---|
| 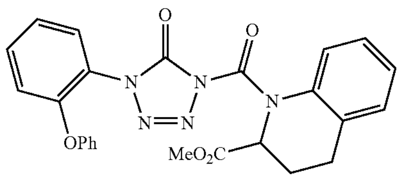 [SMILES: COC(=O)C1CCc2ccccc2N1C(=O)n1nnn(-c2ccccc2Oc2ccccc2)c1=O] | C* | 472.2 |
| | B* | 372.1 |
| 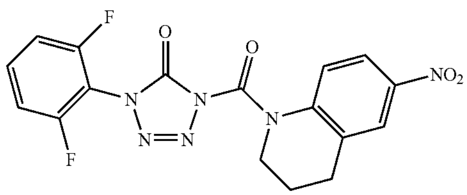 [SMILES: O=C(N1CCCc2cc([N+](=O)[O-])ccc21)n1nnn(-c2c(F)cccc2F)c1=O] | D* | 403.1 |
| | B* | 388.1 |
| | B* | 372.1 |
| | B* | 358.1 |
| | B* | 473.2 |
| | B* | 436.0 |

TABLE 2-continued

| STRUCTURE | ACTIVITY | (M + H)+ |
|---|---|---|
| [structure] | B* | 401.1 |
| [structure] | A | 376.1 |
| [structure] | B* | 373.1 |
| [structure] | B* | 401.1 |
| [structure] | B* | 416.1 |
| [structure] | B* | 372.1 |
| [structure] | B* | 473.2 |

TABLE 2-continued
| STRUCTURE | ACTIVITY | (M + H)+ |
|---|---|---|
| 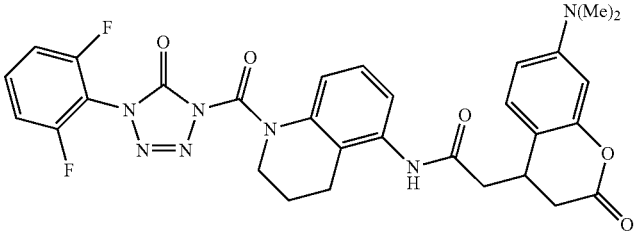 | B | 604.2 |
| 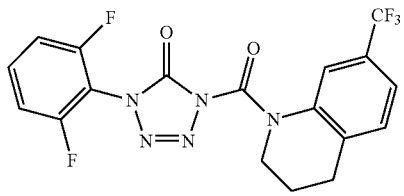 [SMILES: O=C(N1CCCc2ccc(C(F)(F)F)cc21)n1nnn(-c2c(F)cccc2F)c1=O] | C* | 426.1 |
| 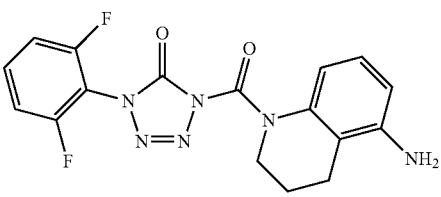 [SMILES: Nc1cccc2c1CCCN2C(=O)n1nnn(-c2c(F)cccc2F)c1=O] | B* | 373.1 |
| 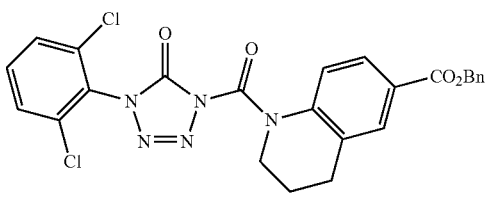 [SMILES: O=C(OCc1ccccc1)c1ccc2c(c1)CCCN2C(=O)n1nnn(-c2c(Cl)cccc2Cl)c1=O] | D* | 524.1 |
| 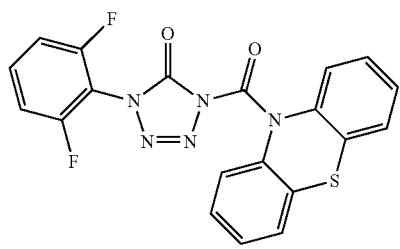 [SMILES: O=C(N1c2ccccc2Sc2ccccc21)n1nnn(-c2c(F)cccc2F)c1=O] | A* | 424.1 |
| 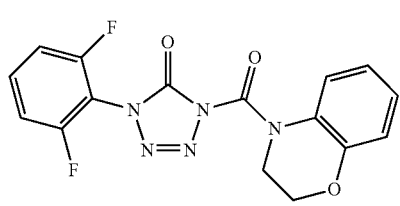 [SMILES: O=C(N1CCOc2ccccc21)n1nnn(-c2c(F)cccc2F)c1=O] | D* | 360.1 |
| 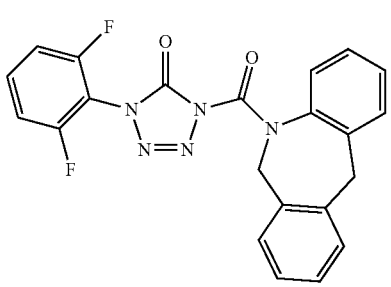 [SMILES: O=C(N1Cc2ccccc2Cc2ccccc21)n1nnn(-c2c(F)cccc2F)c1=O] | B* | 420.1 |

TABLE 2-continued

| STRUCTURE | ACTIVITY | (M + H)+ |
|---|---|---|
| (2,6-difluorophenyl tetrazolinone, 2,3,4,5-tetrahydro-1H-benzo[b]azepine carbonyl) | B* | 372.1 |
| (2-fluoro-6-(o-tolylethynyl)phenyl tetrazolinone, benzazepine carbonyl) | B* | 468.2 |
| (2-fluoro-6-(2-(o-tolyl)ethyl)phenyl tetrazolinone, benzazepine carbonyl) | B* | 472.2 |
| (2-bromo-6-fluorophenyl tetrazolinone, benzazepine carbonyl) | C* | 432.0 |
| (2-bromo-6-fluorophenyl tetrazolinone, indoline carbonyl) | D* | 344.1 |

TABLE 3

| STRUCTURE | ACTIVITY | (M + H)+ |
|---|---|---|
| (2-phenoxyphenyl tetrazolinone, N-allyl-N-(1-Boc-piperidin-4-yl) carboxamide) | D* | 521.2 |

TABLE 3-continued

| STRUCTURE | ACTIVITY | (M + H)⁺ |
|---|---|---|
| 2,6-dichlorophenyl-tetrazolinone-C(O)-N(Et)-piperidine-N-C(=O)CH₂Ph | C* | 503.1 |
| 2,6-dichlorophenyl-tetrazolinone-C(O)-N(Et)-piperidine-N-C(=O)NHEt | D* | 456.1 |
| 2,6-dichlorophenyl-tetrazolinone-C(O)-N(Et)-piperidine-N-CO₂Et | D* | 457.1 |
| 2,6-dichlorophenyl-tetrazolinone-C(O)-N(Et)-piperidine-N-CO₂tBu | D* | 485.1 |
| 2,6-dichlorophenyl-tetrazolinone-C(O)-N(Et)-piperidine-N-C(=O)CH₂CH₂CO₂H | D* | 485.1 |
| 2,6-dichlorophenyl-tetrazolinone-C(O)-N(Et)-piperidine-N-Me | E* | 399.1 |
| 2,6-dichlorophenyl-tetrazolinone-C(O)-N(Et)-piperidine-N-SO₂CH₃ | D* | 463.1 |
| 2,6-dichlorophenyl-tetrazolinone-C(O)-N(Et)-piperidine-N-Ac | D* | 427.1 |

TABLE 3-continued

| STRUCTURE | ACTIVITY | (M + H)⁺ |
|---|---|---|
| [2,6-dichlorophenyl-tetrazolone-C(O)-N(CH₂CH₂Ph)-(N-Me-azabicyclic)] | E* | 501.2 |
| [2,6-dichlorophenyl-tetrazolone-C(O)-N(Et)-piperidin-3-yl-N-C(=O)NHEt] | D* | 456.1 |
| [2,6-dichlorophenyl-tetrazolone-C(O)-N(Et)-piperidin-3-yl-N-Ac] | D* | 427.1 |
| [2,6-dichlorophenyl-tetrazolone-C(O)-N(Et)-piperidin-3-yl-N-C(=O)CH₂CH₂CO₂H] | D* | 485.1 |
| [2,6-dichlorophenyl-tetrazolone-C(O)-N(Et)-piperidin-3-yl-N-CO₂tBu] | D* | 485.1 |
| [2,6-dichlorophenyl-tetrazolone-C(O)-N(Et)-piperidin-3-yl-N-CO₂Et] | D* | 457.1 |
| [2,6-dichlorophenyl-tetrazolone-C(O)-N(Et)-piperidin-3-yl-N-C(=O)CH₂Ph] | D* | 503.1 |
| [2,6-dichlorophenyl-tetrazolone-C(O)-N(Et)-piperidin-3-yl-N-SO₂CH₃] | D* | 463.1 |

TABLE 3-continued

| STRUCTURE | ACTIVITY | (M + H)+ |
|---|---|---|
| | D* | 414.1 |
| | D | 336.1 |
| | D | 350.1 |
| | D | 351.1 |
| | E* | 288.1 |
| | E* | 316.2 |
| | D* | 362.2 |
| | D* | 408.2 |
| | D* | 344.2 |

TABLE 3-continued

| STRUCTURE | ACTIVITY | (M + H)+ |
|---|---|---|
| (2-I-phenyl) tetrazinone-N(Et)(cyclohexyl) carboxamide | D* | 442.1 |
| (2-sec-Butyl-phenyl) tetrazinone-N(Et)(cyclohexyl) carboxamide | D* | 372.2 |
| (2-F-phenyl) tetrazinone-N(Et)(cyclohexyl) carboxamide | D* | 334.2 |
| (2-tBu-phenyl) tetrazinone-N(Et)(cyclohexyl) carboxamide | E* | 315.2 |
| (2-Cl-phenyl) tetrazinone-N(Et)(cyclohexyl) carboxamide | D* | 350.1 |
| (2-Br-phenyl) tetrazinone-N(Et)(cyclohexyl) carboxamide | D* | 394.1 |
| (2-Cl-phenyl) tetrazinone-N(iPr)(cyclohexyl) carboxamide | E* | 364.2 |
| (2-OCF3-phenyl) tetrazinone-N(Et)(cyclohexyl) carboxamide | D* | 400.2 |
| (2-CN-phenyl) tetrazinone-N(Et)(cyclohexyl) carboxamide | D* | 341.2 |

TABLE 3-continued

| STRUCTURE | ACTIVITY | (M + H)+ |
|---|---|---|
| (2-OMe-phenyl tetrazinone, N-Et, N-cyclohexyl carboxamide) | D* | 346.2 |
| (2-Cl-phenyl tetrazinone, N-Me, N-cyclohexyl carboxamide) | D* | 336.1 |
| (2-iPr-phenyl tetrazinone, N-Et, N-cyclohexyl carboxamide) | D* | 358.2 |
| (2-Me-phenyl tetrazinone, N-Et, N-cyclohexyl carboxamide) | D* | 330.2 |
| (2-Cl-phenyl tetrazinone, N-nPr, N-cyclohexyl carboxamide) | D* | 364.2 |
| (4-O2N-phenyl tetrazinone, N-Et, N-cyclohexyl carboxamide) | D* | 361.2 |
| (4-MeO-phenyl tetrazinone, N-Et, N-cyclohexyl carboxamide) | E* | 346.2 |
| (4-F3C-phenyl tetrazinone, N-Et, N-cyclohexyl carboxamide) | E* | 384.2 |
| (4-Cl-phenyl tetrazinone, N-Et, N-cyclohexyl carboxamide) | E* | 350.1 |

TABLE 3-continued

| STRUCTURE | ACTIVITY | (M + H)+ |
|---|---|---|
| 4-(Me2N)C6H4-tetrazolinone-C(O)-N(Et)-cyclohexyl | D* | 359.2 |
| 4-F-C6H4-tetrazolinone-C(O)-N(Et)-cyclohexyl | E* | 334.2 |
| 3-F-C6H4-tetrazolinone-C(O)-N(Et)-cyclohexyl | E* | 334.2 |
| 3-MeO-C6H4-tetrazolinone-C(O)-N(Et)-cyclohexyl | E* | 346.2 |
| 3-Cl-C6H4-tetrazolinone-C(O)-N(Et)-cyclohexyl | E* | 350.1 |
| 3-F3C-C6H4-tetrazolinone-C(O)-N(Et)-cyclohexyl | E* | 384.2 |
| 3-NC-C6H4-tetrazolinone-C(O)-N(Et)-cyclohexyl | E* | 341.2 |
| 2,6-diF-C6H3-tetrazolinone-C(O)-N(OH)-cyclohexyl | B* | 340.1 |
| 2,6-diF-C6H3-tetrazolinone-C(O)-N(Et)-cyclohexyl | C* | 352.2 |

TABLE 3-continued

| STRUCTURE | ACTIVITY | (M + H)⁺ |
|---|---|---|
| | D* | 409.1 |
| | D* | 384.1 |
| | D* | 491.1 |
| | E* | 499.2 |
| | D* | 497.1 |
| | E* | 548.1 |
| | D* | 518.1 |
| | D* | 510.2 |

TABLE 3-continued

| STRUCTURE | ACTIVITY | (M + H)+ |
|---|---|---|
| | E* | 499.2 |
| | D* | 518.1 |
| | D* | 428.1 |
| | D* | 441.1 |
| | E* | 497.1 |
| | D* | 513.2 |
| | D* | 484.1 |

TABLE 3-continued

| STRUCTURE | ACTIVITY | (M + H)+ |
|---|---|---|
| [2,6-dichlorophenyl tetrazolinone-N-cyclohexyl-N-(CH2)3NHAc carboxamide] | D* | 455.1 |
| [2,6-dichlorophenyl tetrazolinone carboxamide with cyclohexyl and propyl-NH-Leu-NHCHO sidechain] | E* | 554.2 |
| [2,6-dichlorophenyl tetrazolinone-N-Et-N-(3-carboxycyclohexyl) carboxamide] | D* | 428.1 |
| [2,6-dichlorophenyl tetrazolinone-N-cyclohexyl-N-CH2C(=O)NHCH3 carboxamide] | D* | 427.1 |
| [2,6-dichlorophenyl tetrazolinone-N-cyclohexyl-N-CH2CH2NHAc carboxamide] | E* | 441.1 |
| [2,6-dichlorophenyl tetrazolinone-N-Et-N-(cyclohexyl-morpholinylcarbonyl) carboxamide] | D* | 497.1 |
| [2,6-dichlorophenyl tetrazolinone-N-Et-N-(cyclohexyl-C(=O)NH-CH(Ph)C(=O)NH2) carboxamide] | D* | 560.2 |

TABLE 3-continued

| STRUCTURE | ACTIVITY | (M + H)+ |
|---|---|---|
| (2,6-dichlorophenyl tetrazolone, N-Et, cyclohexyl-C(=O)NHMe) | D* | 441.1 |
| (2,6-dichlorophenyl tetrazolone, N-cyclohexyl, propyl-NH-C(=O)-CH2-NH-CHO) | D* | 498.1 |
| (2,6-dichlorophenyl tetrazolone, N-cyclohexyl, CH2-furan) | E* | 436.1 |
| (2,6-dichlorophenyl tetrazolone, N-cyclohexyl, CH2-C(=O)-NH-methylfurazan) | E* | 495.1 |
| (2,6-dichlorophenyl tetrazolone, N-Et, cyclohexyl-C(=O)-N-methylpiperazine) | E* | 510.2 |
| (2,6-dichlorophenyl tetrazolone, N-cyclohexyl, propyl-NH-C(=O)-NHEt) | D* | 484.2 |

TABLE 3-continued

| STRUCTURE | ACTIVITY | (M + H)+ |
|---|---|---|
| | E* | 427.1 |
| | E* | 344.2 |
| | E* | 418.1 |
| | D* | 364.2 |
| | D* | 418.2 |
| 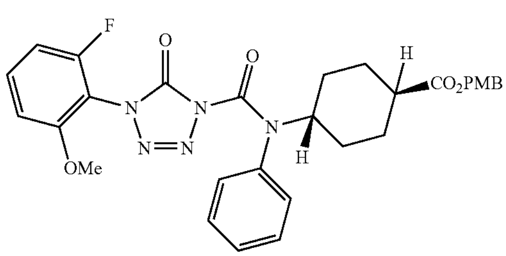 | B | 576.2 |
| 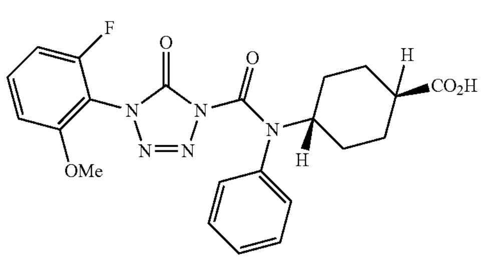 [SMILES: COc1cccc(F)c1-n1nnn(C(=O)N(c2ccccc2)[C@H]2CC[C@H](C(=O)O)CC2)c1=O] | C | 456.2 |

TABLE 3-continued

| STRUCTURE | ACTIVITY | (M + H)+ |
|---|---|---|
| [2-Me-6-tBu-phenyl tetrazolinone N-Et-N-cyclohexyl carboxamide] | E* | 386.3 |
| [4-nBu-2-Me-phenyl tetrazolinone N-Et-N-cyclohexyl carboxamide] | E* | 386.3 |
| [2,4-diCl-phenyl tetrazolinone N-Et-N-cyclohexyl carboxamide] | D* | 384.1 |
| [4-O2N-2-Cl-phenyl tetrazolinone N-Et-N-cyclohexyl carboxamide] | E* | 395.1 |
| [2,4-diF-phenyl tetrazolinone N-Et-N-cyclohexyl carboxamide] | D* | 352.2 |
| [4-F3C-2-Cl-phenyl tetrazolinone N-Et-N-cyclohexyl carboxamide] | E* | 418.1 |
| [2,4-diBr-phenyl tetrazolinone N-Et-N-cyclohexyl carboxamide] | D* | 472.0 |
| [2,5-diCl-phenyl tetrazolinone N-Et-N-cyclohexyl carboxamide] | D* | 384.1 |
| [2,5-diF-phenyl tetrazolinone N-Et-N-cyclohexyl carboxamide] | D* | 352.2 |

TABLE 3-continued

| STRUCTURE | ACTIVITY | (M + H)+ |
|---|---|---|
| | D* | 384.1 |
| | D* | 374.1 |
| | E* | 358.2 |
| | D* | 418.1 |
| | E* | 370.1 |
| | B | 349.1 |
| | B | 393.1 |
| 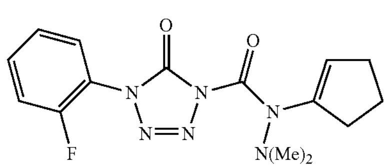 | C | 333.1 |
| | B | 383.1 |

TABLE 3-continued

| STRUCTURE | ACTIVITY | (M + H)+ |
|---|---|---|
| [2,6-difluorophenyl tetrazinone, cyclopentenyl, N(Me)2] | B | 351.1 |
| [2-fluorophenyl tetrazinone, cyclohexenyl, N(Me)2] | C* | 347.2 |
| [2-bromophenyl tetrazinone, cyclohexenyl, N(Me)2] | C* | 407.1 |
| [2-chlorophenyl tetrazinone, cyclohexenyl, N(Me)2] | D* | 363.1 |
| [3-chlorophenyl tetrazinone, cyclohexenyl, N(Me)2] | D* | 363.1 |
| [2-chlorophenyl tetrazinone, cycloheptenyl, N(Me)2] | C | 377.1 |
| [2-chlorophenyl tetrazinone, cyclooctenyl, N(Me)2] | D | 391.2 |
| [phenyl tetrazinone, NH-Et] | E* | 234.1 |
| [2-chlorophenyl tetrazinone, nPr, dienyl chain] | C* | 404.2 |

TABLE 3-continued

| STRUCTURE | ACTIVITY | (M + H)⁺ |
|---|---|---|
| [2-chlorophenyl-tetrazolone-C(O)-N(Me)-undecyl] | C* | 422.2 |
| [2-chlorophenyl-tetrazolone-C(O)-N(Et)(Et)] | D* | 296.1 |
| [2-chlorophenyl-tetrazolone-C(O)-N(Me)-CH₂CH₂CH=CHCH₂CH=CHCH₃] | D* | 376.2 |
| [2-chlorophenyl-tetrazolone-C(O)-N(Et)(Me)] | E* | 282.1 |
| [2-chlorophenyl-tetrazolone-C(O)-N(nPr)(Me)] | E* | 296.1 |
| [2-chlorophenyl-tetrazolone-C(O)-N(nHex)(Me)] | D* | 338.1 |
| [2-chlorophenyl-tetrazolone-C(O)-N(iPr)(iPr)] | E* | 324.1 |
| [2-chlorophenyl-tetrazolone-C(O)-N(Et)(tBu)] | E* | 324.1 |
| [2-chlorophenyl-tetrazolone-C(O)-N(CH₂-cyclopropyl)(nPr)] | D | 336.1 |

TABLE 3-continued

| STRUCTURE | ACTIVITY | (M + H)⁺ |
|---|---|---|
| [structure: 2,6-dichlorophenyl tetrazolone with N-Et, N-CH₂CH₂-O-C(=O)-CH(iBu)-NH-CHO] | D* | 487.1 |

TABLE 4

| STRUCTURE | ACTIVITY | (M + H)⁺ |
|---|---|---|
| [2-thienyl tetrazolone-carboxamide N-Et, N-cyclohexyl] | D* | 322.1 |
| [3-thienyl tetrazolone-carboxamide N-Et, N-cyclohexyl] | E* | 322.1 |
| [1,3,5-trimethylpyrazol-4-yl tetrazolone-carboxamide N-Et, N-cyclohexyl] | E* | 348.2 |
| [3,5-dimethylisoxazol-4-yl tetrazolone-carboxamide N-Et, N-cyclohexyl] | E* | 335.2 |
| [2,6-difluorophenyl tetrazolone-carboxamide N-Boc, N-(2-furyl)] | D* | 408.1 |

TABLE 5

| NAME | ABBREVIATION | STRUCTURE |
|---|---|---|
| methyl | Me | —CH₃ |
| ethyl | Et | —CH₂CH₃ |
| n-propyl | nPr | —CH₂CH₂CH₃ |
| iso-propyl | iPr | —CH(CH₃)₂ |
| n-butyl | nBu | —CH₂CH₂CH₂CH₃ |
| tert-butyl | tBu | —C(CH₃)₃ |
| sec-butyl | | —CH(CH₃)(CH₂CH₃) |
| iso-butyl | iBu | —CH₂CH(CH₃)₂ |
| n-pentyl | nPent | —CH₂CH₂CH₂CH₂CH₃ |

TABLE 5-continued

| NAME | ABBREVIATION | STRUCTURE |
|---|---|---|
| 3-pentanyl or pentan-3-yl | | —CH(CH₂CH₃)₂ |
| amyl | | —CH₂CH(CH₃)CH₂CH₃ |
| neopentyl | | —CH₂C(CH₃)₃ |
| 3-methyl-2-butanyl | | —CH(CH₃)CH(CH₃)₂ |
| tertiary amyl | | —C(CH₃)₂CH₂CH₃ |
| n-hexyl | nHex | —CH₂CH₂CH₂CH₂CH₂CH₃ |
| phenyl | Ph | —C₆H₅ |
| benzyl | Bn | —CH₂C₆H₅ |
| acetyl | Ac | —C(=O)CH₃ |
| tert-butyloxycarbonyl | Boc | —C(=O)OC(CH₃)₃ |
| tert-butyldimethylsilyl | TBDMS | —Si(Me)₂tBu |
| para-methoxybenzyl | PMB | —CH₂C₆H₅(4-OMe) |
| Biotin | | [biotin structure] |

EQUIVALENTS

REFERENCES

All publications and patents mentioned herein are hereby incorporated by reference in their entirety as if each individual publication or patent was specifically and individually incorporated by reference. In case of conflict, the present application, including any definitions herein, will control.

Equivalents

While specific embodiments of the present disclosure have been discussed, the above specification is illustrative and not restrictive. Many variations of this disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A method of inhibiting fatty acid synthase (FASN) in a subject, wherein the subject has a FASN-mediated disorder selected from hyperproliferative disorders, inflammatory disorders, obesity related disorders, Type II diabetes mellitus, fatty liver disease, microbial infections, viral infections, bacterial infections, fungal infections, parasitic infections, and protozoal infections comprising administering to a subject a therapeutically effective amount of a compound of formula (I):

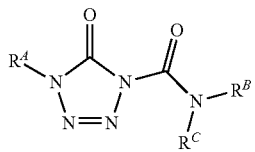

(I)

or a pharmaceutically acceptable salt, hydrate, solvate, tautomer, stereoisomer and/or polymorph thereof;
wherein:
$R^A$ is selected from $C_{3-10}$ carbocyclyl, 3-14 membered heterocyclyl, $C_{6-14}$ aryl and 5-14 membered heteroaryl;
$R^B$ is selected from $C_{1-10}$ alkyl, $C_{2-10}$ alkenyl, $C_{2-10}$ alkynyl, 3-14 membered heteroaliphatic, 3-14 membered heterocyclyl, $C_{6-14}$ aryl and 5-14 membered heteroaryl;
$R^C$ is selected from hydrogen, —OH, —OR$^{C1}$, —ON(R$^{C2}$)$_2$, —N(R$^{C2}$)$_2$, —C(=O)R$^{C1}$, —CHO, —CO$_2$R$^{C1}$, —C(=O)N(R$^{C2}$)$_2$, —C(=NR$^{C2}$)OR$^{C1}$, —C(=NR$^{C2}$)N(R$^{C2}$)$_2$, —SO$_2$R$^{C1}$, —S(=O)R$^{C1}$, —Si(R$^{C1}$)$_3$, $C_{1-10}$ alkyl, $C_{1-10}$ perhaloalkyl, $C_{2-10}$ alkenyl, $C_{2-10}$ alkynyl, 3-14 membered heteroaliphatic, 3-14 membered heterocyclyl, $C_{6-14}$ aryl, and 5-14 membered heteroaryl;
each instance of R$^{C1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; and
each instance of R$^{C2}$ is, independently, selected from hydrogen, —OH, —OR$^{C1}$, —CN, —C(=O)R$^{C1}$, —CO$_2$R$^{C1}$, —SO$_2$R$^{C1}$, —P(=O)$_2$R$^{C1}$, —P(=O)(R$^{C1}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two R$^{C2}$ groups are joined to form a 3-14 membered heterocyclyl or 5-14 membered heteroaryl ring;
or R$^B$ and R$^C$ together with the nitrogen (N) atom to which each is attached are joined to form a 5-14 membered ring.

2. The method of claim 1, wherein the hyperproliferative disorder is selected from prostate cancer and hepatocellular cancer.

3. A method of inhibiting fatty acid synthase (FASN) in a subject, wherein the subject has a FASN-mediated disorder selected from hyperproliferative disorders, inflammatory disorders, obesity related disorders, Type II diabetes mellitus, fatty liver disease, microbial infections, viral infections, bacterial infections, fungal infections, parasitic infections, and protozoal infections comprising administering to & the subject a therapeutically effective amount of a compound of formula (I):

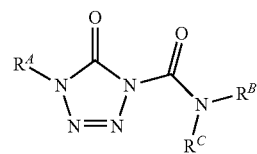

(I)

or a pharmaceutically acceptable salt, hydrate, solvate, tautomer, stereoisomer and/or polymorph thereof;
wherein:
$R^A$ is selected from $C_{6-14}$ aryl and 5-14 membered heteroaryl;
$R^B$ is selected from $C_{6-14}$ aryl and 5-14 membered heteroaryl;
$R^C$ is selected from —OH, —OR$^{C1}$, —ON(R$^{C2}$)$_2$, —N(R$^{C2}$)$_2$, —C(=O)R$^{C1}$, —CHO, —CO$_2$R$^{C1}$, —C(=O)N(R$^{C2}$)$_2$, —C(=NR$^{C2}$)OR$^{C1}$, —C(=NR$^{C2}$)N(R$^{C2}$)$_2$, —SO$_2$R$^{C1}$, —S(=O)R$^{C1}$, —Si(R$^{C1}$)$_3$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$aryl, and 5-14 membered heteroaryl, with the proviso that R$^C$ is not —CH$_3$;
each instance of R$^{C1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;
each instance of R$^{C2}$ is, independently, selected from hydrogen, —OH, —OR$^{C1}$, —CN, —C(=O)R$^{C1}$, —CO$_2$R$^{C1}$, —SO$_2$R$^{C1}$, SOR$^{C1}$, P(=O)$_2$R$^{C1}$, $C_{2-10}$ alkyl, $C_{2-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two R$^{C2}$ groups are joined to form a 3-14 membered heterocyclyl or 5-14 membered heteroaryl ring;
or R$^B$ and R$^C$ together with the nitrogen (N) atom to which each is attached are joined to form a 5-14 membered ring;
wherein:
R$^B$ is substituted with the group:
-L-R$^D$
wherein:
L is a covalent bond or a divalent $C_{1-10}$ hydrocarbon chain, wherein one, two or three methylene units of L are optionally and independently replaced with one or more —O—, —S—, —NR$^{B8}$—, —(C=NR$^{B8}$)—, —C(=O)—, —C(=S)—, —S(=O)—, —S(=O)$_2$—, divalent carbocyclyl, divalent heterocyclyl, divalent aryl or divalent heteroaryl group;

$R^D$ is selected from —CN, —NO$_2$, —N$_3$, —SO$_2$H, —SO$_3$H, —C(=O)R$^{B7}$, —CO$_2$H, —CHO, —C(OR$^{B9}$)$_2$, —CO$_2$R$^{B7}$, —OC(=O)R$^{B7}$, —OCO$_2$R$^{B7}$, —C(=O)N(R$^{B8}$)$_2$, —OC(=O)N(R$^{B8}$)$_2$, —NR$^{B8}$C(=O)R$^{B7}$, —NR$^{B8}$CO$_2$R$^{B7}$, —NR$^{B8}$C(=O)N(R$^{B8}$)$_2$, —C(=NR$^{B8}$)OR$^{B7}$, —OC(=NR$^{B8}$)R$^{B7}$, —OC(=NR$^{B8}$)OR$^{B7}$, —C(=NR$^{B8}$)N(R$^{B8}$)$_2$, —OC(=NR$^{B8}$)N(R$^{B8}$)$_2$, —NR$^{B8}$C(=NR$^{B8}$)N(R$^{B8}$)$_2$, —C(=O)NR$^{B8}$SO$_2$R$^{B7}$, —NR$^{B8}$SO$_2$R$^{B7}$, —SO$_2$N(R$^{B8}$)$_2$, —SO$_2$R$^{B7}$, —SO$_2$OR$^{B7}$, —OSO$_2$R$^{B7}$, —S(=O)R$^{B7}$, —OS(=O)R$^{B7}$, —C(=S)N(R$^{B8}$)$_2$, —C(=O)SR$^{B7}$, —C(=S)SR$^{B7}$, —SC(=S)SR$^{B7}$, —P(=O)$_2$R$^{B7}$, —OP(=O)$_2$R$^{B7}$, —P(=O)(R$^{B7}$)$_2$, —OP(=O)(R$^{B7}$)$_2$, —OP(=O)(OR$^{B9}$)$_2$, —P(=O)$_2$N(R$^{B8}$)$_2$, —OP(=O)$_2$N(R$^{B8}$)$_2$, —P(=O)(NR$^{B8}$)$_2$, —OP(=O)(NR$^{B8}$)$_2$, —NR$^{B8}$P(=O)(OR$^{B9}$)$_2$, —NR$^{B8}$P(=O)(NR$^{B8}$)$_2$, —B(OR$^{B9}$)$_2$, —BR$^{B7}$(OR$^{B9}$), and tetrazolyl;

each instance of $R^{B7}$ is, independently, selected from C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl;

each instance of $R^{B8}$ is, independently, selected from hydrogen, —OH, —OR$^{B7}$, —N(R$^{B9}$)$_2$, —CN, —C(=O)R$^{B7}$, —C(=O)N(R$^{B9}$)$_2$, —CO$_2$R$^{B7}$, —SO$_2$R$^{B7}$, —C(=NR$^{B9}$)OR$^{B7}$, —C(=NR$^{B9}$)N(R$^{B9}$)$_2$, —SO$_2$N(R$^{B9}$)$_2$, —SO$_2$R$^{B9}$, —SO$_2$OR$^{B9}$, —SOR$^{B7}$, —C(=S)N(R$^{B9}$)$_2$, —C(=O)SR$^{B9}$, —C(=S)SR$^{B9}$, —P(=O)$_2$R$^{B7}$, —P(=O)(R$^{B7}$)$_2$, —P(=O)$_2$N(R$^{B9}$)$_2$, —P(=O)(NR$^{B9}$)$_2$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two $R^{B8}$ groups are joined to form a 3-14 membered heterocyclyl or 5-14 membered heteroaryl ring; and each instance of $R^{B9}$ is, independently, selected from hydrogen, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two $R^{B9}$ groups are joined to form a 3-14 membered heterocyclyl or 5-14 membered heteroaryl ring.

4. The method of claim 3, wherein L is a covalent bond.

5. The method of claim 3, wherein L is a divalent C$_{1-10}$ hydrocarbon chain, wherein one methylene unit of L is optionally and independently replaced with a divalent carbocyclyl, divalent heterocyclyl, divalent aryl or divalent heteroaryl group.

6. The method of claim 3, wherein $R^D$ is selected from —CN, —NO$_2$, —SO$_2$H, —SO$_3$H, —C(=O)R$^{B7}$, —CO$_2$H, —CHO, —CO$_2$R$^{B7}$, —C(=O)N(R$^{B8}$)$_2$, —C(=NR$^{B8}$)OR$^{B7}$, —C(=NR$^{B8}$)N(R$^{B8}$)$_2$, —C(=O)NR$^{B8}$SO$_2$R$^{B7}$, —SO$_2$N(R$^{B8}$)$_2$, —SO$_2$R$^{B7}$, —SO$_2$OR$^{B7}$, —S(=O)R$^{B7}$, —C(=S)N(R$^{B8}$)$_2$, —C(=O)SR$^{B7}$, —C(=S)SR$^{B7}$, —P(=O)$_2$R$^{B7}$, —P(=O)(R$^{B7}$)$_2$, —P(=O)$_2$N(R$^{B8}$)$_2$, —P(=O)(NR$^{B8}$)$_2$, —B(OR$^{B9}$)$_2$, —BR$^{B7}$(OR$^{B9}$) and tetrazolyl.

7. The method of claim 6, wherein $R^D$ is selected from —C(=O)R$^{B7}$, —CO$_2$H, —CHO, —CO$_2$R$^{B7}$, —C(=O)N(R$^{B8}$)$_2$, —C(=NR$^{B8}$)OR$^{B7}$, —C(=NR$^{B8}$)N(R$^{B8}$)$_2$, —C(=O)NR$^{B8}$SO$_2$R$^{B7}$, —C(=S)N(R$^{B8}$)$_2$, —C(=O)SR$^{B7}$ and —C(=S)SR$^{B7}$.

8. The method of claim 7, wherein $R^D$ is selected from —C(=O)R$^{B7}$, —CO$_2$H, —CHO, and —CO$_2$R$^{B7}$.

9. The method of claim 8, wherein $R^D$ is —CO$_2$H.

10. The method of claim 3, wherein $R^B$ is further substituted with the group:

—R$^E$ wherein:

$R^E$ is selected from halogen, —OH, —OR$^{B10}$, —ON(R$^{B11}$)$_2$, —N(R$^{B11}$)$_2$, —N(OR$^{B12}$)R$^{B12}$, —SH, —SR$^{B10}$, —SSR$^{B12}$, —OC(=O)R$^{B10}$, —OCO$_2$R$^{B10}$, —OC(=O)N(R$^{B11}$)$_2$, —NR$^{B11}$C(=O)R$^{B10}$, —NR$^{B11}$CO$_2$R$^{B10}$, —NR$^{B11}$C(=O)N(R$^{B11}$)$_2$, —OC(=NR$^{B11}$)R$^{B10}$, —OC(=NR$^{B11}$)OR$^{B10}$, —OC(=NR$^{B11}$)N(R$^{B11}$)$_2$, —NR$^{B11}$(=NR$^{B11}$)N(R$^{B11}$)$_2$, —NR$^{B11}$SO$_2$R$^{B10}$, —OSO$_2$R$^{B10}$, —OS(=O)R$^{B10}$, —Si(R$^{B10}$)$_3$, —OSi(R$^{B10}$)$_3$, —SC(S)SR$^{B10}$, —OP(=O)$_2$R$^{B10}$, —OP(=O)(R$^{B10}$)$_2$, —OP(=O)(OR$^{B12}$)$_2$, —OP(=O)$_2$N(R$^{B11}$)$_2$, —OP(=O)(NR$^{B11}$)$_2$, —NR$^{B11}$P(=O)(OR$^{B12}$)$_2$, —NR$^{B11}$P(=O)(NR$^{B11}$)$_2$, —P(R$^{B12}$)$_2$, —P(R$^{B12}$)$_3$, —OP(R$^{B12}$)$_2$, —OP(R$^{B12}$)$_3$, 3-14 membered heterocyclyl and 5-14 membered heteroaryl, wherein the point of attachment of the 3-14 membered heterocyclyl or 5-14 membered heteroaryl group is on a nitrogen atom;

each instance of $R^{B10}$ is, independently, selected from C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl;

each instance of $R^{B11}$ is, independently, selected from hydrogen, —OH, —OR$^{B10}$, —N(R$^{B12}$)$_2$, —CN, —C(=O)R$^{B10}$, —C(=O)N(R$^{B12}$)$_2$, —CO$_2$R$^{B10}$, —SO$_2$R$^{B10}$, —C(=NR$^{B12}$)OR$^{B10}$, —C(=NR$^{B12}$)N(R$^{B12}$)$_2$, —SO$_2$N(R$^{B12}$)$_2$, —SO$_2$R$^{B12}$, —SO$_2$OR$^{B12}$, —SOR$^{B10}$, —C(=S)N(R$^{B12}$)$_2$, —C(=O)SR$^{B12}$, —C(=S)SR$^{B12}$, —P(=O)$_2$R$^{B10}$, —P(=O)(R$^{B10}$)$_2$, —P(=O)$_2$N(R$^{B12}$)$_2$, —P(=O)(NR$^{B12}$)$_2$, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two $R^{B11}$ groups are joined to form a 3-14 membered heterocyclyl or 5-14 membered heteroaryl ring; and each instance of $R^{B12}$ is, independently, selected from hydrogen, C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl, or two $R^{B12}$ groups are joined to form a 3-14 membered heterocyclyl or 5-14 membered heteroaryl ring.

11. The method of claim 10, wherein $R^E$ is selected from halogen, —OH, —OR$^{B10}$, —ON(R$^{B11}$)$_2$, —N(R$^{B11}$)$_2$, —N(OR$^{B12}$)R$^{B12}$, —SH, —SR$^{B10}$, —SSR$^{B12}$, —Si(R$^{B10}$)$_3$, —OSi(R$^{B10}$)$_3$, —P(R$^{B12}$)$_2$, —P(R$^{B12}$)$_3$, —OP(R$^{B12}$)$_2$, —OP(R$^{B12}$)$_3$, 3-14 membered heterocyclyl and 5-14 membered heteroaryl, wherein the point of attachment of the 3-14 membered heterocyclyl or 5-14 membered heteroaryl group is on a nitrogen atom.

12. The method of claim 11, wherein $R^E$ is selected from halogen, —OR$^{B10}$ and —N(R$^{B11}$)$_2$.

13. The method of claim 3, wherein $R^C$ is selected from C$_{1-10}$ alkyl, C$_{1-10}$ perhaloalkyl, C$_{2-10}$ alkenyl, C$_{2-10}$ alkynyl, 3-14 membered heteroaliphatic, C$_{3-10}$ carbocyclyl, 3-14 membered heterocyclyl, C$_{6-14}$ aryl, and 5-14 membered heteroaryl.

14. The method of claim 13, wherein $R^C$ is C$_{3-10}$ alkyl.

15. The method of claim 13, wherein $R^C$ is C$_{3-10}$ carbocyclyl.

16. The method of claim 3, wherein $R^A$ is $C_{6-14}$ aryl or 5-14 membered heteroaryl, and $R^B$ is $C_{6-14}$ aryl.

17. The method of claim 16, wherein $R^A$ is $C_{6-14}$ aryl and $R^B$ is $C_{6-14}$ aryl.

18. The method of claim 16, wherein $R^A$ is 5-14 membered heteroaryl and $R^B$ is $C_{6-14}$ aryl.

19. The method of claim 3, wherein the compound is of the formula (II):

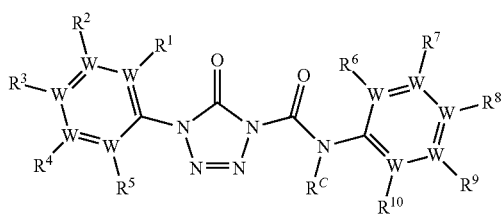

(II)

or a pharmaceutically acceptable salt, hydrate, solvate, tautomer, stereoisomer and/or polymorph thereof;

wherein each group W—$R^1$, W—$R^2$, W—$R^3$, W—$R^4$, and W—$R^5$ independently represents either a nitrogen atom (N) or C—$R^1$, C—$R^2$, C—$R^3$, C—$R^4$, or C—$R^5$, respectively; and wherein $R^1$, $R^2$, $R^3$, $R^4$ and $R^5$ are, independently, selected from the group consisting of hydrogen, halogen, —CN, —NO$_2$, —N$_3$, —SO$_2$H, —SO$_3$H, —OH, —OR$^{A1}$, —ON(R$^{A2}$)$_2$, —N(R$^{A2}$)$_2$, —N(OR$^{A3}$)R$^{A3}$, —SH, —SR$^{A1}$, —SSR$^{A3}$, —C(=O)R$^{A1}$, —CO$_2$H, —CHO, —C(OR$^{A3}$)$_2$, —CO$_2$R$^{A1}$, —OC(=O)R$^{A1}$, —OCO$_2$R$^{A1}$, —C(=O)N(R$^{A2}$)$_2$, —OC(=O)N(R$^{A2}$)$_2$, —NR$^{A2}$C(=O)R$^{A1}$, —NR$^{A2}$CO$_2$R$^{A1}$, —NR$^{A2}$C(=O)N(R$^{A2}$)$_2$, —C(=NR$^{A2}$)OR$^{A1}$, —OC(=NR$^{A2}$)R$^{A1}$, —OC(=NR$^{A2}$)OR$^{A1}$, —C(=NR$^{A2}$)N(R$^{A2}$)$_2$, —OC(=NR$^{A2}$)N(R$^{A2}$)$_2$, —NR$^{A2}$C(=NR$^{A2}$)N(R$^{A2}$)$_2$, —C(=O)NR$^{A2}$SO$_2$R$^{A1}$, —NR$^{A2}$SO$_2$R$^{A1}$, —SO$_2$N(R$^{A2}$)$_2$, —SO$_2$R$^{A1}$, —SO$_2$OR$^{A1}$, —OSO$_2$R$^{A1}$, —S(=O)R$^{A1}$, —OS(=O)R$^{A1}$, —Si(R$^{A1}$)$_3$, —OSi(R$^{A1}$)$_3$—C(=S)N(R$^{A2}$)$_2$, —C(=O)SR$^{A1}$, —C(=S)SR$^{A1}$, —SC(=S)SR$^{A1}$, —P(=O)$_2$R$^{A1}$, —OP(=O)$_2$R$^{A1}$, —P(=O)(R$^{A1}$)$_2$, —OP(=O)(R$^{A1}$)$_2$, —OP(=O)(OR$^{A3}$)$_2$, —P(=O)$_2$N(R$^{A2}$)$_2$, —OP(=O)$_2$N(R$^{A2}$)$_2$, —P(=O)(NR$^{A2}$)$_2$, —OP(=O)(NR$^{A2}$)$_2$, —NR$^{A2}$P(=O)(OR$^{A3}$)$_2$, —NR$^{A2}$P(=O)(NR$^{A2}$)$_2$, —P(R$^{A3}$)$_2$, —P(R$^{A3}$)$_3$, —OP(R$^{A3}$)$_2$, —OP(R$^{A3}$)$_3$, —B(OR$^{A3}$)$_2$, or —BR$^{A1}$(OR$^{A3}$), $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; or one or more of $R^1$ and $R^2$, $R^2$ and $R^3$, $R^3$ and $R^4$ or $R^4$ and $R^5$ are joined to form a $C_{3-10}$ carbocyclyl, 3-14 membered heterocyclyl, $C_{6-14}$ aryl or 5-14 membered heteroaryl ring;

each instance of $R^{A1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{A2}$ is, independently, selected from hydrogen, —OH, —OR$^{A1}$, —N(R$^{A3}$)$_2$, —CN, —C(=O)R$^{A1}$, —C(=O)N(R$^{A3}$)$_2$, —CO$_2$R$^{A1}$, —SO$_2$R$^{A1}$, —C(=NR$^{A3}$)OR$^{A1}$, —C(=NR$^{A3}$)N(R$^{A3}$)$_2$, —SO$_2$N(R$^{A3}$)$_2$, —SO$_2$R$^{A3}$, —SO$_2$OR$^{A3}$, —SOR$^{A1}$, —C(=S)N(R$^{A3}$)$_2$, —C(=O)SR$^{A3}$, —C(=S)SR$^{A3}$, —P(=O)$_2$R$^{A1}$, —P(=O)(R$^{A1}$)$_2$, —P(=O)$_2$N(R$^{A3}$)$_2$, —P(=O)(NR$^{A3}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{A2}$ groups are joined to form a 3-14 membered heterocyclyl or 5-14 membered heteroaryl ring; and each instance of $R^{A3}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{A3}$ groups are joined to form a 3-14 membered heterocyclyl or 5-14 membered heteroaryl ring;

wherein each group W—$R^6$, W—$R^7$, W—$R^8$, W—$R^9$, and W—$R^{10}$ independently represents either a nitrogen atom (N) or C—$R^6$, C—$R^7$, C—$R^8$, C—$R^9$, or C—$R^{10}$, respectively;

$R^6$, $R^7$, $R^7$, $R^9$ and $R^{10}$ are, independently, selected from the group consisting of hydrogen, halogen, —CN, —NO$_2$, —N$_3$, —SO$_2$H, —SO$_3$H, —OH, —OR$^{B1}$, —ON(R$^{B2}$)$_2$, —N(R$^{B2}$)$_2$, —N(OR$^{B3}$)R$^{B3}$, —SH, —SR$^{B1}$, —SSR$^{B3}$, —C(=O)R$^{B1}$, —CO$_2$H, —CHO, —C(OR$^{B3}$)$_2$, —CO$_2$R$^{B1}$, —OC(=O)R$^{B1}$, —OCO$_2$R$^{B1}$, —C(=O)N(R$^{B2}$)$_2$, —OC(=O)N(R$^{B2}$)$_2$, —NR$^{B2}$C(=O)R$^{B1}$, —NR$^{B2}$CO$_2$R$^{B1}$, —NR$^{B2}$C(=O)N(R$^{B2}$)$_2$, —C(=NR$^{B2}$)OR$^{B1}$, —OC(=NR$^{B2}$)R$^{B1}$, —OC(=NR$^{B2}$)OR$^{B1}$, —C(=NR$^{B2}$)N(R$^{B2}$)$_2$, —OC(=NR$^{B2}$)N(R$^{B2}$)$_2$, —NR$^{B2}$C(=NR$^{B2}$)N(R$^{B2}$)$_2$, —C(=O)NR$^{B2}$SO$_2$R$^{B1}$, —NR$^{B2}$SO$_2$R$^{B1}$, —SO$_2$N(R$^{B2}$)$_2$, —SO$_2$R$^{B1}$, —SO$_2$OR$^{B1}$, —OSO$_2$R$^{B1}$, —S(=O)R$^{B1}$, —OS(=O)R$^{B1}$, —Si(R$^{B1}$)$_3$, —OSi(R$^{B1}$)$_3$—C(=S)N(R$^{B2}$)$_2$, —C(=O)SR$^{B1}$, —C(=S)SR$^{B1}$, —SC(S)SR$^{B1}$, —P(=O)$_2$R$^{B1}$, —OP(=O)$_2$R$^{B1}$, —P(=O)(R$^{B1}$)$_2$, —OP(=O)(R$^{B1}$)$_2$, —OP(=O)(OR$^{B3}$)$_2$, —P(=O)$_2$N(R$^{B2}$)$_2$, —OP(=O)$_2$N(R$^{B2}$)$_2$, —P(=O)(NR$^{B2}$)$_2$, —OP(=O)(NR$^{B2}$)$_2$, —NR$^{B2}$P(=O)(OR$^{B3}$)$_2$, —NR$^{B2}$P(=O)(NR$^{B2}$)$_2$, —P(R$^{B3}$)$_2$, —P(R$^{B3}$)$_3$, —OP(R$^{B3}$)$_2$, —OP(R$^{B3}$)$_3$, —B(OR$^{B3}$)$_2$, —BR$^{B1}$(OR$^{B3}$), $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, 5-14 membered heteroaryl, -L-R$^D$ and —R$^E$; or one or more of $R^6$ and $R^7$, $R^7$ and $R^8$, $R^8$ and $R^9$ or $R^9$ and $R^{10}$ are joined to form a $C_{3-10}$ carbocyclyl, 3-14 membered heterocyclyl, $C_{6-14}$ aryl or 5-14 membered heteroaryl ring; or $R^{10}$ and $R^C$ are joined to form a 3-14 membered heterocyclyl or 5-14 membered heteroaryl ring;

wherein at least one of $R^6$, $R^7$, $R^8$, $R^9$, and $R^{10}$ is the group -L-R$^D$;

each instance of $R^{B1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{B2}$ is, independently, selected from hydrogen, —OH, —OR$^{B1}$, —N(R$^{B3}$)$_2$, —CN, —C(=O)R$^{B1}$, —C(=O)N(R$^{B3}$)$_2$, —CO$_2$R$^{B1}$, —SO$_2$R$^{B1}$, —C(=NR$^{B3}$)OR$^{B1}$, —C(=NR$^{B3}$)N(R$^{B3}$)$_2$, —SO$_2$N(R$^{B3}$)$_2$, —SO$_2$R$^{B3}$, —SO$_2$OR$^{B3}$, —SOR$^{B1}$, —C(=S)N(R$^{B3}$)$_2$, —C(=O)SR$^{B3}$, —C(=S)SR$^{B3}$, —P(=O)$_2$R$^{B1}$, —P(=O)(R$^{B1}$)$_2$, —P(=O)$_2$N(R$^{B3}$)$_2$, —P(=O)(NR$^{B3}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B2}$ groups are joined to form a 3-14 membered heterocyclyl or 5-14 membered heteroaryl ring;

each instance of $R^{B3}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B3}$ groups are joined to form a 3-14 membered heterocyclyl or 5-14 membered heteroaryl ring;

L is a covalent bond or a divalent $C_{1-10}$ hydrocarbon chain, wherein one, two or three methylene units of L are optionally and independently replaced with one or more —O—, —S—, —$NR^{B8}$—, —(C=$NR^{B8}$)—, —C(=O)—, —C(=S)—, —S(=O)—, —S(=O)$_2$—, divalent carbocyclyl, divalent heterocyclyl, divalent aryl or divalent heteroaryl group; and wherein $R^D$ is selected from —CN, —NO$_2$, —N$_3$, —SO$_2$H, —SO$_3$H, —C(=O)$R^{B7}$, —CO$_2$H, —CHO, —C(OR$^{B9}$)$_2$, —CO$_2$R$^{B7}$, —OC(=O)R$^{B7}$, —OCO$_2$R$^{B7}$, —C(=O)N(R$^{B8}$)$_2$, —OC(=O)N(R$^{B8}$)$_2$, —NR$^{B8}$C(=O)R$^{B7}$, —NR$^{B8}$CO$_2$R$^{B7}$, —NR$^{B8}$C(=O)N(R$^{B8}$)$_2$, —C(=NR$^{B8}$)OR$^{B7}$, —OC(=NR$^{B8}$)R$^{B7}$, —OC(=NR$^{B8}$)OR$^{B7}$, —C(=NR$^{B8}$)N(R$^{B8}$)$_2$, —OC(=NR$^{B8}$)N(R$^{B8}$)$_2$, —NR$^{B8}$C(=NR$^{B8}$)N(R$^{B8}$)$_2$, —C(=O)NR$^{B8}$SO$_2$R$^{B7}$, —NR$^{B8}$SO$_2$R$^{B7}$, —SO$_2$N(R$^{B8}$)$_2$, —SO$_2$R$^{B7}$, —SO$_2$OR$^{B7}$, —OSO$_2$R$^{B7}$, —S(=O)R$^{B7}$, —OS(=O)R$^{B7}$, —C(=S)N(R$^{B8}$)$_2$, —C(=O)SR$^{B7}$, —C(=S)SR$^{B7}$, —SC(=S)SR$^{B7}$, —P(=O)$_2$R$^{B7}$, —OP(=O)$_2$R$^{B7}$, —P(=O)(R$^{B7}$)$_2$, —OP(=O)(R$^{B7}$)$_2$, —OP(=O)(OR$^{B9}$)$_2$, —P(=O)$_2$N(R$^{B8}$)$_2$, —OP(=O)$_2$N(R$^{B8}$)$_2$, —P(=O)(NR$^{B8}$)$_2$, —OP(=O)(NR$^{B8}$)$_2$, —NR$^{B8}$P(=O)(OR$^{B9}$)$_2$, —NR$^{B8}$P(=O)(NR$^{B8}$)$_2$, —B(OR$^{B9}$)$_2$, —BR$^{B7}$(OR$^{B9}$) and tetrazolyl;

each instance of $R^{B7}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{B8}$ is, independently, selected from hydrogen, —OH, —OR$^{B7}$, —N(R$^{B9}$)$_2$, —CN, —C(=O)R$^{B7}$, —C(=O)N(R$^{B9}$)$_2$, —CO$_2$R$^{B7}$, —SO$_2$R$^{B7}$, —C(=NR$^{B9}$)OR$^{B7}$, —C(=NR$^{B9}$)N(R$^{B9}$)$_2$, —SO$_2$N(R$^{B9}$)$_2$, —SO$_2$R$^{B9}$, —SO$_2$OR$^{B9}$, —SOR$^{B7}$, —C(=S)N(R$^{B9}$)$_2$, —C(=O)SR$^{B9}$, —C(=S)SR$^{B9}$, —P(=O)$_2$R$^{B7}$, —P(=O)(R$^{B7}$)$_2$, —P(=O)$_2$N(R$^{B9}$)$_2$, —P(=O)(NR$^{B9}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B8}$ groups are joined to form a 3-14 membered heterocyclyl or 5-14 membered heteroaryl ring; and each instance of $R^{B9}$ is, independently, selected from hydrogen, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B9}$ groups are joined to form a 3-14 membered heterocyclyl or 5-14 membered heteroaryl ring;

$R^E$ is selected from halogen, —OH, —OR$^{B10}$, —ON(R$^{B11}$)$_2$, —N(R$^{B11}$)$_2$, —N(OR$^{B12}$)R$^{B12}$, —SH, —SR$^{B10}$, —SSR$^{B12}$, —OC(=O)R$^{B10}$, —OCO$_2$R$^{B10}$, —OC(=O)N(R$^{B11}$)$_2$, —NR$^{B11}$C(=O)R$^{B10}$, —NR$^{B11}$CO$_2$R$^{B10}$, —NR$^{B11}$C(=O)N(R$^{B11}$)$_2$, —OC(=NR$^{B11}$)R$^{B10}$, —OC(=NR$^{B11}$)N(R$^{B11}$)$_2$, —NR$^{B11}$C(=NR$^{B11}$)N(R$^{B11}$)$_2$, —NR$^{B11}$SO$_2$R$^{B10}$, —OSO$_2$R$^{B10}$, —OS(=O)R$^{B10}$, —Si(R$^{B10}$)$_3$, —OSi(R$^{B10}$)$_3$, —SC(S)SR$^{B10}$, —OP(=O)$_2$R$^{B10}$, —OP(=O)(R$^{B10}$)$_2$, —OP(=O)(OR$^{B12}$)$_2$, —OP(=O)$_2$N(R$^{B11}$)$_2$, —OP(=O)(NR$^{B11}$)$_2$, —NR$^{B11}$P(=O)(OR$^{B12}$)$_2$, —NR$^{B11}$P(=O)(NR$^{B11}$)$_2$, —P(R$^{B12}$)$_2$, —P(R$^{B12}$)$_3$, —OP(R$^{B12}$)$_2$, —OP(R$^{B12}$)$_3$, 3-14 membered heterocyclyl and 5-14 membered heteroaryl, wherein the point of attachment of the 3-14 membered heterocyclyl or 5-14 membered heteroaryl group is on a nitrogen atom;

each instance of $R^{B10}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl;

each instance of $R^{B11}$ is, independently, selected from hydrogen, —OH, —OR$^{B10}$, —N(R$^{B12}$)$_2$, —CN, —C(=O)R$^{B10}$, —C(=O)N(R$^{B12}$)$_2$, —CO$_2$R$^{B10}$, —SO$_2$R$^{B10}$, —C(=NR$^{B12}$)OR$^{B10}$, —C(=NR$^{B12}$)N(R$^{B12}$)$_2$, —SO$_2$N(R$^{B12}$)$_2$, —SO$_2$R$^{B12}$, —SO$_2$OR$^{B12}$, —SOR$^{B10}$, —C(=S)N(R$^{B12}$)$_2$, —C(=O)SR$^{B12}$, —C(=S)SR$^{B12}$, —P(=O)$_2$R$^{B10}$, —P(=O)(R$^{B10}$)$_2$, —P(=O)$_2$N(R$^{B12}$)$_2$, —P(=O)(NR$^{B12}$)$_2$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B11}$ groups are joined to form a 3-14 membered heterocyclyl or 5-14 membered heteroaryl ring;

each instance of $R^{B12}$ is, independently, selected from hydrogen, $C_{1-10}$ alkyl, $C_{1-10}$ perhaloalkyl, $C_{1-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{B12}$ groups are joined to form a 3-14 membered heterocyclyl or 5-14 membered heteroaryl ring;

$R^C$ is selected from —OH, —OR$^{C1}$, —ON(R$^{C2}$)$_2$, —N(R$^{C2}$)$_2$, —C(=O)R$^{C1}$, —CHO, —CO$_2$R$^{C1}$, —C(=O)N(R$^{C2}$)$_2$, —C(=NR$^{C2}$)OR$^{C1}$, —C(=NR$^{C2}$)N(R$^{C2}$)$_2$, —SO$_2$R$^{C1}$, —S(=O)R$^{C1}$, —Si(R$^{C1}$)$_3$, $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, with the proviso that $R^C$ is not —CH$_3$;

each instance of $R^{C1}$ is, independently, selected from $C_{1-10}$ alkyl, $C_{1-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl; and each instance of $R^{C2}$ is, independently, selected from hydrogen, —OH, —OR$^{C1}$, —CN, —C(=O)R$^{C1}$, —CO$_2$R$^{C1}$, —SO$_2$R$^{C1}$, SOR$^{C1}$, —P(=O)$_2$R$^{C1}$, —P(=O)(R$^{C1}$)$_2$, $C_{2-10}$ alkyl, $C_{2-10}$ perhaloalkyl, $C_{2-10}$ alkenyl, $C_{2-10}$ alkynyl, 3-14 membered heteroaliphatic, $C_{3-10}$ carbocyclyl, 3-14 membered heterocyclyl, $C_{6-14}$ aryl, and 5-14 membered heteroaryl, or two $R^{C2}$ groups are joined to form a 3-14 membered heterocyclyl or 5-14 membered heteroaryl ring.

20. The method of claim 19, wherein at least one of $R^6$, $R^7$, $R^8$, $R^9$ and $R^{10}$ is the group —$R^E$.

21. The method of claim 3, wherein the FASN-mediated disorder is a microbial infection.

22. The method of claim 21, wherein the microbial infection is a viral infection.

23. The method of claim 22, wherein the viral infection is an infection with an enveloped virus or a picornavirus.

24. The method of claim 22, wherein the viral infection is selected from HSV-1, HSV-2, VZV, EBV, CMV, HHV-6, HHV-8, HMCV, CVB3, influenza type A, influenza type B, RSV, PIV, measles virus, rhinovirus, adenovirus, HMPV, SARS virus, vaccinia virus, cowpox virus, ectomelia virus, monkeypox virus, rabbitpox virus, HBV, HCV, papillomavirus, BK virus, VEE virus, Rift Valley fever virus, Tavaribe virus, Yellow fever virus, West Nile virus, dengue virus, PTV or Pichinde virus.

25. The method of claim 24, wherein the viral infection is infection with HCV or dengue virus.

26. The method of claim 22, which further comprises administration of one or more additional anti-viral agents.

27. The method of claim 26, wherein the additional anti-viral agent is an interferon, a protease inhibitor, an integrase inhibitor, a reverse transciptase inhibitor, or a combination thereof.

28. The method of claim 26, wherein the additional anti-viral agent is an interferon, ribavirin or a combination thereof.

29. The method of claim 28, wherein the interferon is interferon type III, interferon type II, interferon type I, peginterferon alfa-2a, peginterferon alfa-2b, standard interferon alfa-2a, standard interferon alfa-2b, consensus interferon, interferon alfacon-1, ALBUFERON, omega interferon, interferon gamma-1b, lymphoblastoid interferon tau, or a combination thereof.

30. The method of claim 21, wherein the microbial infection is a bacterial infection.

31. The method of claim 30, wherein the bacterial infection is selected from *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes, Streptococcus agalactiae, Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia, Actinomyces israelli* or a combination thereof.

32. The method of claim 31, wherein the bacterial infection is *Mycobacteria tuberculosis*.

33. The method of claim 30, wherein the compound is:

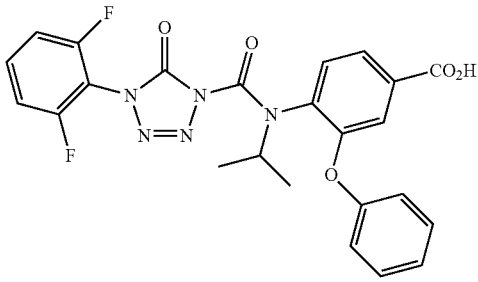 [SMILES: CC(C)N(C(=O)n1nnn(-c2c(F)cccc2F)c1=O)c1ccc(C(=O)O)cc1Oc1ccccc1]

or a pharmaceutically acceptable salt, hydrate, solvate, tautomer, stereoisomer and/or polymorph thereof.

34. The method of claim 21, wherein the microbial infection is a fungal infection.

35. The method of claim 34, wherein the fungal infection is an infection with aspergilliosis, crytococcosis, sporotrichosis, coccidioidomycosis, paracoccidioidomycosis, histoplasmosis, blastomycosis, zygomycosis or candidiasis.

36. The method of claim 21, wherein the microbial infection is a parasitic or protozoal infection.

37. The method of claim 36, wherein the parasitic or protozoal infection is an infection with *P. falcifarium, P. ovale, P. vivax, P. malariae, L. donovari, L. infantum, L. aethiopica, L. major, L. tropica, L. mexicana, L. braziliensis, T. Gondii, B. microti. B. divergens, B. coli, B. hominis, C. parvum, C. cayetanensis, D. fragilis, E. histolytica, I. belli, S. mansonii, S. haematobium, Trypanosoma* ssp. *Toxoplasma* ssp., *O. volvulus, Babesia bovis, Babesia canis, Banesia Gibsoni, Besnoitia darlingi, Cytauxzoon felis, Eimeria* ssp., *Hammondia* ssp., *T. canis, Cestoda, Theileria* ssp. or a combination thereof.

38. The method of claim 36, wherein the parasitic or protozoal infection causes malaria, babesiosis, trypanosomiasis, American trypanosomiasis, leishmaniasis, toxoplasmosis, meningoencephalitis, keratitis, amebiasis, giardiasis, cryptosporidiosis, isosporiasis, cyclosporiasis, microsporidiosis, ascariasis, trichuriasis, ancylostomiasis, strongyloidiasis, toxocariasis, trichinosis, lymphatic filariasis, onchocerciasis, filariasis, schistosomiasis or dermatitis caused by animal schistosomes.

39. The method of claim 38, wherein the parasitic or protozoal infection causes malaria.

40. The method of claim 38, wherein the parasitic or protozoal infection causes leishmaniasis, babesiosis, toxoplasmosis or trypanosomiasis.

41. The method of claim 3, wherein the FASN-mediated disorder is a hyperproliferative disorder.

42. The method of claim 41, wherein the hyperproliferative disorder is cancer.

43. The method of claim 42, wherein the cancer is selected from bladder cancer, brain cancer, breast cancer, colorectal cancer, esophageal cancer, endometrial cancer, gastric cancer, gastrointestinal stromal tumor, kidney cancer, liver cancer, lung cancer, mesothelioma, multiple myeloma, neuroblastoma, oral cancer, ovarian cancer, pancreatic cancer, prostate cancer, Paget's disease of the vulva, retinoblastoma, soft tissue sarcoma, skin cancer or thyroid cancer.

44. The method of claim 42, wherein the cancer is pancreatic cancer.

45. The method of claim 42, wherein the cancer is selected from mesothelioma, multiple myeloma, neuroblastoma, Paget's disease, retinoblastoma, leukemia, myelodisplastic syndrome, and soft tissue sarcoma.

46. The method of claim 42, which further comprises administration of one or more anti-cancer agents.

47. The method of claim 3, wherein the FASN-mediated disorder is an inflammatory disorder.

48. The method of claim 47, wherein the inflammatory disorder is selected from anemia, asthma, arteritis, arthritis, chronic obstructive pulmonary disease, dermatitis, gastroesophageal reflux disease, Crohn's disease, inflammatory bowel syndrome, multiple sclerosis, psoriasis and an autoimmune disease.

49. The method of claim 3, wherein the FASN-mediated disorder is an obesity related disorder.

50. The method of claim 49, wherein the obesity related disorder is selected from Type II diabetes mellitus, elevated blood pressure, elevated cholesterol levels, ischemic heart disease, arterial vascular disease, angina, myocardial infarction, stroke, migraines, congestive heart failure, deep vein thrombosis, pulmonary embolism, gall stones, gastroesophagael reflux disease, obstructive sleep apnea, obesity hypoventilation syndrome, asthma, gout, poor mobility, back pain, erectile dysfunction, urinary incontinence, liver injury, fatty liver, and chronic renal failure.

51. The method of claim 3, wherein the FASN-mediated disorder is Type II diabetes mellitus.

52. The method of claim 3, wherein the FASN-mediated disorder is fatty liver disease.
53. The method of claim 3, wherein the compound is:
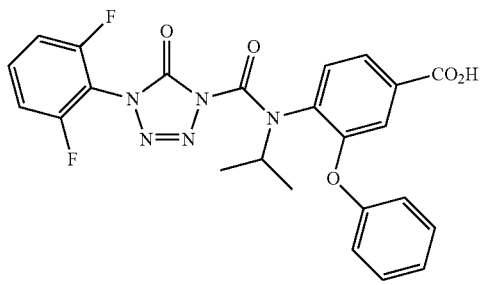 [SMILES: CC(C)N(C(=O)n1nnn(-c2c(F)cccc2F)c1=O)c1ccc(C(=O)O)cc1Oc1ccccc1]
or a pharmaceutically acceptable salt, hydrate, solvate, tautomer, stereoisomer and/or polymorph thereof.
54. The method of claim 3, wherein the compound is:
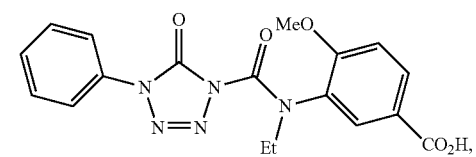
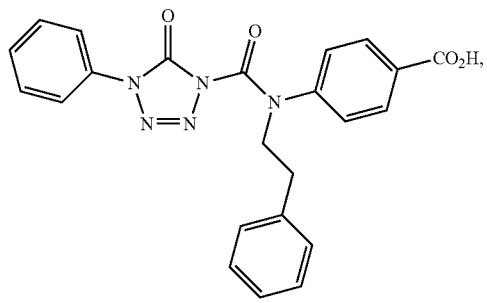
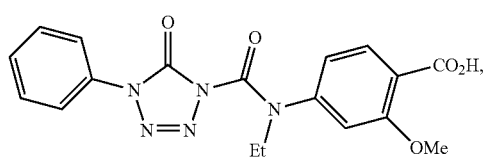
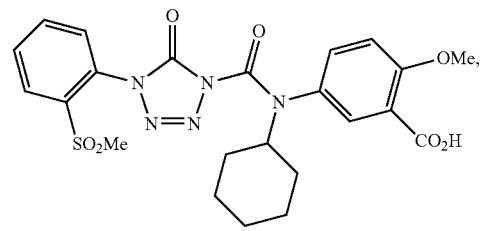
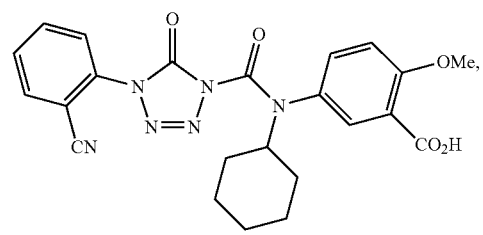
-continued
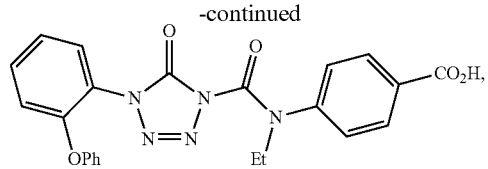
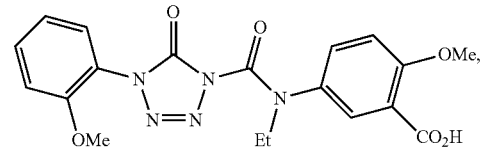
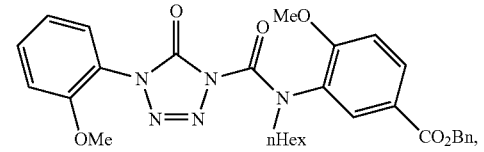
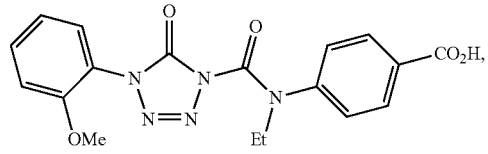
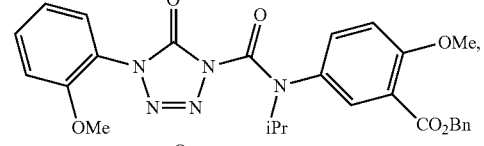
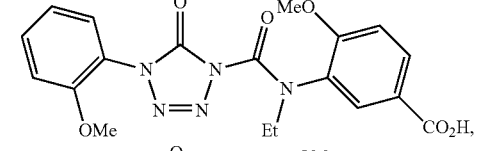
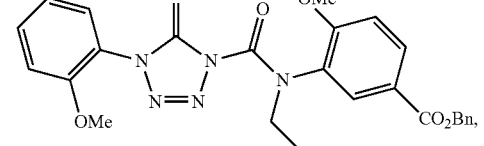
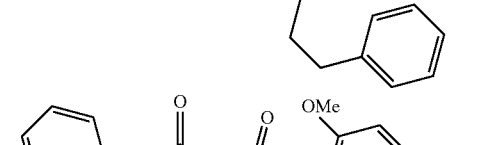
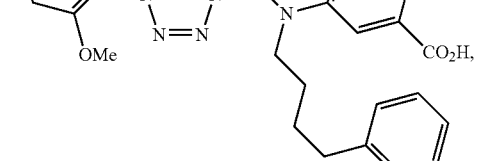
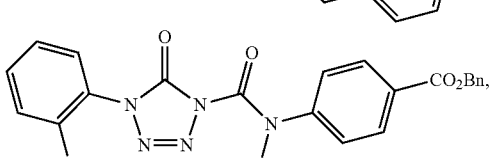
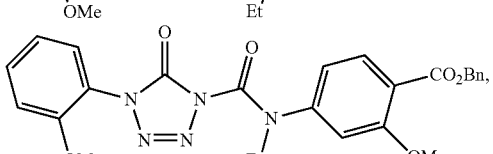

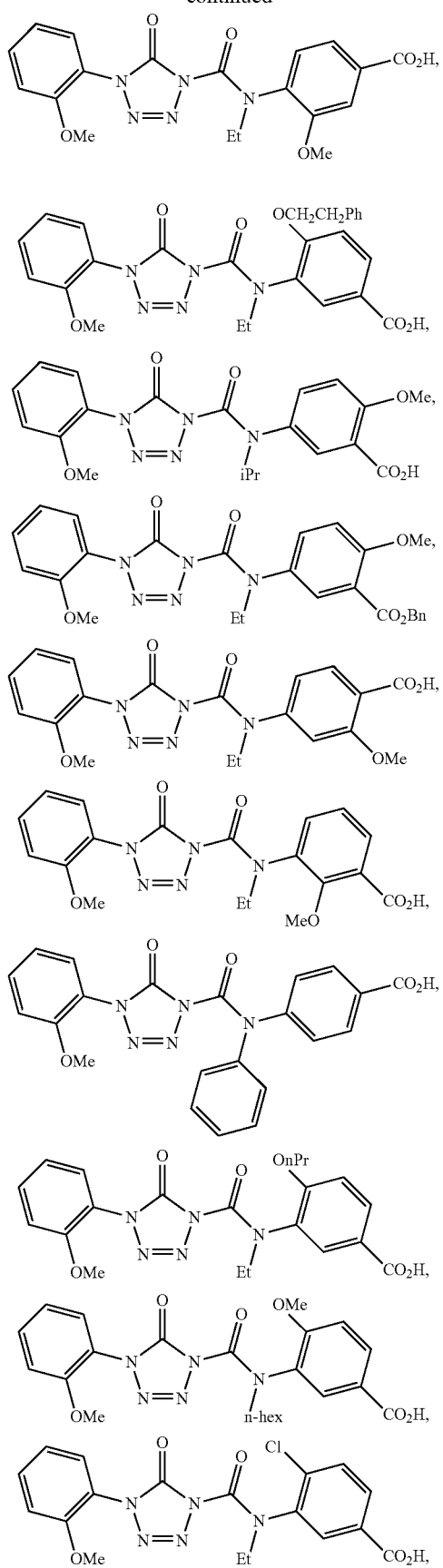
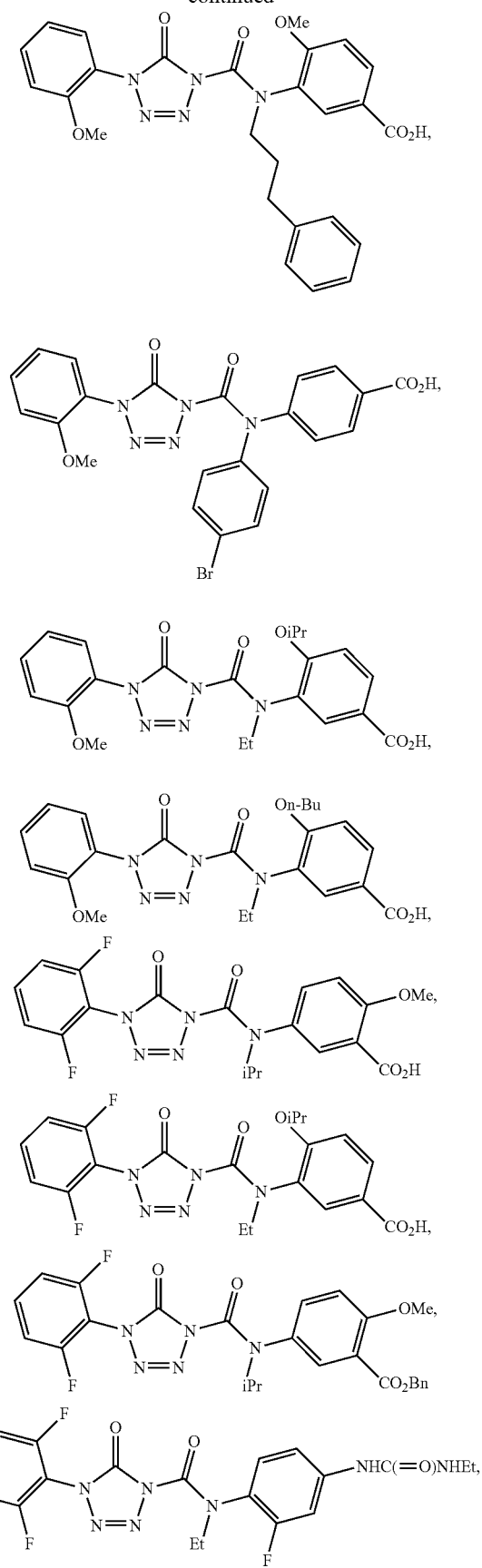

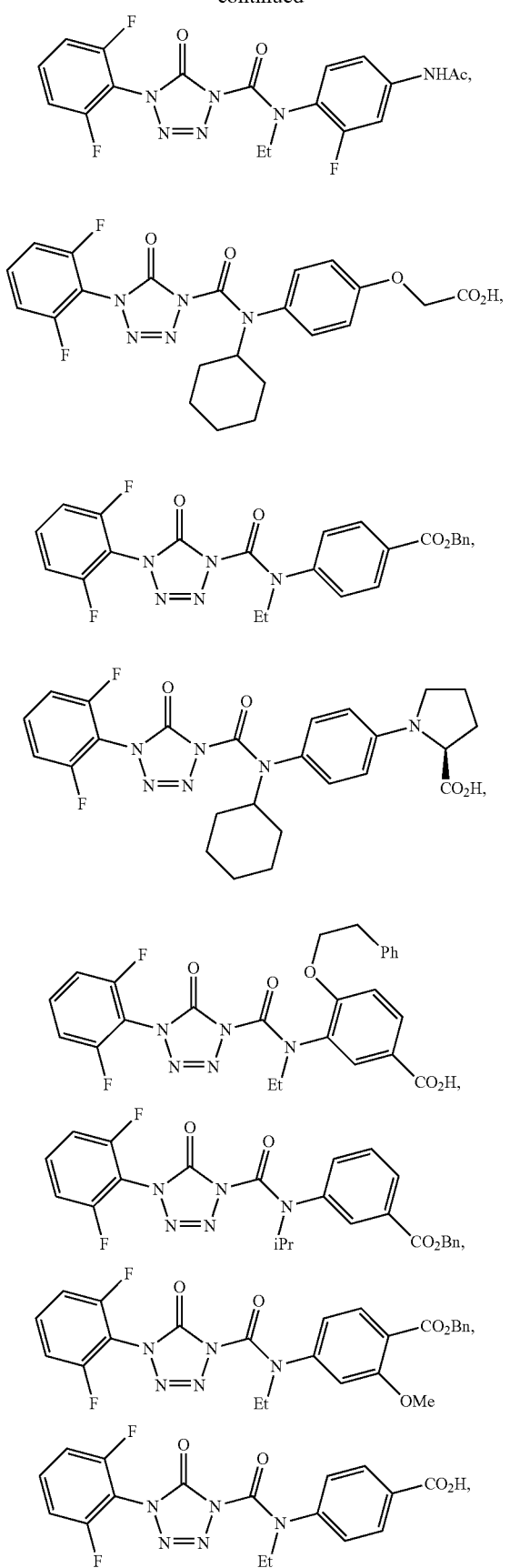
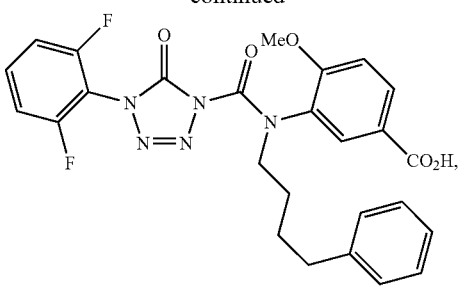
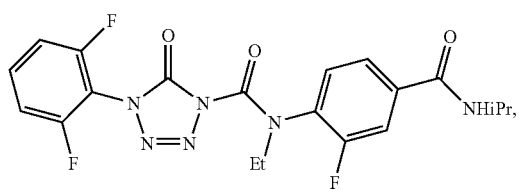
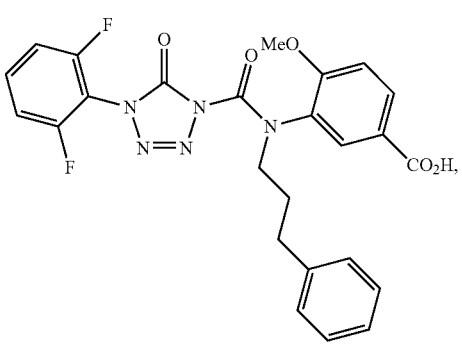
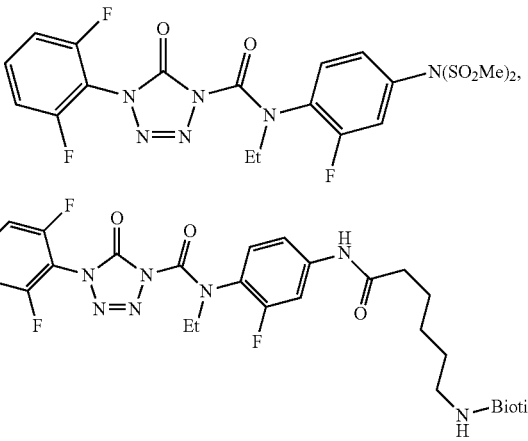

351
-continued
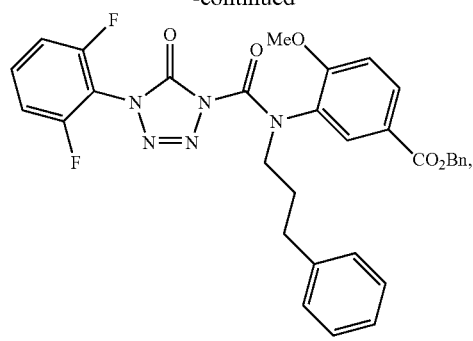
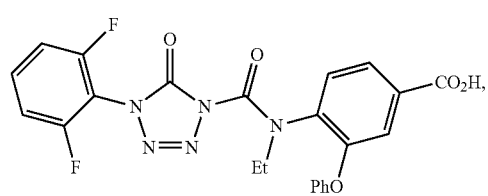
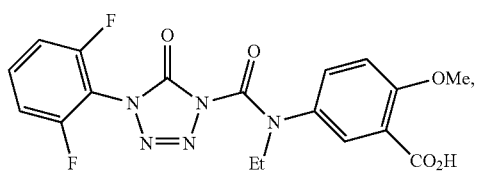
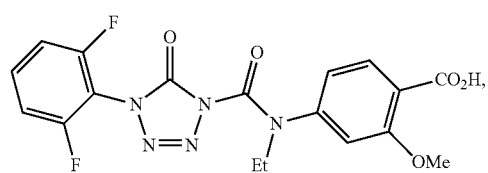
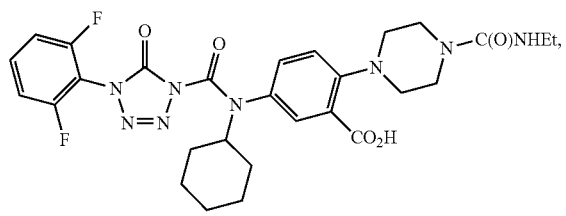
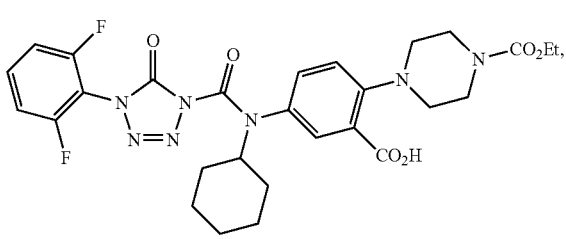
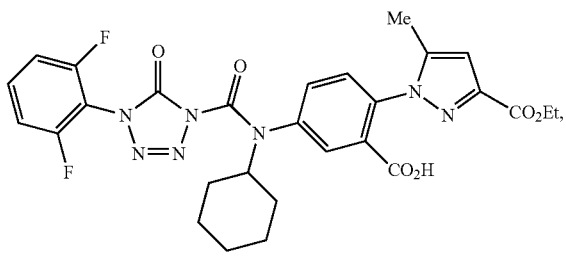
352
-continued
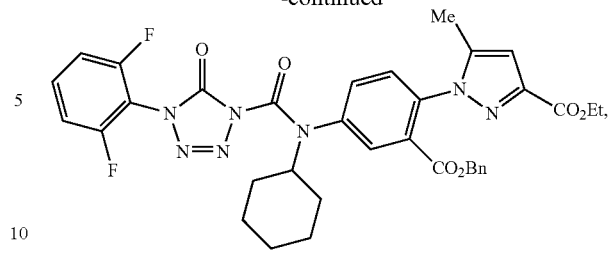
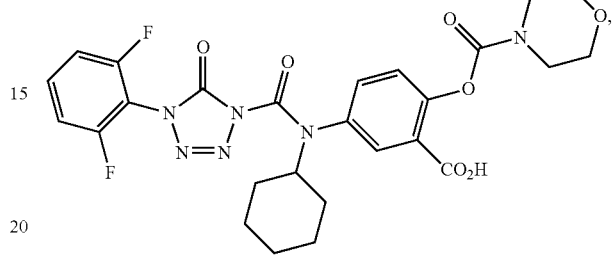
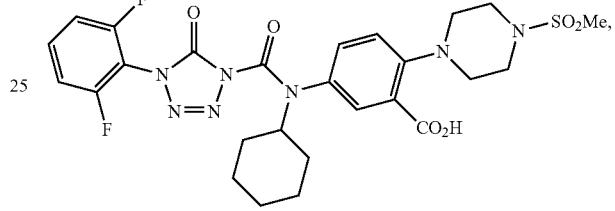
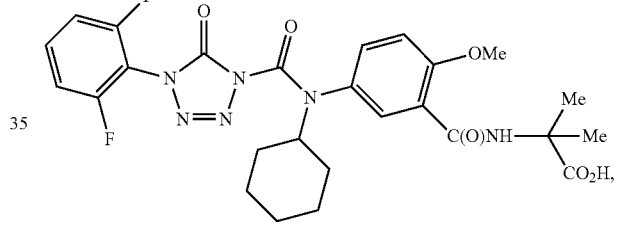
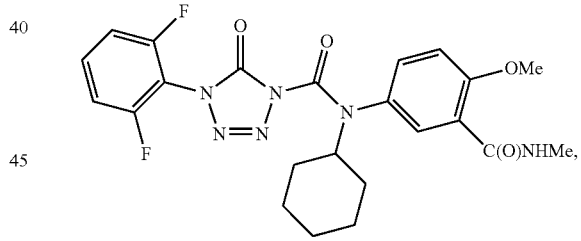
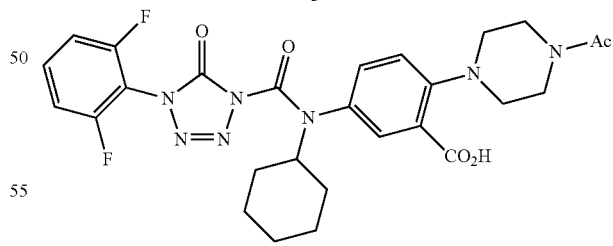
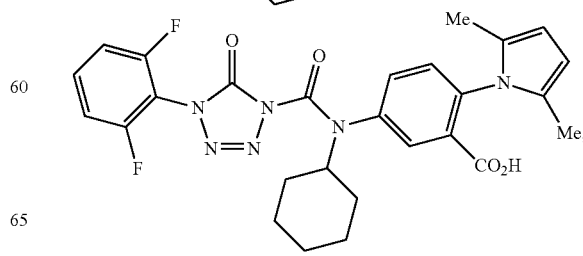

353
-continued
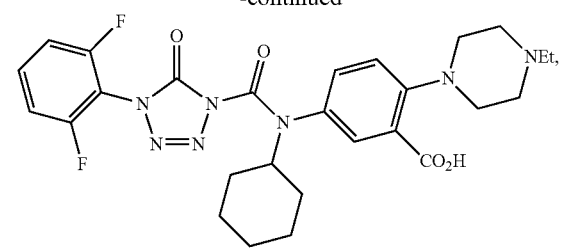
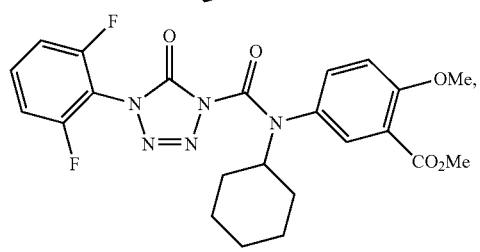
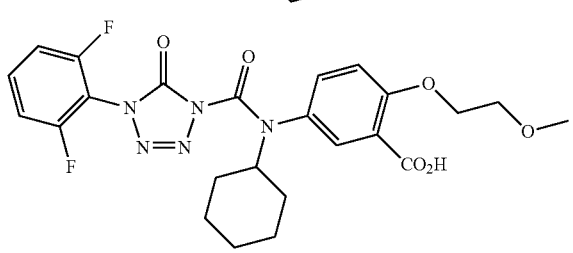
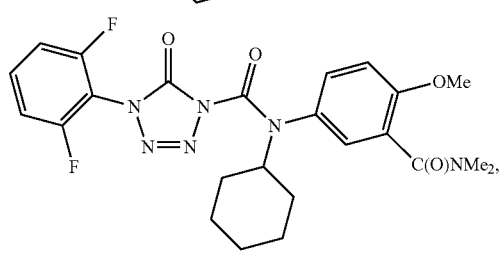
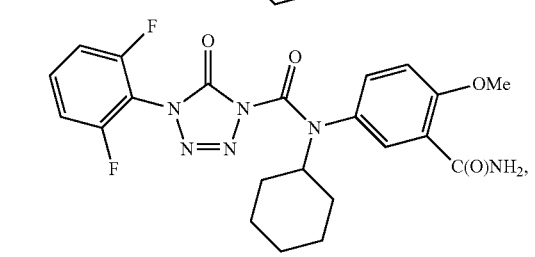
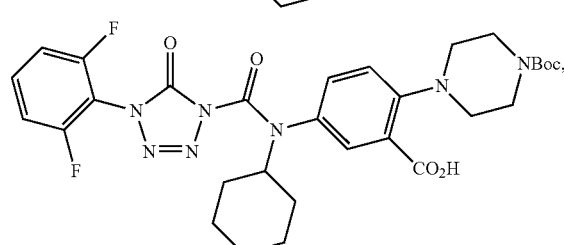
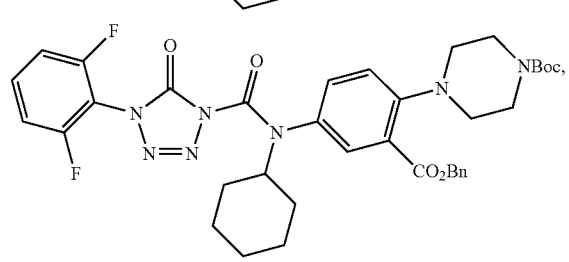
354
-continued
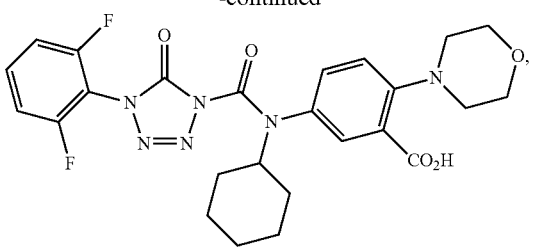
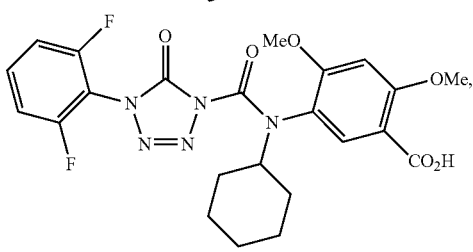
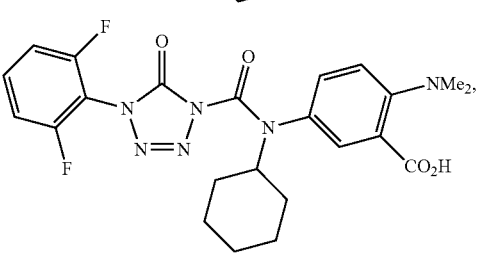
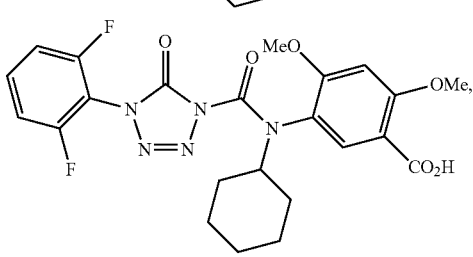
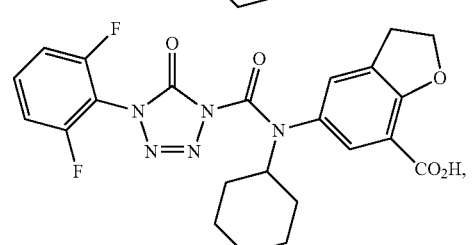
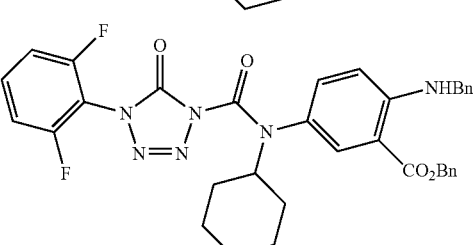
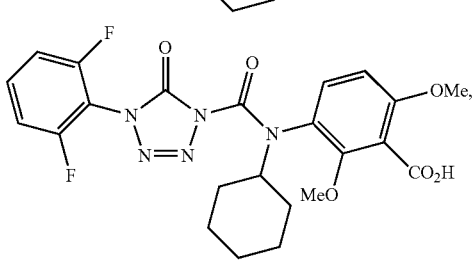

355
-continued
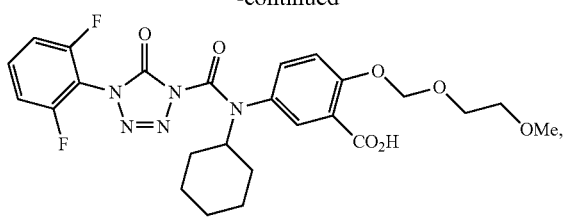
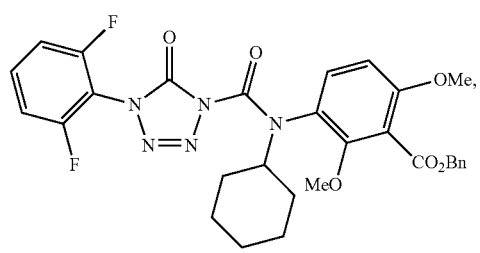
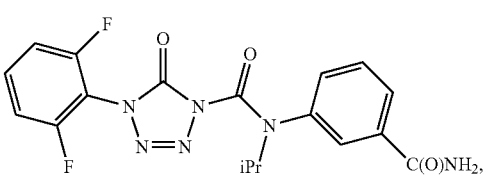
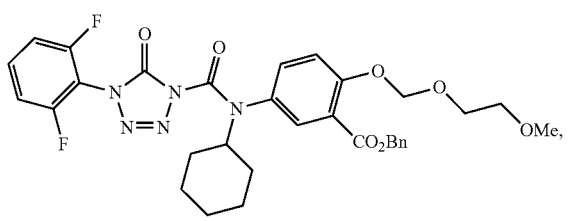
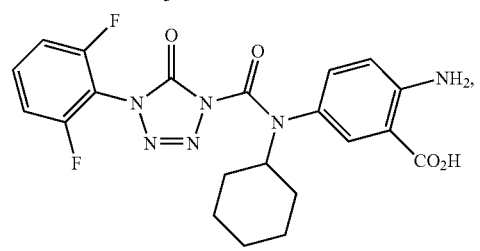
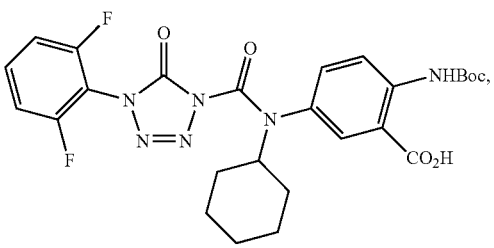
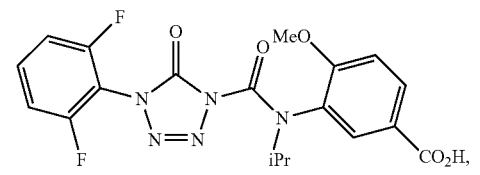
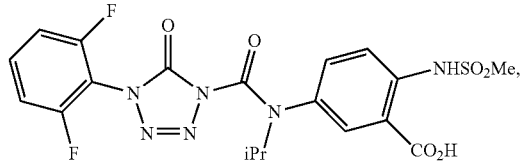
356
-continued
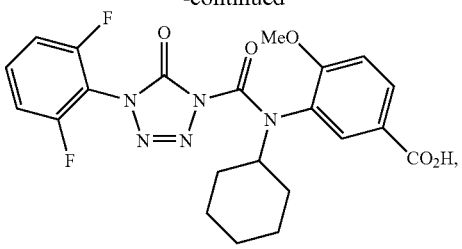
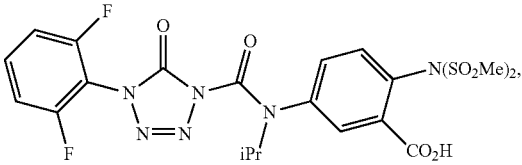
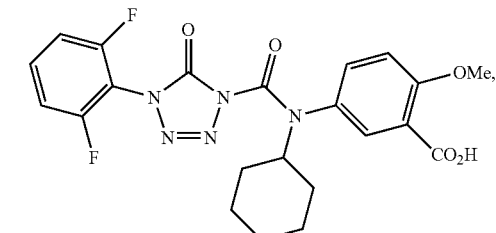
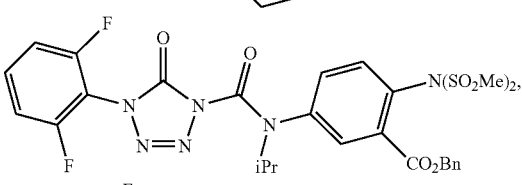
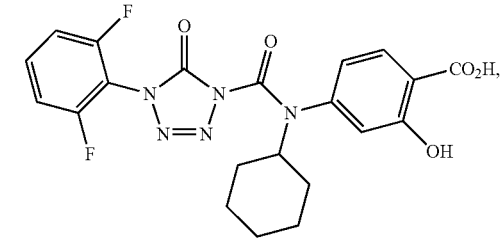
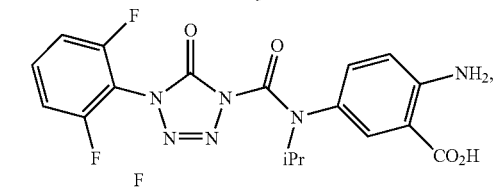
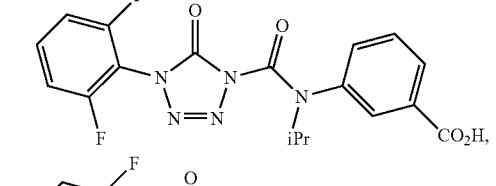
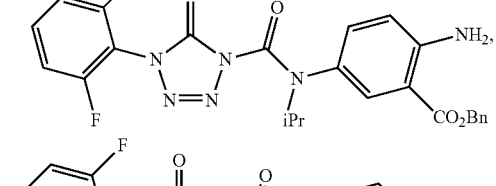
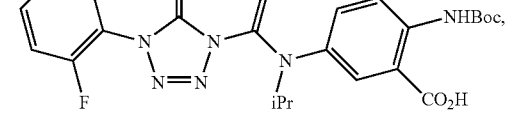

357
-continued
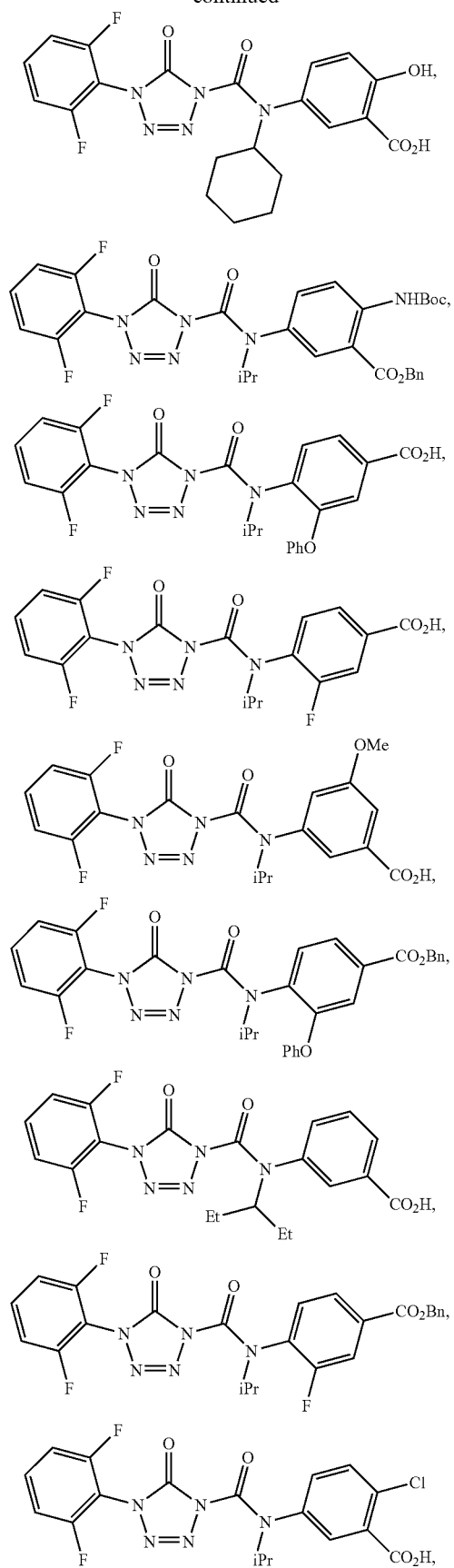
358
-continued
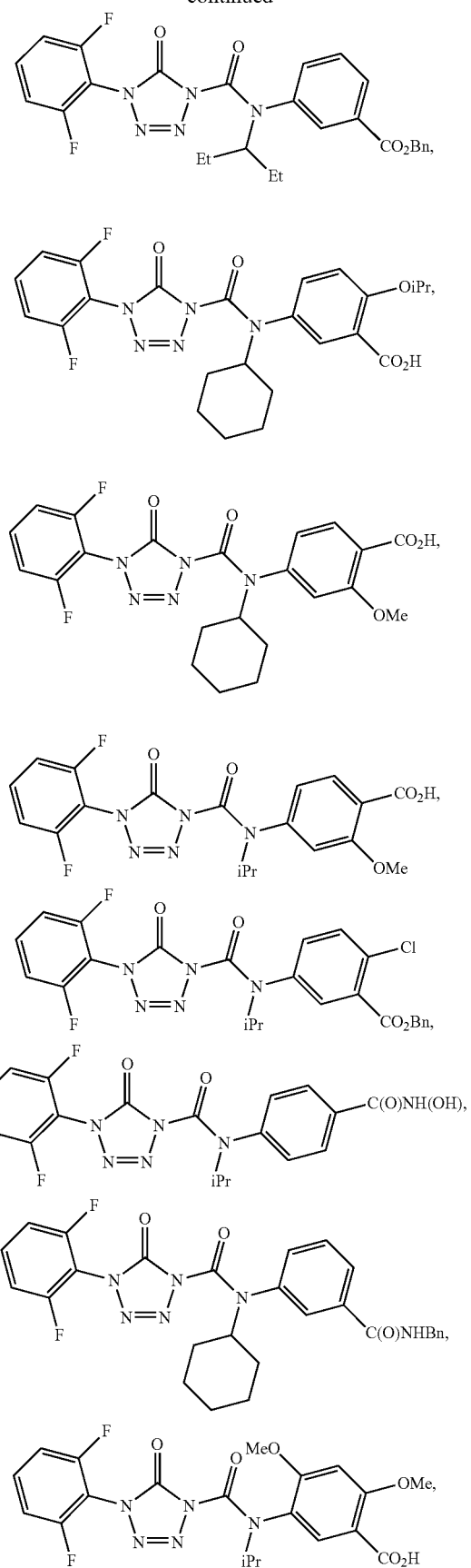

-continued
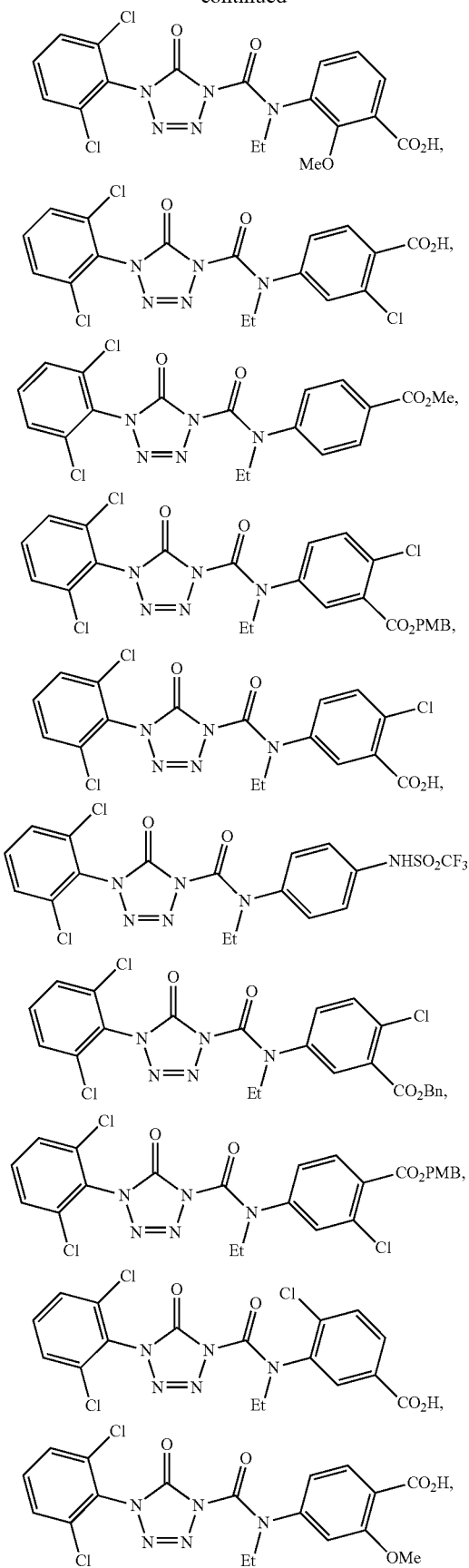
-continued
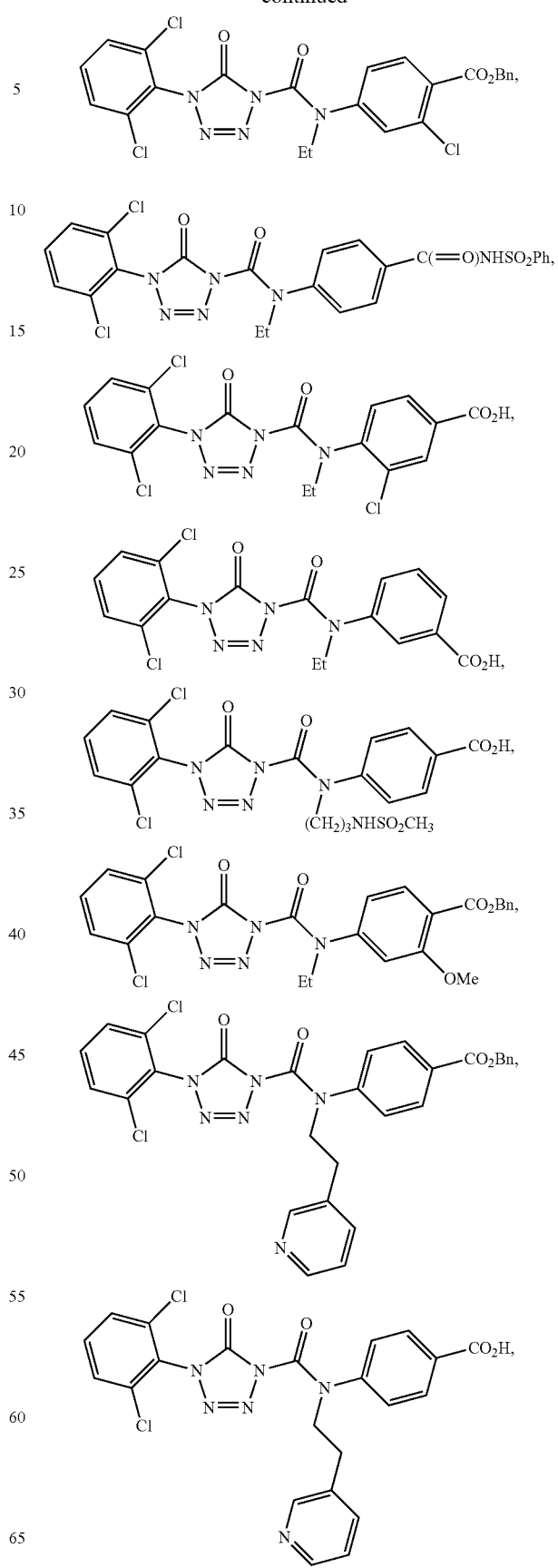

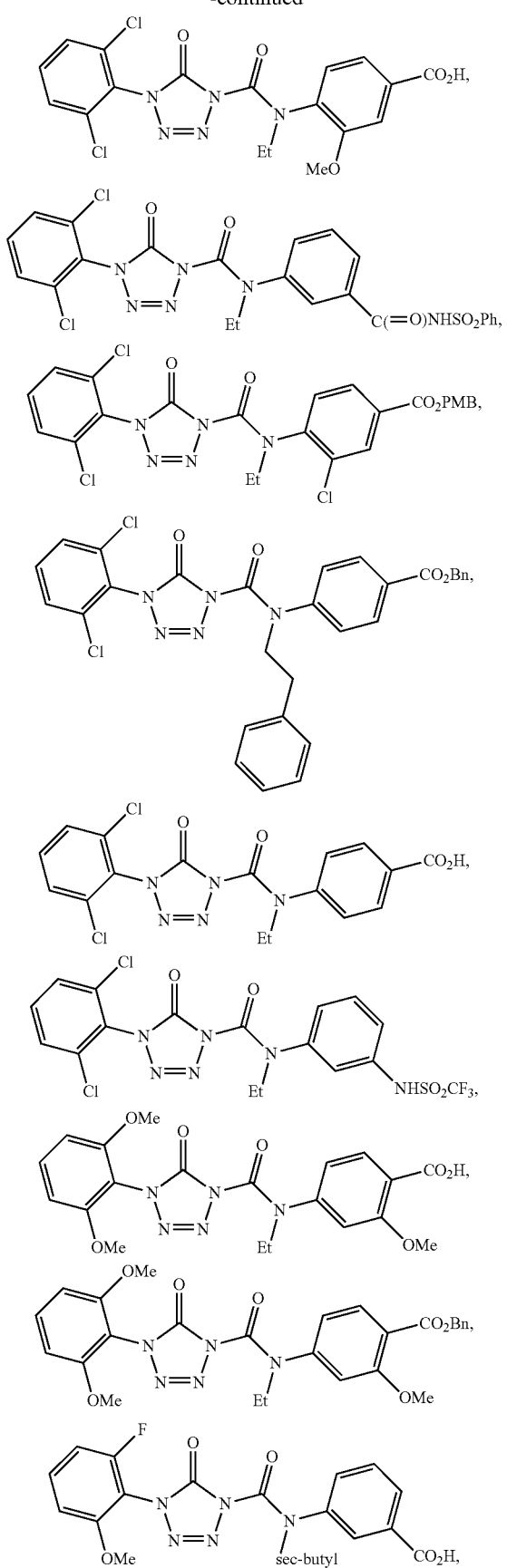
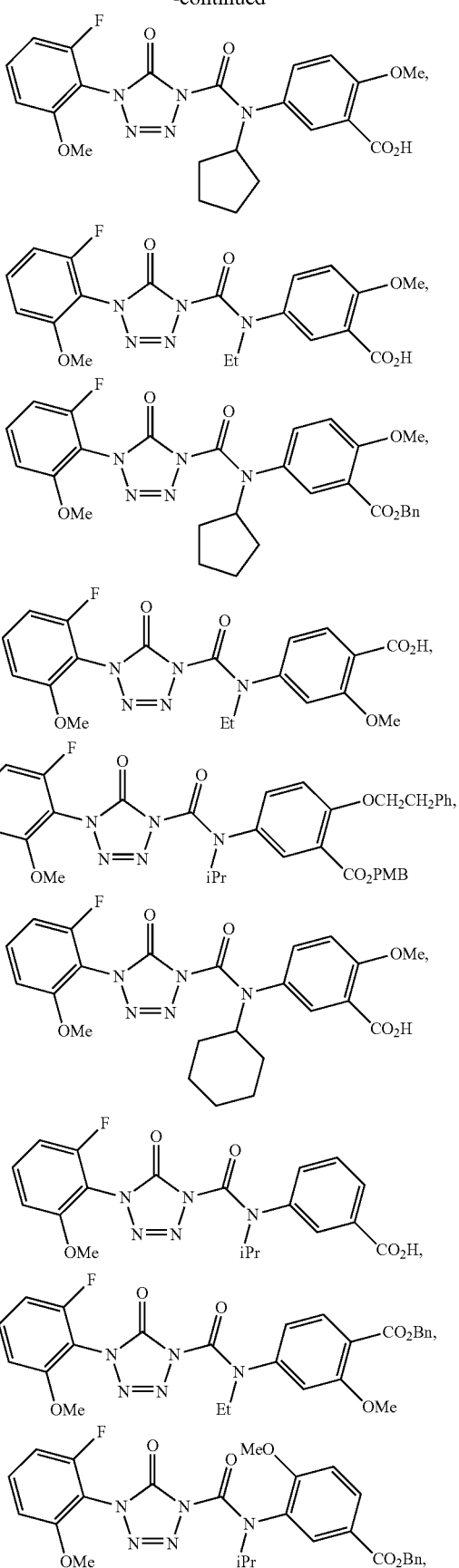

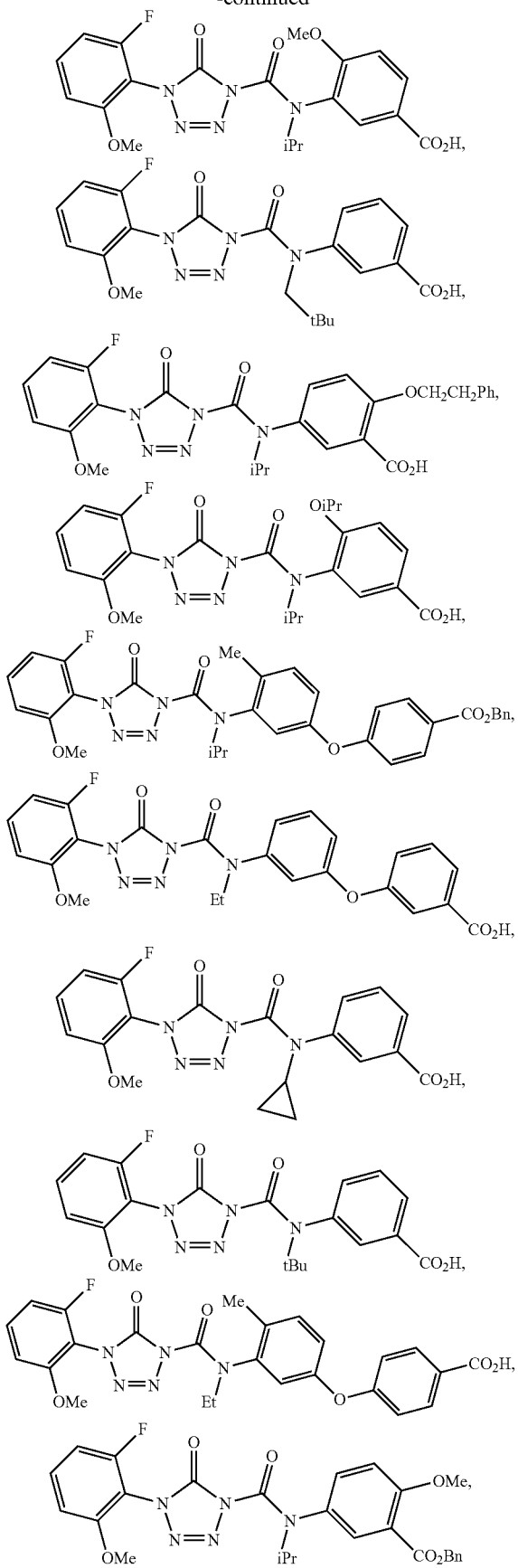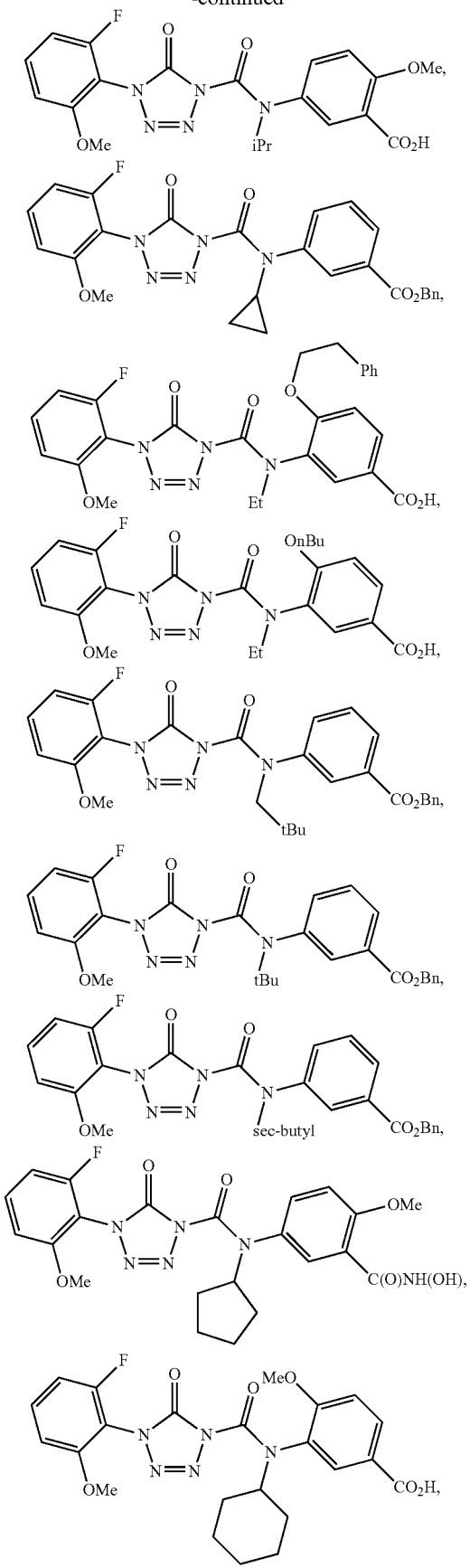

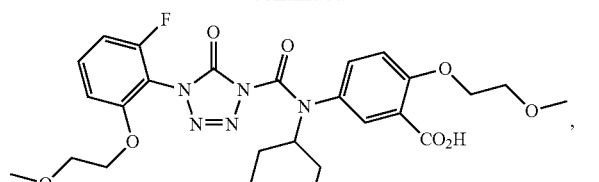
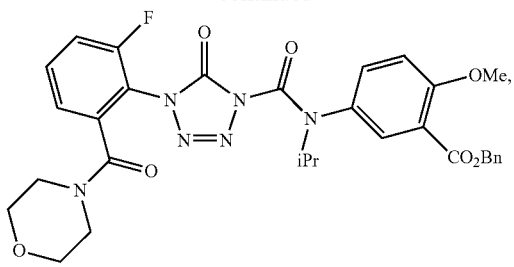
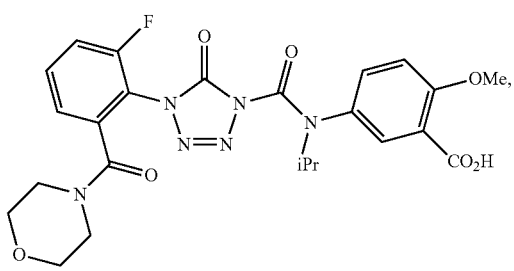
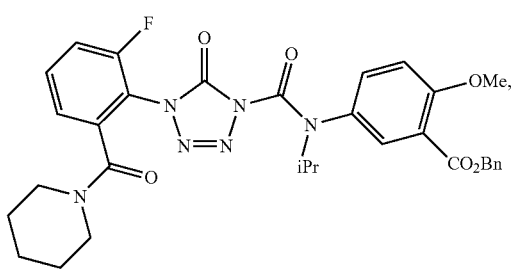
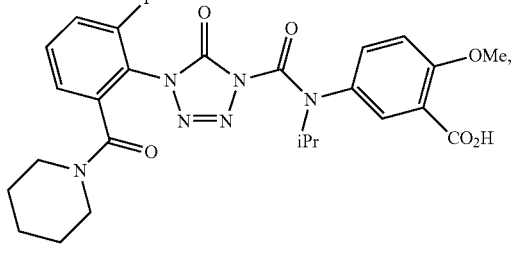
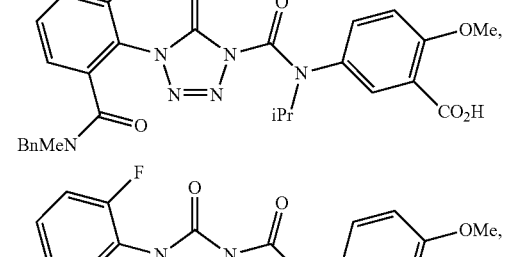
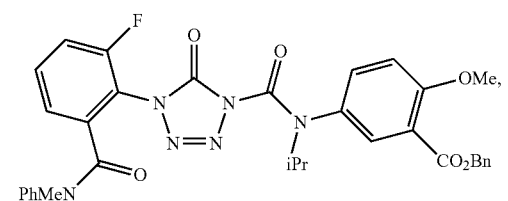

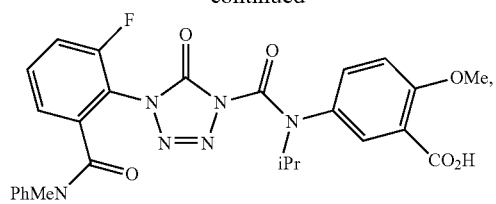
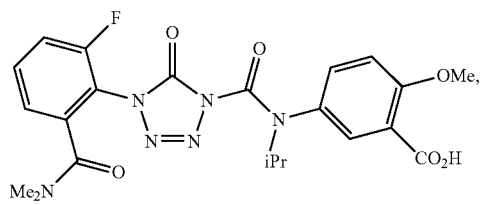
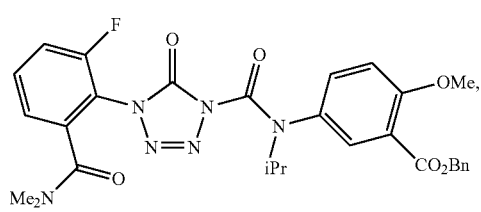
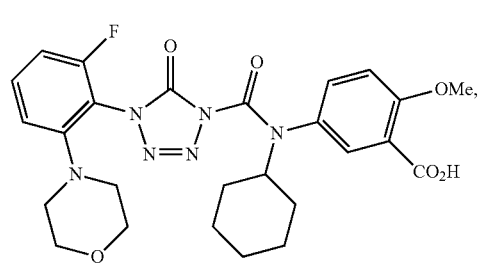
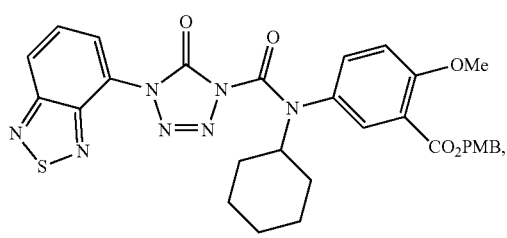
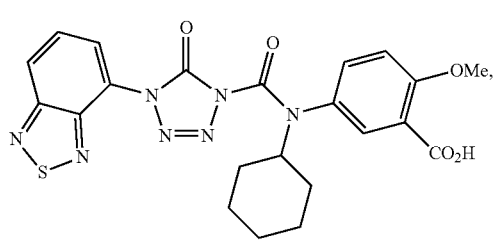
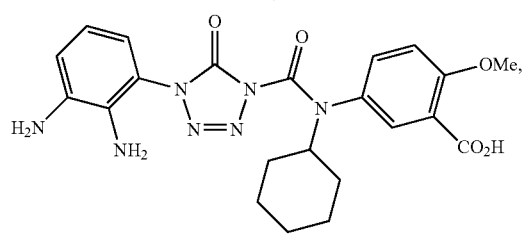
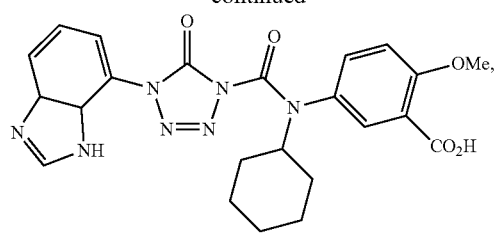
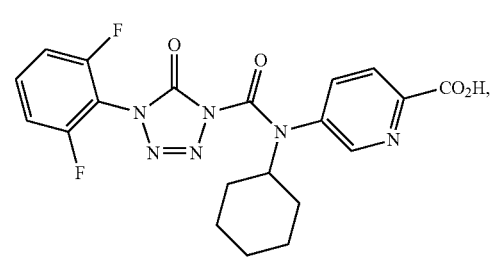
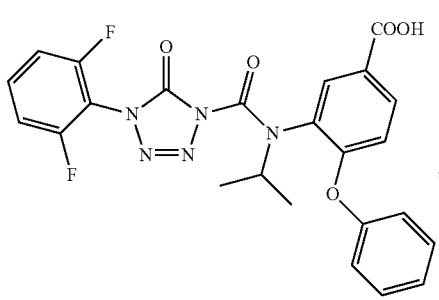
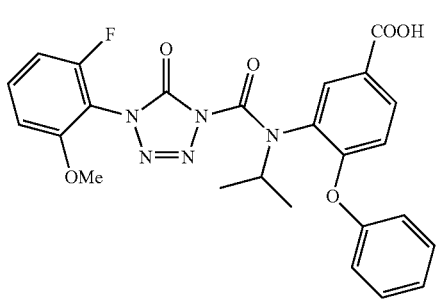
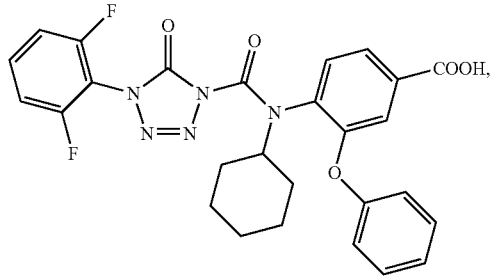
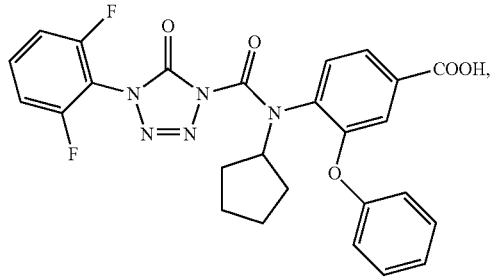

369
-continued
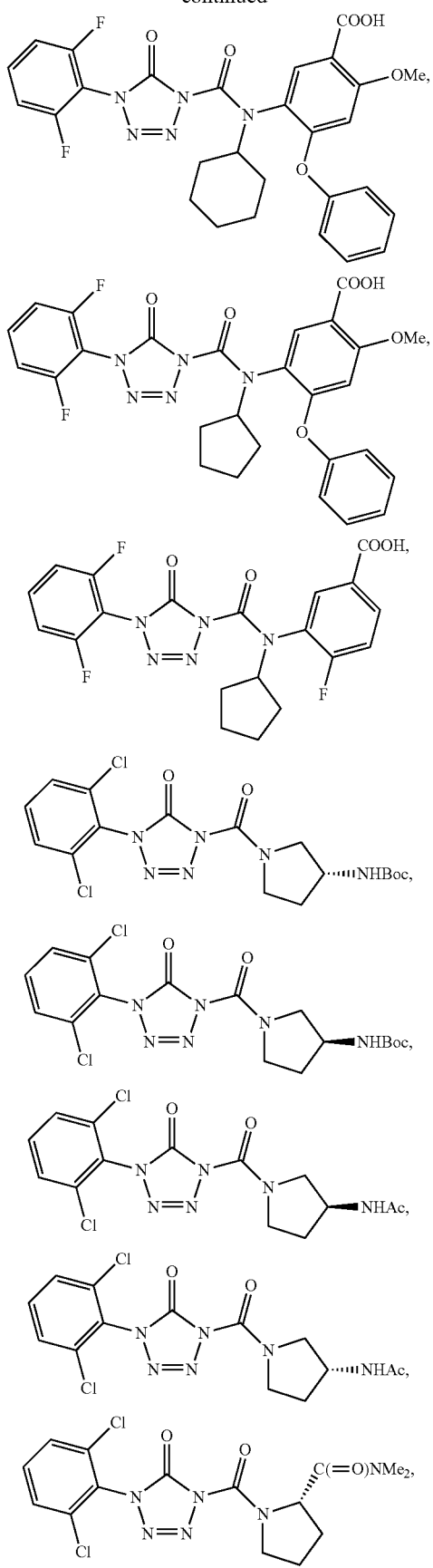
370
-continued
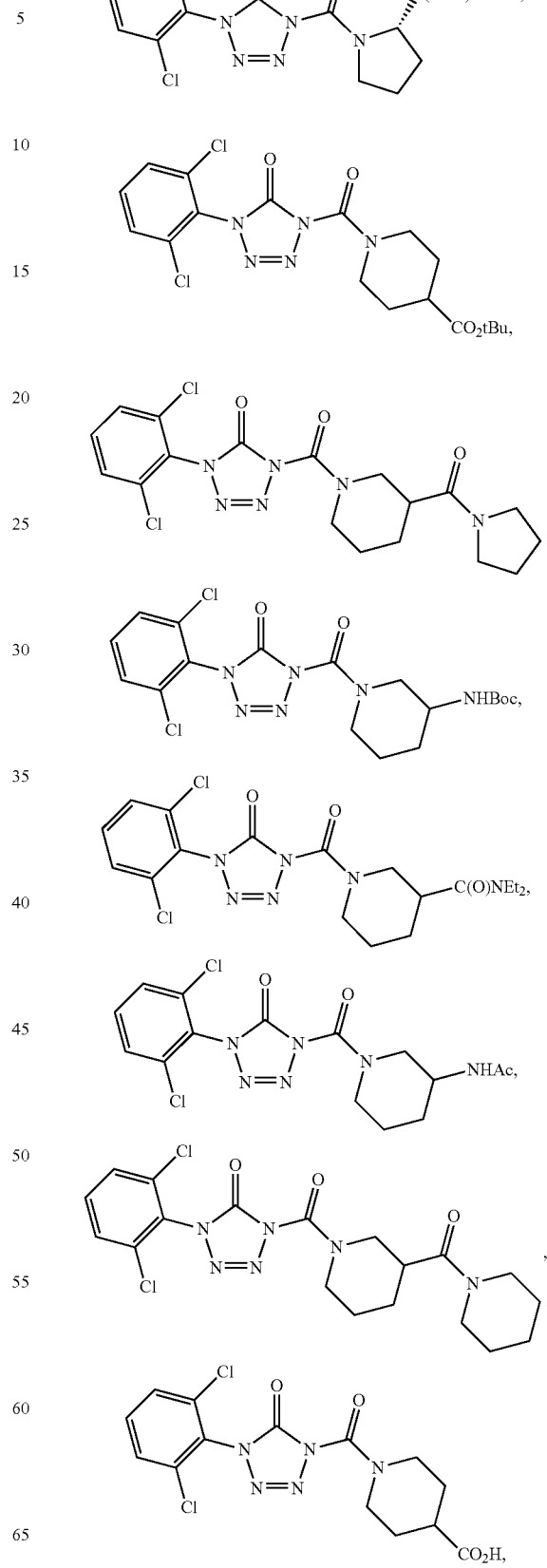

-continued

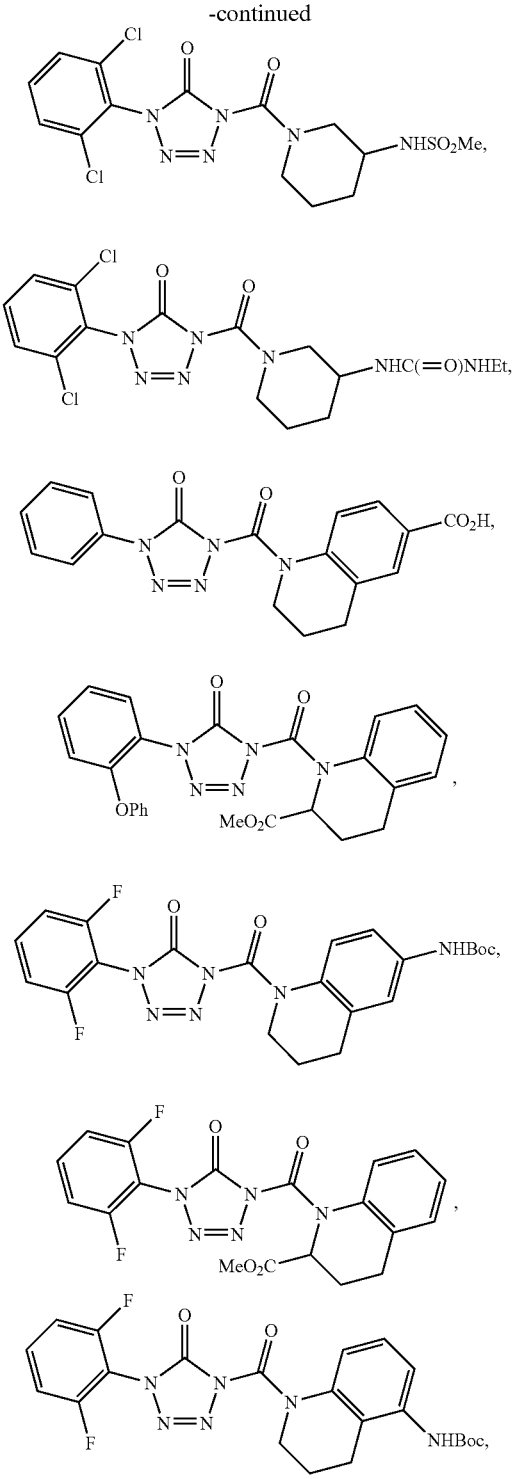

-continued

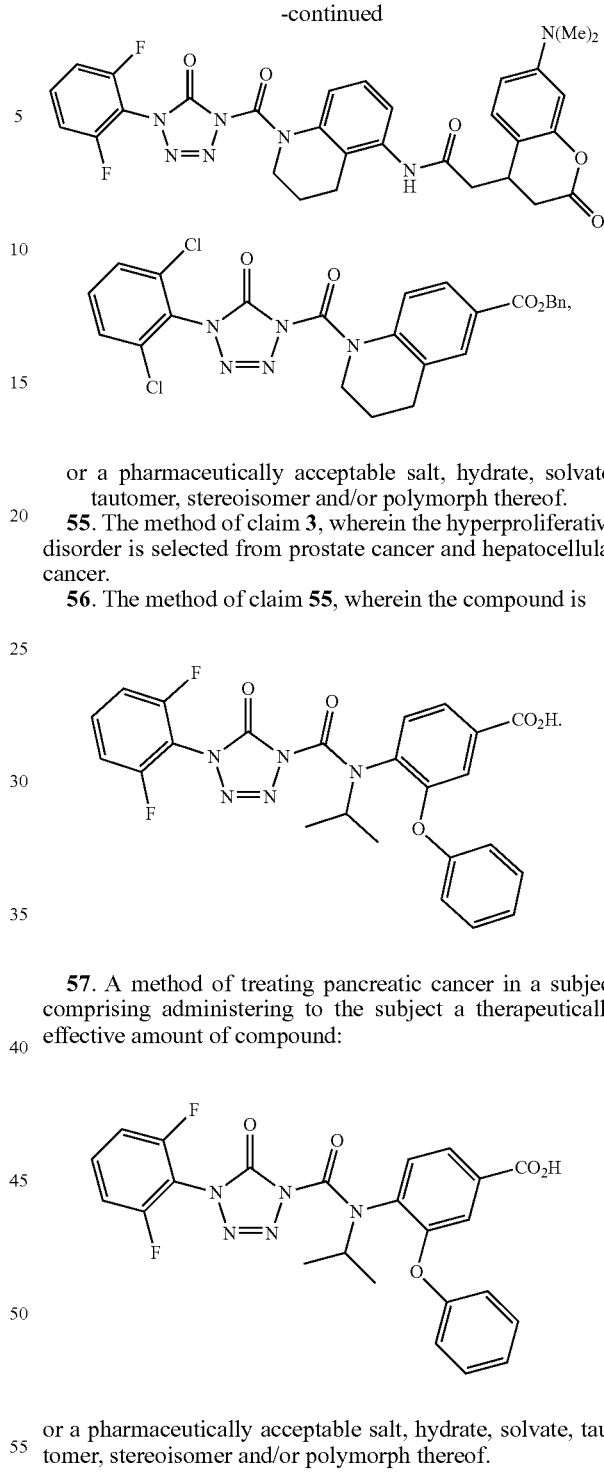

or a pharmaceutically acceptable salt, hydrate, solvate, tautomer, stereoisomer and/or polymorph thereof.

55. The method of claim 3, wherein the hyperproliferative disorder is selected from prostate cancer and hepatocellular cancer.

56. The method of claim 55, wherein the compound is

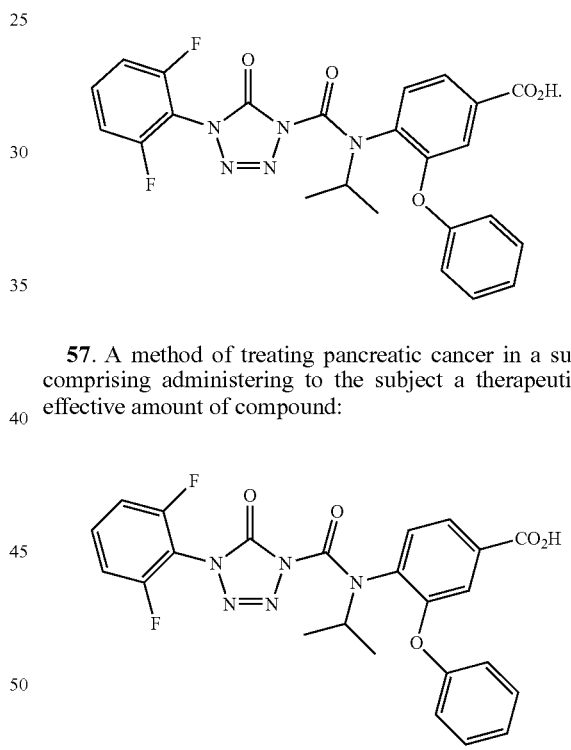

57. A method of treating pancreatic cancer in a subject comprising administering to the subject a therapeutically effective amount of compound:

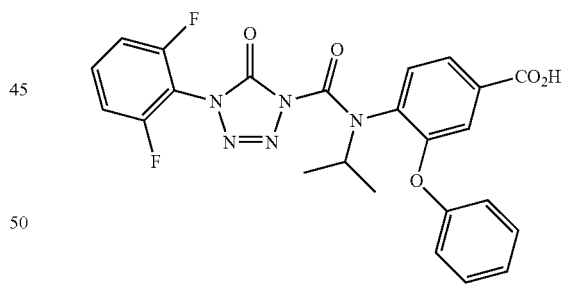

or a pharmaceutically acceptable salt, hydrate, solvate, tautomer, stereoisomer and/or polymorph thereof.

* * * * *